United States Patent
Farnet et al.

(10) Patent No.: US 7,291,490 B2
(45) Date of Patent: *Nov. 6, 2007

(54) NUCLEIC ACID FRAGMENT ENCODING AN NRPS FOR THE BIOSYNTHESIS OF ANTHRAMYCIN

(75) Inventors: Chris M. Farnet, Montreal (CA); Alfredo Staffa, Saint-Laurent (CA)

(73) Assignee: Ecopia Biosciences Inc., Saint Laurent (CA)

( * ) Notice: Subject to any disclaimer, the term of this patent is extended or adjusted under 35 U.S.C. 154(b) by 0 days.

This patent is subject to a terminal disclaimer.

(21) Appl. No.: 11/481,907

(22) Filed: Jul. 7, 2006

(65) Prior Publication Data

US 2007/0117113 A1    May 24, 2007

Related U.S. Application Data

(63) Continuation-in-part of application No. 10/166,087, filed on Jun. 11, 2002, now Pat. No. 7,108,998.

(60) Provisional application No. 60/296,744, filed on Jun. 11, 2001.

(51) Int. Cl.
  C12P 13/00    (2006.01)
  C12N 1/20    (2006.01)
  C07H 21/04    (2006.01)

(52) U.S. Cl. .............. 435/128; 435/252.3; 435/252.33; 435/252.34; 435/252.35; 435/320.1; 536/23.2; 536/23.1; 536/23.7

(58) Field of Classification Search ................ None
See application file for complete search history.

(56) References Cited

U.S. PATENT DOCUMENTS 4,551,433 A    11/1985  DeBoer
4,683,202 A    7/1987   Mullis
4,946,778 A    8/1990   Ladner et al.
5,017,478 A    5/1991   Cashion et al.

FOREIGN PATENT DOCUMENTS

WO    EP 0 246 864    11/1987

OTHER PUBLICATIONS

Marahiel M. et al. (1997) Chem. Rev., vol. 97, pp. 2651-2673 "Modular Peptide Synthetase Involved in Nonribosomal Peptide Synthesis".
Du L. et al. (2001) Metabolic Engineering, vol. 3, pp. 78-95 "Hybrid Peptide-Polyketide Natural Products: Biosynthesis and Prospects toward Engineering Novel Molecules".
Thurston DE et al. (1999) J. Med. Chem 42:1951-1964 "Effect of A-ring modifications on the DNA-binding behavior and cytotoxicity of pyrrolo [2,1-c][1,4] benzodiazepines".
Hurley LH (1977) J. Antibiot (Tokyo) May 30 (5):349-370 "Pyrrolo(1,4)benzodiazepine antitumor antibiotics. Comparative aspects of anthramycin, tomaymycin and sibiromycin".
Stryer, Biochemistry 3rd edition, 1998, W.H. Freeman and Co. New York, pp. 752-754.
Altschul SF et al. (1997) Nucleic Acids Res. vol. 25, pp. 3389-3402 "Grapped BLAST and PSI-BLAST: a new generation of protein database search programs".
Altschul SF et al., J. Mol. Biol., Oct. 5; 215(3) 403-10 , 1990 "Basic Local Alignment Search Tool".
Edge MD (1981) Nature 292:756-62 "Total synthesis of a human leukocyte interferon gene".
Nambiar KP et al. (1984) Science 233(4642):1299-301 "Total synthesis and cloning of a gene coding for the ribonuclease S. Protein".

(Continued)

Primary Examiner—Nashaat T. Nashed

(57) ABSTRACT

Genes and proteins involved in the biosynthesis of benzodiazepines by microorganisms, including the genes and proteins forming the biosynthetic loci for the benzodiazepine anthramycin from Streptomyces refuineus subsp. thermotolerans. The genes and proteins allow direct manipulation of benzodiazepines and related chemical structures via chemical engineering of the enzymes involved in the biosynthesis of anthramycin.

13 Claims, 15 Drawing Sheets

OTHER PUBLICATIONS

Jay E et al. (1984) J. Biol Chem. 259(10):6311-7 "Chemical synthesis of a biologically active gene for human immune interferon-gamma. Prospect for site-specific mutagenesis and structure function studies".

Kieser, T., Hopwood, D.A., Wright, H.M. and Thompson, C.J. (1982) Mol. Gen. Genet. 185(2), 223-8 "pIJ101, a multi-copy broad host-range *Streptomyces plasmid*: functional analysis and development of DNA cloning vetors".

Vara J et al., (1989) J. Bacteriol 171(11):5872-5881 "Cloning of genes governing the deoxysugar portion of the erythromycin biosynthesis pathway in *Saccharopolyspora erythraea (Streptomyces erythreus)*".

Guilfoile PG & Hutchinson CR (1991) Proc. Natl. Acad. Sci. USA, 88:8553-8557 "A bacterial analog of the *mdr* gene of mammalian tumor cells is present in *Streptomyces peuceticus*, the producer of daunorubicine and doxorubicin".

Shen B & Hutchinson CR (1994) J. Biol. Chem. 169(48): 30726-30733 "Triple hydroxylation of tetracenomycin A2 to tetracenomycin C in *Streptomyces glaucescens*. Overexpression of the temG gene in *Streptomyces lividans* and characterization of the tetracenomycin A2 oxygenase".

Pieper et al. (1995) Nature 378(6554):263-266 "Cell-free synthesis of polyketides by recombinant erythromycin polyketide synthases".

Pieper et al. (1995) J. Am. Chem. Soc. 117:11373-11374 "Remarkably Broad Substrate Specificity of a Modular Polyketide Synthase in a Cell-Free System".

Wiesmann KE et al. (1995) Chem. Biol. 2(9):583-589 "Polyketide synthesis in vitro on a modular polyketide synthase".

Quadri et al. (1998) Biochemistry 37:1585-1595 "Characterization of Sfp, a *Bacillus subtilis* Phosphopantetheinyl Transferase for Peptidyl Carrier Protein Domains in Peptide Synthetases".

Nakano MM et al. (1992) Mol. Gen Genet. 232:313-321 "Isolation and characterization of sfp: a gene that functions in the production of the lipopeptide biosurfactant, surfactin, in *Bacillus subtilis*".

Carreras CW & Khosla C (1998) Biochemistry 37(8):2084-2088 "Purification and in vitro reconstitution of the essential protein components of an aromatic polyketide synthase".

Hurley LH et al. (1979) Biochemistry 18(19):4230-4237 "Pyrrolo[1,4]benzodiazepine antibiotics. Biosynthetic conversion of tyrosine to the C2- and C3-proline moieties of anthramycin, tomaymycin, and sibiromycin".

Brahme NM et al. (19884).J. Am. Chem. Soc. 106:7873-7878 "Biosynthesis of the Lincomycins. 1. Studies Using Stable Isotopes on the Biosynthesis of the Propyl- and Ethyl-L-hygric Acid Moieties of Lincomycins A and B".

Kuo MS et al. (1989) J. Antibiot. 42(3):475-478 "Isolation and identification of 7,8-didemethyl-8-hydroxy-5-deazariboflavin, an unusual cosynthetic factor in streptomycetes, from *Streptomyces lincolnensis*".

Peschke U et al. (1995) Molec. Microbiol. 16(6):1137-1156 "Molecular characterization of the lincomycin-production gene cluster of *Streptomyces lincolnensis* 78-11".

Lomovskaya N et al. (1999) J. Bacteriol 181:305-318 "Doxorubicin Overproduction in *Streptomyces peuceticus*: Cloning and Characterization of the *dnrU* Ketoreductase and *dnrV* Genes and the *doxA* Cytochrome P-450 Hydroxylase Gene".

Hurley LH et al. (1975) J. Am. Chem. Soc. 97(15):4372-4378 "Biosynthesis of anthramycin. Determination of the labeling pattern by use of radioactive and stable isotope techniques".

Hurley LH & Gairola C (1979) Antimicrob. Agents Chemother 15(1):42-45 "Pyrrolo (1,4) benzodiazepine antitumor antibiotics: Biosynthetic studies on the conversion of tryptophan to the anthranilic acid moieties of sibiromycin and tomaymicin".

Konz D & Marahiel MA (1999) Chem. Biol., vol. 6(2), pp. R39-R48 "How fo peptide syntetases generate structural diversity?".

May J et al. (2001) J. Biol. Chem. 276:7209-7217 "The *dhb* Operon of *Bacillus subtilis* Encodes the Biosynthetic Template for the Catecholic Siderophore 2,3-Dihydroxybenzoate-Glycine-Threonine Trimeric Ester Bacilliabatin".

Keating TA et al. (2001) Chembiochem 2(2):99-107 "Chain termination steps in nonribosomal peptide synthetase assembly lines: directed acyl-S-enzyme breakdown in antibiotic and siderophore biosynthesis".

Tang MS et al. (1991) J. Mol. Biol. 220(4):855-866 "Repair of helix-stabilizing antrhamycin-N2 guanin DNA adducts by UVRA and UVRB, proteins".

Furuya K & Hutchinson CR (1998) FEMS Microbiol. Lett. 168(2):243-249 "The DrrC protein of *Streptomyces peuceticus*, a UvrA-like protein, is a DNA-binding protein whose gene is induced by daunorubicin".

Gehring AM et al. (1998) Biochemistry 37(8):2648-2659 "Reconstitution and characterization of the *Escherichia coli* enterobactin synthase from EntB, EntE, and EntF".

Walsh CT et al. (1997) Curr. Opin. Chem. Biol. 1:309-315 "Post-translational modification of polyketide and nonribosomal peptide synthases".

Lambalot RH et al. (1996) Chem. Biol. 3:923-936 "A new enzyme superfamily—the phosphopantetheinyl transferases".

Cole SPC et al. (1985) Monoclonal Antibodies, Alan R. Liss, pp. 77-96 "The EBV-Hybridoma technique and its application to human lung cancer".

Admiraal SJ et al. (2001) Biochemistry 40(20):6116-6123 "The loading module of rifamycin synthase is an adenylation-thiolation didomain with substrate tolerance for substituted benzoates".

Lambalot RH & Walsh CT (1995) J. Biol. Chem. 270(42):24658-24661 "Cloning, Overproduction, and Characterization of the *Escheria coli* Holo-acyl Carrier Protein Synthase".

Stachelhaus T et al. (1998) J. Biol. Chem. 273:22773-22781 "Peptide Bond Formation in Nonribosomal Peptide Biosynthesis".

Doekel S & Marahiel MA (2000) Chem. Biol. 7(6):373-384 "Dipeptide formation on engineered hybrid peptide synthetases".

Boojamre CG et al. (1997) J. Org. Chem. 62:1240-1256 "Solid-Phas Synthesis of 1,4-Benzodiazepine 2,5-diones. Library Preparation and Demonstration of Syntehsis Generality".

Mootz HD et al. (2000) Proc. Natl. Acad. Sci. USA 97(11):5848-5853 "Construction of hybrid peptide synthetases by module and domain fusions".

Trauger JW et al. (2000) Nature 407(6801):215-218 "Peptide cyclization catalyzed by the thioesterase domain of tyrocidine synthase".

Walzel B et al. (1997) Chem. Biol. 4(3):223-230 "Mechanism of alkaloid cyclopeptide synthesis in the ergot fungus *Claviceps purpurea*".

Ehmann DE et al. (2000) Chem. Biol. 7(10):765-772 "Aminoacyl-SNACs as small-molecule substrates for the condensation domains of nonribosomal peptide synthetases".

Belshaw PJ et al (1999) Science 284(5413):486-489 "Aminoacyl-CoAs as probes of condensation domain selectivity in nonribosomal peptide synthesis".

Lowden PAS et al. (1996) Chem Int. Ed. Engl. 35:2249-2251 "The Nature of the Starter Unit for the Rapamycin Polyketide Synthase".

Motamedi H & Shafiee A (1998) Eur. J. Biochem 256:528-534 "The biosynthetic gene cluster for macrolactone ring of the immunosuppressant FK506".

Wu K et al. (2000) Gene 251(1):81-90 "The FK520 gene cluster of *Streptomyces hygroscopicus* var. *ascomyceticus* (ATCC 14891) contains genes for biosynthesis of unusual polyketide extender units".

Tillett D et al. (2000) Chem. Biol. 7(10):753-764 "Structural organization of microcystin biosyntesis in *Microcystis aeruginosa* PCC7806: an integrated peptide-polyketide synthetase system".

Aparicio JF et al (2000) Chem. Biol. 7:895-905 "A complex multienzyme system encoded by five polyketide synthase genes is involved in the biosynthesis of the 26-membered polyene macrolide pimaricin in *Streptomyces natalensis*".

Marsden AF et al. (1998) Science, vol. 279, pp. 199-202 "Engineering broader specificity into an antibiotic-producing polyketide synthase".

Chen S et al. (1999) Eur. J. Biochem, vol. 261, pp. 98-107 "Biosynthesis of ansatrienin (mycotrienin) and naphthomycin—Identification and analysis of two separate biosynthetic gene clusters in *Streptomyces collinus* Tü 1892".

Gluzman Y. (1981) Cell., vol. 23, pp. 176-182 "SV40-Transformed Simian Cells Support the Replication of Early SV40 Mutants".

Caldwell R.C. & Joyce G.F. (1992) PCR Methods Applic., vol. 2, pp. 28-33 "Randomization of Genes by PCR Mutagenesis".

Rejdhaar-Olson J.F. and Sauer R.T. (1988) Science, vol. 241, pp. 53-57 "Combinatorial Cassette Mutagenesis as a Probe of the Informational Content of Protein Sequences".

Kholer G. and Milstein C. (1975) Nature, vol. 256, pp. 495-497 "Continuous cultures of fused cells secreting antibody of predefined specificity".

Kozbor D. et al. (1983) Immunology Today, vol. 4 No. 3, pp. 72-79 "The production of monoclonal antibodies from human lymphocytes".

Wood T. and Mahalingeshawara B. (1988) Methods in Enzymology, vol. 160, pp. 87-116 "Methods for Measuring Cellulase Activities".

Person W. and Lipman D. (1988) Proc. Natl. Acad. Sci USA, vol. 85, pp. 2444-2448 "Improved tools for biological sequence database comparison".

Brutlag D.L. et al. (1990) Comp. App. Biosci., vol. 6 no. 3, pp. 237-245 "Improved sensitivity of biological sequence database searches".

Thompson J.D. et al. (1994) Nucleic Acids Res., vol. 22(2), pp. 4673-4680 "Clustal W: improving the sensitivity of progressive multiple sequence alignment through sequence weighting, position-specific gap penalties and weight matrix choice".

Higgins D. et al. (1996) Methods Enzymol., vol. 266, pp. 383-402 "Using CLUSTAL for Multiple Sequence Alignments".

Gish W et al. (1993) Nature Genetics, vol. 3, pp. 266-272 "Identification of protein coding regions by database similarity search".

Eddy S.R. (1998) Bioinformatics, vol. 14 No. 9, pp. 755-763 "Profile hidden Markov models".

Bailey T.L. et al. (1997) J. Steroid Biochem Mol Biol., vol. 62 No. 1, pp. 29-44 "An Artificial Intelligence Approach to Motif Discovery in Protein Sequences: Application to Steroid Dehydrogenases".

Fleishmann R. et al. (1995) Science, vol. 269, pp. 496-512 "Whole-Genome Random Sequencing and Assembly of *Haemophilus influenza* Rd".

Neusser D et al. (1998) Arch. Microbial., vol. 169(4), pp. 322-332 "The genes ImbB1 and ImbB2 of *Streptomyces lincolnensis* encode enzymes involved in the conversion of L-tyrosine to propylproline during the biosynthesis of the antibiotic lincomycin A".

GenBank Accession No. AF319998. *Stigmatella aurantiaca* myxalamid biosynthetic gene cluster, complete sequence. May 2001.

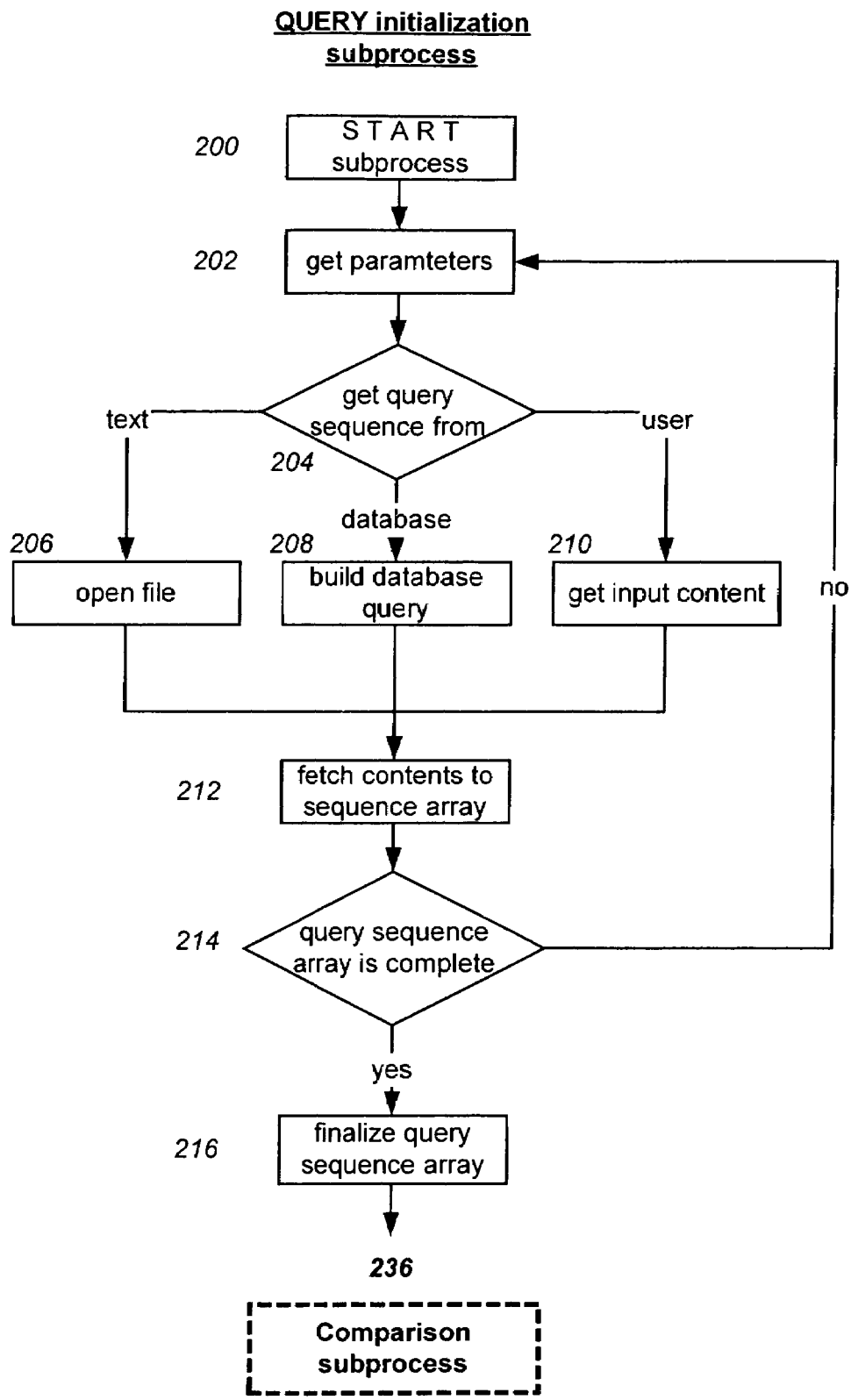
Figure 2-A

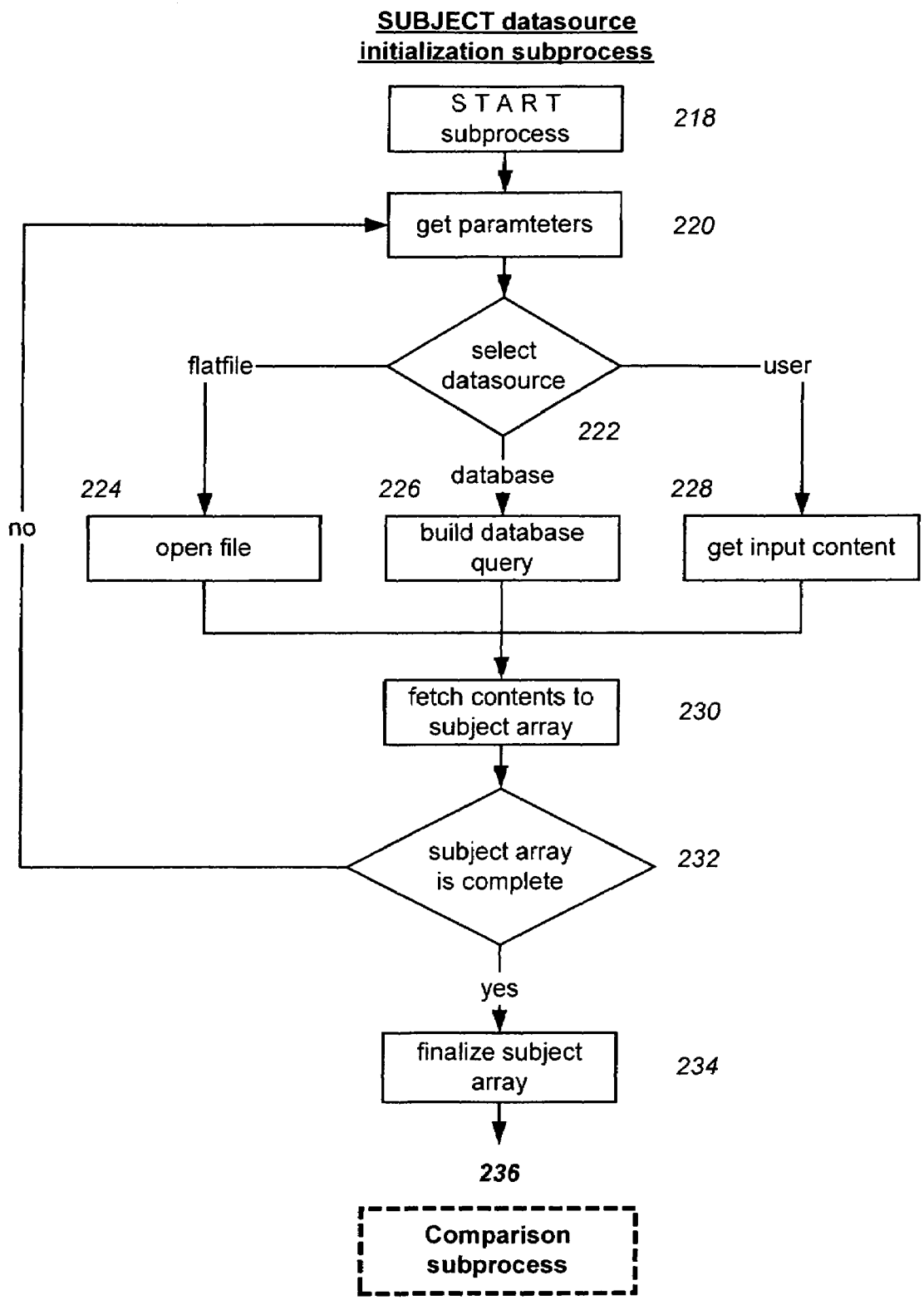
Figure 2-B

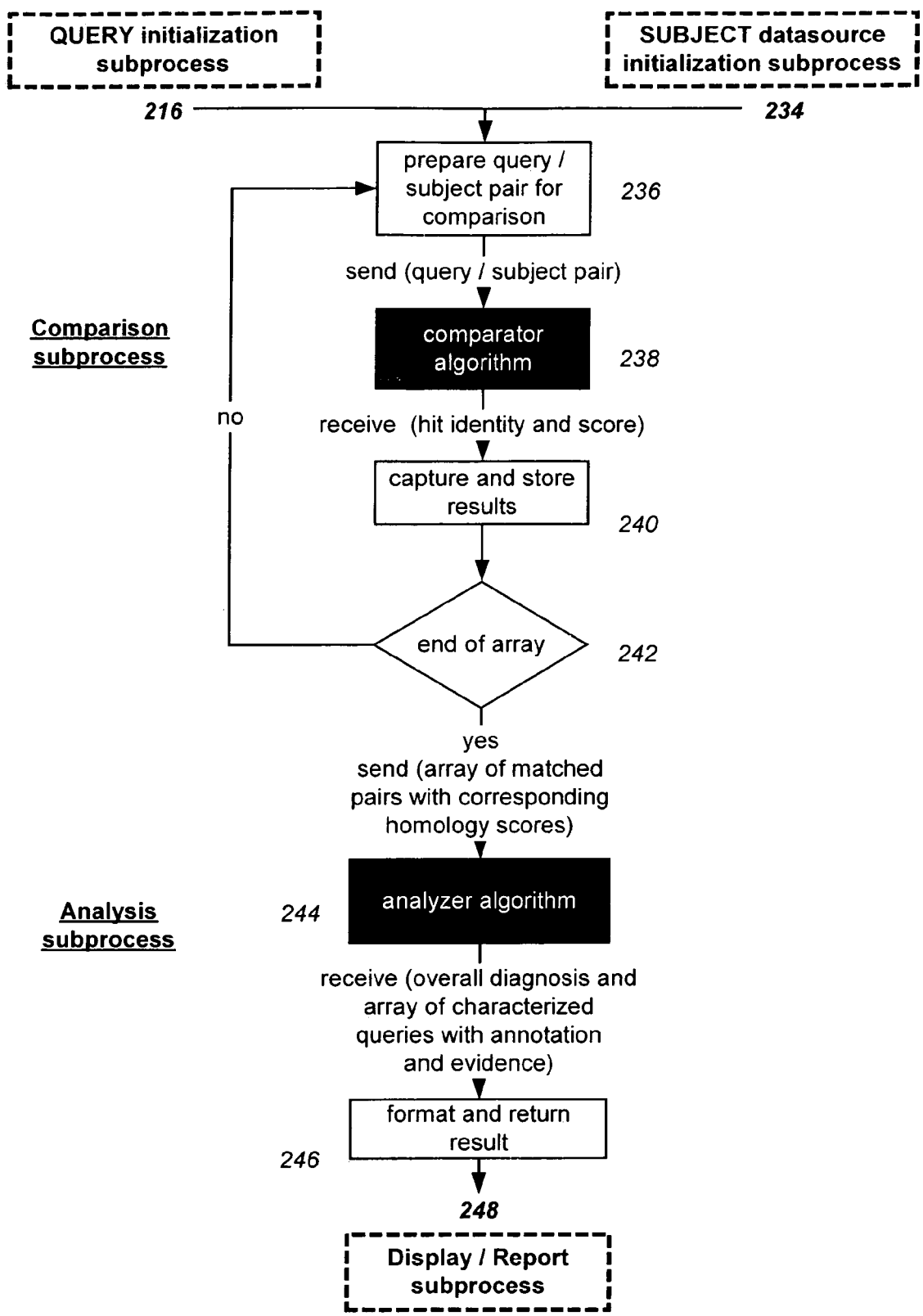
Figure 2-C

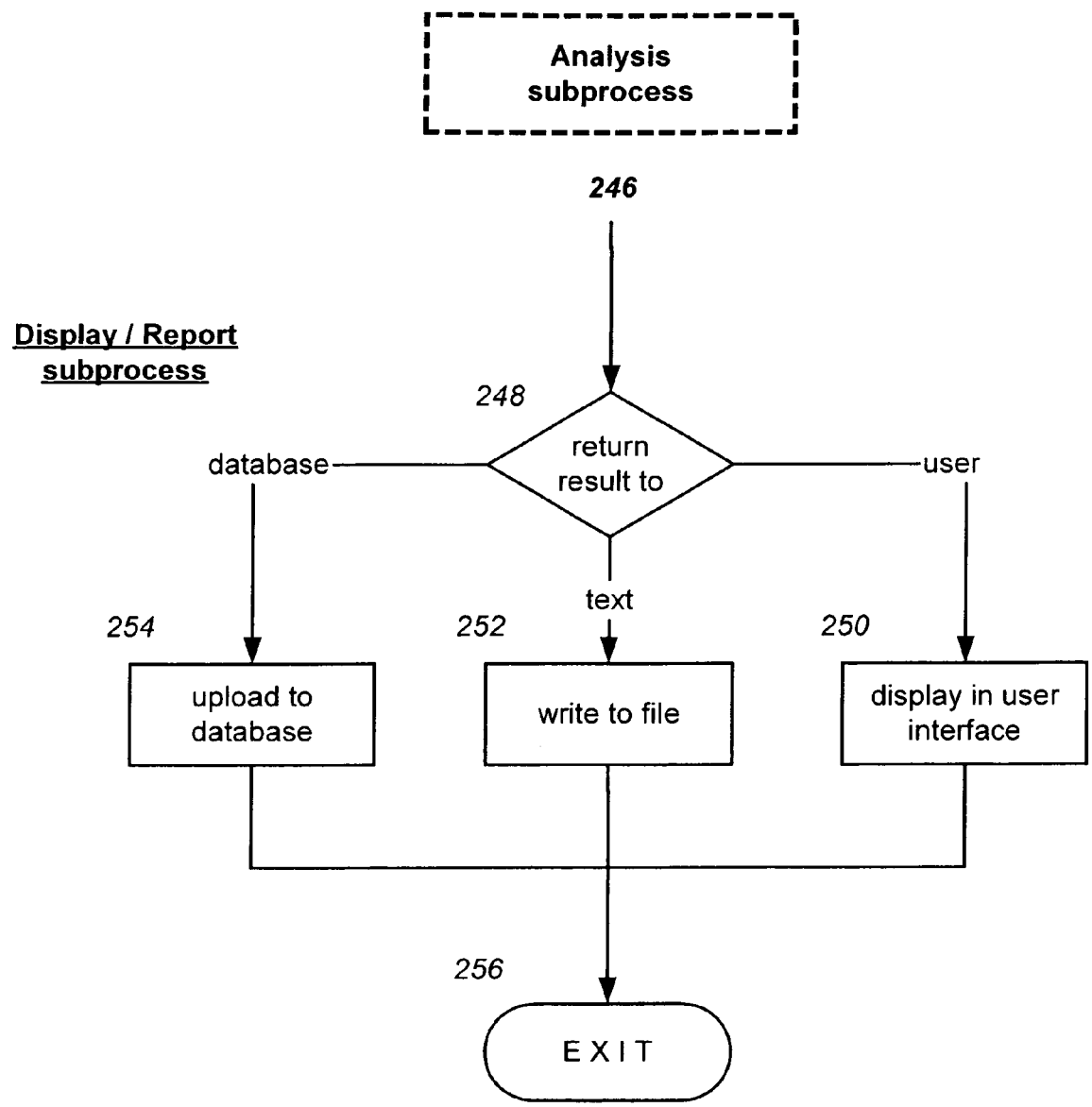
Figure 2-D

Figure 11

Alignment of the Reductase Domain of Anthramycin NRPS (amino acids 1038-1446 of SEQ ID NO:44) and Reductase Domains of other NRPS systems

```
                                                                         R1 (NADPH
                                                                         binding site)                                         R2
SaframycinA (SEQ ID NO:52)    1  --TYQREQLDAVIMNQHATRLDADASLAPDISP-EGELANYIAPSSVLLTGATGFLGAFLLEQLIKRTRATVYCLVRAADPAQAMDRVRATMHQYIVWD
Myxalamid   (SEQ ID NO:53)    1  ARAVEAMGSLPAHDVVEMEADAVDAEIALGKALPPVTG-ALRLHTLLTGATGFLGAFLLECRPIDARTYCLVRSKTEQGNRIRKNLESYSLWN
Myxochelin  (SEQ ID NO:54)    1  --ISKAMLADAFIPEEIVERIPTPGAEADIAPS------PGPAAPLRQVLLTGATGFVGAHLLDLIRCTQAKVCLVRARDEAHAWERLREAMTSQRLST
SEQ ID NO:44 R domain         1  -TVRGMAGSLAGRGASGTVDLREEARLHDLVVG------ERREPADGAVLLTGATGFLGSHLLDELQR-AGRRVCLVRAGSVEEARGRLRAAFEKFALD-
consensus   (SEQ ID NO:56)    1  i  aagdavla dvtvrldada lapli      glppa  g alrsvLLTGATGflGa  LLe Llrrt arvyCLvRa deaeamdRlRaamesy  lw SaframycinA (SEQ ID NO:52)   98  EAYAERLRPMGDIGKPRLGLSREEWELGLEHDSIVHNGALVNFVYPYSALRCPNVHGTQEVLRLCQHRIKAVHVSTIDVILATHMRPFMEDDAPL
Myxalamid   (SEQ ID NO:53)  100  EALAPRIVPVRGDLCQPTLGLSEKEFCRLSEEIDAIVHNGALVNFLYPYEPVMSMRAALVIGTREELILATRTRIKPLHVVSTVLPGFKAP-IREDEPL
Myxochelin  (SEQ ID NO:54)   94  ASLSERVIALPADIGQPWLGLSSARFHGLAPECDMIFNAAVSVREYGSIQATNVRGTRELLRLAASVRPKLPHYVSTLAVAPQNLSP--EVPEAFV
SEQ ID NO:44 R domain        93  PSRIDRAEIWGDLARPRLGIGDG-EAARAHEMGEWYHAAHINEAVPYHTVRTNVDGIRRVIDFCVNR-TPLRIISTLGVFPPDSAPG-VIGEDTVP
consensus   (SEQ ID NO:56)  101  e laeRivplvgDlgqPrlGLseaef rla Eld iyHngAlvnfvypY slratNvHgtrevLrlaa  Rlkplhyvstlavlp ghmpp  i edapl R3                                                                        R4
SaframycinA (SEQ ID NO:52)  198  RNPIEVPGGYTGSKWVABKVVNIARARGPVCIYRPGIILSHEETGATQTNDVLLVAARGYVPMGIIP---DYPRIFDTIPVDMAKAIVHISTQRFALG
Myxalamid   (SEQ ID NO:53)  198  EGPDSLIVGGYAQSKWVABKLVREASRGLPVTILRPGRVTGHSRTGAWNTDDLVCRLKGCVRMGVAP----SVDALDLTPVDYSSAIVDLSMRPFSIG
Myxochelin  (SEQ ID NO:54)  192  PAHPGIRDGVQQSKWMAAERIVEQASERGLPVTVYRIGRVSGALDSCIVNPQDIWRITLAGIPACALP---QLDVGEWTPVDYVARAIVRLSLVPR-PG
SEQ ID NO:44 R domain       190  GDPASIGIGYSQSKWVABHLALQRQAGLPVIWYPVGRIAGHSRIGACRHDFFLQMKGFAILRCPDDIADAPAVDLIPVDYVARAIVRLAEGKP-DD
consensus   (SEQ ID NO:56)  201  gp  sl  gGYtgsKwvAEklv qA  rGlPvtiyRpGritghsrtGa  ntddlvwr lkgyvpmGliP     vd  ldltPvDyvarAivrlsm pe lg R5                                                            R6
SaframycinA (SEQ ID NO:52)  295  RFHLHFNELAPVSLRRFCDWLRSYGYAFDIVPFDEARQALDVDTSHP-IYPIVELIRDAEAEPQESLDPAFIDQLRPDIECRSAVEVLAGSDIRCPMTE
Myxalamid   (SEQ ID NO:53)  295  QTVHIVNPQFVRADEMWNWMYMRAEGYGIRVTHPYDQMLSLGSAASSDSELGDILMFIQOVPPEDRSVGPRMV-----VCDSGDTLZALGCTGTSCSVPA
Myxochelin  (SEQ ID NO:54)  288  TVENLTPAPDVRLSEVEGWMQDYGIEVACICVPEWMRLHVAQSTGSAENSTTLAFFDLRAGAEPIFGLGIIR-----S--ERVLQALSDTGISCPRTDR
SEQ ID NO:44 R domain       289  ANWHLYFQGLAWSVILETTRAEGYAVSPATRSAWLAALERQAGTEAGQGLGPLVPIMREGAMRLGSHSPD------N--GRTMRAVADVGCPFPADT
consensus   (SEQ ID NO:56)  301  fhLfnpq  vrlsemwdwirayGyav  ivpfdew s lg  agsd nl  L p i  a aed svg ptfi     e  grtlkala  tgisCPpmd R7
SaframycinA (SEQ ID NO:52)  394  ELAHRCLVLVDIGFLQRPEVLRA----
Myxalamid   (SEQ ID NO:53)  390  SLISTYISSLVHRGFLKAPEV-----
Myxochelin  (SEQ ID NO:54)  380  FLIHRYLDVCVGGLLQRP--------
SEQ ID NO:44 R domain       381  EWIRRMFEVFRAIGSVPPEDCVTLGGHVA
consensus   (SEQ ID NO:56)  401  elihryldylvgiGflqrPevl
```

Figure 12

Alignment of adenylation domains of ANTH (amino acids 35-522 of SEQ ID NO: 42
and amino acids 481-962 of SEQ ID NO:44) and the adenylation domain of Gramicidin GrsA

SEQUENCE LISTING

```
<160> NUMBER OF SEQ ID NOS: 57

<210> SEQ ID NO 1
<211> LENGTH: 32539
<212> TYPE: DNA
<213> ORGANISM: Streptomyces refuineus subspecies thermotolerans

<400> SEQUENCE: 1
tcaccagtcg agggtcacac cgtaggatcc cagccaggtg tcgagccggg ccggagtctc        60
gtggtgcaga ccgcgcacca gcatcgacga cgccttctcg accggcgtgt cgaggtgacg       120
gcggacggcg tccaggtcga gcaggggcag caccggcgag ctcggctccg cgacgatctt       180
ctccagctcc tgcctgatcg ccctgtcgta gccggcgtcc tgggtggacg ggtagggcgc       240
```

-continued

```
cttgcggcgc tccacgacgg atcggggcag caggtccgcg accgcaccgc gcagcaggct    300
cttctcccgg ccgtcgtagg tcttcatcga ccagggcacg ttgaagacgt actcgaccag    360
gcggtggtcg cagaagggga cgcggacctc cactccgttg gccatgctca gccggtcctt    420
gcgatccagc agcatcggca tgaaccgcgt gatgttcagg tggctcgcga tcctcatccg    480
ccggtcctcg ccggtctccc cggccaggtg cgggacttcc gcgagcgccg tccggtactg    540
gtcggcgatg tactccggga ggttgagctc cgccgtcagg ccggggtcca ggaaggccgt    600
ggacagctcg gccaccggtc gctcgccgag ggcgtgccag gggaacgtgt cggcctggac    660
ggcccgccgg tcgtggaacc acaggtatcc gccgaagacc tcgtccgcgg actcgccgga    720
gagagccacg gtggactcct tccgcacctc cggaagagc aggtacagcg atggtccgag    780 gtcccctca ccgtagggga ggtcccacgc cctcatcacc gtcgaccgca cgcgcggcga    840
cgcaaggtcc gcgttgtcga gcaggatgac ccggtggtcg gtgccgacgt gccgcaccag    900
ctccgccgcg aacggcgcgt ccggggcctc ccggagggt tccggcgcga agttctccac    960
ctgccccacg aagtccacgg agaagctccg tatccggccg ccccgcggg aggcgagccc   1020 gcgctgcgcc agggcggtca gcgcactgga atccaggccg ccggacagga ggctgcacag   1080
ggggacgtcg gcgaccatct gccgggagac gatgtcctcc agcagttcgc ggaccacgcg   1140
gaccgtcgtc ggcacgtcgt cggtgtgcgg ccgggcctcc agcgcccagt acctctcctc   1200
ggaccggtgg ccgtcgcgga ccctcaggac gtggccgggg cggacctcgt acagccccctt   1260 catcggtgtc tgccccggga cccgcacgaa cgacagcacg tcccgcaggc cgtcgaggga   1320
gagcaccgcc cggctctccg ggtgggccat gacggccttc ggctcggacc cgaagaggac   1380
gccgtcgcgg gtggggtagt agaacagcgg cttgatcccc agccggtccc ggtacagcag   1440
cagttcctcg ccgcgggcgt cccagatcgc gaaggcgaac atcccgttca gccgccggac   1500
gaactccggt ccccattcca ggtacgcgcg caggacgacc tcggtgtcgc tcctggtccg   1560
gaagcggtgg ccgcgggcgg cgagttcgcc gcggagttcg gtgaagttgt acacctcacc   1620
gctgtagctg atcgccgcca ggggcgtccc gtcgggcagc gtctccggcg tgaccatggg   1680
ctgcttgccg ccttcgaggt cgatgaccga caggcgccgg tgcccaggg cgacgcgcgg   1740 gcgcacccac acgccctcct cgtccgggcc cggagggcc atcgtgtcca ccatggcctg   1800
gaggacccgc cgttcggcgg tgagatcgcg ggcgaagtcc gcccagccga cgattccgca   1860
cattgcacac ctcatctgcc ggaggtcagg gggcgattga cgtccacacg gtttcagtt   1920 cgaggtaggc gtcgaggccg gcgcgcccca tctcccgccc gaccccggac gccttgagtc   1980
cgccgaacgg ggaagccgga tcgccggcgg cccatgagtt gaggtacacc gaccccgctt   2040
tcagccgggc cgcgaggccg tgcgcggcgc tcaggctccg ggtccacacc ccggccgcca   2100
ggccgtactc ggtgtcgttg gccaggcgga cgacctcgtc gacggtctcg aacgcgccg   2160 ccacgagaac cggtccgaag atctcctcac ggcagatccg catggtcggt gtgacgttcg   2220
tgaacagcgc gggacggacg aagtaccgcc gcccgggtc ggccgcaggc acttcccccg   2280
cccgcagcac ggcgccttcg gagacgccgt cgaggaggta gccgcgcacc cggcggtact   2340
gttcggccga caccacgcgg ccgtactcgg tcgccgggtc gagagccggg ccgacgcgcg   2400
cccgccgggc ccgcgccagc actccctcga ccacgtcgtc gaacacgtcc cggtgcacgt   2460
acagccggga ggcggcgttg caggcctggc cggtgttgaa gaagatgccc tcggcggcgc   2520
ccgagatcgc ggcctcgatg tcggcgtccg ggaggacgat gttggggctc ttcccgccga   2580
```

```
gctccagggt cacccgcttg agccgggcgc cggccttcgc cccgatctcg cgtcccaccg    2640
cggtggagcc ggtgaaagcg atcttgtcga tgcccggatg gtcgaccagc gcggcaccgg    2700
tcggaccgtc accggtgagc acgttgaccg tgccctcggg gaagccggcc tccgcgatca    2760
gttcggccag gcgcagggtg gtcagcgggg tctgctccgc gggcttgagc accacggtgc    2820
acccggcggc gagtgccgct ccgagcttcc aggccgccat cagcagcggg aagttccagg    2880
ggacgatctg cgcgcagaca cccaccggtt ccttgcgcgt gtagcacagc gtgtccggta    2940
ccgcgaccgg gatcgtctcc ccctcgatct tcgtgggcca gccgccgaag tagcggaact    3000
gggctgcggc ggccgggacg tcgagggcgc gggtcttggc gatcggcttg cccacgtcga    3060
gggactcgag ttcggcgagt tcctcggcgt tgcgctcgac gaggtccgcg aggcgggtga    3120
tgagcctgcc gcgctcggcc gcgggaagcg cgccccacgc tccttcgagc gcggtccggg    3180
cggccgcgac ggctgcctcg acatcctccg gtcccgcgtg ggcgacctgc gcgaggcgtt    3240
caccggtgga cgggtcgacg gtggcgaagg tgcgccccgt cgcggaggcc acgaaccggc    3300
cgccgatgaa gagcaggtgg ggacgggaca gaaaggcgcg gcagccact cccggggaag    3360 gattcacaca tgctcccaat gcgctcagaa gcggtcgatg acggtgagcc cgctggtggc    3420
gaaggcgtcc atcgccgcca gcacgtcccc ggcctggtcc agagacacgg tgcgctgcac    3480
gagggtctgc ggcgcgagcc ggccggactc gatcagcgag agcaaccggg ggtaggcggc    3540
gtgcgggttg ccgtgcgagc ccaccacggt cagctcgccg agggtgatca ggtcgatcgg    3600
gagcgcgatc tcgccggcgt cctcggctcc ggtcagcccc acctgtacgt gccggccgcg    3660
tttgcggagc gaacgcacgg agttcaccac cgtcgtccgg atgcccaggg cgtcgatcga    3720
gacgtgggcg ccgccgccgg tgacctcccg gaccgccgcg gggacgtcct gttcggcgcc    3780
ggcgtccacc gtgtgggcgg cgccctgctg ctcggcgagg gcgagcttgg ccgggtcgat    3840
gtccaccgcg acgacggacg ctccggcggc actggcgatc tgcacgcacg acagcccgac    3900
gccgccgaca ccgtgcacgg ccacccactc gcccgggcgc accggccct ggccgtcgac    3960 ggcgtggaac gccgtcatga accggcagcc gatcgcgctg gccgtgagcg gtgtgacgcc    4020
gtccgggatc cgcacgcagt tgaagtccgc gtgcgggatc cgcacgtact cggcgtagcc    4080
gccgtcgcgc cagaagccga gcacctccat ctcgtcgcag aggttggcct gccccgcgcg    4140
gcagtgcgcg cacgtaccgc aggccaggtg aacggcacc gtgacccggt cgcccacccg    4200
cacgcctcgg acgccgggac cggcggccac cacctcgccg gcgatctcgt gtcccggcgt    4260
gcggggcagg gcgatccgcc cgcccagcca ctccagtcg ccccgccacc cgtgccagtc    4320
gctgcggcag atgccggtgg cgaggacggc cacgacgacg ccgcccggct cgggagcggg    4380 gtcgggacc tcgcgtacct ggagcggttc gccgtacccg acgatctgcg ccgctctcac    4440
gtcgatcacc ccttcgctgt tcgccggtgg tcaggagacg cggacgggga gacggtccag    4500
cccccgggtg atgttgttcg cgaccgggt gggctcgccg gcgagctcga tggtggtggc    4560
ccgtctggcg agggcgccga acagggcgtg ggcctccatc gaggccaggg cgcgcccggg    4620
gcaggtgtgg acgccgacgc cgaacccgac ggtgtccacc gggttgcggt gcgcgtcgaa    4680
ccggtcgggg tcggggtagc ggcgctcgtc ccggttggcc gaaccgtagg agtgcacgac    4740
ccgcgcgccc cgcgggatcg tcacgccgtc gatctccacg tcgcgcgtgg tgacgcggga    4800
gaagaactgc agggcgtct ccagccggac gccctccagg aacgtgccgg ggacgagttg    4860
cgggtcctgc cgcacggccc gccactggtc cgggttcaag gccagcagcc acaggtgct    4920 ggccacgccg gcgatcgtgg tgtccagccc ggcgcaggcg taggcgctca tcgccatcag    4980
```

```
ggcctcgttc ccggtgatct ccccgcggtc ggccgcctcc cacacgatct ggccgaaact    5040
gccgggaagc agcctgtcgg gcgtcgcctc ggtcaccagg tactgcatga gggcctgcac    5100
gtcgggggaag gtcgactcct ggcgctcacc gggcggcccc atgaagttga acgcaccgag   5160
ggcccactcc agcaactcct cgcggtgctc gtcgcgcggg aagccgatga ggtccatgac    5220
gatctccacc ggcagcttgc acgcgaagtc cctgacaccg tcgaactcgc cccgccgcac    5280
caggctgtcg acgaggtcgt cggcgaggtg ctcgatgtcg ccggcgaccc tgcgcacgtg    5340
cttgggcgc agggcgtcgt cgaagacctt ccggagggcc cgctgccgcg gcgggtccac     5400
cgagaggatc gagtccgccg agagttcgtt ggcggtcggg ttcatggcga tgccctgcgc    5460
ggagctgaac gtctcccagt cgacgagggc gcgcgcacc tgctcgtacc ggaagagccc     5520
gtacaggtcg tactcggtca ggtagaccac cgggcccatg tcccggagtc tcgcgtagtg    5580
ggggaacgga tcgaggagca cctcggtgga aagaggtcc aggtcggtct cgggcgcggc     5640
ggtcgaagtc cttgctgcgg tcacgctcgg tcctctctga tgtcgttccg cggccgggct    5700
cacctcggcc gtggcgccag gtcgtagaag cacatgcgcg gccccgcgcc cggccgccgg    5760
tacagccgcc ggcactgcag ggtggacttc tcgaagaccg gcagccacgc ggcgcggtcg    5820
cgcgggagcc cctgcccggt caggacgtgg atcaggaaga agtcgtcgtc gttctccctg    5880
ccgtcgtggc ggatctccgg ttcgccgatc agcaggatct tctgctgcgg gaacttcgcc    5940
gagatctcgt ccagcaggtc cacgacggcc tgctcgccct tgcggaagtg ctcgtgcagc    6000
gcgctcatca tgcacagccc gtcggcctcg gcgcagacct cgggccacgt ctggggcgcg    6060
aaggcgtccg cgacgacgaa ctccacccgg tcggacacgc cgtggcggcg cgcgaggtcg    6120
ttggcgaccg cgatggcgtc cgcgtcgatg tccagaccga tgccggtgag ggacgggtcg    6180
cgcagacagg cgtccacgat cagctgcccg ccgccgcagc cgatgtcgag catgcggcgc    6240
actccgcggc cgcgcatggc ctccagcacg accggtgtgt ggaaggtgga gaacaaggtg    6300
gcgcagtgcg cccccagctg ggcgccgtcg cgcgtcacgt ccgtgccgta gacggccttg    6360
ccggtgagca ggtcgccgat ccggctggtg accccgccgt acgcgcccag gtagacgccg    6420
aggcgggcca gcgagacgtc cgtggtcagg aactcgccca gccgcgtcag gaagaactcg    6480
tcaccgcggg tctccaggac gccccggttc accaggtagc gcaggaaacc cgcaccgatg    6540
tcggggtcga ggccggccag caggccgtcg tcgggccgcc gggggccgtt gcgcagccgt    6600
tccagcagcg gggtctcggc gatcgcccgc acggcgtggc agacgtgcag ggcgctgatc    6660
atctcgggga ggccggacag caggaaggcc tgccactccc ggcgctgctt ctcgtcctgc    6720
agctcgatga tctccgggcc gtcggtgctg agcgtcatgg atctcttccc ttcgaaggtc    6780
gtcgcccggt cctactcgca taccgcgtac gcgtgccggc cgcgcgggct ggccgcggcc    6840
cgcacgaacc cctccccgtc ggtcagcccg gtggcgcaga ccctgcccag cgagtacgcc    6900
ggtacgagtt ccacctcgtg gccgcgccgg ccgagttcct cgaccacctc cggggcgcag    6960
gtctcctcgg cgaccagcac gccgggacgg tgcgcgtgcg gggtgaagga agcgggcacc    7020
tggtcggtgt ggaaggccgt cgtctcggtc gcgctctgca ggtcgagccc gaagtcggcg    7080
acgttgagga agaactgcag cgtccactgg tcctgccggt cgccgccggg gtcccgaac     7140
gcgacgaacg ggcgtccgtc ccgcagcacc acggtgggc tgagcgtcgt cctcggccgc     7200
ttgccgggcg ccagggagtt ggggtgcccg tcgacgagga acatggactg ccgcgggtg     7260
ccgaggggga agccgaggcc ggggatggcg ggcgaactct tcagccaccc cccgctgggg    7320
```

```
gtcgcggcca ccatgttgcc gtgccggtcg acggcggtga ccgtgcaggt gtcgcccttc   7380
gccgccgtgg cccgcaggat cgtcggcagt ccgttgcgca gctgggacat ccactccgtg   7440
tccggttccg ggtcgtccgg ggcggacagc gaggggatga acgacgtccg gccgccgggc   7500
tcgcccggac gcagcgtcag ctcggcgcgg gcaccgacca gttcgcggcg ccgccgggtg   7560
tactcctcgt cgagcagggc ggccaacggc acgtcgctgt gggccggatc gccgtaccac   7620
gcctcgcggt cggccatggc gagcttcgtg cactccacca cggtgtgcag atagtcggca   7680
ctgcccagcc ccatgcccgc caggtcgaag ccgtcgagca gcgcgagctg ctgcaggaac   7740
accgggccct gcgaccacgg ccccggcttg aagacctggt aggacttgta gacgcggctc   7800
ggcgccgtct ccacggacgc ctcccagccg gctaggtcgt ccccggtcag cagccccttg   7860
tgccgcctgc cggtggcgtc gagcacgggc cccgaggcga ggaagtcggc gatctccccg   7920
gcgacgaacc ccttgtagaa ggcgtcgtgc gcggcctgga tctgggcgtc gcggtcggcc   7980
gacgcggcct ccgcctcctt gatcagccgc tggtaggtgc cggccagcgc cggattgcgg   8040
aaccggctgc ccgccgcggg ggccttcccg cccggcaggt acgtccgggc ggagccctgc   8100
cactcctcgc ggaacagcgg ggcgagcacc tcgatggcgg tcgcggtctc gggaagcagc   8160
gggaagccgt tgtccgcgta ccgatcgcc ggtgccagga cgtcggccag gcgcatcgtc   8220
ccgaactcgg cgagcagccg catccagccg ccgaacgctc ccggcacgca ggccggcagc   8280
agccccgatc ccggaatgct gctcaacccc aggtcggtga aggtgtcgat gtccgcggcg   8340
cggggcatcg gccctgccc gcagatggcc tgcacgtcgc cgctgccggc tcggtgcacc   8400
acgatggaca cgtcaccgcc ggggccgttg aagtggggtt ccactacctg gaggacgaag   8460
ccggcggcga cggcggcgtc gaacgcgttg ccgccgttgg cgaggatcct catgcccgcg   8520
gccgaggcga gccagtgggt gctggccacg cgccgaggg tcccggtcag ctcgggcttg   8580
gacgaagca tgccgctact ccatggtcgg gaggtgggtg tacggtccgg aacgggcggt   8640
cgctccgccg gcgtcatccg ttccggaaga tcccggggcc ggggtgagg acggagtcgg   8700
ggtcgtagcg cttcttcgcc tcacggaagg tctcccactg gtcgccgtag tgggcacgcc   8760
agtcctgctc ggtgaacggc accgagccga tcgggtagag caccgcaccg tagcggtcgc   8820
gtgcgcgggc gaacagccgg gtgttgcggt cgagcatctc cttgacgaag gccggatcgt   8880
cccccggggt ctcggcgacg gtgttgatgt cgaggacgaa aacccagggg gagccgtccg   8940
gttcgggcag ccggggaagc ggccgggtga cggccgagcg ccgctgcggg tagatcaggc   9000
tgatgccgta gggcccgatg tcgcgtgcgg tcagcgtcgg gtggacctcg gcgatgtagt   9060
cctccacggc ggaccggggg agccacacgt cgtaccaggg cttgaggagc ccgtcccagc   9120
ccacggtctc ccgcatcccg tcgacgagcc ggtcgatcga gaacacgtag tccaggtagc   9180
cggtgtcgtc gacgaccggt tcggtgctca ggccggcgac ggccgcctcg tcgtccggcg   9240
cggccccgtc gtggaagacg gtcgcgtagc acttgtgggt cggcctggag cctggcgcgt   9300
acagctcggc gtagacgtgg tcgatgccgg ccgctcgat acggtgcgc aggtcgcgga   9360
agaacgcggc gttgtcggtg tactccagca cgtaggtgcg ggcgcgctcc ttggcgggga   9420
cgagttcgac gaccgccttg gtgatgatgc cgcactggcc gagcccgccg agcaccgcct   9480
cgaacaggtc gcgcctgtgg tggagggagc agcgttcgat gtcaccggtc ccggtgacga   9540
cctccagctc gcggacgtgg tccacctgca gtccggtgcg cagggcgccg acgagaccgc   9600
cgagcccgcc gaccgagagc gttccgccca cggtcagcga ggtgtaccg gtgaccgccg   9660
gcggggtgag cctcggcgac tgcccgaagg cggcggtgac caggtccttc cagtggacgc   9720
```

-continued

```
cggcgtcgac ctcggcaacg tccggaccga gcgagtggat ccggttcagg gaccgggcct   9780
cgacgacgag tccgtcggtg aggccctggc cgagcgtggt gtgcgcctgc cctctggtgg   9840
agaccgtgat gccgtgcgct cggcagaagc ggaccatcgc ggcgatgtcc cgggccgagc   9900
gcggtcgcag caccgcgccc ggcttgtgga cggcgatgtt gcccaggtcg gtggcgaccg   9960
cctggcggga cgcctcgtcg atcagaagct cgccctccag cgccggcgcg gcggcgaacg  10020
acgacgccgt cgtcgcgggg ccggtgaccc acgtgcgttc ggccgggtcg aagcccagga  10080
ctgcggcgtt cgcggaggga accggccggc tcgtcatgtc gtctcccgtc atgtcccgtc  10140
gggcgtcttc ggctccgcgg ccacggcaac gcgatatgcc ggcgctcagc ccgggcgcgg  10200
tgaactcctc ccacgcggcg gccacggctc gaattgctct cgccgaaaca ctagccgtgg  10260
gtgccgccgg acacactcag acgattttca agttgctgtc agatcctctt taaaaaacat  10320
ttcacacaag cgccggacgg ggggcggccc ctgtgtgcgc aggtgcggta gcgtctgaac  10380
ggggaccaat cggggtgatt tcacccgagt ggcgccaggg gtgccgcgcg ggatgtcatt  10440
cacaaattgc cggatggtcg tgccgctgat aagatttccg atccgtggaa agctgccgga  10500
aggccgagga ggattcatgg aaagccgggg cgggcggcgg gcgagcgaca ccatcgcgct  10560
ggacggcatc cgggagaaca acctgaagga cgtgtcgctg cgcatcccga agggaagct  10620
gaccgtgttc acgggtgtgt cgggatccgg taagtcgtca ctggttttca gtacgatcgc  10680
cgtcgagtcc caacggcagc tcaacgcgac cttccctgg ttcatccgca accggctgcc  10740
gaaatacgag cgcccgaacg ccaggggat ggccaacctg tccaccgcca tcgtggtcga  10800
ccagaagccg atcggcggca actccaggtc gacggtgggc accatgacgg agatcaacgc  10860
ggctttacgt gtcctgttct cccggcacg caagcccagc gccggtccgt ccaccgtgta  10920
ctcgttcaac gacccgcagg ggatgtgcac cgagtgcgag gggctgggcc gcaccgcgcg  10980
cctggatctc gggctgcttc tcgacgagag caagtcgctc aatgacggtg ccatcatgtc  11040
gccgctgttc gccgtgggca gtttcaactg gcagctgtat gcccaatcgg ccttttcga  11100
ccccgacaag ccgctgaaga aattcaccgc gaaggatcgg gagctgctgc tttacgagaa  11160
gggtttcaag gtccagcgcc ccggccgtga actgacgtat tccaacgaat acgaaggaat  11220
tgtggtccga ttcaaccgcc gctacctcaa gaacggcatg gacgcgctga gggcaagga  11280
gcgccaggcc gtcgagcagg tcgtccgggt cggcacctgc gaggtgtgcg cggtggccg  11340
gctcaaccag gcgcgctcg cctccaggat cgacggcaag aacatcgccg actacgccgc  11400
catggaggtg agcgaactga tcaccgagct ggggcgcatc gacgacccgg tggccgaacc  11460
catcgtgcag gcggtcaccg cggccctgcg cgtgtggag gcgatcgggc tgggctacct  11520
cagtctcggc cgcgagacgt ccacctctc cggcggcgag ggccagcggc tgaagacggt  11580
gcggcacctc ggcagcagtc tgagcgacct gaccttcatc ttcgacgagc cgagcgtcgc  11640
cctgcacccg cgggacgtgc accggctcaa cgaactcctc gccgagctgc gggacaaggg  11700
caacaccgtg ctcgtcgtgg aacacaatcc ggacgtcatg gccgccgccg accacatcgt  11760
cgacatgggg cccggagccg gtgtgcacgg cggcgaggtc gtgttcgagg ggtcctatca  11820
ggagctgcgc gaagccgaca cgctcaccgg ccgcaagctc cgccagcgcc gcggcctgaa  11880
ggaggagctg cgcacccca ccggcttcct gaccgtccgc gacgccacgc tgaacaacct  11940
gaagaacgtc accgtcgaca ttcccacggg gatcatgacc gcggtgaccg gagtggccgg  12000
gtccgggaag agctcgctga tctccggggc gttcgccgcc cagtaccctg aagcggtcat  12060
```

```
gatcgaccag tcgagcatcg gcatctcctc gcggtccacg ccggccacct acgtggacat   12120
catggacacg atccgcacga tgttcgccaa ggccaacgac gccgagcccg gcctgttcag   12180
cttcaactcc atgggcggct gcccggcctg ccaggggcgc ggcgtgatcc agacggacct   12240
cgcctacatg gacccggtga ccgtgacctg cgaggtgtgc gagggccgca ggtaccgggc   12300
cgaagcgctc gagaagacgc tgcgcggcaa gaacatcgcc gaagtgctcg cgctcaccgt   12360
cgaagagggg ctgtccttct tcgacgagga cgccgcggtg gtccggaagc tggcgatgct   12420
ccaggacgtc ggactgtcct acctgaccct gggccagccg ctgtcgaccc tctcgggagg   12480
cgagcggcag cggctcaagc tcgcccaccg gctccaggac accggcaacg tcttcgtctt   12540
cgacgaaccg acgaccggac tgcacatggc cgacgtcgac acgctgctcg cgctgttcga   12600
ccgcatcgtg gacgacggga acacggtcgt cgtcgtggag cacgacctcc aggtcgtcaa   12660
acacgccgac tgggtgatcg acctcggacc ggacgccggc cggcacggcg ccgggtggt   12720 cttcgagggc acaccgaagg agctcgccgc ccacgagcac tcggtcaccg cccggtacct   12780
gcgggccgat ctcgcgcagg tgcggggctg acgccgcacc gccaccgcca tgtcgacaca   12840
acgggaggga agcgacagtg aacacgtccg aagtccgtcc ggtgaccgtg ggtggttcg   12900 agatcaccac caccgatccg gcgcgcagca aggagttcta ccagggctc ttcgactgga   12960 agctcaccgc cttcgccgat gacgacgcct actccacgat caccgcgccc ggtgccgcgg   13020
ccgccatggg ggcactgcgg cggggcgacc acgacgcggt gtgcatcagc gtcgtgtgcg   13080
acgacgtggc ggcggtgatc tcggagctgc gggcgctggg cgccacgctc gtcgagcccc   13140
ccgcccgcac gatggcgggc gacgtgcacg cggtggtcac cgacgtgcgc ggaaacaggc   13200
tggggttgtt cgagcccggg gagcggcgtg atccggagcc gacccgaccg gtgccgaacg   13260
ccacggcctg gttcgagatc gggacgaccg acctcgcggc gacgcggacg ttctacgaga   13320
aggccttcgg ctggacccag gtgcgcgacg aggcggccga gggagcggag tactacagca   13380
tcatgccccc ctcgtcgcag caggccatcg ggggagtcct cgacctgtcc gcaacgcccg   13440
gcgcagcgga ctacgcggtg cccgggctgc tggtaaccga tgtcccggac ctgctcgagc   13500
ggtgtgaggc agccggcggc cgacgtgtgg cgggcccgtt ctccgacgcc gacggactgg   13560
tcatcggaca gttcaccgac cccttcggca acaagtggag cgctttcgcc cagcccgccg   13620
gcgagtgacc gccggccgag accccgggg agagagatgc ctgtcgctgt gtacgtgctg   13680
gcggtggccg tctgctgcct caacacgacc gagatcatgg tcgccggtct gatccagggc   13740
atctcgagcg acctgggcgt gtccgtcgcg gccgtcggct acctcgtgtc ggtctacgcc   13800
ttcggcatgg tcgtcggcgg cccgctgctg accatcggcc tgtcccgggt gccgcagaag   13860
aggtcgctgg tctggctgct ggcggtgttc gtcgtcgggc aggcgatcgg ggccctggcc   13920
gtcgactact ggatgctcgt ggtcgcacgg gtgctgaccg cactggccgc ctcggccttc   13980
ttcggggtga gcgccgcggt gtgcatccgc ctcgtcggcg ccgagcggcg cgggcgtgcg   14040
atgtcggccc tgtacggcgg catcatggtg gcccaggtcg tcggcctgcc gcgggccgcc   14100
ttcatcgagc agcgtgtcga ctggcgggcc agcttctggg cggtcgacct gctggcgctc   14160
gtgtgcatcg cggcggtcgt gctgaaggtc ccggccggcg gtgatcccga cacgctcgac   14220
ctccgtgcgg agatccgggg tttccgcaac ctgcggctgt ggggcgcgta cggaccaac   14280 gccctcgcca tcggatcggt cgtggcgggg ttcacctacc tctcccgat cctcaccgac   14340 gccgcccact tcacgccgtc gaccgtgccg gtgctgttcg cggtgtacgg agcggccacc   14400
gtggtgggca acaccgtcgt cggccggttc gcggaccgtc atacgcgacc ggtcctcttc   14460
```

```
ggcggcctga gcacggtcac cctcgtcctc gtcggattcg ccctgaccgt ctcgcaccag   14520
gtgccggtgg ccgtcttcac cgttctgctc ggtctgatcg gcctgccgct caaccccgcg   14580
ctggccgccc gggtgatgtc cgtgtccaat gagggcgcgc tggtcaacac ggtcaacggg   14640
tccgcgatca acgtcggcgt ggtcctcggc ccctggctcg gcggcatggg gatcagcgcg   14700
gggctcggtc tcgcggcgcc gttgtggatc ggggcggcca tggcgctgtg cgcactgatc   14760
acgctgctgc ccgacctccg gaagcgctcg ggcgcctcgg cgcccgagcg cggcgaaacg   14820
ggccgcgacg agaccgcggt gagagcctga tccgaccggg aacgtcccgc gtgccagccg   14880
tacggacgct tcccgccgcc cgacggccga atgcgcagcc gcggcgagaa cacctcgcc    14940
gcggctgttt tcatgccgct ttccggccgg tgccgcatgg cggcccgacc cgcgtggaag   15000
gaaaagggcc gacagaccgc gcaaggcggg acatcccgga gaggcccgcg atgcccgcgc   15060
gtgaccgagc cgtcgccggg gccgtccggc cgccggcccg tccggcggtg cacgcggcgt   15120
gctgcgaccg tgcggccgag cggttccccg cccttcgccg gcgcagccgc ggaccgcgcc   15180
gggccgcctc ggccgaccgc ctgaagtggg gcctaaaaga attcctgaaa gcgatttaag   15240
gcttcttta agatgatctg attgctgtcc acgacctcat acgccgacca ttgaggccga   15300
ttgcttccac tccgcggaga cagtgaacac gccgagcaca cccgcgacgg aagggctttc   15360
gatggagggg cttgacatcg cgccggggtt tcaccatgtc gccgtccaga cggacgacgt   15420
ggacgccacg gtcaggtggt acgaggaatt cctcggggcc acggtggagt ggtcgctcga   15480
caccttctca ccactcactc acgcgcggct ccccggaatc aagaagctgg tcgaagtgaa   15540
gaagggcac gtgcgtttcc acgtcttcga ccgggcgggg cacagccggg gcggaccgga   15600
tccgctcggc taccagtacc agcacatcgg gatcaccgtg aaccgccgg aagacctcgc   15660
gcggctccgt gagcggtggt tgcgcgtgcg cgaacggacc gacctccggt gggccaggga   15720
cgagccgccg tccgacatcg tggccgacgc cgacggcgta cagagcctct acgtcctgga   15780
ccccaacggt ctcgaactcg agttcatcta ctttccagga gcgggaacgt gagcaacggc   15840
cgaggacatg ccgccgcacc gggcgggggg cactcgcccc tgctgcaacc gcaactgctg   15900
ttcatgcccc cggtgggcca cgcgtacgag accccgtccg aggaggtgcc gcacaccacc   15960
ggggccgccg accgggacgc gccggactac gacctcttcg gcgaacgccc ggtcgaggcg   16020
cagcggctgt tctggtaccg ctggatcgcc ggccaccaga tctcgttcgt gctctggcgg   16080
gccatgggg acatcctgtg gcaccacccc catgacgtgc ccggcgcccg cgaactcgac   16140
gtgctgaccg cctgcgtcga cggatacagc gcgatgctgc tctactcggc caccgtcccg   16200
cgtgcccact accactccta caccagagcg cgcatgcgc tgcagcaccc gtcgttcagc   16260
ggcgcgtggg cgccggacta ccggccgatc cgccggctct tccgcaacag gttgccctgg   16320
cagggcgatc cgtcgtgcag ggccctgggc gaggcggtcg cgcgcaacgg cgtgacccac   16380
gaccacatcg ccaaccacct cgtgcccgac gggcggtccc tgctgcagca gtccgccggc   16440
gcaccgggag tgaccgtgtc ccgggagaag gaggacctct acgacaactt cttcctgacc   16500
gtccggcggc cggtcagcca ccgcgaactc gtcgcgcagc tggacgcgcg cgtcacggag   16560
gtcgcggcgg acctccggca caacgggctc taccccaacg tcgacggacg ccaccacccg   16620
gtcgtcacct ggcagtcgga cggagtgatg gggtcgctgc cgaccggtgt cctgcggacg   16680
ctgaaccggg cgacgcggat ggtcgcgcag acgcgcctcg aggaagcccg gtcatgaggc   16740
acggcgtcgt actgctgccc gaacacgact ggaagaccgc cgccgagcgg tggcgggccg   16800
```

```
cggagcagct cggctaccac cacgcctgga cctacgacca cctgatgtgg cgctggttcg    16860
ccgaccggcg gtggtacggc tcgatcccga cactcgccgc cgcggccgtc gtgaccgaca    16920
ccatcggact cggtgtgctc gtggccaccc cgaacttccg ccacccggtc gtgctggcca    16980
aggacctcgt ctccgtcgac gacatcgcgg agggccgtct gatctgcggc ctgggctccg    17040
gcgcccccgg ctacgacaac agcatcctcg gcggggccgc gctcggtccc ggcgagcgcg    17100
ccgaccgctt cgaggcgttc gtggagctgc tcgacgcggt gctggtcgac ggcgacgtgg    17160
accggtccac gccctggtac accgcgcgcg gcgtgacgtt tcacccgcgg gccgaaggcg    17220
gtcggcgact gcccttcgcg gtggctgcgg ccgggccgag gggcatggcg ctgaccgccc    17280
gcttcgggca gtactgggtc acctccgggc cgcccaacga cttccgcacg cggccgctgc    17340
gcgaggtcct gccggagctg cgggcccaac tgcgcggcgt cgacgaggcc tgcgagcgag    17400
cgggccgcga cccggccacg ctgcgtcggc tgctggtggc cgacgcggcg gtcggcggga    17460
tcaccgcctc gctgtcggcg tacgaggacg cggcgggcga gctggaggag gccggcttca    17520
ccgacctcgt cgtgcactgg ccgcgccccg accagccgta ccaggagac gagcaggtcc    17580 tcgtcgactt cgcggccgag cacctggtgg agaagtcatg cgtgtgacca cggtggacat    17640
gttcggtgcg gccccgggcc gggggagcgc cctggacgtg ctcgtcccgg acggtccgtg    17700
cggcgaggcg gcgccgagg aggccgcggc gcacgcacgc cggagcgccg cggacgagag    17760
cgtgctggtc gtcgagtgcc gcagggcgca gcggaccttc gcgtcgcggg tcttcaacgc    17820
gggtggggag acgccgttcg ccacccactc cctggcgggc gcggccgcct gcctggtcgg    17880
cgcggggcac ctgccgccgg gtgaggtggg gcggacggcc gagagcggat cccagtggct    17940
gtggaccgac ggccacgagg tccgggtgcc cttcgacggg cccgtggtgc accgggggat    18000
cccgcacgac cccgcgctgt cggcccgta cgccggcacg ccgtacgccg gcggcgtcgg    18060
ccgggccttc aacctgctgc gcgtcgcgga agaccccgg acgctgcccg cccccgatcc    18120
cgggcgcatg cgggaactgg ggttcacgga cctcaccgtc ttccggtggg acccggaccg    18180
gggcgaggtg ctggcgcggg tgttcgcccc gggcttcggc atcccggagg acgccggctg    18240
cctgccggcg gccgccgcgc tcggcgtcgc cgcactgcgc ctggccgccg acgaccggac    18300
gtccgtgacg gtccgccagg tcaccgtccg cggcaccgag tcggtcttcc gctgtaccgg    18360
ctccgcccgc ggcggcagcg cgaacgtgac gatcaccgga cgcgtgtgga ccggcgggac    18420
ggccggccgg gaagtgggtg gatcatgacc acacggaaga cggcgcccgc ggcgaccgcg    18480
gcacggaccg gccggtccgc cctgcgggac gaggcgcgg gccgcgacga ccgcgatccg    18540
ctgtccgcgc acgcgcccg gttcgccacc ggcggcgtcg tccacctcaa cggcaactcg    18600 ctcgaccgc ccaggagag cctcgtgcac gcgctcgacc gcgtggtgtc cggccagtgg    18660
gcgcccccgc aggtacgggg ctggttccgc gacggatggc tcgagctgcc ccgcaccgtc    18720
ggggacaagc tggccgcact gctcggcgcg ggcccggac aggtggtggt cgccggcgag    18780
acgacgtcca cgacgctgtt caacgcgctg gtcgccgcct ccgcctgcg cgacgaccgg    18840 cccgtgctgc tcgccgaggc cgagtccttc cccaccgact tgtacatcgc ggactcggtg    18900
gcgcggctcc ttggccgtcg gctcgtcgtc gaaccgcgcg gcggcttcga cgcgttcctc    18960
gccgagcacg gcggcaggt ggcggccgcg atccgcgcgc cggtggactt ccgcaccggc    19020
gagcggcgcg agatcgggcc caccaccgcg ctgtgccacg ccgccggagc cgtgtccgtg    19080
tgggacctca gccacgccgc cggcgtcctg ccgaccgaac tggacgccca ggggtggac    19140 ctggcgatcg ggtgcggcta caagtacctg ggcggggcc cggggcgcc ggcgttcctc    19200
```

```
tacgtccgct ccggactcca gccggaggtg gacttccccc tgtcggggtg gcacggacac   19260
gcgcggccgt tcgacatggc gccccggttc gtgccggccg ggggagtgga ccgcgcgcgc   19320
accggcaccc cgccgctgct cagcatcgtc gcgctggacc acgccctcga accactggtg   19380
cagaccggca tccgggcgct gcaccggcgc agccggtccc tgggcgagtt cttcctgacc   19440
tgcctggggg aaggccgccc cgacctgctg cggcgactgg cctcgccccg cgacccggac   19500
cgccggggcg ggcacctcgc actgcgcgtc cccgatgccg acgggctcga acgcgcgctg   19560
gccgacagcg gcgtgctcgt cgacgcccgg ccgccggacc tggtccgttt cgcgttcgcc   19620
ccgctgtatg tgacctacga gcaggtatgg cgcgcagtga acgaggtgca ccgtgccctg   19680
ccgtgaaagg agtgagatga accgggcgcc cgagtacgtc tcctacgccc gcatggacga   19740
actgcacgaa ctgcagcgcc cgcggagcga cgcccgaggc gagctgaact tcatcctgct   19800
cagccacgtc aaggagctgc tgttccgcgc ggtcaccgac gacctggaca cggcccgcca   19860
cgcactggcg ggcgacgacg tcgcggacgc gtgcctggcg ctgtcgcggg cggccgcac   19920 ccagcgggtg ctcgtggcct gctgggagtc gatgaacggc atgtcggccg acgagttcgt   19980
ggcgttccgg cacgtgctca acgacgcgtc ggggtgcag tccttcgcct accgcaccct   20040
ggagttcgtc atgggcaacc ggccgccccg gcaggtggag gcggcgtacc gggaagggca   20100
cccgctggtg cgcgcggaac tggccaggcc gtcggtgtac gacgaggcgc tgcggtacct   20160
ggcgcggcgg gggttcgcgg tcccggccga ctgcgtgacc aggccaccgg aggagcagca   20220
cgagccggat ccccgcatcg aggaggtgtg gctggagatc taccggcacc cggaccggta   20280
ccgcgacgcg caccgcctgg cggagtgcct gatcgaggtc gcctaccagt tctcccactg   20340
gcgggccacg cacctgctgg tcgtcgagcg gatgctcggc ggcaagagcg gaacgggcgg   20400
cagcgacggc gccgcgtggc tgcgcaccgt caacgagcac cgcttcttcc cggagctgtg   20460
gaccttccgc acccggctct gaacccggag cgagaaccga cccacggagg aaagtgatga   20520 aggaacccg cacggggctg ccgatcggca cgccccaccc gccggtcgcg cggtgcgccc   20580 acgacccgg gtccgtcccg cacggcggac ggggaacgg gctcgtccgc ccgtcttgcg   20640
gcacgcacgg gccggcgtgg gaggccaccg gcctgccggg aggcacgtcg tgacgaaacc   20700
ggtcgacctc aagccgctcg ttccggtgct cttcgggttc gccgccttcc agcaactgcg   20760
ggccgcgtcg gaactgcagc tgttcgagta cctcacccct aacggcccct cgacctgtga   20820
ccaggtcgcc gccggactgc ggctgccgcc caagtcggcg cgcaagctgc tgctcggcac   20880
gacggcgctc ggcctgaccg agcacgagga ggggcggtac gcgccgagcc ggatgctgcg   20940
cgacgcgatc gacggaggcg tctggccgct gatccgcaac atcatcgact ccagcaccg   21000 cctgtcgtac ctgccggcca tggagtacac ggagtcgttg cggaccggca ggaacgaggg   21060
gctcaagcac ctgcccggct cggcagcga cctgtactcg cggctggaac aggccctgga   21120
cctggagaac ctgttcttcc ggggaatgaa ctcctggtcg gagctgtcca accggtgct   21180 gctgcaccag gtggactacc gggacgtgcg cgacctgctg gacgtcggcg gcggcgacgc   21240
cgtcaacgcc atcgcgctgg cgcgggcaca cccgcacctg agggtgacgg tgttcgacct   21300
cgaaggggcc gccgaggtgg ccaggggacaa catcgccgac gccggcctcg cgaccggat   21360 ccgggtggtg gccggcgaca tgttcggcga tccgctgccc gacgggttcg acctggtgct   21420
gttcgcccac cagttcgtga tctggtcgcc ggagcagaac cgggcgctgc tcaagcgggc   21480
ctacgaggcg ctgcgtcccg gcggccgggt ggccgtgttc aacgcgttcg ccgacgacga   21540
```

```
cggatgcggg ccgctctaca cggcgctgga caacgtctac ttcgcgacac tgccgtccga   21600
ggagtcgacg atctaccgct ggagcgagca cgaggagtgg ctcaccgccg ccggattcgt   21660
cgacgtcacg cgcgtccaca acgacggctg accccgcac ggcgtcatcg agggcgcaa    21720
gcccgatgcg tgagccaggc cggctggacc gcgagtactc gccgagcacc gtcgcccgcg   21780
acccggcccg ctcgctgcgg ctctaccgca cgcgcagcga cgacgccggg tcccggcccg   21840
gcgcgcacac gacggtccgg tacggcaccg agagcggcga gcggtgccat gtgttcccgg   21900
ccgccgcgcc cggcacaccg ggaccccgga ccccgccct ggtcttcgtg cacggcggcc    21960
actggcagga gtccggcatc gacgacgcct gcttcgcggc acgcaacgcg ctggcgcacg   22020
gatgcgcgtt cgtggccgtg ggctacgggc tcgccccgga ccgcacgctg cccgacatga   22080
tcgcctcggt ggcccgggcc ctggagtggc tcgcccgcac cgggccgcgg ttcggcatcg   22140
atccggagcg cctgcacgtg gcgggcagca gcgcgggcgc gcacctgctc gccgcggcgc   22200
tcgccggcgg cgcggccccc cggtccgca gcgcgtgcct gctgagcggc ctgtacgacc    22260
tcaccgagat cccgcgcacc tacgtcaacg aagccgtcgg cctgaccgcg gagctcgccc   22320
gcgactgcag cccgctgcgg atgcccgcac cgcgctgcga ctccgtgctg ctcgccgccg   22380
ggcagcacga gacgcggacg tacctgcgcc agcacgaggc gtacgccgct cacctggccg   22440
cccacgcggt cccggtgaca gcccgggtgg tacccgaccg ggaccacttc gacctgccgc   22500
tggacctggc ggacgcctcc accccgttcg gccggaccac cctgaaccac ctgggcctgg   22560
cggcgcccac cggaaccgag cccacacgag aagggacggt gacatccgcg cgatgacagt   22620
acgcagcacc gccacggcgg ccggcacggc cgtcgcggcc cggaccaccg ttgagacgat   22680
cccgcaggcg ttcacccggg cggcgcggca gcacgcggcg cgcgaggcgc tctccgacgg   22740
tgcgacgacc ctgacctacg ccgaactgga cgacgccgcc aaccggatcg cccgcgccct   22800
gcgcgagcgc gggctccggc cggggagcg ggtcggcgtg cgcctcgacc gcggcctcgc    22860
cctctacgag gtcttcctcg gcgcgctgaa agccggcctg gtggtggtcc cgttcaaccc   22920
cgggcaccccc gcggaccaca cgtcgcggat gcaccggatg agcgggccgg ccctgacggt   22980
gacggactcc ggtgccgccg aggggatccc cgcggcgacc cgtctgccgg tcgacgagct   23040
gctggccgac gcggcgccgc tgtccgcgca gccggtggac ccggaggtga cggcggaagc   23100
acccgcgttc atcctgttca cctccggctc caccggcgct cccaagggag tggtgatcgc   23160
ccaccgcggg atcgccaggg tcgcccggca cctcaccggt ttcacgcccg gcccgcagga   23220
ccgcttcctg cagctcgcgc agccgtcgtt cgccgcgtcg accaccgaca tctggacgtg   23280
cctgctgcgg ggcggccggc tctcggtcgc cccgcaggag ctgccgccgc tcggtgacct   23340
ggcacggctc atcgtccgcg agcggaccac cgtcctcaac ctgcccgtcg gcctgttcaa   23400
cctgctggtc gaacaccatc cgcagaccct cgcgcagacc cggtcggtga tcgtcagcgg   23460
tgacttcccc tcgccgcgc acctcgaacg cgccctcgcc gtcgtcggcg gtgacctgtt    23520
caacgccttc ggatgcacgg agaactccgc gctcaccgca gtccacaaga tcaccccgc    23580
ggacctgtcc ggcaccgaca tcccggtcgg acggcccatg ccgaccgttg acatgacggt   23640
ccgcgacgag cggctggagg agtgcgcgcc cgggcagatc ggcgagctgt gcatcgccgg   23700
cgacggcctc gccctcggat acctcgacga cccggaactc acggaccgga agttcgtccg   23760
gcaccgcggg aggcggctgc tgcggaccgg ggacctggcc aagcggaccg aggaggggga   23820
gatcgtactc gccggccgca cggaccagat gctgaaggtg aggggttcc gggtcgaacc    23880
gcggcagatc gaggtgacgg ccgaggcgta ccccggcgtc gagcgcgcgg tggcgcaggc   23940
```

-continued

```
cgtgccgagc gacggggcgg cggaccggct cgccctgtgg tgcgtgcccg cgccgggaca    24000
cgaactcgcc gaacgcggcc tcgtggacca cctgcgcggg cgcctgcccg actacatggt    24060
gccgtccgtg gtgctggtcc tcgactcctt cccgctcaac gcgaacggca agatcgaccg    24120
cagggagctc gccgcgcggc tcgcggcccg catggccacc gggacgcacg gcggtggcgc    24180
ggaggaccgg ctgcggcgg tcgtgcgcgc caccctggcg gacgtgaccg gccagggccc    24240
gctcggcccg gacgacggcc tggtggagaa cggggtcacc tccctgcacc tgatcgacct    24300
cggcgcccgc ctcgaggacg tggtgggcgt cgccctggca cccgacgaga tcttcggcgc    24360
cggcaccgtg cgcggtgtgg ccgacctgat acgcaccaag cgttcccgag gctgagatga    24420
ctgctgccga ttaccgcaa gcgaccgaca cccggtgctt cccgccgtcg ccggcccagg    24480
ccggcctgtg gttcgcgagc acctacggga ccgatcccac cgcgtacaac cagcccctgg    24540
tcctgcgcct gggcaccctg gtggaccaca ccctcctcca ccgggcgctg cgcctggtcc    24600
accgggagca ctgcgcgctg cgcaccacgt tcgacatgga tgcggacggt gagctgcggc    24660
agatcgtgca cggcgagctg gaaccgatcg tcgacgtgcg cgtccacgcc ggcggcgact    24720
ccgaggcctg ggtggccgag caggtggagc aggtcgcggc caccgtcttc gacctgcgca    24780
ggggcccgct cgcgcgggtg cggcacctgc gcctggtggc ggagggccgg agcctgctgg    24840
tcttcaacat ccaccacacc gtcttcgacg gcctgtcgtg aagccctac ctcagccggc    24900
tggaagcggt ctacaccgcc ctcgcccgcg gacaggaacc accccggaag ccccggcgcc    24960
aggcggtcga ggcgtacgcg cggtggtccg agcggtgggc ggactccgga tcgctgtccc    25020
actggctgga caagctggcg gacgcgcccg cggcggcgcc cgtcggactg ccgggggagg    25080
gccccgcgcg ccacgtgacc cacaaggccg tcctcgacga ccggctgtcc gcgcaggtga    25140
agacgttctg cgccaccgag ggcatcacca ccggcatgtt cttcgccgcc ctcgccttcg    25200
tgctgctgca ccggcacacc gggcaggacg acatcctcct cggcgtcccg gtcaccgtgc    25260
ggggagcgg cgacgccgag gtcgtcgggc acctgaccaa cacggtcgtg ctgcggcacc    25320
ggctggcccc cggagcgacc gcccgcgacg tcctgcacgc ggtgaagcgg acatgctcg    25380
acgcgctgcg gcaccggcat gtcccgctgg aggcggtggt cggcgaactc cgcgccctgg    25440
gaggcggcaa ggacgcgtc ggcgaccgt tcaacgcgat gctcacggtg atgccggcct    25500
ccgcccgccg cctggacctg cgcgagtggg gagtggagac gtgggaacac gtctccgggg    25560
gcgccaagta cgaactggcg gtcgtggtgg acgagacgcc gggccgctac acgctggtcg    25620
tcgagcacac ctcggcctcg gccggcgccg gaagcctcgc ggcgtacctg gcgcggcgcc    25680
tggagacgct cgtgcgcagc gtgatggccg acccggacac ggacgtccgc cggctgcgct    25740
gggtgagcgc ggaggaggag cgggcggtca ccggcctgtg cgcgcgcagg caggacgcgc    25800
ccgagctggg caccgaggtg acggccgacc tgttcgccga ggccgccgcg gcggcggccg    25860
ccgaccccgc cgtggtcgcg gacggcgtgg tgacgtccta cgccgagctg gcgcggcagg    25920
ccgacgccgt ggcggcggac ctggccgccc ggggagtgcg ggacggcggg ccggtggccg    25980
tgctgatgcg gccggggctc gacctggtgg cgaccgtcgt cggcatcctg cggcggggcg    26040
gcagctacgt ggtcctcgac gccgaccaac cgcgggaacg gctgtctttc gcgctggccg    26100
acagcggcgc gaagatcctg ctgcacgacc cggacgccga cctcgcgggc gtacggctgc    26160
ccgacgggat gcagaccgcc accatgcccg gcacggaggg cggggtcgtt ctcgagcccg    26220
gtcgcaggaa gtcgccggac gaccaggtgt acgtcgtcta cacatcgggg tccaccgggc    26280
```

```
gccccaaggg ggtggtgctg ctggagccga ccctgaccaa cctcgtgcgc aaccaggccg   26340
tactgtcctc gcaccgccgg atgcgcaccc tgcagtacat gccgccggcc ttcgacgtgt   26400
tcaccctgga ggtcttcggg accctgtgca ccggcggcac gctggtcgtc ccgccccgc    26460 acgcccgcac cgacttcgag gccctggccg cgctgctggc cgagcagcgc atcgagcggg   26520
cgtacttccc gtacgtcgcg ctccgcgagc tcgccgccgt cctgcgctcg tccgggacgc   26580
gcctgccgga cctgcgcgag gtgtacgtca ccggcgagcg actggtggtc accgaggatc   26640
tgcgggagat gttccggcgg caccccggag cccggctgat caacgcctac gggccgtccg   26700
aggcccacct ggtcagcgcg gagtggctgc cggccgatcc cgatacctgg cccgcggtcc   26760
cgccgatcgg ccgggtggtc gccggcctcg acgcccgggt gctcctggag ggggacgagc   26820
cggcgccgtt cggcgtcgag ggggagctgt gcgtggccgg accggtcgtc tcgcccggat   26880
acatcggact gccggagaag acccgccagg cgatggtccc cgaccgttc gtccccggcc    26940 agctgatgta ccggaccggc gacgtggtcg tgctggaccc ggacgggcgc ctgcactacc   27000
ggggccgggc cgacgaccag atcaagatcc gcgggtaccg cgtcgaaccc ggtgaggtcg   27060
aggcggccct ggagcgggtg ctgcacgtgg aagcggccgc ggtgatcgcc gtaccggcgg   27120
gccacgaccg ggcgctgcac gccttcgtgc ggagcggcca ggagccgccc tcgaactggc   27180
gctcccgcct cgggaccgtc ctgcccggat acatgatccc gcggggatc acccgggtcg    27240 acgccatccc ggtgacgccg aacgggaaga ccgaccgccg cgcactcgag gcacggctcg   27300
ccgaccgcgc cgggacggag cccgccgggg gcggcggcat ggactggacg gactgcgaac   27360
gcgcgatcgc cgacctgtgg acggaggtcc tcggacacgg gcccgcgaca ccggacgacg   27420
acttcttcga gctgggcggg cactcactgc tcgccgcccg cctgcaccgg ctggtccggc   27480
agcgcctgga cagcgacgtc ccgctctcgg tgctgctcgg cacgcccacc gtgcgcggca   27540
tggccggcag cctcgccggc cggggcgcct cggggacggt cgacctgcgc gaagaggccc   27600
gactgcacga cctcgtcgtg ggcgagcgcc gggaaccggc cgacggcgcg gtgctgctca   27660
ccggggcgac cggcttcctc ggcagccacc tcctcgacga actccagcgt gccgggcgcc   27720
gcgtgtgctg cctggtccgc gccggcagcg tcgaggaggc gcggggccgg ctgcgggcgg   27780
cgttcgagaa gttcgcgctc gaccccctccc ggctcgaccg ggccgagata tggctgggcg   27840
acctcgcccg gccccggctc ggtctcggcg acgggttcgc ggcgcgcgca cacgaggtcg   27900
gcgaggtgta ccacgcggcc gcgcacatca acttcgccgt tccgtaccac accgtcaagc   27960
gcaccaacgt cgacggcctg cggcgcgtgc tcgacttctg cggcgtcaac cgcacgccgt   28020
tgcgcctgat ctccaccctg gcgtcttcc cgccggactc cgcgcccggt gtgatcggcg    28080
aggacacggt tccgggcgac ccggcgtcgc tcggcatcgg gtactcgcag agcaagtggg   28140
tcgccgagca cctcgcgttg caggcgcggc aggccggact gccggtcacc gtgtaccgcg   28200
tcggccggat cgccgggcac agccgcaccg gggcgtgccg gcacgacgac ttcttctggc   28260
tgcagatgaa gggcttcgcg ctgctcggcc gctgcccgga cgacatcgcc gacgcaccgg   28320
ccgtcgacct gctgccggtg gattacgtgg cccgggcgat cgtccggctg ccgagggca    28380 agccggacga cgccaactgg cacctgtacc acccgcaggg gctcgcctgg tccgtgatcc   28440
tggagacgat ccgcgcggaa gggtacgcgg tgagcccggc cacccgatcc gcgtggctgg   28500
ccgcactgga acggcaggcc gggaccgagg cccagggcca gggactcggg ccgctggtgc   28560
ccctgatgcg ggagggcgcg atgcgtctcg gctcccattc gttcgacaac gggagaacca   28620
tgcgtgctgt ggccgatgtc ggatgcccgt gtccgccggc ggacacggaa tggatccggc   28680
```

```
gaatgttcga gtacttccgt gccatcggct cggtgccgcc gccggacggg gtcaccctgg   28740
gaggtcatgt tgcctgagct gcacaggcgc tcggtggtgg tcatcggcgc cggaccggtc   28800
ggttgcgccc tggcgctgct gctgcggcgg cagggcgctgg aggtggacgt cttcgaacgg   28860
gagccggagt cggtgggcgg cgggtccggt cactccttca acctcacgct caccctgcgc   28920
gggctcggct gcctgccccg atccgtcagg cgccgcctct acctgcaggg cgcggtgctg   28980
gtgaaacgca tcatccacca ccgcgacggc gcgatctcca cgcagccgta cggcacgtcg   29040
gacacccatc acctgctgtc cattccgcgc cgggtcctcc aggacatcct gcgcgaccag   29100
gccctgcggg tcggcgcgcg gatccactac ggacgcgcgt gcgtcgacgt ggacaccgga   29160 cgcccgcgg cgctgctgcg cgacggcgac ggcggcacct cgtgggtgga ggcggacctg   29220
ctggtcggtt gcgacggggc caacagcgcg gtgcgcggcg ccgtcgccgc ggcccacccg   29280
gccgacatgt gggtgcggcg ccgcacgatc gcccatggcc acgcggagat cacgatggac   29340
tacggggacg ccgacccgac cggcatgcac ctgtggccgc ggggcgacca cttcctgcag   29400
gcccagccca accgcgacag gacgttcacc acgagtctgt tcaagccgct gacgggcgac   29460
ggcccgcggc cgcacttcac cggcctgccg tcggccgacg cggtcagcga gtactgcgcg   29520
acggagttcc ccgacgtctt cggccggatg gccggggtcg gcagggacct caccgcccgt   29580
cgtcccggca ggctgcggat catcgactgc gccccgtacc accaccggcg caccgtgctg   29640
gtcggagacg ccgcgcacac ggtcgtcccg ttcttcggac agggcatcaa ctgcagtttc   29700
gaggacgccc ccacgcttgc cgggctgctg gagaagttcc agttcgcccg ccgcgacgag   29760
agcgggacca tcgtggaggc cgtcgccgac gagtacagcg acgcacgggt gaaggcgggc   29820
cacgcactgg ccgagctgtc gctgcgcaac ctcgaggagc tgtcggacca cgtgaacagc   29880
cgcgcgttcc tggcccgccg tgcgctggag cgccggctgc acgagctgca ccccgacctg   29940
ttcaccccgc tctaccagct ggtcgcgttc accaacgtgc cctatgacgc ggtgcagcgg   30000
atgcacggcg agttcggcgc cgtactggac tcgctgtgcc gcgggcgtga cctacggcgc   30060
gaacgggacg ccatcatcag ggagttcgtc gacgtgtacg attccggatt cgcggccggg   30120
agactgcgca cggggtgagg gggaccgcgg ccgcggcacc gaccgcagcg cgtggacgcc   30180
gcatcctgac acgccgcgc cggcgggccc cgggcccgcc ggcgcggccg tcaccggcga   30240
cgagacgagg tcacggggac gacatctcca tgagcacccg gatcgacgac tccagcgcgt   30300
agttcatcga cccgccgttg ggctcgaacg cggtgtgctc gcccgcgaag tggatgcgcc   30360
cctccggggc cctgatggcc gccatcagtt cgctgtggcc cttctccggg aggatgtacg   30420 cgcccgccg gtacggctcg ttgtcccagg ccaccgaggt gcccagctcg aagttctccc   30480
gcgctccggg aaggatcggc tccagttcgt tcagcgcgta ggcgacgcgc tcctcggggc   30540
tcatggccgc ggccgcctgc gcctgccatc cggtgagcca gcactcgacg atcctgcggg   30600
gcccgggcag gtgcggtgtg gcatcgcgga ccgtgcggac cgccgtgtcc gtggacagca   30660
tcaaccgcct ctccggccag aacttcctgc gcatctgcag gaagacacgg accgtcgacg   30720
cgtagcggag ccgccggatc gccgcgtgct tcgccgccga caggcgggcc atcgacaagt   30780
tgacgcgccg catgctgctg aacgcgcgcg tgacgacgac ccggtccgcg cacaacgtcc   30840
ggagccggcc gtggtcgagg aaggtcacct gcgcctcgcg gtcgtcctgg gcgatgcgga   30900
cgaccggctt gcggtagagg atccgctccc cgagcctgct cgccagcgcc cgggcgagca   30960
tgtccgtacc gccctcgacc ttgtaccact gggcgcccgc cgtggagaag gaccgtgggc   31020
```

```
ccgactcgta gcgggcccac gccatggccg aggcggattc cagctcgcct ccgcgcatct    31080
ccaggaagaa cggttccatg aggccgatcg cggcggcgga agcgccacgc tcctcgagca    31140
cccggcgcac ggagacccgg tcgagctcca gcagacgcgg tgtcggtgcc cagacgggct    31200
gcgcgatctc cgggccgagc ttctcgttga actcggtcac atatctggcg atcatgccct    31260
cgacggtgag gtgccgctcg tcggggtgca ggcccaggag gtcggcgtgc tcgccgacct    31320
tgtcgggggg tattcgcacg ccgttgcggt ggtacccgaa gtccgtgtcg acgaggtcgc    31380
tcggttcggt cccgatcccc atctccttca gatagtgcat ggtgtagtgg cagtgctccg    31440
tcaccgtcat ggcgccggcc tccgcgcgga ggccgtcggc gaacggctcg cgcagggtcc    31500
acgtccgtcc tcccggacgg ctgtcggctt cgagcacggt gaccgtgacg ccctgcctcg    31560
tcaattcgtg ggccgcggcc agaccggcca gcccggcgcc gaccacgatg accgaggagg    31620
tgccgtgctg aggcgggatg ccgctgtcga aggtctccct gacgctgtgc tgggttggct    31680
ccggcacggt tgtcctttcg tccacacgag ggccggctca ctgcggcgcc gagttcacct    31740
cacggaagat cctgcgcgac ggcggccagg gcgcgtggtg tcccgaggtg ccgttcgcgc    31800
gggccggctc cttgcccggg cagggctcgt cgcgggtcgc ttccccgttg aaccggaagc    31860
cgaccccgcg gacggtgatg atccaatcgg gcgagccgag cttcttgcgc aggctgctga    31920
cgtgtgtgtc gatcgtgcgg ctggccagcg atgtcacttc cgcgctgacg tcgtcgtagt    31980
cccatacccg ccgcagcagc tcggctctgg agaagagctt gtcgggttcg gcggcgagca    32040
ggtggagcag ttcgaactcc ttgcgggtgg tctcgatcgg ccggttctcg accctcacct    32100
ggcgcagggt ggggtagatc tgcagcttgc cgaccgtcag cgccggtggg gacagcacgc    32160
gggcccgtcg gagcagcgcg cccaggcgcg ccacgagttc acggctgtgg tacggcttca    32220
ccacgcagtc gtcgcagccc gcctccaggg cgaggacgcg ctcgagcgcg cggagcagg    32280 cgaagccgat catcgggatg tcactggcgt tgcggatctg ccggcacagg gtcagaccgt    32340
cgaagtcctt cagatcgagg tcgatcagga ccacgtcgtg ttcgcggtag gaggccatgg    32400
cctcggcgcc ggtcgtcacc gactcggcct cgaaaccgtg ccgcttgagg tctctgatca    32460
tttctgcgag gccctcgcag tcccccacga tcagcacctt taagccgttg tcaagcaatg    32520
tccaaccccc ttcggtcac                                                 32539
```

<210> SEQ ID NO 2
<211> LENGTH: 620
<212> TYPE: PRT
<213> ORGANISM: Streptomyces refuineus subspecies thermotolerans

<400> SEQUENCE: 2

Met Cys Gly Ile Val Gly Trp Ala Asp Phe Ala Arg Asp Leu Thr Ala
1               5                   10                  15

Glu Arg Arg Val Leu Gln Ala Met Val Asp Thr Met Ala Leu Arg Gly
            20                  25                  30

Pro Asp Glu Glu Gly Val Trp Val Arg Pro Arg Val Ala Leu Gly His
        35                  40                  45

Arg Arg Leu Ser Val Ile Asp Leu Glu Gly Gly Lys Gln Pro Met Val
    50                  55                  60

Thr Pro Glu Thr Leu Pro Asp Gly Thr Pro Leu Ala Ala Ile Ser Tyr
65                  70                  75                  80

Ser Gly Glu Val Tyr Asn Phe Thr Glu Leu Arg Gly Glu Leu Ala Ala
                85                  90                  95

Arg Gly His Arg Phe Arg Thr Arg Ser Asp Thr Glu Val Val Leu Arg

-continued

```
                    100                 105                 110
Ala Tyr Leu Glu Trp Gly Pro Glu Phe Val Arg Arg Leu Asn Gly Met
                115                 120                 125
Phe Ala Phe Ala Ile Trp Asp Ala Arg Gly Glu Glu Leu Leu Leu Tyr
            130                 135                 140
Arg Asp Arg Leu Gly Ile Lys Pro Leu Phe Tyr Tyr Pro Thr Arg Asp
145                 150                 155                 160
Gly Val Leu Phe Gly Ser Glu Pro Lys Ala Val Met Ala His Pro Glu
                    165                 170                 175
Ser Arg Ala Val Leu Ser Leu Asp Gly Leu Arg Asp Val Leu Ser Phe
                180                 185                 190
Val Arg Val Pro Gly Gln Thr Pro Met Lys Gly Leu Tyr Glu Val Arg
            195                 200                 205
Pro Gly His Val Leu Arg Val Arg Asp Gly His Arg Ser Glu Glu Arg
210                 215                 220
Tyr Trp Ala Leu Glu Ala Arg Pro His Thr Asp Asp Val Pro Thr Thr
225                 230                 235                 240
Val Arg Val Val Arg Glu Leu Glu Asp Ile Val Ser Arg Gln Met
                245                 250                 255
Val Ala Asp Val Pro Leu Cys Ser Leu Leu Ser Gly Gly Leu Asp Ser
                260                 265                 270
Ser Ala Leu Thr Ala Leu Ala Gln Arg Gly Leu Ala Ser Arg Gly Gly
            275                 280                 285
Gly Arg Ile Arg Ser Phe Ser Val Asp Phe Val Gly Gln Val Glu Asn
            290                 295                 300
Phe Ala Pro Glu Pro Leu Arg Glu Ala Pro Asp Ala Pro Phe Ala Ala
305                 310                 315                 320
Glu Leu Val Arg His Val Gly Thr Asp His Arg Val Ile Leu Leu Asp
                    325                 330                 335
Asn Ala Asp Leu Ala Ser Pro Arg Val Arg Ser Thr Val Met Arg Ala
                340                 345                 350
Trp Asp Leu Pro Tyr Gly Glu Gly Asp Leu Gly Pro Ser Leu Tyr Leu
            355                 360                 365
Leu Phe Arg Glu Val Arg Lys Glu Ser Thr Val Ala Leu Ser Gly Glu
            370                 375                 380
Ser Ala Asp Glu Val Phe Gly Gly Tyr Leu Trp Phe His Asp Arg Arg
385                 390                 395                 400
Ala Val Gln Ala Asp Thr Phe Pro Trp His Ala Leu Gly Glu Arg Pro
                    405                 410                 415
Val Ala Glu Leu Ser Thr Ala Phe Leu Asp Pro Gly Leu Thr Ala Glu
                420                 425                 430
Leu Asn Leu Pro Glu Tyr Ile Ala Asp Gln Tyr Arg Thr Ala Leu Ala
            435                 440                 445
Glu Val Pro His Leu Ala Gly Glu Thr Gly Glu Asp Arg Arg Met Arg
            450                 455                 460
Ile Ala Ser His Leu Asn Ile Thr Arg Phe Met Pro Met Leu Leu Asp
465                 470                 475                 480
Arg Lys Asp Arg Leu Ser Met Ala Asn Gly Val Glu Val Arg Val Pro
                    485                 490                 495
Phe Cys Asp His Arg Leu Val Glu Tyr Val Phe Asn Val Pro Trp Ser
                500                 505                 510
Met Lys Thr Tyr Asp Gly Arg Glu Lys Ser Leu Leu Arg Gly Ala Val
            515                 520                 525
```

```
Ala Asp Leu Leu Pro Arg Ser Val Val Glu Arg Arg Lys Ala Pro Tyr
    530                 535                 540

Pro Ser Thr Gln Asp Ala Gly Tyr Asp Arg Ala Ile Arg Gln Glu Leu
545                 550                 555                 560

Glu Lys Ile Val Ala Glu Pro Ser Ser Pro Val Leu Pro Leu Leu Asp
                565                 570                 575

Leu Asp Ala Val Arg Arg His Leu Asp Thr Pro Val Glu Lys Ala Ser
                580                 585                 590

Ser Met Leu Val Arg Gly Leu His His Glu Thr Pro Ala Arg Leu Asp
        595                 600                 605

Thr Trp Leu Gly Ser Tyr Gly Val Thr Leu Asp Trp
610                 615                 620

<210> SEQ ID NO 3
<211> LENGTH: 1863
<212> TYPE: DNA
<213> ORGANISM: Streptomyces refuineus subspecies thermotolerans

<400> SEQUENCE: 3
```

| | | | | |
|---|---|---|---|---|
| atgtgcggaa | tcgtcggctg | gcggacttc | gcccgcgatc | tcaccgccga acggcgggtc | 60 |
| ctccaggcca | tggtggacac | gatggccctc | gcgggcccgg | acgaggaggg cgtgtgggtg | 120 |
| cgcccgcgcg | tcgccctggg | ccaccggcgc | ctgtcggtca | tcgacctcga aggcggcaag | 180 |
| cagcccatgg | tcacgccgga | gacgctgccc | gacgggacgc | ccctggcggc gatcagctac | 240 |
| agcggtgagg | tgtacaactt | caccgaactc | gcggcgaac | tcgccgcccg cggccaccgc | 300 |
| ttccggacca | ggagcgacac | cgaggtcgtc | ctgcgcgcgt | acctggaatg gggaccggag | 360 |
| ttcgtccggc | ggctgaacgg | gatgttcgcc | ttcgcgatct | gggacgcccg cggcgaggaa | 420 |
| ctgctgctgt | accgggaccg | gctggggatc | aagccgctgt | tctactaccc cacccgcgac | 480 |
| ggcgtcctct | tcgggtccga | gccgaaggcc | gtcatggccc | accggagag ccgggcggtg | 540 |
| ctctcctcg | acggcctgcg | ggacgtgctg | tcgttcgtgc | gggtcccggg gcagacaccg | 600 |
| atgaaggggc | tgtacgaggt | ccgccccggc | cacgtcctga | gggtccgcga cggccaccgg | 660 |
| tccgaggaga | ggtactgggc | gctggaggcc | cggccgcaca | ccgacgacgt gccgacgacg | 720 |
| gtccgcgtgg | tccgcgaact | gctggaggac | atcgtctccc | ggcagatggt cgccgacgtc | 780 |
| cccctgtgca | gcctcctgtc | cggcggcctg | gattccagtg | cgctgaccgc cctggcgcag | 840 |
| cgcgggctcg | cctcccgcgg | gggcggccgg | atacggagct | ctccgtgga cttcgtgggg | 900 |
| caggtggaga | acttcgcgcc | ggaaccctc | cgggaggccc | cggacgcgcc gttcgcggcg | 960 |
| gagctggtgc | ggcacgtcgg | caccgaccac | cgggtcatcc | tgctcgacaa cgcggacctt | 1020 |
| gcgtcgccgc | gcgtgcggtc | gacggtgatg | agggcgtggg | acctccccta cggtgagggg | 1080 |
| gacctcggac | catcgctgta | cctgctcttc | cggaggtgc | ggaaggagtc caccgtggct | 1140 |
| ctctccggcg | agtccgcgga | cgaggtcttc | ggcggatacc | tgtggttcca cgaccggcgg | 1200 |
| gccgtccagg | ccgacacgtt | cccctggcac | gccctcggcg | agcgaccggt ggccgagctg | 1260 |
| tccacggcct | tcctggaccc | cggcctgacg | gcggagctca | acctcccgga gtacatcgcc | 1320 |
| gaccagtacc | ggacgcgct | cgcggaagtc | ccgcacctgg | ccggggagac cggcgaggac | 1380 |
| cggcggatga | ggatcgcgag | ccacctgaac | atcacgcggt | tcatgccgat gctgctggat | 1440 |
| cgcaaggacc | ggctgagcat | ggccaacgga | gtggaggtcc | gcgtcccctt ctgcgaccac | 1500 |
| cgcctggtcg | agtacgtctt | caacgtgccc | tggtcgatga | agacctacga cggccgggag | 1560 |

-continued

```
aagagcctgc tgcgcggtgc ggtcgcggac ctgctgcccc gatccgtcgt ggagcgccgc    1620
aaggcgccct acccgtccac ccaggacgcc ggctacgaca gggcgatcag gcaggagctg    1680
gagaagatcg tcgcggagcc gagctcgccg gtgctgcccc tgctcgacct ggacgccgtc    1740
cgccgtcacc tcgacacgcc ggtcgagaag gcgtcgtcga tgctggtgcg cggtctgcac    1800
cacgagactc cggcccggct cgacacctgg ctgggatcct acggtgtgac cctcgactgg    1860
tga                                                                  1863
```

<210> SEQ ID NO 4
<211> LENGTH: 500
<212> TYPE: PRT
<213> ORGANISM: Streptomyces refuineus subspecies thermotolerans

<400> SEQUENCE: 4

```
Leu Ser Ala Leu Gly Ala Cys Val Asn Pro Ser Pro Gly Val Ala Ala
1               5                   10                  15

Arg Ala Phe Leu Ser Arg Pro His Leu Leu Phe Ile Gly Gly Arg Phe
            20                  25                  30

Val Ala Ser Ala Thr Gly Arg Thr Phe Ala Thr Val Asp Pro Ser Thr
        35                  40                  45

Gly Glu Arg Leu Ala Gln Val Ala His Ala Gly Pro Glu Asp Val Glu
    50                  55                  60

Ala Ala Val Ala Ala Arg Thr Ala Leu Glu Gly Ala Trp Gly Ala
65                  70                  75                  80

Leu Pro Ala Ala Glu Arg Gly Arg Leu Ile Thr Arg Leu Ala Asp Leu
                85                  90                  95

Val Glu Arg Asn Ala Glu Glu Leu Ala Glu Leu Glu Ser Leu Asp Val
            100                 105                 110

Gly Lys Pro Ile Ala Lys Thr Arg Ala Leu Asp Val Pro Ala Ala Ala
        115                 120                 125

Ala Gln Phe Arg Tyr Phe Gly Gly Trp Pro Thr Lys Ile Glu Gly Glu
    130                 135                 140

Thr Ile Pro Val Ala Val Pro Asp Thr Leu Cys Tyr Thr Arg Lys Glu
145                 150                 155                 160

Pro Val Gly Val Cys Ala Gln Ile Val Pro Trp Asn Phe Pro Leu Leu
                165                 170                 175

Met Ala Ala Trp Lys Leu Gly Ala Ala Leu Ala Ala Gly Cys Thr Val
            180                 185                 190

Val Leu Lys Pro Ala Glu Gln Thr Pro Leu Thr Leu Arg Leu Ala
        195                 200                 205

Glu Leu Ile Ala Glu Ala Gly Phe Pro Glu Gly Thr Val Asn Val Leu
    210                 215                 220

Thr Gly Asp Gly Pro Thr Gly Ala Ala Leu Val Asp His Pro Gly Ile
225                 230                 235                 240

Asp Lys Ile Ala Phe Thr Gly Ser Thr Ala Val Gly Arg Glu Ile Gly
                245                 250                 255

Ala Lys Ala Gly Ala Arg Leu Lys Arg Val Thr Leu Glu Leu Gly Gly
            260                 265                 270

Lys Ser Pro Asn Ile Val Leu Pro Asp Ala Asp Ile Glu Ala Ala Ile
        275                 280                 285

Ser Gly Ala Ala Glu Gly Ile Phe Phe Asn Thr Gly Gln Ala Cys Asn
    290                 295                 300

Ala Ala Ser Arg Leu Tyr Val His Arg Asp Val Phe Asp Asp Val Val
305                 310                 315                 320
```

```
Glu Gly Val Leu Ala Arg Ala Arg Arg Ala Arg Val Gly Pro Ala Leu
            325                 330                 335

Asp Pro Ala Thr Glu Tyr Gly Pro Leu Val Ser Ala Glu Gln Tyr Arg
            340                 345                 350

Arg Val Arg Gly Tyr Leu Leu Asp Gly Val Ser Glu Gly Ala Val Leu
            355                 360                 365

Arg Ala Gly Glu Val Pro Ala Ala Asp Pro Gly Gly Tyr Phe Val
            370                 375                 380

Arg Pro Ala Leu Phe Thr Asn Val Thr Pro Thr Met Arg Ile Cys Arg
385                 390                 395                 400

Glu Glu Ile Phe Gly Pro Val Leu Val Ala Ala Pro Phe Glu Thr Val
            405                 410                 415

Asp Glu Val Val Arg Leu Ala Asn Asp Thr Glu Tyr Gly Leu Ala Ala
            420                 425                 430

Gly Val Trp Thr Arg Ser Leu Ser Ala Ala His Gly Leu Ala Ala Arg
            435                 440                 445

Leu Lys Ala Gly Ser Val Tyr Leu Asn Ser Trp Ala Pro Gly Asp Pro
450                 455                 460

Ala Ser Pro Phe Gly Gly Leu Lys Ala Ser Gly Val Gly Arg Glu Met
465                 470                 475                 480

Gly Arg Ala Gly Leu Asp Ala Tyr Leu Glu Leu Lys Thr Val Trp Thr
            485                 490                 495

Ser Ile Ala Pro
            500

<210> SEQ ID NO 5
<211> LENGTH: 1503
<212> TYPE: DNA
<213> ORGANISM: Streptomyces refuineus subspecies thermotolerans

<400> SEQUENCE: 5
ctgagcgcat tgggagcatg tgtgaatcct tccccgggag tggctgcccg cgcctttctg      60
tcccgtcccc acctgctctt catcggcggc cggttcgtgg cctccgcgac ggggcgcacc     120
ttcgccaccg tcgacccgtc caccggtgaa cgcctcgcgc aggtcgccca cgcgggaccg     180
gaggatgtcg aggcagccgt cgcggccgcc cggaccgcgc tcgaaggagc gtggggcgcg     240
cttcccgcgg ccgagcgcgg caggctcatc acccgcctcg cggacctcgt cgagcgcaac     300
gccgaggaac tcgccgaact cgagtccctc gacgtgggca agccgatcgc caagacccgc     360
gccctcgacg tcccggccgc cgcagcccag ttccgctact tcggcggctg cccacgaag      420 atcgaggggg agacgatccc ggtcgcggta ccggacacgc tgtgctacac gcgcaaggaa     480
ccggtgggtg tctgcgcgca gatcgtcccc tggaacttcc cgctgctgat ggcggcctgg     540
aagctcggag cggcactcgc cgccgggtgc accgtggtgc tcaagcccgc ggagcagacc     600
ccgctgacca ccctgcgcct ggccgaactg atcgcggagg ccggcttccc cgagggcacg     660
gtcaacgtgc tcaccggtga cggtccgacc ggtgccgcgc tggtcgacca tccgggcatc     720
gacaagatcg cttttcaccgg ctccaccgcg gtgggacgcg agatcggggc gaaggccggc     780
gcccggctca gcggggtgac cctggagctc ggcgggaaga gccccaacat cgtcctcccg     840
gacgccgaca tcgaggccgc gatctcgggc gccgccgagg gcatcttctt caacaccggc     900
caggcctgca acgccgcctc ccggctgtac gtgcaccggg acgtgttcga cgacgtggtc     960
gagggagtgc tggcgcgggc ccggcggcgc gcgtcggcc cggctctcga cccggcgacc    1020
```

-continued

```
gagtacgggc cgctggtgtc ggccgaacag taccgccggg tgcgcggcta cctcctcgac   1080
ggcgtctccg aaggcgccgt gctgcgggcg ggggaagtgc ctgcggccga cccgggcggc   1140
gggtacttcg tccgtcccgc gctgttcacg aacgtcacac cgaccatgcg gatctgccgt   1200
gaggagatct tcggaccggt tctcgtggcg gcgccgttcg agaccgtcga cgaggtcgtc   1260
cgcctggcca acgacaccga gtacggcctg gcggccgggg tgtggacccg gagcctgagc   1320
gccgcgcacg gcctcgcggc ccggctgaaa gcggggtcgg tgtacctcaa ctcatgggcg   1380
cccggcgatc cggcttcccc gttcggcgga ctcaaggcgt ccggggtcgg gcgggagatg   1440
gggcgcgccg gcctcgacgc ctacctcgaa ctgaaaaccg tgtggacgtc aatcgccccc   1500
tga                                                                 1503
```

<210> SEQ ID NO 6
<211> LENGTH: 354
<212> TYPE: PRT
<213> ORGANISM: Streptomyces refuineus subspecies thermotolerans

<400> SEQUENCE: 6

```
Val Ile Asp Val Arg Ala Ala Gln Ile Val Gly Tyr Gly Glu Pro Leu
1               5                   10                  15

Gln Val Arg Glu Val Pro Asp Pro Ala Pro Glu Pro Gly Gly Val Val
            20                  25                  30

Val Ala Val Leu Ala Thr Gly Ile Cys Arg Ser Asp Trp His Gly Trp
        35                  40                  45

Arg Gly Asp Trp Glu Trp Leu Gly Gly Arg Ile Ala Leu Pro Arg Thr
    50                  55                  60

Pro Gly His Glu Ile Ala Gly Glu Val Ala Ala Gly Pro Gly Val
65                  70                  75                  80

Arg Gly Val Arg Val Gly Asp Arg Val Thr Val Pro Phe His Leu Ala
                85                  90                  95

Cys Gly Thr Cys Ala His Cys Arg Ala Gly Gln Ala Asn Leu Cys Asp
            100                 105                 110

Glu Met Glu Val Leu Gly Phe Trp Arg Asp Gly Gly Tyr Ala Glu Tyr
        115                 120                 125

Val Arg Ile Pro His Ala Asp Phe Asn Cys Val Arg Ile Pro Asp Gly
    130                 135                 140

Val Thr Pro Leu Thr Ala Ser Ala Ile Gly Cys Arg Phe Met Thr Ala
145                 150                 155                 160

Phe His Ala Val Asp Gly Gln Gly Arg Val Arg Pro Gly Glu Trp Val
                165                 170                 175

Ala Val His Gly Val Gly Gly Val Gly Leu Ser Cys Val Gln Ile Ala
            180                 185                 190

Ser Ala Ala Gly Ala Ser Val Val Ala Val Asp Ile Asp Pro Ala Lys
        195                 200                 205

Leu Ala Leu Ala Glu Gln Gln Gly Ala Ala His Thr Val Asp Ala Gly
    210                 215                 220

Ala Glu Gln Asp Val Pro Ala Val Arg Glu Val Thr Gly Gly Gly
225                 230                 235                 240

Ala His Val Ser Ile Asp Ala Leu Gly Ile Arg Thr Thr Val Asn
                245                 250                 255

Ser Val Arg Ser Leu Arg Lys Arg Gly Arg His Val Gln Val Gly Leu
            260                 265                 270

Thr Gly Ala Glu Asp Ala Gly Glu Ile Ala Leu Pro Ile Asp Leu Ile
        275                 280                 285
```

Thr Leu Gly Glu Leu Thr Val Val Gly Ser His Gly Asn Pro His Ala
    290                 295                 300

Ala Tyr Pro Arg Leu Leu Ser Leu Ile Glu Ser Gly Arg Leu Ala Pro
305                 310                 315                 320

Gln Thr Leu Val Gln Arg Thr Val Ser Leu Asp Gln Ala Gly Asp Val
            325                 330                 335

Leu Ala Ala Met Asp Ala Phe Ala Thr Ser Gly Leu Thr Val Ile Asp
        340                 345                 350

Arg Phe

<210> SEQ ID NO 7
<211> LENGTH: 1065
<212> TYPE: DNA
<213> ORGANISM: Streptomyces refuineus subspecies thermotolerans

<400> SEQUENCE: 7

```
gtgatcgacg tgagagcggc gcagatcgtc gggtacggcg aaccgctcca ggtacgcgag     60
gtccccgacc ccgctcccga gccgggcggc gtcgtcgtgg ccgtcctcgc caccggcatc    120
tgccgcagcg actggcacgg gtggcggggc gactgggagt ggctgggcgg gcggatcgcc    180
ctgccccgca cgccgggaca cgagatcgcc ggcgaggtgg tggccgccgg tcccggcgtc    240
cgaggcgtgc gggtgggcga ccgggtcacg gtgccgttcc acctggcctg cggtacgtgc    300
gcgcactgcc gcgcggggca ggccaacctc tgcgacgaga tggaggtgct cggcttctgg    360
cgcgacggcg gctacgccga gtacgtgcgg atcccgcacg cggacttcaa ctgcgtgcgg    420
atcccggacg gcgtcacacc gctcacggcc agcgcgatcg gctgccggtt catgacggcg    480
ttccacgccg tcgacggcca gggccgggtg cgcccgggcg agtgggtggc cgtgcacggt    540
gtcggcggcg tcgggctgtc gtgcgtgcag atcgccagtg ccgccggagc gtccgtcgtc    600
gcggtggaca tcgacccggc caagctcgcc ctcgccgagc agcagggcgc cgcccacacg    660
gtggacgccg cgccgaacag gacgtcccc gcggcggtcc gggaggtcac cggcggcggc    720
gcccacgtct cgatcgacgc cctgggcatc cggacgacgg tggtgaactc cgtgcgttcg    780
ctccgcaaac gcggccggca cgtacaggtg gggctgaccg agccgaggac gccggcgag    840
atcgcgctcc cgatcgacct gatcaccctc ggcgagctga ccgtggtggg ctcgcacggc    900
aacccgcacg ccgcctaccc ccggttgctc tcgctgatcg agtccggccg gctcgcgccg    960
cagaccctcg tgcagcgcac cgtgtctctg gaccaggccg gggacgtgct ggcggcgatg   1020
gacgccttcg ccaccagcgg gctcaccgtc atcgaccgct ctga                    1065
```

<210> SEQ ID NO 8
<211> LENGTH: 410
<212> TYPE: PRT
<213> ORGANISM: Streptomyces refuineus subspecies thermotolerans

<400> SEQUENCE: 8

Val Ser Pro Ala Ala Glu Arg His Gln Arg Gly Pro Ser Val Thr Ala
1               5                   10                  15

Ala Arg Thr Ser Thr Ala Ala Pro Glu Thr Asp Leu Asp Leu Phe Ser
            20                  25                  30

Thr Glu Val Leu Leu Asp Pro Phe Pro His Tyr Ala Arg Leu Arg Asp
        35                  40                  45

Met Gly Pro Val Val Tyr Leu Thr Glu Tyr Asp Leu Tyr Gly Leu Phe
    50                  55                  60

-continued

```
Arg Tyr Glu Gln Val Arg Ala Ala Leu Val Asp Trp Glu Thr Phe Ser
 65                  70                  75                  80

Ser Ala Gln Gly Ile Ala Met Asn Pro Thr Ala Asn Glu Leu Ser Ala
                 85                  90                  95

Asp Ser Ile Leu Ser Val Asp Pro Arg Gln Arg Ala Leu Arg Lys
            100                 105                 110

Val Phe Asp Asp Ala Leu Arg Pro Lys His Val Arg Val Ala Gly
        115                 120                 125

Asp Ile Glu His Leu Ala Asp Leu Val Asp Ser Leu Val Arg Arg
130                 135                 140

Gly Glu Phe Asp Gly Val Arg Asp Phe Ala Cys Lys Leu Pro Val Glu
145                 150                 155                 160

Ile Val Met Asp Leu Ile Gly Phe Pro Arg Asp Glu His Arg Glu Glu
                165                 170                 175

Leu Leu Glu Trp Ala Leu Gly Ala Phe Asn Phe Met Gly Pro Pro Gly
            180                 185                 190

Glu Arg Gln Glu Ser Thr Phe Pro Asp Val Gln Ala Leu Met Gln Tyr
        195                 200                 205

Leu Val Thr Glu Ala Thr Pro Asp Arg Leu Leu Pro Gly Ser Phe Gly
210                 215                 220

Gln Ile Val Trp Glu Ala Ala Asp Arg Gly Glu Ile Thr Gly Asn Glu
225                 230                 235                 240

Ala Leu Met Ala Met Ser Ala Tyr Ala Cys Ala Gly Leu Asp Thr Thr
                245                 250                 255

Ile Ala Gly Val Ala Ser Thr Leu Trp Leu Leu Ala Leu Asn Pro Asp
            260                 265                 270

Gln Trp Arg Ala Val Arg Gln Asp Pro Gln Leu Val Pro Gly Thr Phe
        275                 280                 285

Leu Glu Gly Val Arg Leu Glu Thr Pro Leu Gln Phe Phe Ser Arg Val
290                 295                 300

Thr Thr Arg Asp Val Glu Ile Asp Gly Val Thr Ile Pro Arg Gly Ala
305                 310                 315                 320

Arg Val Val His Ser Tyr Gly Ser Ala Asn Arg Asp Glu Arg Tyr
                325                 330                 335

Pro Asp Pro Asp Arg Phe Asp Ala His Arg Asn Pro Val Asp Thr Val
            340                 345                 350

Gly Phe Gly Val Gly Val His Thr Cys Pro Gly Arg Ala Leu Ala Ser
        355                 360                 365

Met Glu Ala His Ala Leu Phe Gly Ala Leu Ala Arg Arg Ala Thr Thr
370                 375                 380

Ile Glu Leu Ala Gly Glu Pro Thr Arg Ser Pro Asn Asn Ile Thr Arg
385                 390                 395                 400

Gly Leu Asp Arg Leu Pro Val Arg Val Ser
                405                 410
```

<210> SEQ ID NO 9
<211> LENGTH: 1233
<212> TYPE: DNA
<213> ORGANISM: Streptomyces refuineus subspecies thermotolerans

<400> SEQUENCE: 9

```
gtgagcccgg ccgcggaacg acatcagaga ggaccgagcg tgaccgcagc aaggacttcg    60
accgccgcgc ccgagaccga cctggacctc ttctccaccg aggtgctcct cgatccgttc   120
ccccactacg cgagactccg ggacatgggc ccggtggtct acctgaccga gtacgacctg   180
```

-continued

```
tacgggctct tccggtacga gcaggtgcgc gcggccctcg tcgactggga gacgttcagc    240
tccgcgcagg gcatcgccat gaacccgacc gccaacgaac tctcggcgga ctcgatcctc    300
tcggtggacc cgccgcggca gcgggccctc cggaaggtct tcgacgacgc cctgcgcccc    360
aagcacgtgc gcagggtcgc cggcgacatc gagcacctcg ccgacgacct cgtcgacagc    420
ctggtgcggc ggggcgagtt cgacggtgtc agggacttcg cgtgcaagct gccggtggag    480
atcgtcatgg acctcatcgg cttcccgcgc gacgagcacc gcgaggagtt gctggagtgg    540
gccctcggtg cgttcaactt catggggccg cccggtgagc gccaggagtc gaccttcccc    600
gacgtgcagg ccctcatgca gtacctggtg accgaggcga cgcccgacag gctgcttccc    660
ggcagtttcg ccagatcgt gtgggaggcg gccgaccgcg gggagatcac cgggaacgag    720
gccctgatgg cgatgagcgc ctacgcctgc gccgggctgg acaccacgat cgccggcgtg    780
gccagcaccc tgtggctgct ggccttgaac ccggaccagt ggcgggccgt gcggcaggac    840
ccgcaactcg tccccggcac gttcctggag ggcgtccggc tggagacgcc cctgcagttc    900
ttctcccgcg tcaccacgcg cgacgtggag atcgacggcg tgacgatccc gcggggcgcg    960
cgggtcgtgc actcctacgg ttcggccaac cgggacgagc gccgctaccc cgaccccgac   1020
cggttcgacg cgcaccgcaa cccggtggac accgtcgggt tcggcgtcgg cgtccacacc   1080
tgccccgggc gcgccctggc ctcgatggag gcccacgccc tgttcggcgc cctcgccaga   1140
cgggccacca ccatcgagct cgccggcgag cccacccggt cgccgaacaa catcacccgg   1200
gggctggacc gtctccccgt ccgcgtctcc tga                                1233
```

<210> SEQ ID NO 10
<211> LENGTH: 352
<212> TYPE: PRT
<213> ORGANISM: Streptomyces refuineus subspecies thermotolerans

<400> SEQUENCE: 10

```
Met Thr Leu Ser Thr Asp Gly Pro Glu Ile Ile Glu Leu Gln Asp Glu
1               5                   10                  15

Lys Gln Arg Arg Glu Trp Gln Ala Phe Leu Leu Ser Gly Leu Pro Glu
            20                  25                  30

Met Ile Ser Ala Leu His Val Cys His Ala Val Arg Ala Ile Ala Glu
        35                  40                  45

Thr Pro Leu Leu Glu Arg Leu Arg Asn Gly Pro Arg Arg Pro Asp Asp
    50                  55                  60

Gly Leu Leu Ala Gly Leu Asp Pro Asp Ile Gly Ala Gly Phe Leu Arg
65                  70                  75                  80

Tyr Leu Val Asn Arg Gly Val Leu Glu Thr Arg Gly Asp Glu Phe Phe
                85                  90                  95

Leu Thr Arg Leu Gly Glu Phe Leu Thr Thr Asp Val Ser Leu Ala Arg
            100                 105                 110

Leu Gly Val Tyr Leu Gly Ala Tyr Gly Gly Val Thr Ser Arg Ile Gly
        115                 120                 125

Asp Leu Leu Thr Gly Lys Ala Val Tyr Gly Thr Asp Val Thr Arg Asp
    130                 135                 140

Gly Ala Gln Leu Gly Ala His Cys Ala Thr Leu Phe Ser Thr Phe His
145                 150                 155                 160

Thr Pro Val Val Leu Glu Ala Met Arg Gly Arg Gly Val Arg Arg Met
                165                 170                 175

Leu Asp Ile Gly Cys Gly Gly Gly Gln Leu Ile Val Asp Ala Cys Leu
```

```
                   180              185              190
Arg Asp Pro Ser Leu Thr Gly Ile Gly Leu Asp Ile Asp Ala Asp Ala
            195                 200             205

Ile Ala Val Ala Asn Asp Leu Ala Arg Arg His Gly Val Ser Asp Arg
            210                 215             220

Val Glu Phe Val Val Ala Asp Ala Phe Ala Pro Gln Thr Trp Pro Glu
225                 230             235                     240

Val Cys Ala Glu Ala Asp Gly Leu Cys Met Met Ser Ala Leu His Glu
                245             250                 255

His Phe Arg Lys Gly Glu Gln Ala Val Val Asp Leu Leu Asp Glu Ile
            260                 265             270

Ser Ala Lys Phe Pro Gln Gln Lys Ile Leu Leu Ile Gly Glu Pro Glu
            275                 280             285

Ile Arg His Asp Gly Arg Glu Asn Asp Asp Asp Phe Phe Leu Ile His
            290                 295             300

Val Leu Thr Gly Gln Gly Leu Pro Arg Asp Arg Ala Ala Trp Leu Pro
305                 310             315                     320

Val Phe Glu Lys Ser Thr Leu Gln Cys Arg Arg Leu Tyr Arg Arg Pro
                325             330                 335

Gly Ala Gly Pro Arg Met Cys Phe Tyr Asp Leu Ala Pro Arg Pro Arg
            340                 345             350
```

<210> SEQ ID NO 11
<211> LENGTH: 1059
<212> TYPE: DNA
<213> ORGANISM: Streptomyces refuineus subspecies thermotolerans

<400> SEQUENCE: 11

```
atgacgctca gcaccgacgg cccggagatc atcgagctgc aggacgagaa gcagcgccgg      60
gagtggcagg ccttcctgct gtccggcctc cccgagatga tcagcgccct gcacgtctgc     120
cacgccgtgc gggcgatcgc cgagaccccg ctgctggaac ggctgcgcaa cggccccggg     180
cggcccgacg acggcctgct ggccggcctc gaccccgaca tcggtgcggg tttcctgcgc     240
tacctggtga accggggcgt cctggagacc cgcggtgacg agttcttcct gacgcggctg     300
ggcgagttcc tgaccacgga cgtctcgctg gcccgcctcg cgtctacct gggcgcgtac      360
ggcggggtca ccagccggat cggcgacctg ctcaccggca aggccgtcta cggcacggac     420
gtgacgcgcg acggcccca gctgggggcg cactgcgcca ccttgttctc caccttccac      480
acaccggtcg tgctggaggc catgcgcggc gcggagtgc gccgcatgct cgacatcggc      540
tgcggcggcg ggcagctgat cgtggacgcc tgtctgcgcg acccgtccct caccggcatc     600
ggtctggaca tcgacgcgga cgccatcgcg gtcgccaacg acctcgcgcg ccgccacggc     660
gtgtccgacc gggtggagtt cgtcgtcgcg gacgccttcg cgccccagac gtggcccgag     720
gtctgcgccg aggccgacgg gctgtgcatg atgagcgcgc tgcacgagca cttccgcaag     780
ggcgagcagg ccgtcgtgga cctgctggac gagatctcgg cgaagttccc gcagcagaag     840
atcctgctga tcggcgaacc ggagatccgc cacgacggca gggagaacga cgacgacttc     900
ttcctgatcc acgtcctgac cgggcagggg ctcccgcgcg accgcgccgc gtggctgccg     960
gtcttcgaga agtccaccct gcagtgccgg cggctgtacc ggcggccggg cgcggggccg    1020
cgcatgtgct tctacgacct ggcgccacgg ccgaggtga                           1059
```

<210> SEQ ID NO 12
<211> LENGTH: 621

<212> TYPE: PRT
<213> ORGANISM: Streptomyces refuineus subspecies thermotolerans

<400> SEQUENCE: 12

```
Met Thr Pro Ala Glu Arg Pro Val Pro Asp Arg Thr Pro Thr Ser
 1               5                  10                  15

Arg Pro Trp Ser Ser Gly Met Leu Pro Ser Lys Pro Glu Leu Thr Gly
             20                  25                  30

Thr Leu Gly Ala Val Ala Ser Thr His Trp Leu Ala Ser Ala Ala Gly
             35                  40                  45

Met Arg Ile Leu Ala Asn Gly Gly Asn Ala Phe Asp Ala Ala Val Ala
 50                      55                  60

Ala Gly Phe Val Leu Gln Val Val Glu Pro His Phe Asn Gly Pro Gly
 65                  70                      75                  80

Gly Asp Val Ser Ile Val Val His Arg Ala Gly Ser Gly Asp Val Gln
                 85                  90                  95

Ala Ile Cys Gly Gln Gly Pro Met Pro Arg Ala Ala Asp Ile Asp Thr
            100                 105                 110

Phe Thr Asp Leu Gly Leu Ser Ser Ile Pro Gly Ser Gly Leu Leu Pro
            115                 120                 125

Ala Cys Val Pro Gly Ala Phe Gly Gly Trp Met Arg Leu Leu Ala Glu
            130                 135                 140

Phe Gly Thr Met Arg Leu Ala Asp Val Leu Ala Pro Ala Ile Gly Tyr
145                 150                 155                 160

Ala Asp Asn Gly Phe Pro Leu Leu Pro Glu Thr Ala Thr Ala Ile Glu
                165                 170                 175

Val Leu Ala Pro Leu Phe Arg Glu Glu Trp Gln Gly Ser Ala Arg Thr
            180                 185                 190

Tyr Leu Pro Gly Gly Lys Ala Pro Ala Ala Gly Ser Arg Phe Arg Asn
            195                 200                 205

Pro Ala Leu Ala Gly Thr Tyr Gln Arg Leu Ile Lys Glu Ala Glu Ala
            210                 215                 220

Ala Ser Ala Asp Arg Asp Ala Gln Ile Gln Ala Ala His Asp Ala Phe
225                 230                 235                 240

Tyr Lys Gly Phe Val Ala Gly Glu Ile Ala Asp Phe Leu Ala Ser Gly
                245                 250                 255

Pro Val Leu Asp Ala Thr Gly Arg Arg His Lys Gly Leu Leu Thr Gly
            260                 265                 270

Asp Asp Leu Ala Gly Trp Glu Ala Ser Val Glu Thr Ala Pro Ser Arg
            275                 280                 285

Val Tyr Lys Ser Tyr Gln Val Phe Lys Pro Gly Pro Trp Ser Gln Gly
            290                 295                 300

Pro Val Phe Leu Gln Gln Leu Ala Leu Leu Asp Gly Phe Asp Leu Ala
305                 310                 315                 320

Gly Met Gly Leu Gly Ser Ala Asp Tyr Leu His Thr Val Val Glu Cys
                325                 330                 335

Thr Lys Leu Ala Met Ala Asp Arg Glu Ala Trp Tyr Gly Asp Pro Ala
            340                 345                 350

His Ser Asp Val Pro Leu Ala Ala Leu Leu Asp Glu Glu Tyr Thr Arg
            355                 360                 365

Arg Arg Arg Glu Leu Val Gly Ala Arg Ala Glu Leu Thr Leu Arg Pro
            370                 375                 380

Gly Glu Pro Gly Gly Arg Thr Ser Phe Ile Pro Ser Leu Ser Ala Pro
385                 390                 395                 400
```

-continued

```
Asp Asp Pro Glu Pro Asp Thr Glu Trp Met Ser Gln Leu Arg Asn Gly
            405                 410                 415
Leu Pro Thr Ile Leu Arg Ala Thr Ala Ala Lys Gly Asp Thr Cys Thr
            420                 425                 430
Val Thr Ala Val Asp Arg His Gly Asn Met Val Ala Ala Thr Pro Ser
            435                 440                 445
Gly Gly Trp Leu Lys Ser Ser Pro Ala Ile Pro Gly Leu Gly Phe Pro
    450                 455                 460
Leu Gly Thr Arg Gly Gln Ser Met Phe Leu Val Asp Gly His Pro Asn
465                 470                 475                 480
Ser Leu Ala Pro Gly Lys Arg Pro Arg Thr Thr Leu Ser Pro Thr Val
            485                 490                 495
Val Leu Arg Asp Gly Arg Pro Phe Val Ala Phe Gly Thr Pro Gly Gly
            500                 505                 510
Asp Arg Gln Asp Gln Trp Thr Leu Gln Phe Phe Leu Asn Val Ala Asp
            515                 520                 525
Phe Gly Leu Asp Leu Gln Ser Ala Thr Glu Thr Thr Ala Phe His Thr
    530                 535                 540
Asp Gln Val Pro Ala Ser Phe Thr Pro His Ala His Arg Pro Gly Val
545                 550                 555                 560
Leu Val Ala Glu Glu Thr Cys Ala Pro Glu Val Val Glu Glu Leu Gly
            565                 570                 575
Arg Arg Gly His Glu Val Glu Leu Val Pro Ala Tyr Ser Leu Gly Arg
            580                 585                 590
Val Cys Ala Thr Gly Leu Thr Asp Gly Glu Gly Phe Val Arg Ala Ala
            595                 600                 605
Ala Ser Pro Arg Gly Arg His Ala Tyr Ala Val Cys Glu
    610                 615                 620

<210> SEQ ID NO 13
<211> LENGTH: 1866
<212> TYPE: DNA
<213> ORGANISM: Streptomyces refuineus subspecies thermotolerans

<400> SEQUENCE: 13
atgacgccgg cggagcgacc gcccgttccg gaccgtacac ccacctcccg accatggagt     60
agcggcatgc ttccgtccaa gcccgagctg accgggaccc tcggcgccgt ggccagcacc    120
cactggctcg cctcggccgc gggcatgagg atcctcgcca acggcggcaa cgcgttcgac    180
gccgccgtcg ccgccggctt cgtcctccag gtagtggaac ccacttcaa cggccccggc    240
ggtgacgtgt ccatcgtggt gcaccgagcc ggcagcggcg acgtgcaggc catctgcggg    300
cagggcccga tgccccgcgc cgcggacatc gacaccttca ccgacctggg gttgagcagc    360
attccgggat cggggctgct gccggcctgc gtgccgggag cgttcggcgg ctggatgcgg    420
ctgctcgccg agttcgggac gatgcgcctg ccgacgtcc tggcaccggc gatcggctac    480
gcggacaacg gcttcccgct gcttcccgag accgcgaccg ccatcgaggt gctcgccccg    540
ctgttccgcg aggagtggca gggctccgcc cggacgtacc tgccgggcgg gaaggccccc    600
gcggcgggca gccggttccg caatccggcc ctggccggca cctaccagcg gctgatcaag    660
gaggcggagg ccgcgtcggc cgaccgcgac gcccagatcc aggccgcgca cgacgccttc    720
tacaaggggt tcgtcgccgg ggagatcgcc gacttcctcg cctcgggccc cgtgctcgac    780
gccaccggca ggcggcacaa ggggctgctg accggggacg acctagccgg ctgggaggcg    840
```

| | |
|---|---|
| tccgtggaga cggcgccgag ccgcgtctac aagtcctacc aggtcttcaa gccggggccg | 900 |
| tggtcgcagg gcccggtgtt cctgcagcag ctcgcgctgc tcgacggctt cgacctggcg | 960 |
| ggcatggggc tgggcagtgc cgactatctg cacaccgtgg tggagtgcac gaagctcgcc | 1020 |
| atggccgacc gcgaggcgtg gtacggcgat ccggcccaca gcgacgtgcc gttggccgcc | 1080 |
| ctgctcgacg aggagtacac ccggcggcgc cgcgaactgg tcggtgcccg cgccgagctg | 1140 |
| acgctgcgtc cgggcgagcc cggcggccgg acgtcgttca tccctcgct gtccgccccg | 1200 |
| gacgacccgg aaccggacac ggagtggatg tcccagctgc gcaacggact gccgacgatc | 1260 |
| ctgcgggcca cggcggcgaa gggcgacacc tgcacggtca ccgccgtcga ccggcacggc | 1320 |
| aacatggtgg ccgcgacccc cagcgggggg tggctgaaga gttcgcccgc catccccggc | 1380 |
| ctcggcttcc ccctcggcac ccgcggccag tccatgttcc tcgtcgacgg caccccaac | 1440 |
| tccctggcgc ccggcaagcg gccgaggacg acgctcagcc ccaccgtggt gctgcgggac | 1500 |
| ggacgcccgt tcgtcgcgtt cgggaccccg ggcggcgacc ggcaggacca gtggacgctg | 1560 |
| cagttcttcc tcaacgtcgc cgacttcggg ctcgacctgc agagcgcgac cgagacgacg | 1620 |
| gccttccaca ccgaccaggt gcccgcttcc ttcaccccgc acgcgcaccg tcccggcgtg | 1680 |
| ctggtcgccg aggagacctg cgccccggag gtggtcgagg aactcggccg cgcggccac | 1740 |
| gaggtggaac tcgtaccggc gtactcgctg gcagggtct cgccaccgg gctgaccgac | 1800 |
| ggggaggggt tcgtgcgggc cgcggccagc ccgcgcggcc ggcacgcgta cgcggtatgc | 1860 |
| gagtag | 1866 |

<210> SEQ ID NO 14
<211> LENGTH: 487
<212> TYPE: PRT
<213> ORGANISM: Streptomyces refuineus subspecies thermotolerans

<400> SEQUENCE: 14

```
Met Thr Ser Arg Pro Val Pro Ser Ala Asn Ala Ala Val Leu Gly Phe
1               5                   10                  15

Asp Pro Ala Glu Arg Thr Trp Val Thr Gly Pro Ala Thr Thr Ala Ser
            20                  25                  30

Ser Phe Ala Ala Pro Ala Leu Glu Gly Glu Leu Leu Ile Asp Glu
        35                  40                  45

Ala Ser Arg Gln Ala Val Ala Thr Asp Leu Gly Asn Ile Ala Val His
    50                  55                  60

Lys Pro Gly Ala Val Leu Arg Pro Arg Ser Ala Arg Asp Ile Ala Ala
65                  70                  75                  80

Met Val Arg Phe Cys Arg Ala His Gly Ile Thr Val Ser Thr Arg Gly
                85                  90                  95

Gln Ala His Thr Thr Leu Gly Gln Gly Leu Thr Asp Gly Leu Val Val
            100                 105                 110

Glu Ala Arg Ser Leu Asn Arg Ile His Ser Leu Gly Pro Asp Val Ala
        115                 120                 125

Glu Val Asp Ala Gly Val His Trp Lys Asp Leu Val Thr Ala Ala Phe
    130                 135                 140

Gly Gln Ser Pro Arg Leu Thr Pro Pro Ala Val Thr Gly Tyr Thr Ser
145                 150                 155                 160

Leu Thr Val Gly Gly Thr Leu Ser Val Gly Leu Gly Leu Val
                165                 170                 175

Gly Ala Leu Arg Thr Gly Leu Gln Val Asp His Val Arg Glu Leu Glu
            180                 185                 190
```

```
Val Val Thr Gly Thr Gly Asp Ile Glu Arg Cys Ser Leu His His Arg
        195                 200                 205

Arg Asp Leu Phe Glu Ala Val Leu Gly Gly Leu Gly Gln Cys Gly Ile
    210                 215                 220

Ile Thr Lys Ala Val Val Glu Leu Val Pro Ala Lys Glu Arg Ala Arg
225                 230                 235                 240

Thr Tyr Val Leu Glu Tyr Thr Asp Asn Ala Ala Phe Phe Arg Asp Leu
                245                 250                 255

Arg Thr Val Ile Glu Arg Pro Gly Ile Asp His Val Tyr Ala Glu Leu
            260                 265                 270

Tyr Ala Pro Gly Ser Arg Pro Thr His Lys Cys Tyr Ala Thr Val Phe
        275                 280                 285

His Asp Gly Ala Ala Pro Asp Glu Ala Ala Val Ala Gly Leu Ser
    290                 295                 300

Thr Glu Pro Val Val Asp Asp Thr Gly Tyr Leu Asp Tyr Val Phe Ser
305                 310                 315                 320

Ile Asp Arg Leu Val Asp Gly Met Arg Glu Thr Val Gly Trp Asp Gly
                325                 330                 335

Leu Leu Lys Pro Trp Tyr Asp Val Trp Leu Pro Gly Ser Ala Val Glu
            340                 345                 350

Asp Tyr Ile Ala Glu Val His Pro Thr Leu Thr Ala Arg Asp Ile Gly
        355                 360                 365

Pro Tyr Gly Ile Ser Leu Ile Tyr Pro Gln Arg Arg Ser Ala Val Thr
    370                 375                 380

Arg Pro Leu Pro Arg Leu Pro Glu Pro Asp Gly Ser Pro Trp Val Phe
385                 390                 395                 400

Val Leu Asp Ile Asn Thr Val Ala Glu Thr Pro Gly Asp Asp Pro Ala
                405                 410                 415

Phe Val Lys Glu Met Leu Asp Arg Asn Thr Arg Leu Phe Ala Arg Ala
            420                 425                 430

Arg Asp Arg Tyr Gly Ala Val Leu Tyr Pro Ile Gly Ser Val Pro Phe
        435                 440                 445

Thr Glu Gln Asp Trp Arg Ala His Tyr Gly Asp Gln Trp Glu Thr Phe
    450                 455                 460

Arg Glu Ala Lys Lys Arg Tyr Asp Pro Asp Ser Val Leu Thr Pro Gly
465                 470                 475                 480

Pro Gly Ile Phe Arg Asn Gly
                485

<210> SEQ ID NO 15
<211> LENGTH: 1464
<212> TYPE: DNA
<213> ORGANISM: Streptomyces refuineus subspecies thermotolerans

<400> SEQUENCE: 15
atgacgagcc gcccggttcc ctccgcgaac gccgcagtcc tgggcttcga cccggccgaa     60
cgcacgtggg tcaccggccc cgcgacgacg cgtcgtcgt tcgccgccgc gccggcgctg    120
gagggcgagc ttctgatcga cgaggcgtcc cgccaggcgg tcgccaccga cctgggcaac    180
atcgccgtcc acaagccggg cgcggtgctg cgaccgcgct cggcccggga catcgccgcg    240
atggtccgct tctgccgagc gcacggcatc acgtctcca ccagagggca ggcgcacacc    300
acgctcggcc agggcctcac cgacggactc gtcgtcgagg cccggtccct gaaccggatc    360
cactcgctcg gtccggacgt tgccgaggtc gacgccggcg tccactggaa ggacctggtc    420
```

```
accgccgcct tcgggcagtc gccgaggctc accccgccgg cggtcaccgg gtacacctcg    480
ctgaccgtgg gcggaacgct ctcggtcggc gggctcggcg gtctcgtcgg cgccctgcgc    540
accggactgc aggtggacca cgtccgcgag ctggaggtcg tcaccgggac cggtgacatc    600
gaacgctgct ccctccacca caggcgcgac ctgttcgagg cggtgctcgg cgggctcggc    660
cagtgcggca tcatcaccaa ggcggtcgtc gaactcgtcc ccgccaagga gcgcgcccgc    720
acctacgtgc tggagtacac cgacaacgcc gcgttcttcc gcgacctgcg caccgtcatc    780
gagcggcccg gcatcgacca cgtctacgcc gagctgtacg cgccaggctc caggccgacc    840
cacaagtgct acgcgaccgt cttccacgac ggggccgcgc cggacgacga ggcggccgtc    900
gccggcctga gcaccgaacc ggtcgtcgac gacaccggct acctggacta cgtgttctcg    960
atcgaccggc tcgtcgacgg gatgcgggag accgtgggct gggacgggct cctcaagccc   1020
tggtacgacg tgtggctccc cgggtccgcc gtggaggact acatcgccga ggtccacccg   1080
acgctgaccg cacgcgacat cgggccctac ggcatcagcc tgatctaccc gcagcggcgc   1140
tcggccgtca cccggccgct tccccggctg cccgaaccgg acggctcccc ctgggttttc   1200
gtcctcgaca tcaacaccgt cgccgagacc ccgggggacg atccggcctt cgtcaaggag   1260
atgctcgacc gcaacacccg gctgttcgcc cgcgcacgcg accgctacgg tgcggtgctc   1320
tacccgatcg gctcggtgcc gttcaccgag caggactggc gtgcccacta cggcgaccag   1380
tgggagacct ccgtgaggc gaagaagcgc tacgaccccg actccgtcct caccccggc    1440 cccgggatct tccggaacgg atga                                          1464
```

<210> SEQ ID NO 16
<211> LENGTH: 764
<212> TYPE: PRT
<213> ORGANISM: Streptomyces refuineus subspecies thermotolerans

<400> SEQUENCE: 16

```
Met Glu Ser Arg Gly Gly Arg Arg Ala Ser Asp Thr Ile Ala Leu Asp
1               5                   10                  15

Gly Ile Arg Glu Asn Asn Leu Lys Asp Val Ser Leu Arg Ile Pro Lys
            20                  25                  30

Gly Lys Leu Thr Val Phe Thr Gly Val Ser Gly Ser Gly Lys Ser Ser
        35                  40                  45

Leu Val Phe Ser Thr Ile Ala Val Glu Ser Gln Arg Gln Leu Asn Ala
    50                  55                  60

Thr Phe Pro Trp Phe Ile Arg Asn Arg Leu Pro Lys Tyr Glu Arg Pro
65                  70                  75                  80

Asn Ala Arg Gly Met Ala Asn Leu Ser Thr Ala Ile Val Val Asp Gln
                85                  90                  95

Lys Pro Ile Gly Gly Asn Ser Arg Ser Thr Val Gly Thr Met Thr Glu
            100                 105                 110

Ile Asn Ala Ala Leu Arg Val Leu Phe Ser Arg His Gly Lys Pro Ser
        115                 120                 125

Ala Gly Pro Ser Thr Val Tyr Ser Phe Asn Asp Pro Gln Gly Met Cys
    130                 135                 140

Thr Glu Cys Glu Gly Leu Gly Arg Thr Ala Arg Leu Asp Leu Gly Leu
145                 150                 155                 160

Leu Leu Asp Glu Ser Lys Ser Leu Asn Asp Gly Ala Ile Met Ser Pro
                165                 170                 175

Leu Phe Ala Val Gly Ser Phe Asn Trp Gln Leu Tyr Ala Gln Ser Gly
```

```
                    180                 185                 190
Leu Phe Asp Pro Asp Lys Pro Leu Lys Lys Phe Thr Ala Lys Asp Arg
            195                 200                 205

Glu Leu Leu Leu Tyr Gly Glu Gly Phe Lys Val Gln Arg Pro Gly Arg
            210                 215                 220

Glu Leu Thr Tyr Ser Asn Glu Tyr Glu Gly Ile Val Arg Phe Asn
225                 230                 235                 240

Arg Arg Tyr Leu Lys Asn Gly Met Asp Ala Leu Lys Gly Lys Glu Arg
                245                 250                 255

Gln Ala Val Glu Gln Val Val Arg Val Gly Thr Cys Glu Val Cys Gly
            260                 265                 270

Gly Gly Arg Leu Asn Gln Ala Ala Leu Ala Ser Arg Ile Asp Gly Lys
            275                 280                 285

Asn Ile Ala Asp Tyr Ala Ala Met Glu Val Ser Glu Leu Ile Thr Glu
            290                 295                 300

Leu Gly Arg Ile Asp Asp Pro Val Ala Glu Pro Ile Val Gln Ala Val
305                 310                 315                 320

Thr Ala Ala Leu Arg Arg Val Glu Ala Ile Gly Leu Gly Tyr Leu Ser
                325                 330                 335

Leu Gly Arg Glu Thr Ser Thr Leu Ser Gly Glu Gly Gln Arg Leu
            340                 345                 350

Lys Thr Val Arg His Leu Gly Ser Ser Leu Ser Asp Leu Thr Phe Ile
                355                 360                 365

Phe Asp Glu Pro Ser Val Ala Leu His Pro Arg Asp Val His Arg Leu
            370                 375                 380

Asn Glu Leu Leu Ala Glu Leu Arg Asp Lys Gly Asn Thr Val Leu Val
385                 390                 395                 400

Val Glu His Asn Pro Asp Val Met Ala Ala Asp His Ile Val Asp
                405                 410                 415

Met Gly Pro Gly Ala Gly Val His Gly Gly Glu Val Val Phe Glu Gly
                420                 425                 430

Ser Tyr Gln Glu Leu Arg Glu Ala Asp Thr Leu Thr Gly Arg Lys Leu
            435                 440                 445

Arg Gln Arg Arg Gly Leu Lys Glu Glu Leu Arg Thr Pro Thr Gly Phe
    450                 455                 460

Leu Thr Val Arg Asp Ala Thr Leu Asn Asn Leu Lys Asn Val Thr Val
465                 470                 475                 480

Asp Ile Pro Thr Gly Ile Met Thr Ala Val Thr Gly Val Ala Gly Ser
                485                 490                 495

Gly Lys Ser Ser Leu Ile Ser Gly Ala Phe Ala Ala Gln Tyr Pro Glu
            500                 505                 510

Ala Val Met Ile Asp Gln Ser Ser Ile Gly Ile Ser Ser Arg Ser Thr
            515                 520                 525

Pro Ala Thr Tyr Val Asp Ile Met Asp Thr Ile Arg Thr Met Phe Ala
            530                 535                 540

Lys Ala Asn Asp Ala Glu Pro Gly Leu Phe Ser Phe Asn Ser Met Gly
545                 550                 555                 560

Gly Cys Pro Ala Cys Gln Gly Arg Gly Val Ile Gln Thr Asp Leu Ala
                565                 570                 575

Tyr Met Asp Pro Val Thr Val Thr Cys Glu Val Cys Glu Gly Arg Arg
                580                 585                 590

Tyr Arg Ala Glu Ala Leu Glu Lys Thr Leu Arg Gly Lys Asn Ile Ala
            595                 600                 605
```

```
Glu Val Leu Ala Leu Thr Val Glu Gly Leu Ser Phe Phe Asp Glu
        610                 615                 620

Asp Ala Ala Val Val Arg Lys Leu Ala Met Leu Gln Asp Val Gly Leu
625                 630                 635                 640

Ser Tyr Leu Thr Leu Gly Gln Pro Leu Ser Thr Leu Ser Gly Gly Glu
                645                 650                 655

Arg Gln Arg Leu Lys Leu Ala His Arg Leu Gln Asp Thr Gly Asn Val
                660                 665                 670

Phe Val Phe Asp Glu Pro Thr Thr Gly Leu His Met Ala Asp Val Asp
                675                 680                 685

Thr Leu Leu Ala Leu Phe Asp Arg Ile Val Asp Asp Gly Asn Thr Val
        690                 695                 700

Val Val Val Glu His Asp Leu Gln Val Val Lys His Ala Asp Trp Val
705                 710                 715                 720

Ile Asp Leu Gly Pro Asp Ala Gly Arg His Gly Gly Arg Val Val Phe
                725                 730                 735

Glu Gly Thr Pro Lys Glu Leu Ala Ala His Glu His Ser Val Thr Ala
                740                 745                 750

Arg Tyr Leu Arg Ala Asp Leu Ala Gln Val Arg Gly
        755                 760

<210> SEQ ID NO 17
<211> LENGTH: 2295
<212> TYPE: DNA
<213> ORGANISM: Streptomyces refuineus subspecies thermotolerans

<400> SEQUENCE: 17
atggaaagcc gggcggggcg gcgggcgagc gacaccatcg cgctggacgg catccgggag      60
aacaacctga aggacgtgtc gctgcgcatc ccgaagggga agctgaccgt gttcacgggt     120
gtgtcgggat ccgtaagtc gtcactggtt ttcagtacga tcgccgtcga gtcccaacgg     180
cagctcaacg cgacctttcc ctggttcatc cgcaaccggc tgccgaaata cgagcgcccg     240
aacgccaggg ggatggccaa cctgtccacc gccatcgtgg tcgaccagaa gccgatcggc     300
ggcaactcca ggtcgacggt gggcaccatg acggagatca acgcggcttt acgtgtcctg     360
ttctcccggc acggcaagcc cagcgccggt ccgtccaccg tgtactcgtt caacgacccg     420
caggggatgt gcaccgagtg cgaggggctg gccgcaccg cgcgcctgga tctcgggctg     480
cttctcgacg agagcaagtc gctcaatgac ggtgccatca tgtcgccgct gttcgccgtg     540
ggcagtttca actggcagct gtatgcccaa tcgggccttt tcgaccccga caagccgctg     600
aagaaattca ccgcgaagga tcgggagctg ctgctttacg agagggtttt caaggtccag     660
cgccccggcc gtgaactgac gtattccaac gaatacgaag gaattgtggt ccgattcaac     720
cgccgctacc tcaagaacgg catggacgcg ctgaagggca aggagcgcca ggccgtcgag     780
caggtcgtcc gggtcggcac ctgcgaggtg tgcggcggtg gccggctcaa ccaggcggcg     840
ctcgcctcca ggatcgacgg caagaacatc gccgactacg ccgccatgga ggtgagcgaa     900
ctgatcaccg agctggggcg catcgacgac ccggtggccg aacccatcgt gcaggcggtc     960
accgcggccc tgcggcgtgt ggaggcgatc gggctgggct acctcagtct cggccgcgag    1020
acgtccaccc tctccggcgg cgagggccag cggctgaaga cggtgcggca cctcggcagc    1080
agtctgagcg aactgacctt catcttcgac gagccgagcg tcgccctgca cccgcgggac    1140
gtgcaccggc tcaacgaact cctcgccgag ctgcgggaca aggcaacac cgtgctcgtc    1200
```

```
gtggaacaca atccggacgt catggccgcc gccgaccaca tcgtcgacat ggggcccgga    1260
gccggtgtgc acggcggcga ggtcgtgttc gagggtgtcct atcaggagct gcgcgaagcc   1320
gacacgctca ccggccgcaa gctccgccag cgccgcggcc tgaaggagga gctgcgcacc   1380
cccaccggct tcctgaccgt ccgcgacgcc acgctgaaca acctgaagaa cgtcaccgtc   1440
gacattccca cggggatcat gaccgcggtg accggagtgg ccgggtccgg gaagagctcg   1500
ctgatctccg ggcgttcgc cgcccagtac cctgaagcgg tcatgatcga ccagtcgagc    1560
atcggcatct cctcgcggtc cacgccggcc acctacgtgg acatcatgga cacgatccgc   1620
acgatgttcg ccaaggccaa cgacgccgag cccggcctgt tcagcttcaa ctccatgggc   1680
ggctgcccgg cctgccaggg gcgcggcgtg atccagacgg acctcgccta catggacccg   1740
gtgaccgtga cctgcgaggt gtgcgagggc cgcaggtacc gggccgaagc gctcgagaag   1800
acgctgcgcg gcaagaacat cgccgaagtg ctcgcgctca ccgtcgaaga ggggctgtcc   1860
ttcttcgacg aggacgccgc ggtggtccgg aagctggcga tgctccagga cgtcggactg   1920
tcctacctga ccctgggcca gccgctgtcg accctctcgg gaggcgagcg gcagcggctc   1980
aagctcgccc accggctcca ggacaccggc aacgtcttcg tcttcgacga accgacgacc   2040
ggactgcaca tggccgacgt cgacacgctg ctcgcgctgt tcgaccgcat cgtggacgac   2100
gggaacacgg tcgtcgtcgt ggagcacgac ctccaggtcg tcaaacacgc cgactgggtg   2160
atcgacctcg gaccggacgc cggccggcac ggcggccggg tggtcttcga gggcacaccg   2220
aaggagctcg ccgcccacga gcactcggtc accgcccggt acctgcgggc cgatctcgcg   2280
caggtgcggg gctga                                                     2295
```

<210> SEQ ID NO 18
<211> LENGTH: 256
<212> TYPE: PRT
<213> ORGANISM: Streptomyces refuineus subspecies thermotolerans

<400> SEQUENCE: 18

```
Val Asn Thr Ser Glu Val Arg Pro Val Thr Val Gly Trp Phe Glu Ile
1               5                   10                  15

Thr Thr Thr Asp Pro Ala Arg Ser Lys Glu Phe Tyr Gln Gly Leu Phe
            20                  25                  30

Asp Trp Lys Leu Thr Ala Phe Ala Asp Asp Ala Tyr Ser Thr Ile
        35                  40                  45

Thr Ala Pro Gly Ala Ala Ala Met Gly Ala Leu Arg Arg Gly Asp
    50                  55                  60

His Asp Ala Val Cys Ile Ser Val Val Cys Asp Val Ala Ala Val
65                  70                  75                  80

Ile Ser Glu Leu Arg Ala Leu Gly Ala Thr Leu Val Glu Pro Pro Ala
                85                  90                  95

Arg Thr Met Ala Gly Asp Val His Ala Val Val Thr Asp Val Arg Gly
            100                 105                 110

Asn Arg Leu Gly Leu Phe Glu Pro Gly Glu Arg Arg Asp Pro Glu Pro
        115                 120                 125

Thr Arg Pro Val Pro Asn Ala Thr Ala Trp Phe Glu Ile Gly Thr Thr
    130                 135                 140

Asp Leu Ala Ala Thr Arg Thr Phe Tyr Glu Lys Ala Phe Gly Trp Thr
145                 150                 155                 160

Gln Val Arg Asp Glu Ala Ala Glu Gly Ala Glu Tyr Tyr Ser Ile Met
                165                 170                 175
```

```
Pro Pro Ser Ser Gln Gln Ala Ile Gly Gly Val Leu Asp Leu Ser Ala
        180                 185                 190

Thr Pro Gly Ala Ala Asp Tyr Ala Val Pro Gly Leu Leu Val Thr Asp
        195                 200                 205

Val Pro Asp Leu Leu Glu Arg Cys Glu Ala Ala Gly Gly Arg Arg Val
        210                 215                 220

Ala Gly Pro Phe Ser Asp Ala Asp Gly Leu Val Ile Gly Gln Phe Thr
225                 230                 235                 240

Asp Pro Phe Gly Asn Lys Trp Ser Ala Phe Ala Gln Pro Ala Gly Glu
                245                 250                 255

<210> SEQ ID NO 19
<211> LENGTH: 771
<212> TYPE: DNA
<213> ORGANISM: Streptomyces refuineus subspecies thermotolerans

<400> SEQUENCE: 19
gtgaacacgt ccgaagtccg tccggtgacc gtggggtggt tcgagatcac caccaccgat      60
ccggcgcgca gcaaggagtt ctaccagggg ctcttcgact ggaagctcac cgccttcgcc     120
gatgacgacg cctactccac gatcaccgcg cccggtgccg cggccgccat ggggggcactg     180
cggcggggcg accacgacgc ggtgtgcatc agcgtcgtgt gcgacgacgt ggcggcggtg     240
atctcggagc tgcgggcgct gggcgccacg ctcgtcgagc ccccgcccg cacgatggcg     300
ggcgacgtgc acgcggtggt caccgacgtg cgcggaaaca ggctggggtt gttcgagccc     360
ggggagcggc gtgatccgga gccgacccga ccggtgccga acgccacggc ctggttcgag     420
atcgggacga ccgacctcgc ggcgacgcgg acgttctacg agaaggcctt cggctggacc     480
caggtgcgcg acgaggcggc cgaggagcg gagtactaca gcatcatgcc ccctcgtcg     540
cagcaggcca tcgggggagt cctcgacctg tccgcaacgc cggcgcagc ggactacgcg     600
gtgcccgggc tgctggtaac cgatgtcccg gacctgctcg agcggtgtga ggcagccggc     660
ggccgacgtg tggcgggccc gttctccgac gccgacggac tggtcatcgg acagttcacc     720
gaccccttcg gcaacaagtg gagcgctttc gcccagcccg ccggcgagtg a             771

<210> SEQ ID NO 20
<211> LENGTH: 397
<212> TYPE: PRT
<213> ORGANISM: Streptomyces refuineus subspecies thermotolerans

<400> SEQUENCE: 20

Met Pro Val Ala Val Tyr Val Leu Ala Val Ala Val Cys Cys Leu Asn
1               5                   10                  15

Thr Thr Glu Ile Met Val Ala Gly Leu Ile Gln Gly Ile Ser Ser Asp
        20                  25                  30

Leu Gly Val Ser Val Ala Ala Val Gly Tyr Leu Val Ser Val Tyr Ala
        35                  40                  45

Phe Gly Met Val Val Gly Gly Pro Leu Leu Thr Ile Gly Leu Ser Arg
    50                  55                  60

Val Pro Gln Lys Arg Ser Leu Val Trp Leu Leu Ala Val Phe Val Val
65                  70                  75                  80

Gly Gln Ala Ile Gly Ala Leu Ala Val Asp Tyr Trp Met Leu Val Val
                85                  90                  95

Ala Arg Val Leu Thr Ala Leu Ala Ala Ser Ala Phe Phe Gly Val Ser
            100                 105                 110

Ala Ala Val Cys Ile Arg Leu Val Gly Ala Glu Arg Arg Gly Arg Ala
```

```
              115                 120                 125
Met Ser Ala Leu Tyr Gly Gly Ile Met Val Ala Gln Val Val Gly Leu
        130                 135                 140
Pro Ala Ala Ala Phe Ile Glu Gln Arg Val Asp Trp Arg Ala Ser Phe
145                 150                 155                 160
Trp Ala Val Asp Leu Leu Ala Leu Val Cys Ile Ala Ala Val Val Leu
                165                 170                 175
Lys Val Pro Ala Gly Gly Asp Pro Asp Thr Leu Asp Leu Arg Ala Glu
            180                 185                 190
Ile Arg Gly Phe Arg Asn Leu Arg Leu Trp Gly Ala Tyr Gly Thr Asn
        195                 200                 205
Ala Leu Ala Ile Gly Ser Val Val Ala Gly Phe Thr Tyr Leu Ser Pro
    210                 215                 220
Ile Leu Thr Asp Ala Ala His Phe Thr Pro Ser Thr Val Pro Val Leu
225                 230                 235                 240
Phe Ala Val Tyr Gly Ala Ala Thr Val Val Gly Asn Thr Val Val Gly
                245                 250                 255
Arg Phe Ala Asp Arg His Thr Arg Pro Val Leu Phe Gly Gly Leu Ser
            260                 265                 270
Thr Val Thr Leu Val Leu Val Gly Phe Ala Leu Thr Val Ser His Gln
        275                 280                 285
Val Pro Val Ala Val Phe Thr Val Leu Leu Gly Leu Ile Gly Leu Pro
    290                 295                 300
Leu Asn Pro Ala Leu Ala Ala Arg Val Met Ser Val Ser Asn Glu Gly
305                 310                 315                 320
Ala Leu Val Asn Thr Val Asn Gly Ser Ala Ile Asn Val Gly Val Val
                325                 330                 335
Leu Gly Pro Trp Leu Gly Gly Met Gly Ile Ser Ala Gly Leu Gly Leu
            340                 345                 350
Ala Ala Pro Leu Trp Ile Gly Ala Ala Met Ala Leu Cys Ala Leu Ile
        355                 360                 365
Thr Leu Leu Pro Asp Leu Arg Lys Arg Ser Gly Ala Ser Ala Pro Glu
    370                 375                 380
Arg Gly Glu Thr Gly Arg Asp Glu Thr Ala Val Arg Ala
385                 390                 395
```

<210> SEQ ID NO 21
<211> LENGTH: 1194
<212> TYPE: DNA
<213> ORGANISM: Streptomyces refuineus subspecies thermotolerans

<400> SEQUENCE: 21

```
atgcctgtcg ctgtgtacgt gctggcggtg ccgtctgct gcctcaacac gaccgagatc      60
atggtcgccg gtctgatcca gggcatctcg agcgacctgg gcgtgtccgt cgcggccgtc     120
ggctacctcg tgtcggtcta cgccttcggc atggtcgtcg gcggcccgct gctgaccatc     180
ggcctgtccc gggtgccgca gaagaggtcg ctggtctggc tgctggcggt gttcgtcgtc     240
gggcaggcga tcgggccct ggccgtcgac tactggatgc tcgtggtcgc acgggtgctg     300
accgcactgg ccgcctcggc cttcttcggg gtgagcgccg cggtgtgcat ccgcctcgtc     360
ggcgccgagc ggcgcgggcg tgcgatgtcg gccctgtacg gcggcatcat ggtggcccag     420
gtcgtcggcc tgcccgcggc cgccttcatc gagcagcgtg tcgactggcg gccagcttc     480
tgggcggtcg acctgctggc gctcgtgtgc atcgcggcgg tcgtgctgaa ggtcccggcc     540
```

```
ggcggtgatc ccgacacgct cgacctccgt gcggagatcc ggggtttccg caacctgcgg      600
ctgtggggcg cgtacgggac caacgccctc gccatcggat cggtcgtggc ggggttcacc      660
tacctctccc cgatcctcac cgacgccgcc cacttcacgc cgtcgaccgt gccggtgctg      720
ttcgcggtgt acggagcggc caccgtggtg gcaacaccg tcgtcggccg gttcgcggac       780
cgtcatacgc gaccggtcct cttcggcggc ctgagcacgg tcaccctcgt cctcgtcgga      840
ttcgccctga ccgtctcgca ccaggtgccg gtggccgtct tcaccgttct gctcggtctg      900
atcggcctgc cgctcaaccc cgcgctggcc gcccgggtga tgtccgtgtc caatgagggc      960
gcgctggtca acacggtcaa cggtccgcg atcaacgtcg gcgtggtcct cggcccctgg      1020
ctcggcggca tggggatcag cgcggggctc ggtctcgcgg cgccgttgtg gatcggggcg      1080
gccatggcgc tgtgcgcact gatcacgctg ctgcccgacc tccggaagcg ctcgggcgcc      1140
tcggcgcccg agcgcggcga acgggccgc gacgagaccg cggtgagagc ctga             1194
```

<210> SEQ ID NO 22
<211> LENGTH: 89
<212> TYPE: PRT
<213> ORGANISM: Streptomyces refuineus subspecies thermotolerans

<400> SEQUENCE: 22

```
Val Pro His Gly Gly Pro Thr Arg Val Glu Gly Lys Gly Pro Thr Asp
1               5                   10                  15

Arg Ala Arg Arg Asp Ile Pro Glu Arg Pro Ala Met Pro Ala Arg Asp
            20                  25                  30

Arg Ala Val Ala Gly Ala Val Arg Pro Pro Ala Arg Pro Ala Val His
        35                  40                  45

Ala Ala Cys Cys Asp Arg Ala Ala Glu Arg Phe Pro Ala Leu Arg Arg
    50                  55                  60

Arg Ser Arg Gly Pro Arg Arg Ala Ala Ser Ala Asp Arg Leu Lys Trp
65                  70                  75                  80

Gly Leu Lys Glu Phe Leu Lys Ala Ile
                85
```

<210> SEQ ID NO 23
<211> LENGTH: 270
<212> TYPE: DNA
<213> ORGANISM: Streptomyces refuineus subspecies thermotolerans

<400> SEQUENCE: 23

```
gtgccgcatg gcggcccgac ccgcgtggaa ggaaaagggc cgacagaccg cgcaaggcgg       60
gacatcccgg agaggcccgc gatgcccgcg cgtgaccgag ccgtcgccgg ggccgtccgg      120
ccgccggccc gtccggcggt gcacgcggcg tgctgcgacc gtgcggccga gcggttcccc      180
gcccttcgcc ggcgcagccg cggaccgcgc cgggccgcct cggccgaccg cctgaagtgg      240
ggcctaaaag aattcctgaa agcgatttaa                                       270
```

<210> SEQ ID NO 24
<211> LENGTH: 169
<212> TYPE: PRT
<213> ORGANISM: Streptomyces refuineus subspecies thermotolerans

<400> SEQUENCE: 24

```
Val Asn Thr Pro Ser Thr Pro Ala Thr Glu Gly Leu Ser Met Glu Gly
1               5                   10                  15

Leu Asp Ile Ala Pro Gly Phe His His Val Ala Val Gln Thr Asp Asp
            20                  25                  30
```

```
Val Asp Ala Thr Val Arg Trp Tyr Glu Glu Phe Leu Gly Ala Thr Val
            35                  40                  45

Glu Trp Ser Leu Asp Thr Phe Ser Pro Leu Thr His Ala Arg Leu Pro
 50                  55                  60

Gly Ile Lys Lys Leu Val Glu Val Lys Lys Gly His Val Arg Phe His
 65                  70                  75                  80

Val Phe Asp Arg Ala Gly His Ser Arg Gly Pro Asp Pro Leu Gly
                 85                  90                  95

Tyr Gln Tyr Gln His Ile Gly Ile Thr Val Asn Arg Pro Glu Asp Leu
                100                 105                 110

Ala Arg Leu Arg Glu Arg Trp Leu Arg Val Arg Glu Arg Thr Asp Leu
            115                 120                 125

Arg Trp Ala Arg Asp Glu Pro Pro Ser Asp Ile Val Ala Asp Ala Asp
130                 135                 140

Gly Val Gln Ser Leu Tyr Val Leu Asp Pro Asn Gly Leu Glu Leu Glu
145                 150                 155                 160

Phe Ile Tyr Phe Pro Gly Ala Gly Thr
                165

<210> SEQ ID NO 25
<211> LENGTH: 510
<212> TYPE: DNA
<213> ORGANISM: Streptomyces refuineus subspecies thermotolerans

<400> SEQUENCE: 25
gtgaacacgc cgagcacacc cgcgacggaa gggctttcga tggagggggct tgacatcgcg      60 ccggggtttc accatgtcgc cgtccagacg gacgacgtgg acgccacggt caggtggtac     120
gaggaattcc tcgggccacc ggtggagtgg tcgctcgaca ccttctcacc actcactcac     180
gcgcggctcc ccggaatcaa gaagctggtc gaagtgaaga aggggcacgt gcgtttccac     240
gtcttcgacc gggcggggca cagccggggc ggaccggatc cgctcggcta ccagtaccag     300
cacatcggga tcaccgtgaa ccggccggaa gacctcgcgc ggctccgtga gcggtggttg     360
cgcgtgcgcg aacggaccga cctccggtgg gccagggacg agccgccgtc cgacatcgtg     420
gccgacgccg acggcgtaca gagcctctac gtcctggacc caacggtct cgaactcgag     480 ttcatctact tccaggagc gggaacgtga                                       510

<210> SEQ ID NO 26
<211> LENGTH: 302
<212> TYPE: PRT
<213> ORGANISM: Streptomyces refuineus subspecies thermotolerans

<400> SEQUENCE: 26

Val Ser Asn Gly Arg Gly His Ala Ala Ala Pro Gly Gly Gly His Ser
 1                   5                  10                  15

Pro Leu Leu Gln Pro Gln Leu Leu Phe Met Pro Pro Val Gly His Ala
             20                  25                  30

Tyr Glu Thr Pro Ser Glu Glu Val Pro His Thr Thr Gly Ala Ala Asp
             35                  40                  45

Arg Asp Ala Pro Asp Tyr Asp Leu Phe Gly Glu Arg Pro Val Glu Ala
 50                  55                  60

Gln Arg Leu Phe Trp Tyr Arg Trp Ile Ala Gly His Gln Ile Ser Phe
 65                  70                  75                  80

Val Leu Trp Arg Ala Met Gly Asp Ile Leu Trp His His Pro His Asp
             85                  90                  95
```

```
Val Pro Gly Ala Arg Glu Leu Asp Val Leu Thr Ala Cys Val Asp Gly
            100                 105                 110

Tyr Ser Ala Met Leu Leu Tyr Ser Ala Thr Val Pro Arg Ala His Tyr
        115                 120                 125

His Ser Tyr Thr Arg Ala Arg Met Ala Leu Gln His Pro Ser Phe Ser
    130                 135                 140

Gly Ala Trp Ala Pro Asp Tyr Arg Pro Ile Arg Arg Leu Phe Arg Asn
145                 150                 155                 160

Arg Leu Pro Trp Gln Gly Asp Pro Ser Cys Arg Ala Leu Gly Glu Ala
                165                 170                 175

Val Ala Arg Asn Gly Val Thr His Asp His Ile Ala Asn His Leu Val
            180                 185                 190

Pro Asp Gly Arg Ser Leu Leu Gln Gln Ser Ala Gly Ala Pro Gly Val
        195                 200                 205

Thr Val Ser Arg Glu Lys Glu Asp Leu Tyr Asp Asn Phe Phe Leu Thr
    210                 215                 220

Val Arg Arg Pro Val Ser His Ala Glu Leu Val Ala Gln Leu Asp Ala
225                 230                 235                 240

Arg Val Thr Glu Val Ala Ala Asp Leu Arg His Asn Gly Leu Tyr Pro
                245                 250                 255

Asn Val Asp Gly Arg His His Pro Val Val Thr Trp Gln Ser Asp Gly
            260                 265                 270

Val Met Gly Ser Leu Pro Thr Gly Val Leu Arg Thr Leu Asn Arg Ala
        275                 280                 285

Thr Arg Met Val Ala Gln Thr Arg Leu Glu Glu Ala Arg Ser
    290                 295                 300

<210> SEQ ID NO 27
<211> LENGTH: 909
<212> TYPE: DNA
<213> ORGANISM: Streptomyces refuineus subspecies thermotolerans

<400> SEQUENCE: 27
gtgagcaacg gccgaggaca tgccgccgca ccgggcgggg ggcactcgcc cctgctgcaa     60
ccgcaactgc tgttcatgcc cccggtgggc cacgcgtacg agaccccgtc cgaggaggtg    120
ccgcacacca ccggggccgc cgaccgggac gcgccggact acgacctctt cggcgaacgc    180
ccggtcgagg cgcagcggct gttctggtac cgctggatcg ccggccacca gatctcgttc    240
gtgctctggc gggccatggg ggacatcctg tggcaccacc cccatgacgt gcccggcgcc    300
cgcgaactcg acgtgctgac cgcctgcgtc gacggataca gcgcgatgct gctctactcg    360
gccaccgtcc cgcgtgccca ctaccactcc tacaccagag cgcgcatggc gctgcagcac    420
ccgtcgttca gcggcgcgtg ggcgccggac taccggccga tccgccggct cttccgcaac    480
aggttgccct gcagggcgga tccgtcgtgc agggccctgg gcgaggcggt cgcgcgcaac    540
ggcgtgaccc acgaccacat cgccaaccac ctcgtgcccg acggcggtc cctgctgcag    600
cagtccgccg gcgcaccggg agtgaccgtg tcccgggaga aggaggacct ctacgacaac    660
ttcttcctga ccgtccggcg gccggtcagc cacgccgaac tcgtcgcgca gctggacgcg    720
cgcgtcacgg aggtcgcggc ggacctccgg cacaacgggc tctacccaa cgtcgacgga    780
cgccaccacc cggtcgtcac ctggcagtcg gacggagtga tggggtcgct gccgaccggt    840
gtcctgcgga cgctgaaccg ggcgacgcgg atggtcgcgc agacgcgcct cgaggaagcc    900
cggtcatga                                                            909
```

<210> SEQ ID NO 28
<211> LENGTH: 297
<212> TYPE: PRT
<213> ORGANISM: Streptomyces refuineus subspecies thermotolerans

<400> SEQUENCE: 28

```
Met Arg His Gly Val Leu Leu Pro Glu His Asp Trp Lys Thr Ala
1               5                   10                  15

Ala Glu Arg Trp Arg Ala Ala Glu Gln Leu Gly Tyr His His Ala Trp
                20                  25                  30

Thr Tyr Asp His Leu Met Trp Arg Trp Phe Ala Asp Arg Arg Trp Tyr
            35                  40                  45

Gly Ser Ile Pro Thr Leu Ala Ala Ala Val Thr Asp Thr Ile
50                  55                  60

Gly Leu Gly Val Leu Val Ala Thr Pro Asn Phe Arg His Pro Val Val
65                  70                  75                  80

Leu Ala Lys Asp Leu Val Ser Val Asp Asp Ile Ala Glu Gly Arg Leu
                85                  90                  95

Ile Cys Gly Leu Gly Ser Gly Ala Pro Gly Tyr Asp Asn Ser Ile Leu
            100                 105                 110

Gly Gly Ala Ala Leu Gly Pro Gly Glu Arg Ala Asp Arg Phe Glu Ala
        115                 120                 125

Phe Val Glu Leu Leu Asp Ala Val Leu Val Asp Gly Asp Val Asp Arg
    130                 135                 140

Ser Thr Pro Trp Tyr Thr Ala Arg Gly Val Thr Phe His Pro Arg Ala
145                 150                 155                 160

Glu Gly Gly Arg Arg Leu Pro Phe Ala Val Ala Ala Gly Pro Arg
                165                 170                 175

Gly Met Ala Leu Thr Ala Arg Phe Gly Gln Tyr Trp Val Thr Ser Gly
            180                 185                 190

Pro Pro Asn Asp Phe Arg Thr Arg Pro Leu Arg Glu Val Leu Pro Glu
        195                 200                 205

Leu Arg Ala Gln Leu Arg Gly Val Asp Glu Ala Cys Glu Arg Ala Gly
    210                 215                 220

Arg Asp Pro Ala Thr Leu Arg Arg Leu Leu Val Ala Asp Ala Ala Val
225                 230                 235                 240

Gly Gly Ile Thr Ala Ser Leu Ser Ala Tyr Glu Asp Ala Ala Gly Glu
                245                 250                 255

Leu Glu Glu Ala Gly Phe Thr Asp Leu Val Val His Trp Pro Arg Pro
            260                 265                 270

Asp Gln Pro Tyr Gln Gly Asp Glu Gln Val Leu Val Asp Phe Ala Ala
        275                 280                 285

Glu His Leu Val Glu Lys Ser Cys Val
    290                 295
```

<210> SEQ ID NO 29
<211> LENGTH: 894
<212> TYPE: DNA
<213> ORGANISM: Streptomyces refuineus subspecies thermotolerans

<400> SEQUENCE: 29

```
atgaggcacg gcgtcgtact gctgcccgaa cacgactgga agaccgccgc cgagcggtgg      60
cgggccgcgg agcagctcgg ctaccaccac gcctggacct acgaccacct gatgtggcgc     120
tggttcgccg accggcggtg gtacggctcg atcccgacac tcgccgccgc ggccgtcgtg     180
```

```
accgacacca tcggactcgg tgtgctcgtg gccaccccga acttccgcca cccggtcgtg    240
ctggccaagg acctcgtctc cgtcgacgac atcgcggagg gccgtctgat ctgcggcctg    300
ggctccggcg cccccggcta cgacaacagc atcctcggcg gggccgcgct cggtcccggc    360
gagcgcgccg accgcttcga ggcgttcgtg gagctgctcg acgcggtgct ggtcgacggc    420
gacgtggacc ggtccacgcc ctggtacacc gcgcgcggcg tgacgtttca cccgcgggcc    480
gaaggcggtc ggcgactgcc cttcgcggtg gctgcggccg gccgaggggg catggcgctg    540
accgcccgct cgggcagta ctgggtcacc tccgggccgc caacgactt ccgcacgcgg    600 ccgctgcgcg aggtcctgcc ggagctgcgg gcccaactgc gcggcgtcga cgaggcctgc    660
gagcgagcgg gccgcgaccc ggccacgctg cgtcggctgc tggtggccga cgcggcggtc    720
ggcgggatca ccgcctcgct gtcggcgtac gaggacgcgg cgggcgagct ggaggaggcc    780
ggcttcaccg acctcgtcgt gcactggccg cgccccgacc agccgtacca gggagacgag    840
caggtcctcg tcgacttcgc ggccgagcac ctggtggaga agtcatgcgt gtga          894
```

<210> SEQ ID NO 30
<211> LENGTH: 274
<212> TYPE: PRT
<213> ORGANISM: Streptomyces refuineus subspecies thermotolerans

<400> SEQUENCE: 30

```
Val Thr Thr Val Asp Met Phe Gly Ala Ala Pro Gly Arg Gly Ser Ala
1               5                   10                  15

Leu Asp Val Leu Val Pro Asp Gly Pro Cys Gly Glu Ala Ala Ala Glu
                20                  25                  30

Glu Ala Ala His Ala Arg Arg Ser Ala Ala Asp Glu Ser Val Leu
            35                  40                  45

Val Val Glu Cys Arg Arg Ala Gln Arg Thr Phe Ala Ser Arg Val Phe
    50                  55                  60

Asn Ala Gly Gly Glu Thr Pro Phe Ala Thr His Ser Leu Ala Gly Ala
65                  70                  75                  80

Ala Ala Cys Leu Val Gly Ala Gly His Leu Pro Pro Gly Glu Val Gly
                85                  90                  95

Arg Thr Ala Glu Ser Gly Ser Gln Trp Leu Trp Thr Asp Gly His Glu
            100                 105                 110

Val Arg Val Pro Phe Asp Gly Pro Val His Arg Gly Ile Pro His
    115                 120                 125

Asp Pro Ala Leu Phe Gly Pro Tyr Ala Gly Thr Pro Tyr Ala Gly Gly
    130                 135                 140

Val Gly Arg Ala Phe Asn Leu Leu Arg Val Ala Glu Asp Pro Arg Thr
145                 150                 155                 160

Leu Pro Ala Pro Asp Pro Gly Arg Met Arg Glu Leu Gly Phe Thr Asp
                165                 170                 175

Leu Thr Val Phe Arg Trp Asp Pro Asp Arg Gly Glu Val Leu Ala Arg
            180                 185                 190

Val Phe Ala Pro Gly Phe Gly Ile Pro Glu Asp Ala Gly Cys Leu Pro
    195                 200                 205

Ala Ala Ala Ala Leu Gly Val Ala Ala Leu Arg Leu Ala Ala Asp Asp
    210                 215                 220

Arg Thr Ser Val Thr Val Arg Gln Val Thr Val Arg Gly Thr Glu Ser
225                 230                 235                 240

Val Phe Arg Cys Thr Gly Ser Ala Arg Gly Gly Ser Ala Asn Val Thr
```

```
                   245                 250                 255
Ile Thr Gly Arg Val Trp Thr Gly Gly Thr Ala Gly Arg Glu Val Gly
            260                 265                 270

Gly Ser

<210> SEQ ID NO 31
<211> LENGTH: 825
<212> TYPE: DNA
<213> ORGANISM: Streptomyces refuineus subspecies thermotolerans

<400> SEQUENCE: 31
gtgaccacgg tggacatgtt cggtgcggcc ccgggccggg ggagcgccct ggacgtgctc      60
gtcccggacg gtccgtgcgg cgaggcggcg gccgaggagg ccgcggcgca cgcacgccgg     120
agcgccgcgg acgagagcgt gctggtcgtc gagtgccgca gggcgcagcg gaccttcgcg     180
tcgcgggtct tcaacgcggg tggggagacg ccgttcgcca cccactccct ggcgggcgcg     240
gccgcctgcc tggtcggcgc ggggcacctg ccgccgggtg aggtggggcg gacggccgag     300
agcggatccc agtggctgtg gaccgacggc cacgaggtcc gggtgccctt cgacgggccc     360
gtggtgcacc gggggatccc gcacgacccc gcgctgttcg gcccgtacgc cggcacgccg     420
tacgccggcg cgtcggccg  ggccttcaac ctgctgcgcg tcgcggaaga ccccggacg      480 ctgcccgccc ccgatcccgg gcgcatgcgg gaactggggt tcacgaccct caccgtcttc     540
cggtgggacc cggaccgggg cgaggtgctg gcgcgggtgt cgccccgggg cttcggcatc     600
ccggaggacg ccggctgcct gccggcggcc gccgcgctcg gcgtcgccgc actgcgcctg     660
gccgccgacg accggacgtc cgtgacggtc cgccaggtca ccgtccgcgg caccgagtcg     720
gtcttccgct gtaccggctc cgcccgcggc ggcagcgcga acgtgacgat caccggacgc     780
gtgtggaccg gcgggacggc cggccgggaa gtgggtggat catga                     825

<210> SEQ ID NO 32
<211> LENGTH: 413
<212> TYPE: PRT
<213> ORGANISM: Streptomyces refuineus subspecies thermotolerans

<400> SEQUENCE: 32

Met Thr Thr Arg Lys Thr Ala Pro Ala Ala Thr Ala Ala Arg Thr Gly
1               5                  10                  15

Arg Ser Ala Leu Arg Asp Glu Ala Arg Arg Arg Asp Asp Arg Asp Pro
            20                  25                  30

Leu Ser Ala His Ala Ala Arg Phe Ala Thr Gly Gly Val Val His Leu
        35                  40                  45

Asn Gly Asn Ser Leu Gly Pro Pro Arg Glu Ser Leu Val His Ala Leu
    50                  55                  60

Asp Arg Val Val Ser Gly Gln Trp Ala Pro Arg Gln Val Arg Gly Trp
65                  70                  75                  80

Phe Arg Asp Gly Trp Leu Glu Leu Pro Arg Thr Val Gly Asp Lys Leu
                85                  90                  95

Ala Ala Leu Leu Gly Ala Gly Pro Gly Gln Val Val Ala Gly Glu
            100                 105                 110

Thr Thr Ser Thr Thr Leu Phe Asn Ala Leu Val Ala Ala Cys Arg Leu
        115                 120                 125

Arg Asp Asp Arg Pro Val Leu Leu Ala Glu Ala Glu Ser Phe Pro Thr
    130                 135                 140

Asp Leu Tyr Ile Ala Asp Ser Val Ala Arg Leu Leu Gly Arg Arg Leu
```

```
                145                 150                 155                 160
Val Val Glu Pro Arg Gly Gly Phe Asp Ala Phe Leu Ala Glu His Gly
                    165                 170                 175

Arg Gln Val Ala Ala Ile Ala Ala Pro Val Asp Phe Arg Thr Gly
            180                 185                 190

Glu Arg Arg Glu Ile Gly Pro Thr Thr Ala Leu Cys His Ala Ala Gly
        195                 200                 205

Ala Val Ser Val Trp Asp Leu Ser His Ala Ala Gly Val Leu Pro Thr
    210                 215                 220

Glu Leu Asp Ala His Gly Val Asp Leu Ala Ile Gly Cys Gly Tyr Lys
225                 230                 235                 240

Tyr Leu Gly Gly Gly Pro Gly Ala Pro Ala Phe Leu Tyr Val Arg Ser
                245                 250                 255

Gly Leu Gln Pro Glu Val Asp Phe Pro Leu Ser Gly Trp His Gly His
            260                 265                 270

Ala Arg Pro Phe Asp Met Ala Pro Arg Phe Val Pro Ala Gly Gly Val
        275                 280                 285

Asp Arg Ala Arg Thr Gly Thr Pro Pro Leu Leu Ser Ile Val Ala Leu
    290                 295                 300

Asp His Ala Leu Glu Pro Leu Val Gln Thr Gly Ile Arg Ala Leu His
305                 310                 315                 320

Arg Arg Ser Arg Ser Leu Gly Glu Phe Phe Leu Thr Cys Leu Gly Glu
                325                 330                 335

Gly Arg Pro Asp Leu Leu Arg Arg Leu Ala Ser Pro Arg Asp Pro Asp
            340                 345                 350

Arg Arg Gly Gly His Leu Ala Leu Arg Val Pro Asp Ala Asp Gly Leu
        355                 360                 365

Glu Arg Ala Leu Ala Asp Ser Gly Val Leu Val Asp Ala Arg Pro Pro
    370                 375                 380

Asp Leu Val Arg Phe Ala Phe Ala Pro Leu Tyr Val Thr Tyr Glu Gln
385                 390                 395                 400

Val Trp Arg Ala Val Asn Glu Val His Arg Ala Leu Pro
                405                 410

<210> SEQ ID NO 33
<211> LENGTH: 1242
<212> TYPE: DNA
<213> ORGANISM: Streptomyces refuineus subspecies thermotolerans

<400> SEQUENCE: 33
atgaccacac ggaagacggc gcccgcggcg accgcggcac ggaccggccg gtccgccctg      60
cgggacgagg cgcggcgccg cgacgaccgc gatccgctgt ccgcgcacgc ggcccggttc     120
gccaccggcg gcgtcgtcca cctcaacggc aactcgctcg accgcccag ggagagcctc     180 gtgcacgcgc tcgaccgcgt ggtgtccggc cagtgggcgc ccggcaggt acggggctgg     240 ttccgcgacg gatggctcga gctgccccgc accgtcgggg acaagctggc cgcactgctc     300
ggcgcgggcc cggacaggt ggtggtcgcc ggcgagacga cgtccacgac gctgttcaac     360
gcgctggtcg ccgcctgccg cctgcgcgac gaccggcccg tgctgctcgc cgaggccgag     420
tccttcccca ccgacttgta catcgcggac tcggtggcgc ggctccttgg ccgtcggctc     480
gtcgtcgaac cgcgcggcgg cttcgacgcg ttcctcgccg agcacgggcg gcaggtggcg     540
gccgcgatcg ccgcgccggt ggacttccgc accggcgagc ggcgcgagat cgggcccacc     600
accgcgctgt gccacgccgc cggagccgtg tccgtgtggg acctcagcca cgccgccggc     660
```

```
gtcctgccga ccgaactgga cgcccacggg gtggacctgg cgatcgggtg cggctacaag    720
tacctgggcg ggggcccggg ggcgccggcg ttcctctacg tccgctccgg actccagccg    780
gaggtggact tccccctgtc ggggtggcac ggacacgcgc ggccgttcga catggcgccc    840
cggttcgtgc cggccggggg agtggaccgc gcgcgcaccg gcaccccgcc gctgctcagc    900
atcgtcgcgc tggaccacgc cctcgaacca ctggtgcaga ccggcatccg ggcgctgcac    960
cggcgcagcc ggtccctggg cgagttcttc ctgacctgcc tgggggaagg ccgccccgac   1020
ctgctgcggc gactggcctc gccccgcgac ccggaccgcc ggggcgggca cctcgcactg   1080
cgcgtccccg atgccgacgg gctcgaacgc gcgctggccg acagcggcgt gctcgtcgac   1140
gcccggccgc cggacctggt ccgtttcgcg ttcgccccgc tgtatgtgac ctacgagcag   1200
gtatggcgcg cagtgaacga ggtgcaccgt gccctgccgt ga                      1242
```

<210> SEQ ID NO 34
<211> LENGTH: 261
<212> TYPE: PRT
<213> ORGANISM: Streptomyces refuineus subspecies thermotolerans

<400> SEQUENCE: 34

```
Met Asn Arg Ala Pro Glu Tyr Val Ser Tyr Ala Arg Met Asp Glu Leu
1               5                   10                  15

His Glu Leu Gln Arg Pro Arg Ser Asp Ala Arg Gly Glu Leu Asn Phe
            20                  25                  30

Ile Leu Leu Ser His Val Lys Glu Leu Leu Phe Arg Ala Val Thr Asp
        35                  40                  45

Asp Leu Asp Thr Ala Arg His Ala Leu Ala Gly Asp Asp Val Ala Asp
    50                  55                  60

Ala Cys Leu Ala Leu Ser Arg Ala Ala Arg Thr Gln Arg Val Leu Val
65                  70                  75                  80

Ala Cys Trp Glu Ser Met Asn Gly Met Ser Ala Asp Glu Phe Val Ala
                85                  90                  95

Phe Arg His Val Leu Asn Asp Ala Ser Gly Val Gln Ser Phe Ala Tyr
            100                 105                 110

Arg Thr Leu Glu Phe Val Met Gly Asn Arg Pro Pro Arg Gln Val Glu
        115                 120                 125

Ala Ala Tyr Arg Glu Gly His Pro Leu Val Arg Ala Glu Leu Ala Arg
    130                 135                 140

Pro Ser Val Tyr Asp Glu Ala Leu Arg Tyr Leu Ala Arg Arg Gly Phe
145                 150                 155                 160

Ala Val Pro Ala Asp Cys Val Thr Arg Pro Glu Glu Gln His Glu
                165                 170                 175

Pro Asp Pro Arg Ile Glu Glu Val Trp Leu Glu Ile Tyr Arg His Pro
            180                 185                 190

Asp Arg Tyr Arg Asp Ala His Arg Leu Ala Glu Cys Leu Ile Glu Val
        195                 200                 205

Ala Tyr Gln Phe Ser His Trp Arg Ala Thr His Leu Leu Val Val Glu
    210                 215                 220

Arg Met Leu Gly Gly Lys Ser Gly Thr Gly Gly Ser Asp Gly Ala Ala
225                 230                 235                 240

Trp Leu Arg Thr Val Asn Glu His Arg Phe Phe Pro Glu Leu Trp Thr
                245                 250                 255

Phe Arg Thr Arg Leu
            260
```

<210> SEQ ID NO 35
<211> LENGTH: 786
<212> TYPE: DNA
<213> ORGANISM: Streptomyces refuineus subspecies thermotolerans

<400> SEQUENCE: 35

| | | | | | |
|---|---|---|---|---|---|
| atgaaccggg | cgcccgagta | cgtctcctac | gcccgcatgg | acgaactgca | cgaactgcag | 60 |
| cgcccgcgga | gcgacgcccg | aggcgagctg | aacttcatcc | tgctcagcca | cgtcaaggag | 120 |
| ctgctgttcc | gcgcggtcac | cgacgacctg | gacacggccc | gccacgcact | ggcgggcgac | 180 |
| gacgtcgcgg | acgcgtgcct | ggcgctgtcg | cgggcggccc | gcacccagcg | ggtgctcgtg | 240 |
| gcctgctggg | agtcgatgaa | cggcatgtcg | gccgacgagt | tcgtggcgtt | ccggcacgtg | 300 |
| ctcaacgacg | cgtcgggggt | gcagtccttc | gcctaccgca | ccctggagtt | cgtcatgggc | 360 |
| aaccggccgc | cccggcaggt | ggaggcggcg | taccgggaag | gcacccgct | ggtgcgcgcg | 420 |
| gaactggcca | ggccgtcggt | gtacgacgag | gcgctgcggt | acctggcgcg | gcggggggttc | 480 |
| gcggtcccgg | ccgactgcgt | gaccaggcca | ccggaggagc | agcacgagcc | ggatccccgc | 540 |
| atcgaggagg | tgtggctgga | gatctaccgg | caccggacc | ggtaccgcga | cgcgcaccgc | 600 |
| ctggcggagt | gcctgatcga | ggtcgcctac | cagttctccc | actggcgggc | cacgcacctg | 660 |
| ctggtcgtcg | agcggatgct | cggcggcaag | agcggaacgg | gcggcagcga | cggcgccgcg | 720 |
| tggctgcgca | ccgtcaacga | gcaccgcttc | ttcccggagc | tgtggacctt | ccgcacccgg | 780 |
| ctctga | | | | | | 786 |

<210> SEQ ID NO 36
<211> LENGTH: 58
<212> TYPE: PRT
<213> ORGANISM: Streptomyces refuineus subspecies thermotolerans

<400> SEQUENCE: 36

Met Lys Glu Pro Arg Thr Gly Leu Pro Ile Gly Thr Pro His Pro Pro
1               5                   10                  15

Val Ala Arg Cys Ala His Asp Pro Gly Ser Val Pro His Gly Gly Arg
            20                  25                  30

Gly Asn Gly Leu Val Arg Pro Ser Cys Gly Thr His Gly Pro Ala Trp
        35                  40                  45

Glu Ala Thr Gly Leu Pro Gly Gly Thr Ser
    50                  55

<210> SEQ ID NO 37
<211> LENGTH: 177
<212> TYPE: DNA
<213> ORGANISM: Streptomyces refuineus subspecies thermotolerans

<400> SEQUENCE: 37

| | | | | | |
|---|---|---|---|---|---|
| atgaaggaac | cccgcacggg | gctgccgatc | ggcacgcccc | acccgccggt | cgcgcggtgc | 60 |
| gcccacgacc | ccgggtccgt | cccgcacggc | ggacggggga | acgggctcgt | ccgcccgtct | 120 |
| tgcggcacgc | acgggccggc | gtgggaggcc | accggcctgc | cgggaggcac | gtcgtga | 177 |

<210> SEQ ID NO 38
<211> LENGTH: 347
<212> TYPE: PRT
<213> ORGANISM: Streptomyces refuineus subspecies thermotolerans

<400> SEQUENCE: 38

| | | | | | | | | | | | | | | |
|---|---|---|---|---|---|---|---|---|---|---|---|---|---|---|
|Val|Thr|Lys|Pro|Val|Asp|Leu|Lys|Pro|Leu|Val|Pro|Val|Leu|Phe|Gly|
|1| | | |5| | | | |10| | | | |15|

Phe Ala Ala Phe Gln Gln Leu Arg Ala Ala Ser Glu Leu Gln Leu Phe
                    20                  25                  30

Glu Tyr Leu Thr Leu Asn Gly Pro Ser Thr Cys Asp Gln Val Ala Ala
             35                  40                  45

Gly Leu Arg Leu Pro Pro Lys Ser Ala Arg Lys Leu Leu Leu Gly Thr
 50                  55                  60

Thr Ala Leu Gly Leu Thr Glu His Glu Glu Gly Arg Tyr Ala Pro Ser
 65                  70                  75                  80

Arg Met Leu Arg Asp Ala Ile Asp Gly Val Trp Pro Leu Ile Arg
                 85                  90                  95

Asn Ile Ile Asp Phe Gln His Arg Leu Ser Tyr Leu Pro Ala Met Glu
                 100                 105                 110

Tyr Thr Glu Ser Leu Arg Thr Gly Arg Asn Glu Gly Leu Lys His Leu
             115                 120                 125

Pro Gly Ser Gly Ser Asp Leu Tyr Ser Arg Leu Glu Gln Ala Leu Asp
         130                 135                 140

Leu Glu Asn Leu Phe Phe Arg Gly Met Asn Ser Trp Ser Glu Leu Ser
145                 150                 155                 160

Asn Pro Val Leu Leu His Gln Val Asp Tyr Arg Asp Val Arg Asp Leu
                 165                 170                 175

Leu Asp Val Gly Gly Gly Asp Ala Val Asn Ala Ile Ala Leu Ala Arg
             180                 185                 190

Ala His Pro His Leu Arg Val Thr Val Phe Asp Leu Glu Gly Ala Ala
         195                 200                 205

Glu Val Ala Arg Asp Asn Ile Ala Asp Ala Gly Leu Gly Asp Arg Ile
210                 215                 220

Arg Val Val Ala Gly Asp Met Phe Gly Asp Pro Leu Pro Asp Gly Phe
225                 230                 235                 240

Asp Leu Val Leu Phe Ala His Gln Phe Val Ile Trp Ser Pro Glu Gln
                 245                 250                 255

Asn Arg Ala Leu Leu Lys Arg Ala Tyr Glu Ala Leu Arg Pro Gly Gly
             260                 265                 270

Arg Val Ala Val Phe Asn Ala Phe Ala Asp Asp Gly Cys Gly Pro
         275                 280                 285

Leu Tyr Thr Ala Leu Asp Asn Val Tyr Phe Ala Thr Leu Pro Ser Glu
     290                 295                 300

Glu Ser Thr Ile Tyr Arg Trp Ser Glu His Glu Glu Trp Leu Thr Ala
305                 310                 315                 320

Ala Gly Phe Val Asp Val Thr Arg Val His Asn Asp Gly Trp Thr Pro
                 325                 330                 335

His Gly Val Ile Glu Gly Arg Lys Pro Asp Ala
             340                 345

<210> SEQ ID NO 39
<211> LENGTH: 1044
<212> TYPE: DNA
<213> ORGANISM: Streptomyces refuineus subspecies thermotolerans

<400> SEQUENCE: 39
gtgacgaaac cggtcgacct caagccgctc gttccggtgc tcttcgggtt cgccgccttc      60
cagcaactgc gggccgcgtc ggaactgcag ctgttcgagt acctcaccct caacggcccc     120
tcgacctgtg accaggtcgc cgccggactg cggctgccgc ccaagtcggc gcgcaagctg     180

-continued

```
ctgctcggca cgacggcgct cggcctgacc gagcacgagg aggggcggta cgcgccgagc      240
cggatgctgc gcgacgcgat cgacggaggc gtctggccgc tgatccgcaa catcatcgac      300
ttccagcacc gcctgtcgta cctgccggcc atggagtaca cggagtcgtt gcggaccggc      360
aggaacgagg ggctcaagca cctgcccggc tcgggcagcg acctgtactc gcggctggaa      420
caggccctgg acctggagaa cctgttcttc cggggaatga actcctggtc ggagctgtcc      480
aacccggtgc tgctgcacca ggtggactac cgggacgtgc gcgacctgct ggacgtcggc      540
ggcggcgacg ccgtcaacgc catcgcgctg gcgcgggcac acccgcacct gagggtgacg      600
gtgttcgacc tcgaaggggc cgccgaggtg gccagggaca catcgccga cgccggcctc      660 ggcgaccgga tccgggtggt ggccggcgac atgttcggcg atccgctgcc cgacgggttc      720
gacctggtgc tgttcgccca ccagttcgtg atctggtcgc cggagcagaa ccgggcgctg      780
ctcaagcggg cctacgaggc gctgcgtccc ggcggccggg tggccgtgtt caacgcgttc      840
gccgacgacg acggatgcgg gccgctctac acggcgctgg acaacgtcta cttcgcgaca      900
ctgccgtccg aggagtcgac gatctaccgc tggagcgagc acgaggagtg gctcaccgcc      960
gccggattcg tcgacgtcac gcgcgtccac aacgacggct ggaccccgca cggcgtcatc     1020 gagggggcgca agcccgatgc gtga                                            1044
```

<210> SEQ ID NO 40
<211> LENGTH: 296
<212> TYPE: PRT
<213> ORGANISM: Streptomyces refuineus subspecies thermotolerans

<400> SEQUENCE: 40

```
Met Arg Glu Pro Gly Arg Leu Asp Arg Glu Tyr Ser Pro Ser Thr Val
1               5                   10                  15

Ala Arg Asp Pro Ala Arg Ser Leu Arg Leu Tyr Arg Thr Arg Ser Asp
            20                  25                  30

Asp Ala Arg Ser Arg Pro Gly Ala His Thr Thr Val Arg Tyr Gly Thr
        35                  40                  45

Glu Ser Gly Glu Arg Cys His Val Phe Pro Ala Ala Pro Gly Thr
    50                  55                  60

Pro Gly Pro Arg Thr Pro Ala Leu Val Phe Val His Gly Gly His Trp
65                  70                  75                  80

Gln Glu Ser Gly Ile Asp Asp Ala Cys Phe Ala Ala Arg Asn Ala Leu
                85                  90                  95

Ala His Gly Cys Ala Phe Val Ala Val Gly Tyr Gly Leu Ala Pro Asp
            100                 105                 110

Arg Thr Leu Pro Asp Met Ile Ala Ser Val Ala Arg Ala Leu Glu Trp
        115                 120                 125

Leu Ala Arg Thr Gly Pro Arg Phe Gly Ile Asp Pro Glu Arg Leu His
    130                 135                 140

Val Ala Gly Ser Ser Ala Gly Ala His Leu Leu Ala Ala Leu Ala
145                 150                 155                 160

Gly Gly Ala Ala Pro Arg Val Arg Ser Ala Cys Leu Leu Ser Gly Leu
                165                 170                 175

Tyr Asp Leu Thr Glu Ile Pro Arg Thr Tyr Val Asn Glu Ala Val Gly
            180                 185                 190

Leu Thr Ala Glu Leu Ala Arg Asp Cys Ser Pro Leu Arg Met Pro Ala
        195                 200                 205

Pro Arg Cys Asp Ser Val Leu Leu Ala Ala Gly Gln His Glu Thr Arg
```

```
                   210                 215                 220
Thr Tyr Leu Arg Gln His Glu Ala Tyr Ala Ala His Leu Ala Ala His
225                 230                 235                 240

Ala Val Pro Val Thr Ala Arg Val Val Pro Asp Arg Asp His Phe Asp
                245                 250                 255

Leu Pro Leu Asp Leu Ala Asp Ala Ser Thr Pro Phe Gly Arg Thr Thr
            260                 265                 270

Leu Asn His Leu Gly Leu Ala Ala Pro Thr Gly Thr Glu Pro Thr Arg
        275                 280                 285

Glu Gly Thr Val Thr Ser Ala Arg
        290                 295

<210> SEQ ID NO 41
<211> LENGTH: 891
<212> TYPE: DNA
<213> ORGANISM: Streptomyces refuineus subspecies thermotolerans

<400> SEQUENCE: 41
atgcgtgagc caggccggct ggaccgcgag tactcgccga gcaccgtcgc ccgcgacccg     60
gcccgctcgc tgcggctcta ccgcacgcgc agcgacgacg cccggtcccg gcccggcgcg    120
cacacgacgg tccggtacgg caccgagagc ggcgagcggt gccatgtgtt cccgccgcc    180 gcgcccggca ccgggacc ccggaccccc gccctggtct tcgtgcacgg cggccactgg     240
caggagtccg gcatcgacga cgcctgcttc gcggcacgca acgcgctggc cacggatgc    300 gcgttcgtgg ccgtgggcta cgggctcgcc ccggaccgca cgctgcccga catgatcgcc    360
tcggtggccc gggccctgga gtggctcgcc cgcaccgggc gcggttcgg catcgatccg    420 gagcgcctgc acgtggcggg cagcagcgcg ggcgcgcacc tgctcgccgc ggcgctcgcc    480
ggcggcgcgg ccccccgggt ccgcagcgcg tgcctgctga cggcctgta cgacctcacc    540 gagatcccgc gcacctacgt caacgaagcc gtcggcctga ccgcggagct cgcccgcgac    600
tgcagcccgc tgcggatgcc cgcaccgcgc tgcgactccg tgctgctcgc cgccgggcag    660
cacgagacgg gacgtacct cgccagcac gaggcgtacg ccgctcacct ggccgcccac    720
gcggtcccgg tgacagcccg ggtggtaccc gaccgggacc acttcgacct gccgctggac    780
ctggcggacg cctccacccc gttcggccgg accaccctga ccacctgggg cctggcggcg    840
cccaccggaa ccgagcccac acgagaaggg acggtgacat ccgcgcgatg a             891

<210> SEQ ID NO 42
<211> LENGTH: 600
<212> TYPE: PRT
<213> ORGANISM: Streptomyces refuineus subspecies thermotolerans

<400> SEQUENCE: 42

Met Thr Val Arg Ser Thr Ala Thr Ala Ala Gly Thr Ala Val Ala Ala
1               5                   10                  15

Arg Thr Thr Val Glu Thr Ile Pro Gln Ala Phe Thr Arg Ala Ala Arg
                20                  25                  30

Gln His Ala Ala Arg Glu Ala Leu Ser Asp Gly Ala Thr Thr Leu Thr
            35                  40                  45

Tyr Ala Glu Leu Asp Asp Ala Ala Asn Arg Ile Ala Arg Ala Leu Arg
        50                  55                  60

Glu Arg Gly Leu Arg Pro Gly Glu Arg Val Gly Val Arg Leu Asp Arg
65                  70                  75                  80

Gly Leu Ala Leu Tyr Glu Val Phe Leu Gly Ala Leu Lys Ala Gly Leu
```

-continued

```
                85                  90                  95
Val Val Val Pro Phe Asn Pro Gly His Pro Ala Asp His Thr Ser Arg
            100                 105                 110
Met His Arg Met Ser Gly Pro Ala Leu Thr Val Thr Asp Ser Gly Ala
            115                 120                 125
Ala Glu Gly Ile Pro Ala Ala Thr Arg Leu Pro Val Asp Glu Leu Leu
            130                 135                 140
Ala Asp Ala Ala Pro Leu Ser Ala Gln Pro Val Asp Pro Glu Val Thr
145                 150                 155                 160
Ala Glu Ala Pro Ala Phe Ile Leu Phe Thr Ser Gly Ser Thr Gly Ala
            165                 170                 175
Pro Lys Gly Val Val Ile Ala His Arg Gly Ile Ala Arg Val Ala Arg
            180                 185                 190
His Leu Thr Gly Phe Thr Pro Gly Pro Gln Asp Arg Phe Leu Gln Leu
            195                 200                 205
Ala Gln Pro Ser Phe Ala Ala Ser Thr Thr Asp Ile Trp Thr Cys Leu
            210                 215                 220
Leu Arg Gly Gly Arg Leu Ser Val Ala Pro Gln Glu Leu Pro Pro Leu
225                 230                 235                 240
Gly Asp Leu Ala Arg Leu Ile Val Arg Glu Arg Thr Thr Val Leu Asn
            245                 250                 255
Leu Pro Val Gly Leu Phe Asn Leu Leu Val Glu His Pro Gln Thr
            260                 265                 270
Leu Ala Gln Thr Arg Ser Val Ile Val Ser Gly Asp Phe Pro Ser Ala
            275                 280                 285
Ala His Leu Glu Arg Ala Leu Ala Val Val Gly Gly Asp Leu Phe Asn
            290                 295                 300
Ala Phe Gly Cys Thr Glu Asn Ser Ala Leu Thr Ala Val His Lys Ile
305                 310                 315                 320
Thr Pro Ala Asp Leu Ser Gly Thr Asp Ile Pro Val Gly Arg Pro Met
            325                 330                 335
Pro Thr Val Asp Met Thr Val Arg Asp Glu Arg Leu Glu Glu Cys Ala
            340                 345                 350
Pro Gly Gln Ile Gly Glu Leu Cys Ile Ala Gly Asp Gly Leu Ala Leu
            355                 360                 365
Gly Tyr Leu Asp Asp Pro Glu Leu Thr Asp Arg Lys Phe Val Arg His
            370                 375                 380
Arg Gly Arg Arg Leu Leu Arg Thr Gly Asp Leu Ala Lys Arg Thr Glu
385                 390                 395                 400
Glu Gly Glu Ile Val Leu Ala Gly Arg Thr Asp Gln Met Leu Lys Val
            405                 410                 415
Arg Gly Phe Arg Val Glu Pro Arg Gln Ile Glu Val Thr Ala Glu Ala
            420                 425                 430
Tyr Pro Gly Val Glu Arg Ala Val Ala Gln Ala Val Pro Ser Asp Gly
            435                 440                 445
Ala Ala Asp Arg Leu Ala Leu Trp Cys Val Pro Ala Pro Gly His Glu
450                 455                 460
Leu Ala Glu Arg Gly Leu Val Asp His Leu Arg Gly Arg Leu Pro Asp
465                 470                 475                 480
Tyr Met Val Pro Ser Val Val Leu Val Leu Asp Ser Phe Pro Leu Asn
            485                 490                 495
Ala Asn Gly Lys Ile Asp Arg Arg Glu Leu Ala Ala Arg Leu Ala Ala
            500                 505                 510
```

```
Arg Met Ala Thr Gly Thr His Gly Gly Gly Ala Glu Asp Arg Leu Ala
            515                 520                 525

Ala Val Val Arg Ala Thr Leu Ala Asp Val Thr Gly Gln Gly Pro Leu
        530                 535                 540

Gly Pro Asp Asp Gly Leu Val Glu Asn Gly Val Thr Ser Leu His Leu
545                 550                 555                 560

Ile Asp Leu Gly Ala Arg Leu Glu Asp Val Val Gly Val Ala Leu Ala
                565                 570                 575

Pro Asp Glu Ile Phe Gly Ala Gly Thr Val Arg Gly Val Ala Asp Leu
            580                 585                 590

Ile Arg Thr Lys Arg Ser Arg Gly
            595                 600

<210> SEQ ID NO 43
<211> LENGTH: 1803
<212> TYPE: DNA
<213> ORGANISM: Streptomyces refuineus subspecies thermotolerans

<400> SEQUENCE: 43
atgacagtac gcagcaccgc cacggcggcc ggcacggccg tcgcggcccg gaccaccgtt      60
gagacgatcc cgcaggcgtt cacccgggcg gcgcggcagc acgcggcgcg cgaggcgctc     120
tccgacggtg cgacgaccct gacctacgcc gaactggacg acgccgccaa ccggatcgcc     180
cgcgccctgc gcgagcgcgg gctccggccc ggggagcggg tcggcgtgcg cctcgaccgc     240
ggcctcgccc tctacgaggt cttcctcggc gcgctgaaag ccggcctggt ggtggtcccg     300
ttcaaccccg gcaccccgc ggaccacacg tcgcggatgc accggatgag cgggccggcc     360
ctgacggtga cggactccgg tgccgccgag gggatccccg cggcgacccg tctgccggtc     420
gacgagctgc tggccgacgc ggcgccgctg tccgcgcagc cggtggaccc ggaggtgacg     480
gcggaagcac ccgcgttcat cctgttcacc tccggctcca ccggcgctcc caagggagtg     540
gtgatcgccc accgcgggat cgccagggtc gcccggcacc tcaccggttt cacgcccggc     600
ccgcaggacc gcttcctgca gctcgcgcag ccgtcgttcg ccgcgtcgac caccgacatc     660
tggacgtgcc tgctgcgggg cggccggctc tcggtcgccc cgcaggagct gccgccgctc     720
ggtgacctgg cacggctcat cgtccgcgag cggaccaccg tcctcaacct gcccgtcggc     780
ctgttcaacc tgctggtcga acaccatccg cagaccctcg cgcagacccg gtcggtgatc     840
gtcagcggtg acttcccctc ggccgcgcac ctcgaacgcg ccctcgccgt cgtcggcggt     900
gacctgttca acgccttcgg atgcacggag aactccgcgc tcaccgcagt ccacaagatc     960 accccgcgg acctgtccgg caccgacatc ccggtcggac ggcccatgcc gaccgttgac    1020
atgacggtcc gcgacgagcg gctggaggag tgcgcgcccg ggcagatcgg cgagctgtgc    1080
atcgccggcg acgcctcgc cctcggatac ctcgacgacc cggaactcac ggaccggaag    1140
ttcgtccggc accgcggcag gcggctgctg cggaccgggg acctggccaa gcggaccgag    1200
gaggggagga tcgtactcgc cggccgcacg gaccagatgc tgaaggtgag ggggttccgg    1260
gtcgaaccgc ggcagatcga ggtgacggcc gaggcgtacc ccggcgtcga gcgcgcggtg    1320
gcgcaggccg tgccgagcga cggggcggcg gaccggctcg ccctgtggtg cgtgcccgcg    1380
ccgggacacg aactcgccga acgcggcctc gtggaccacc tgcgcgggcg cctgcccgac    1440
tacatggtgc cgtccgtggt gctggtcctc gactccttcc cgctcaacgc gaacggcaag    1500
atcgaccgca gggagctcgc cgcgcggctc gcggcccgca tggccaccgg gacgcacggc    1560
```

-continued

```
ggtggcgcgg aggaccggct ggcggcggtc gtgcgcgcca ccctggcgga cgtgaccggc    1620
cagggcccgc tcggcccgga cgacggcctg gtggagaacg gggtcacctc cctgcacctg    1680
atcgacctcg cgcccggct cgaggacgtg gtgggcgtcg ccctggcacc cgacgagatc     1740
ttcggcgccg gcaccgtgcg cggtgtggcc gacctgatac gcaccaagcg ttcccgaggc    1800
tga                                                                   1803
```

<210> SEQ ID NO 44
<211> LENGTH: 1446
<212> TYPE: PRT
<213> ORGANISM: Streptomyces refuineus subspecies thermotolerans

<400> SEQUENCE: 44

```
Met Thr Ala Ala Asp Tyr Pro Gln Ala Thr Asp Thr Arg Cys Phe Pro
1               5                   10                  15

Pro Ser Pro Ala Gln Ala Gly Leu Trp Phe Ala Ser Thr Tyr Gly Thr
            20                  25                  30

Asp Pro Thr Ala Tyr Asn Gln Pro Leu Val Leu Arg Leu Gly Thr Leu
        35                  40                  45

Val Asp His Thr Leu Leu His Arg Ala Leu Arg Leu Val His Arg Glu
    50                  55                  60

His Cys Ala Leu Arg Thr Thr Phe Asp Met Asp Ala Asp Gly Glu Leu
65                  70                  75                  80

Arg Gln Ile Val His Gly Glu Leu Glu Pro Ile Val Asp Val Arg Val
                85                  90                  95

His Ala Gly Gly Asp Ser Glu Ala Trp Val Ala Glu Gln Val Glu Gln
            100                 105                 110

Val Ala Ala Thr Val Phe Asp Leu Arg Arg Gly Pro Leu Ala Arg Val
        115                 120                 125

Arg His Leu Arg Leu Val Ala Glu Gly Arg Ser Leu Leu Val Phe Asn
    130                 135                 140

Ile His His Thr Val Phe Asp Gly Leu Ser Trp Lys Pro Tyr Leu Ser
145                 150                 155                 160

Arg Leu Glu Ala Val Tyr Thr Ala Leu Ala Arg Gly Gln Glu Pro Pro
                165                 170                 175

Arg Lys Pro Arg Arg Gln Ala Val Glu Ala Tyr Ala Arg Trp Ser Glu
            180                 185                 190

Arg Trp Ala Asp Ser Gly Ser Leu Ser His Trp Leu Asp Lys Leu Ala
        195                 200                 205

Asp Ala Pro Ala Ala Pro Val Gly Leu Pro Gly Glu Gly Pro Ala
    210                 215                 220

Arg His Val Thr His Lys Ala Val Leu Asp Asp Arg Leu Ser Ala Gln
225                 230                 235                 240

Val Lys Thr Phe Cys Ala Thr Glu Gly Ile Thr Thr Gly Met Phe Phe
                245                 250                 255

Ala Ala Leu Ala Phe Val Leu Leu His Arg His Thr Gly Gln Asp Asp
            260                 265                 270

Ile Leu Leu Gly Val Pro Val Thr Val Arg Gly Ser Gly Asp Ala Glu
        275                 280                 285

Val Val Gly His Leu Thr Asn Thr Val Leu Arg His Arg Leu Ala
    290                 295                 300

Pro Gly Ala Thr Ala Arg Asp Val Leu His Ala Val Lys Arg Asp Met
305                 310                 315                 320

Leu Asp Ala Leu Arg His Arg His Val Pro Leu Glu Ala Val Val Gly
```

-continued

```
                325                 330                 335
Glu Leu Arg Ala Leu Gly Gly Gly Lys Asp Gly Val Gly Asp Leu Phe
            340                 345                 350
Asn Ala Met Leu Thr Val Met Pro Ala Ser Ala Arg Arg Leu Asp Leu
            355                 360                 365
Arg Glu Trp Gly Val Glu Thr Trp Glu His Val Ser Gly Gly Ala Lys
370                 375                 380
Tyr Glu Leu Ala Val Val Asp Glu Thr Pro Gly Arg Tyr Thr Leu
385                 390                 395                 400
Val Val Glu His Thr Ser Ala Ser Ala Gly Ala Gly Ser Leu Ala Ala
            405                 410                 415
Tyr Leu Ala Arg Arg Leu Glu Thr Leu Val Arg Ser Val Met Ala Asp
            420                 425                 430
Pro Asp Thr Asp Val Arg Arg Leu Arg Trp Val Ser Ala Glu Glu Glu
            435                 440                 445
Arg Ala Val Thr Gly Leu Cys Ala Arg Arg Gln Asp Ala Pro Glu Leu
            450                 455                 460
Gly Thr Glu Val Thr Ala Asp Leu Phe Ala Glu Ala Ala Ala Ala
465                 470                 475                 480
Ala Ala Asp Pro Ala Val Val Ala Asp Gly Val Val Thr Ser Tyr Ala
            485                 490                 495
Glu Leu Ala Arg Gln Ala Asp Ala Val Ala Ala Asp Leu Ala Ala Arg
            500                 505                 510
Gly Val Arg Asp Gly Arg Pro Val Ala Val Leu Met Arg Pro Gly Leu
            515                 520                 525
Asp Leu Val Ala Thr Val Gly Ile Leu Arg Ala Gly Gly Ser Tyr
            530                 535                 540
Val Val Leu Asp Ala Asp Gln Pro Arg Glu Arg Leu Ser Phe Ala Leu
545                 550                 555                 560
Ala Asp Ser Gly Ala Lys Ile Leu Leu His Asp Pro Asp Ala Asp Leu
            565                 570                 575
Ala Gly Val Arg Leu Pro Asp Gly Met Gln Thr Ala Thr Met Pro Gly
            580                 585                 590
Thr Glu Gly Gly Val Val Leu Glu Pro Gly Arg Arg Lys Ser Pro Asp
            595                 600                 605
Asp Gln Val Tyr Val Val Tyr Thr Ser Gly Ser Thr Gly Arg Pro Lys
            610                 615                 620
Gly Val Val Leu Leu Glu Pro Thr Leu Thr Asn Leu Val Arg Asn Gln
625                 630                 635                 640
Ala Val Leu Ser Ser His Arg Arg Met Arg Thr Leu Gln Tyr Met Pro
            645                 650                 655
Pro Ala Phe Asp Val Phe Thr Leu Glu Val Phe Gly Thr Leu Cys Thr
            660                 665                 670
Gly Gly Thr Leu Val Pro Pro His Ala Arg Thr Asp Phe Glu
            675                 680                 685
Ala Leu Ala Ala Leu Leu Ala Glu Gln Arg Ile Glu Arg Ala Tyr Phe
            690                 695                 700
Pro Tyr Val Ala Leu Arg Glu Leu Ala Ala Val Leu Arg Ser Ser Gly
705                 710                 715                 720
Thr Arg Leu Pro Asp Leu Arg Glu Val Tyr Val Thr Gly Glu Arg Leu
            725                 730                 735
Val Val Thr Glu Asp Leu Arg Glu Met Phe Arg Arg His Pro Gly Ala
            740                 745                 750
```

```
Arg Leu Ile Asn Ala Tyr Gly Pro Ser Glu Ala His Leu Val Ser Ala
        755                 760                 765

Glu Trp Leu Pro Ala Asp Pro Asp Thr Trp Pro Ala Val Pro Pro Ile
    770                 775                 780

Gly Arg Val Val Ala Gly Leu Asp Ala Arg Val Leu Leu Glu Gly Asp
785                 790                 795                 800

Glu Pro Ala Pro Phe Gly Val Glu Gly Leu Cys Val Ala Gly Pro
                805                 810                 815

Val Val Ser Pro Gly Tyr Ile Gly Leu Pro Glu Lys Thr Arg Gln Ala
        820                 825                 830

Met Val Pro Asp Pro Phe Val Pro Gly Gln Leu Met Tyr Arg Thr Gly
        835                 840                 845

Asp Val Val Leu Asp Pro Asp Gly Arg Leu His Tyr Arg Gly Arg
        850                 855                 860

Ala Asp Asp Gln Ile Lys Ile Arg Gly Tyr Arg Val Glu Pro Gly Glu
865                 870                 875                 880

Val Glu Ala Ala Leu Glu Arg Val Leu His Val Glu Ala Ala Val
                885                 890                 895

Ile Ala Val Pro Ala Gly His Asp Arg Ala Leu His Ala Phe Val Arg
                900                 905                 910

Ser Gly Gln Glu Pro Pro Ser Asn Trp Arg Ser Arg Leu Gly Thr Val
        915                 920                 925

Leu Pro Gly Tyr Met Ile Pro Arg Gly Ile Thr Arg Val Asp Ala Ile
    930                 935                 940

Pro Val Thr Pro Asn Gly Lys Thr Asp Arg Arg Ala Leu Glu Ala Arg
945                 950                 955                 960

Leu Ala Asp Arg Ala Gly Thr Glu Pro Ala Gly Gly Gly Met Asp
                965                 970                 975

Trp Thr Asp Cys Glu Arg Ala Ile Ala Asp Leu Trp Thr Glu Val Leu
        980                 985                 990

Gly His Gly Pro Ala Thr Pro Asp Asp Asp Phe Phe Glu Leu Gly Gly
        995                 1000                1005

His Ser Leu Leu Ala Ala Arg Leu His Arg Leu Val Arg Gln Arg
    1010                1015                1020

Leu Asp Ser Asp Val Pro Leu Ser Val Leu Leu Gly Thr Pro Thr
    1025                1030                1035

Val Arg Gly Met Ala Gly Ser Leu Ala Gly Arg Gly Ala Ser Gly
    1040                1045                1050

Thr Val Asp Leu Arg Glu Glu Ala Arg Leu His Asp Leu Val Val
    1055                1060                1065

Gly Glu Arg Arg Glu Pro Ala Asp Gly Ala Val Leu Leu Thr Gly
    1070                1075                1080

Ala Thr Gly Phe Leu Gly Ser His Leu Leu Asp Glu Leu Gln Arg
    1085                1090                1095

Ala Gly Arg Arg Val Cys Cys Leu Val Arg Ala Gly Ser Val Glu
    1100                1105                1110

Glu Ala Arg Gly Arg Leu Arg Ala Ala Phe Glu Lys Phe Ala Leu
    1115                1120                1125

Asp Pro Ser Arg Leu Asp Arg Ala Glu Ile Trp Leu Gly Asp Leu
    1130                1135                1140

Ala Arg Pro Arg Leu Gly Leu Gly Asp Gly Phe Ala Ala Arg Ala
    1145                1150                1155
```

```
His Glu Val Gly Glu Val Tyr His Ala Ala His Ile Asn Phe
    1160                1165            1170

Ala Val Pro Tyr His Thr Val Lys Arg Thr Asn Val Asp Gly Leu
    1175                1180            1185

Arg Arg Val Leu Asp Phe Cys Gly Val Asn Arg Thr Pro Leu Arg
    1190                1195            1200

Leu Ile Ser Thr Leu Gly Val Phe Pro Pro Asp Ser Ala Pro Gly
    1205                1210            1215

Val Ile Gly Glu Asp Thr Val Pro Gly Asp Pro Ala Ser Leu Gly
    1220                1225            1230

Ile Gly Tyr Ser Gln Ser Lys Trp Val Ala Glu His Leu Ala Leu
    1235                1240            1245

Gln Ala Arg Gln Ala Gly Leu Pro Val Thr Val Tyr Arg Val Gly
    1250                1255            1260

Arg Ile Ala Gly His Ser Arg Thr Gly Ala Cys Arg His Asp Asp
    1265                1270            1275

Phe Phe Trp Leu Gln Met Lys Gly Phe Ala Leu Leu Gly Arg Cys
    1280                1285            1290

Pro Asp Asp Ile Ala Asp Ala Pro Ala Val Asp Leu Leu Pro Val
    1295                1300            1305

Asp Tyr Val Ala Arg Ala Ile Val Arg Leu Ala Glu Gly Lys Pro
    1310                1315            1320

Asp Asp Ala Asn Trp His Leu Tyr His Pro Gln Gly Leu Ala Trp
    1325                1330            1335

Ser Val Ile Leu Glu Thr Ile Arg Ala Glu Gly Tyr Ala Val Ser
    1340                1345            1350

Pro Ala Thr Arg Ser Ala Trp Leu Ala Ala Leu Glu Arg Gln Ala
    1355                1360            1365

Gly Thr Glu Ala Gln Gly Gln Gly Leu Gly Pro Leu Val Pro Leu
    1370                1375            1380

Met Arg Glu Gly Ala Met Arg Leu Gly Ser His Ser Phe Asp Asn
    1385                1390            1395

Gly Arg Thr Met Arg Ala Val Ala Asp Val Gly Cys Pro Cys Pro
    1400                1405            1410

Pro Ala Asp Thr Glu Trp Ile Arg Arg Met Phe Glu Tyr Phe Arg
    1415                1420            1425

Ala Ile Gly Ser Val Pro Pro Asp Gly Val Thr Leu Gly Gly
    1430                1435            1440

His Val Ala
    1445
```

<210> SEQ ID NO 45
<211> LENGTH: 4341
<212> TYPE: DNA
<213> ORGANISM: Streptomyces refuineus subspecies thermotolerans

<400> SEQUENCE: 45

```
atgactgctg ccgattaccc gcaagcgacc gacacccggt gcttcccgcc gtcgccggcc    60
caggccggcc tgtggttcgc gagcacctac gggaccgatc ccaccgcgta caaccagccc   120
ctggtcctgc gcctgggcac cctggtggac cacaccctcc tccaccgggc gctgcgcctg   180
gtccaccggg agcactgcgc gctgcgcacc acgttcgaca tggatgcgga cggtgagctg   240
cggcagatcg tgcacggcga gctggaaccg atcgtcgacg tgcgcgtcca cgccggcggc   300
gactccgagg cctgggtggc cgagcaggtg gagcaggtcg cggccaccgt cttcgacctg   360
```

-continued

```
cgcaggggcc cgctcgcgcg ggtgcggcac ctgcgcctgg tggcggaggg ccggagcctg      420
ctggtcttca acatccacca caccgtcttc gacggcctgt cgtggaagcc ctacctcagc      480
cggctggaag cggtctacac cgccctcgcc cgcggacagg aaccaccccg gaagcccgg       540 cgccaggcgg tcgaggcgta cgcgcggtgg tccgagcggt gggcggactc cggatcgctg      600
tcccactggc tggacaagct ggcggacgcg cccgcggcgg cgcccgtcgg actgccgggg      660
gagggccccg cgcgccacgt gacccacaag gccgtcctcg acgaccggct gtccgcgcag      720
gtgaagacgt tctgcgccac cgagggcatc accaccggca tgttcttcgc cgccctcgcc      780
ttcgtgctgc tgcaccggca caccgggcag gacgacatcc tcctcggcgt cccggtcacc      840
gtgcggggga gcgcgacgc cgaggtcgtc gggcacctga ccaacacggt cgtgctgcgg       900
caccggctgg ccccggagc gaccgcccgc gacgtcctgc acgcggtgaa gcgggacatg       960
ctcgacgcgc tgcggcaccg gcatgtcccg ctggaggcgg tggtcggcga actccgcgcc     1020
ctgggaggcg gcaaggacgg cgtcggcgac ctgttcaacg cgatgctcac ggtgatgccg     1080
gcctccgccc gccgcctga cctgcgcgag tggggagtgg agacgtggga acacgtctcc      1140
gggggcgcca agtacgaact ggcggtcgtg gtggacgaga cgccgggccg ctacacgctg     1200
gtcgtcgagc acacctcggc ctcggccggc gccggaagcc tcgcggcgta cctggcgcgg     1260
cgcctggaga cgctcgtgcg cagcgtgatg gccgacccgg acacgacgt ccgccggctg      1320 cgctgggtga gcgcggagga ggagcgggcg gtcaccggcc tgtgcgcgcg caggcaggac     1380
gcgcccgagc tgggcaccga ggtgacggcc gacctgttcg ccgaggccgc cgcggcggcg     1440
gccgccgacc ccgccgtggt cgcggacggc gtggtgacgt cctacgccga gctggcgcgg     1500
caggccgacg ccgtggcggc ggacctggcc gcccggggag tgcgggacgg gcggccggtg     1560
gccgtgctga tgcggccggg gctcgacctg gtggcgaccg tcgtcggcat cctgcgggcg     1620
ggcggcagct acgtggtcct cgacgccgac caaccgcggg aacggctgtc tttcgcgctg     1680
gccgacagcg cgcgcaagat cctgctgcac gacccggacg ccgacctcgc gggcgtacgg     1740
ctgcccgacg ggatgcagac cgccaccatg cccggcacgg agggcgggt cgttctcgag      1800 cccggtcgca ggaagtcgcc ggacgaccag gtgtacgtcg tctacacatc ggggtccacc     1860
gggcgcccca aggggtggt gctgctggag ccgaccctga ccaacctcgt gcgcaaccag      1920
gccgtactgt cctcgcaccg ccggatgcgc accctgcagt acatgccgcc ggccttcgac     1980
gtgttcaccc tggaggtctt cgggaccctg tgcaccggcg gcacgctggt cgtcccgccc     2040
ccgcacgccc gcaccgactt cgaggccctg gccgcgctgc tggccgagca gcgcatcgag     2100
cgggcgtact tcccgtacgt cgcgctccgc gagctcgccg ccgtcctgcg ctcgtccggg     2160
acgcgcctgc cggacctgcg cgaggtgtac gtcaccggcg agcgactggt ggtcaccgag     2220
gatctgcggg agatgttccg gcggcacccc ggagcccggc tgatcaacgc ctacgggccg     2280
tccgaggccc acctggtcag cgcggagtgg ctgccggccg atcccgatac ctggcccgcg     2340
gtcccgccga tcgccgggt ggtcgccggc ctcgacgccc gggtgctcct ggaggggac       2400 gagccggcgc cgttcggcgt cgaggggag ctgtgcgtgg ccggaccggt cgtctcgccc      2460
ggatacatcg gactgccgga gaagacccgc caggcgatgg tccccgaccc gttcgtcccc     2520
ggccagctga tgtaccggac cggcgacgtg gtcgtgctgg accggacgg gcgcctgcac      2580 taccgggcc gggccgacga ccagatcaag atccgcgggt accgcgtcga acccggtgag      2640
gtcgaggcgg ccctggagcg ggtgctgcac gtggaagcgg ccgcgtgat cgccgtaccg     2700
```

-continued

```
gcgggccacg accgggcgct gcacgccttc gtgcggagcg ccaggagcc gccctcgaac    2760
tggcgctccc gcctcgggac cgtcctgccc ggatacatga tcccgcgggg gatcacccgg    2820
gtcgacgcca tcccggtgac gccgaacggg aagaccgacc gccgcgcact cgaggcacgg    2880
ctcgccgacc gcgccgggac ggagcccgcc ggggcggcg gcatggactg gacggactgc    2940
gaacgcgcga tcgccgacct gtggacggag gtcctcggac acgggcccgc gacaccggac    3000
gacgacttct tcgagctggg cggcactca ctgctcgccg cccgcctgca ccggctggtc    3060
cggcagcgcc tggacagcga cgtcccgctc tcggtgctgc tcggcacgcc caccgtgcgc    3120
ggcatggccg gcagcctcgc cggccggggc gcctcgggga cggtcgacct cgcgaagag    3180
gcccgactgc acgacctcgt cgtgggcgag cgccgggaac cggccgacgg cgcggtgctg    3240
ctcaccgggg cgaccggctt cctcggcagc cacctcctcg acgaactcca gcgtgccggg    3300
cgccgcgtgt gctgcctggt ccgcgccggc agcgtcgagg aggcgcgggg ccggctgcgg    3360
gcggcgttcg agaagttcgc gctcgacccc tcccggctcg accgggccga gatatgcctg    3420
ggcgacctcg cccggccccg gctcggtctc ggcgacgggt tcggcggcg cgcacacgag    3480
gtcggcgagg tgtaccacgc ggccgcgcac atcaacttcg ccgttccgta ccacaccgtc    3540
aagcgcacca acgtcgacgg cctgcggcgc gtgctcgact tctgcggcgt caaccgcacg    3600
ccgttgcgcc tgatctccac cctgggcgtc ttcccgccgg actccgcgcc cggtgtgatc    3660
ggcgaggaca cggttccggg cgacccggcg tcgctcggca tcgggtactc gcagagcaag    3720
tgggtcgccg agcacctcgc gttgcaggcg cggcaggccg gactgccggt caccgtgtac    3780
cgcgtcggcc ggatcgccgg gcacagccgc accggggcgt gccggcacga cgacttcttc    3840
tggctgcaga tgaagggctt cgcgctgctc ggccgctgcc cggacgacat cgccgacgca    3900
ccggccgtcg acctgctgcc ggtggattac gtggcccggg cgatcgtccg gctggccgag    3960
ggcaagccgg acgacgccaa ctggcacctg taccacccgc aggggctcgc ctggtccgtg    4020
atcctggaga cgatccgcgc ggaagggtac gcggtgagcc cggccacccg atccgcgtgg    4080
ctggccgcac tggaacggca ggccgggacc gaggcccagg gccagggact cgggccgctg    4140
gtgcccctga tgcgggaggg cgcgatgcgt ctcggctccc attcgttcga caacgggaga    4200
accatgcgtg ctgtgccga tgtcggatgc ccgtgtccgc cggcggacac ggaatggatc    4260
cggcgaatgt tcgagtactt ccgtgccatc ggctcggtgc cgccgccgga cggggtcacc    4320
ctgggaggtc atgttgcctg a                                              4341
```

<210> SEQ ID NO 46
<211> LENGTH: 454
<212> TYPE: PRT
<213> ORGANISM: Streptomyces refuineus subspecies thermotolerans

<400> SEQUENCE: 46

```
Val Val Val Ile Gly Ala Gly Pro Val Gly Cys Ala Leu Ala Leu Leu
1               5                   10                  15

Leu Arg Arg Gln Gly Leu Glu Val Asp Val Phe Glu Arg Glu Pro Glu
            20                  25                  30

Ser Val Gly Gly Gly Ser Gly His Ser Phe Asn Leu Thr Leu Thr Leu
        35                  40                  45

Arg Gly Leu Gly Cys Leu Pro Arg Ser Val Arg Arg Leu Tyr Leu
    50                  55                  60

Gln Gly Ala Val Leu Val Lys Arg Ile Ile His His Arg Asp Gly Ala
65                  70                  75                  80
```

```
Ile Ser Thr Gln Pro Tyr Gly Thr Ser Asp Thr His His Leu Leu Ser
                85                  90                  95

Ile Pro Arg Arg Val Leu Gln Asp Ile Leu Arg Asp Gln Ala Leu Arg
            100                 105                 110

Val Gly Ala Arg Ile His Tyr Gly Arg Ala Cys Val Asp Val Asp Thr
            115                 120                 125

Gly Arg Pro Ala Ala Leu Leu Arg Asp Gly Asp Gly Thr Ser Trp
        130                 135                 140

Val Glu Ala Asp Leu Leu Val Gly Cys Asp Gly Ala Asn Ser Ala Val
145                 150                 155                 160

Arg Gly Ala Val Ala Ala His Pro Ala Asp Met Trp Val Arg Arg
                165                 170                 175

Arg Thr Ile Ala His Gly His Ala Glu Ile Thr Met Asp Tyr Gly Asp
            180                 185                 190

Ala Asp Pro Thr Gly Met His Leu Trp Pro Arg Gly Asp His Phe Leu
            195                 200                 205

Gln Ala Gln Pro Asn Arg Asp Arg Thr Phe Thr Thr Ser Leu Phe Lys
            210                 215                 220

Pro Leu Thr Gly Asp Gly Pro Arg Pro His Phe Thr Gly Leu Pro Ser
225                 230                 235                 240

Ala Asp Ala Val Ser Glu Tyr Cys Ala Thr Glu Phe Pro Asp Val Phe
                245                 250                 255

Gly Arg Met Ala Gly Val Gly Arg Asp Leu Thr Ala Arg Arg Pro Gly
            260                 265                 270

Arg Leu Arg Ile Ile Asp Cys Ala Pro Tyr His His Arg Arg Thr Val
        275                 280                 285

Leu Val Gly Asp Ala Ala His Thr Val Pro Phe Phe Gly Gln Gly
    290                 295                 300

Ile Asn Cys Ser Phe Glu Asp Ala Ala Thr Leu Ala Gly Leu Leu Glu
305                 310                 315                 320

Lys Phe Gln Phe Ala Arg Arg Asp Glu Ser Gly Thr Ile Val Glu Ala
                325                 330                 335

Val Ala Asp Glu Tyr Ser Asp Ala Arg Val Lys Ala Gly His Ala Leu
            340                 345                 350

Ala Glu Leu Ser Leu Arg Asn Leu Glu Leu Ser Asp His Val Asn
        355                 360                 365

Ser Arg Ala Phe Leu Ala Arg Ala Leu Glu Arg Leu His Glu
370                 375                 380

Leu His Pro Asp Leu Phe Thr Pro Leu Tyr Gln Leu Val Ala Phe Thr
385                 390                 395                 400

Asn Val Pro Tyr Asp Ala Val Gln Arg Met His Gly Glu Phe Gly Ala
                405                 410                 415

Val Leu Asp Ser Leu Cys Arg Gly Arg Asp Leu Arg Arg Glu Arg Asp
            420                 425                 430

Ala Ile Ile Arg Glu Phe Val Asp Val Tyr Asp Ser Gly Phe Ala Ala
        435                 440                 445

Gly Arg Leu Arg Thr Gly
    450
```

<210> SEQ ID NO 47
<211> LENGTH: 1365
<212> TYPE: DNA
<213> ORGANISM: Streptomyces refuineus subspecies thermotolerans

<400> SEQUENCE: 47

```
gtggtggtca tcggcgccgg accggtcggt tgcgccctgg cgctgctgct gcggcggcag      60
gggctggagg tggacgtctt cgaacgggag ccggagtcgg tgggcggcgg gtccggtcac     120
tccttcaacc tcacgctcac cctgcgcggg ctcggctgcc tgccccgatc cgtcaggcgc     180
cgcctctacc tgcagggcgc ggtgctggtg aaacgcatca tccaccaccg cgacggcgcg     240
atctccacgc agccgtacgg cacgtcggac acccatcacc tgctgtccat tccgcgccgg     300
gtcctccagg acatcctgcg cgaccaggcc ctgcgggtcg gcgcgcggat ccactacgga     360
cgcgcgtgcg tcgacgtgga caccggacgc ccggcgcgc tgctgcgcga cggcgacggc     420
ggcacctcgt gggtggaggc ggacctgctg gtcggttgcg acggggccaa cagcgcggtg     480
cgcggcgccg tcgccgcggc ccacccggcc gacatgtggg tgcggcgccg cacgatcgcc     540
catggccacg cggagatcac gatggactac ggggacgccg acccgaccgg catgcacctg     600
tggccgcggg cgaccacttc ctgcaggcc cagcccaacc gcgacaggac gttcaccacg     660
agtctgttca agccgctgac gggcgacggc ccgcggccgc acttcaccgg cctgccgtcg     720
gccgacgcgg tcagcgagta ctgcgcgacg gagttccccg acgtcttcgg ccggatggcc     780
ggggtcggca gggacctcac cgcccgtcgt cccggcaggc tgcggatcat cgactgcgcc     840
ccgtaccacc accggcgcac cgtgctggtc ggagacgccg cgcacaccgt cgtcccgttc     900
ttcggacagg gcatcaactg cagtttcgag gacgccgcca cgcttgccgg gctgctggag     960
aagttccagt tcgcccgccg cgacgagagc gggaccatcg tggaggccgt cgccgacgag    1020
tacagcgacg cacgggtgaa ggcgggccac gcactggccg agctgtcgct gcgcaacctc    1080
gaggagctgt cggaccacgt gaacagccgc gcgttcctgg cccgccgtgc gctggagcgc    1140
cggctgcacg agctgcaccc cgacctgttc accccgctct accagctggt cgcgttcacc    1200
aacgtgccct atgacgcggt gcagcggatg cacggcgagt tcggcgccgt actggactcg    1260
ctgtgccgcg ggcgtgacct acggcgcgaa cgggacgcca tcatcaggga gttcgtcgac    1320
gtgtacgatt ccggattcgc ggccgggaga ctgcgcacgg ggtga                    1365
```

<210> SEQ ID NO 48
<211> LENGTH: 478
<212> TYPE: PRT
<213> ORGANISM: Streptomyces refuineus subspecies thermotolerans

<400> SEQUENCE: 48

```
Val Pro Glu Pro Thr Gln His Ser Val Arg Glu Thr Phe Asp Ser Gly
1               5                   10                  15

Ile Pro Pro Gln His Gly Thr Ser Ser Val Ile Val Val Gly Ala Gly
            20                  25                  30

Leu Ala Gly Leu Ala Ala Ala His Glu Leu Thr Arg Gln Gly Val Thr
        35                  40                  45

Val Thr Val Leu Glu Ala Asp Ser Arg Pro Gly Gly Arg Thr Trp Thr
    50                  55                  60

Leu Arg Glu Pro Phe Ala Asp Gly Leu Arg Ala Glu Gly Ala Met
65                  70                  75                  80

Thr Val Thr Glu His Cys His Tyr Thr Met His Tyr Leu Lys Glu Met
                85                  90                  95

Gly Ile Gly Thr Glu Pro Ser Asp Leu Val Asp Thr Asp Phe Gly Tyr
            100                 105                 110

His Arg Asn Gly Val Arg Ile Pro Pro Asp Lys Val Gly Glu His Ala
        115                 120                 125
```

-continued

```
Asp Leu Leu Gly Leu His Pro Asp Glu Arg His Leu Thr Val Glu Gly
            130                 135                 140

Met Ile Ala Arg Tyr Val Thr Glu Phe Asn Glu Lys Leu Gly Pro Glu
145                 150                 155                 160

Ile Ala Gln Pro Val Trp Ala Pro Thr Pro Arg Leu Leu Glu Leu Asp
                165                 170                 175

Arg Val Ser Val Arg Arg Val Leu Glu Glu Arg Gly Ala Ser Ala Ala
            180                 185                 190

Ala Ile Gly Leu Met Glu Pro Phe Phe Leu Glu Met Arg Gly Gly Glu
        195                 200                 205

Leu Glu Ser Ala Ser Ala Met Ala Trp Ala Arg Tyr Glu Ser Gly Pro
    210                 215                 220

Arg Ser Phe Ser Thr Ala Gly Ala Gln Trp Tyr Lys Val Glu Gly Gly
225                 230                 235                 240

Thr Asp Met Leu Ala Arg Ala Leu Ala Ser Arg Leu Gly Glu Arg Ile
                245                 250                 255

Leu Tyr Arg Lys Pro Val Val Arg Ile Ala Gln Asp Asp Arg Glu Ala
            260                 265                 270

Gln Val Thr Phe Leu Asp His Gly Arg Leu Arg Thr Leu Cys Ala Asp
        275                 280                 285

Arg Val Val Thr Ala Pro Phe Ser Ser Met Arg Arg Val Asn Leu
    290                 295                 300

Ser Met Ala Arg Leu Ser Ala Ala Lys His Ala Ala Ile Arg Arg Leu
305                 310                 315                 320

Arg Tyr Ala Ser Thr Val Arg Val Phe Leu Gln Met Arg Arg Lys Phe
                325                 330                 335

Trp Pro Glu Arg Arg Leu Met Leu Ser Thr Asp Thr Ala Val Arg Thr
            340                 345                 350

Val Arg Asp Ala Thr Pro His Leu Pro Gly Pro Arg Arg Ile Val Glu
        355                 360                 365

Cys Trp Leu Thr Gly Trp Gln Ala Gln Ala Ala Ala Met Ser Pro
    370                 375                 380

Glu Glu Arg Val Ala Tyr Ala Leu Asn Glu Leu Glu Pro Ile Leu Pro
385                 390                 395                 400

Gly Ala Arg Glu Asn Phe Glu Leu Gly Thr Ser Val Ala Trp Asp Asn
                405                 410                 415

Glu Pro Tyr Ala Ala Gly Ala Tyr Ile Leu Pro Glu Lys Gly His Ser
            420                 425                 430

Glu Leu Met Ala Ala Ile Arg Ala Pro Glu Gly Arg Ile His Phe Ala
        435                 440                 445

Gly Glu His Thr Ala Phe Glu Pro Asn Gly Gly Ser Met Asn Tyr Ala
    450                 455                 460

Leu Glu Ser Ser Ile Arg Val Leu Met Glu Met Ser Ser Pro
465                 470                 475
```

<210> SEQ ID NO 49
<211> LENGTH: 1437
<212> TYPE: DNA
<213> ORGANISM: Streptomyces refuineus subspecies thermotolerans

<400> SEQUENCE: 49
gtgccggagc caacccagca cagcgtcagg gagaccttcg acagcggcat cccgcctcag    60
cacggcacct cctcggtcat cgtggtcggc gccgggctgg ccggtctggc gcggccccac    120
gaattgacga ggcagggcgt cacggtcacc gtgctcgaag ccgacagccg tccgggagga    180

-continued

```
cggacgtgga ccctgcgcga gccgttcgcc gacggcctcc gcgcggaggc cggcgccatg      240
acggtgacgg agcactgcca ctacaccatg cactatctga aggagatggg gatcgggacc      300
gaaccgagcg acctcgtcga cacggacttc gggtaccacc gcaacggcgt gcgaataccc      360
cccgacaagg tcggcgagca cgccgacctc ctgggcctgc accccgacga gcggcacctc      420
accgtcgagg gcatgatcgc cagatatgtg accgagttca cgagaagct cggcccggag       480 atcgcgcagc ccgtctgggc accgacaccg cgtctgctgg agctcgaccg ggtctccgtg      540
cgccgggtgc tcgaggagcg tggcgcttcc gccgccgcga tcggcctcat ggaaccgttc      600
ttcctggaga tgcgcggagg cgagctggaa tccgcctcgg ccatggcgtg ggcccgctac      660
gagtcgggcc cacggtcctt ctccacggcg ggcgcccagt ggtacaaggt cgagggcggt      720
acggacatgc tcgcccgggc gctggcgagc aggctcgggg agcggatcct ctaccgcaag      780
ccggtcgtcc gcatcgccca ggacgaccgc gaggcgcagg tgaccttcct cgaccacggc      840
cggctccgga cgttgtgcgc ggaccgggtc gtcgtcaccg cgccgttcag cagcatgcgg      900
cgcgtcaact tgtcgatggc ccgcctgtcg gcggcgaagc acgcggcgat ccggcggctc      960
cgctacgcgt cgacggtccg tgtcttcctg cagatgcgca ggaagttctg gccggagagg      1020
cggttgatgc tgtccacgga cacggcggtc cgcacggtcc gcgatgccac accgcacctg      1080
cccgggcccc gcaggatcgt cgagtgctgg ctcaccggat ggcaggcgca ggcggccgcg      1140
gccatgagcc ccgaggagcg cgtcgcctac gcgctgaacg aactggagcc gatccttccc      1200
ggagcgcggg agaacttcga gctgggcacc tcggtggcct gggacaacga gccgtacgcg      1260
gcgggcgcgt acatcctccc ggagaagggc cacagcgaac tgatggcggc catcagggcc      1320
ccggaggggc gcatccactt cgcgggcgag cacaccgcgt cgagcccaa cggcgggtcg       1380 atgaactacg cgctggagtc gtcgatccgg gtgctcatgg agatgtcgtc cccgtga         1437
```

<210> SEQ ID NO 50
<211> LENGTH: 273
<212> TYPE: PRT
<213> ORGANISM: Streptomyces refuineus subspecies thermotolerans

<400> SEQUENCE: 50

```
Val Thr Glu Gly Gly Trp Thr Leu Leu Asp Asn Gly Leu Lys Val Leu
1               5                   10                  15

Ile Val Gly Asp Cys Glu Gly Leu Ala Glu Met Ile Arg Asp Leu Lys
            20                  25                  30

Arg His Gly Phe Glu Ala Glu Ser Val Thr Thr Gly Ala Glu Ala Met
        35                  40                  45

Ala Ser Tyr Arg Glu His Asp Val Val Leu Ile Asp Leu Asp Leu Lys
    50                  55                  60

Asp Phe Asp Gly Leu Thr Leu Cys Arg Gln Ile Arg Asn Ala Ser Asp
65                  70                  75                  80

Ile Pro Met Ile Gly Phe Ala Cys Ser Ala Ala Leu Glu Arg Val Leu
                85                  90                  95

Ala Leu Glu Ala Gly Cys Asp Asp Cys Val Val Lys Pro Tyr His Ser
            100                 105                 110

Arg Glu Leu Val Ala Arg Leu Gly Ala Leu Leu Arg Arg Ala Arg Val
        115                 120                 125

Leu Ser Pro Pro Ala Leu Thr Val Gly Lys Leu Gln Ile Tyr Pro Thr
    130                 135                 140

Leu Arg Gln Val Arg Val Glu Asn Arg Pro Ile Glu Thr Thr Arg Lys
```

-continued

```
               145                 150                 155                 160
Glu Phe Glu Leu Leu His Leu Leu Ala Ala Glu Pro Asp Lys Leu Phe
                165                 170                 175
Ser Arg Ala Glu Leu Leu Arg Arg Val Trp Asp Tyr Asp Asp Val Ser
            180                 185                 190
Ala Glu Val Thr Ser Leu Ala Ser Arg Thr Ile Asp Thr His Val Ser
        195                 200                 205
Ser Leu Arg Lys Lys Leu Gly Ser Pro Asp Trp Ile Ile Thr Val Arg
    210                 215                 220
Gly Val Gly Phe Arg Phe Asn Gly Glu Ala Thr Arg Asp Glu Pro Cys
225                 230                 235                 240
Pro Gly Lys Glu Pro Ala Arg Ala Asn Gly Thr Ser Gly His His Ala
                245                 250                 255
Pro Trp Pro Pro Ser Arg Arg Ile Phe Arg Glu Val Asn Ser Ala Pro
                260                 265                 270
Gln
```

<210> SEQ ID NO 51
<211> LENGTH: 822
<212> TYPE: DNA
<213> ORGANISM: Streptomyces refuineus subspecies thermotolerans

<400> SEQUENCE: 51

```
gtgaccgaag ggggttggac attgcttgac aacggcttaa aggtgctgat cgtggggac      60
tgcgagggcc tcgcagaaat gatcagagac ctcaagcggc acggtttcga ggccgagtcg    120
gtgacgaccg cgccgaggc catggcctcc taccgcgaac acgacgtggt cctgatcgac     180
ctcgatctga aggacttcga cggtctgacc ctgtgccggc agatccgcaa cgccagtgac    240
atcccgatga tcggcttcgc ctgctccgcc gcgctcgagc gcgtcctcgc cctggaggcg    300
ggctgcgacg actgcgtggt gaagccgtac acagccgtg aactcgtggc gcgcctgggc     360
gcgctgctcc gacgggcccg cgtgctgtcc ccaccggcgc tgacggtcgg caagctgcag    420
atctaccca ccctgcgcca ggtgagggtc gagaaccggc cgatcgagac cacccgcaag     480
gagttcgaac tgctccacct gctcgccgcc gaacccgaca gctcttctc cagagccgag     540
ctgctgcggc gggtatggga ctacgacgac gtcagcgcgg aagtgacatc gctggccagc    600
cgcacgatcg acacacacgt cagcagcctg cgcaagaagc tcggctcgcc cgattggatc    660
atcaccgtcc gcggggtcgg cttccggttc aacggggaag cgacccgcga cgagccctgc    720
ccgggcaagg agccggcccg cgcgaacggc acctcgggac accacgcgcc ctggccgccg    780
tcgcgcagga tcttccgtga ggtgaactcg gcgccgcagt ga                       822
```

<210> SEQ ID NO 52
<211> LENGTH: 417
<212> TYPE: PRT
<213> ORGANISM: Myxococcus xanthus

<400> SEQUENCE: 52

```
Thr Tyr Gln Arg Glu Gly Leu Asp Ala Val Leu Met Asn Gln His Ala
1               5                   10                  15
Thr Arg Leu Asp Ala Asp Ala Ser Leu Ala Pro Asp Ile Ser Pro Glu
            20                  25                  30
Gly Leu Pro Leu Ala Asn Tyr Leu Ala Pro Ser Ser Val Leu Leu Thr
        35                  40                  45
Gly Ala Thr Gly Tyr Leu Gly Ala Phe Leu Leu Glu Gln Leu Leu Lys
```

```
            50                  55                  60
Arg Thr Arg Ala Thr Val Tyr Cys Leu Val Arg Ala Ala Asp Pro Ala
 65                  70                  75                  80

Gln Ala Met Asp Arg Val Arg Ala Thr Met His Gln Tyr Leu Val Trp
                 85                  90                  95

Asp Glu Ala Tyr Ala Glu Arg Ile Arg Pro Leu Val Gly Asp Leu Gly
                100                 105                 110

Lys Pro Arg Leu Gly Leu Ser Arg Glu Glu Trp Glu Arg Leu Gly Leu
                115                 120                 125

Glu Leu Asp Ser Ile Tyr His Asn Gly Ala Leu Val Asn Phe Val Tyr
130                 135                 140

Pro Tyr Ser Ala Leu Arg Gly Pro Asn Val His Gly Thr Gln Glu Val
145                 150                 155                 160

Leu Arg Leu Gly Cys Gln His Arg Leu Lys Ala Val His Tyr Val Ser
                165                 170                 175

Thr Ile Asp Val Leu Leu Ala Thr His Met Pro Arg Pro Phe Met Glu
                180                 185                 190

Asp Asp Ala Pro Leu Arg Asn Pro Ile Glu Val Pro Gly Gly Tyr Thr
                195                 200                 205

Gly Ser Lys Trp Val Ala Glu Lys Val Val Asn Ile Ala Arg Ala Arg
210                 215                 220

Gly Ile Pro Val Cys Ile Tyr Arg Pro Gly Leu Ile Leu Ser His Glu
225                 230                 235                 240

Glu Thr Gly Ala Thr Gln Thr Asn Asp Tyr Leu Leu Val Ala Phe Arg
                245                 250                 255

Gly Tyr Val Pro Met Gly Ile Ile Pro Asp Tyr Pro Arg Ile Phe Asp
                260                 265                 270

Thr Ile Pro Val Asp Tyr Ala Ala Lys Ala Ile Val His Ile Ser Thr
                275                 280                 285

Gln Arg Glu Ala Leu Gly Arg Phe Phe His Leu Phe Asn Pro Ala Pro
                290                 295                 300

Val Ser Leu Arg Arg Phe Cys Asp Trp Ile Arg Ser Tyr Gly Tyr Ala
305                 310                 315                 320

Phe Asp Ile Val Pro Phe Asp Glu Ala Arg Arg Gln Ala Leu Asp Val
                325                 330                 335

Asp Thr Ser His Pro Leu Tyr Pro Leu Val Pro Leu Ile Arg Asp Ala
                340                 345                 350

Glu Ala Glu Pro Gln Glu Ser Leu Asp Pro Ala Phe Ile Asp Gln Leu
                355                 360                 365

Arg Pro Asp Leu Glu Cys Arg Ser Ala Val Glu Val Leu Ala Gly Ser
                370                 375                 380

Asp Ile Arg Cys Pro Pro Met Thr Glu Glu Leu Ala His Arg Cys Leu
385                 390                 395                 400

Gln Tyr Leu Val Asp Ile Gly Phe Leu Gln Arg Pro Glu Val Leu Arg
                405                 410                 415

Ala
```

<210> SEQ ID NO 53
<211> LENGTH: 410
<212> TYPE: PRT
<213> ORGANISM: Stigmatella aurantiaca

<400> SEQUENCE: 53

Ala Arg Ala Val Glu Ala Ala Lys Thr Gly Ser Leu Pro Ala His Asp

```
1               5                    10                   15
Val Thr Val Glu Met Glu Ala Asp Ala Val Leu Asp Ala Glu Ile Ala
            20                  25                  30
Leu Gly Lys Ala Leu Pro Pro Val Thr Gly Ala Leu Arg Thr Ile Leu
            35                  40              45
Leu Thr Gly Ala Thr Gly Phe Leu Gly Ala Phe Leu Leu Glu Glu Leu
50                      55                  60
Cys Arg Arg Thr Asp Ala Arg Ile Tyr Cys Leu Val Arg Ser Lys Thr
65                  70              75                      80
Glu Gln Glu Gly Met Asn Arg Ile Arg Lys Asn Leu Glu Ser Tyr Ser
                85                  90                  95
Leu Trp Asn Glu Ala Leu Ala Pro Arg Ile Val Pro Val Arg Gly Asp
            100                 105                 110
Ile Gly Gln Pro Leu Leu Gly Leu Ser Glu Lys Glu Phe Gln Arg Leu
            115                 120                 125
Ser Glu Glu Ile Asp Ala Ile Tyr His Asn Gly Ala Leu Val Asn Phe
            130                 135             140
Leu Tyr Pro Tyr Glu Ser Met Arg Ala Ala Asn Val Leu Gly Thr Arg
145                     150                 155                 160
Glu Ile Leu Arg Leu Ala Thr Arg Thr Arg Ile Lys Pro Leu His Tyr
                165                 170                 175
Val Ser Thr Val Ser Val Leu Pro Leu Gly Arg Lys Ala Pro Ile Arg
                180                 185                 190
Glu Asp Glu Pro Leu Glu Gly Pro Ser Ser Leu Val Gly Gly Tyr Ala
            195                 200                 205
Gln Ser Lys Trp Val Ala Glu Lys Leu Val Arg Glu Ala Ser Arg Arg
            210                 215                 220
Gly Leu Pro Val Thr Ile Leu Arg Pro Gly Arg Val Thr Gly His Ser
225                     230                 235                 240
Arg Thr Gly Ala Trp Asn Thr Asp Asp Leu Val Cys Arg Thr Leu Lys
                245                 250                 255
Gly Cys Val Arg Met Gly Val Ala Pro Ser Val Asp Ala Leu Leu Asp
                260                 265                 270
Leu Thr Pro Val Asp Tyr Val Ser Ser Ala Ile Val Asp Leu Ser Met
            275                 280                 285
Arg Pro Glu Ser Ile Gly Gln Thr Tyr His Leu Val Asn Pro Gln Phe
            290                 295                 300
Val Arg Ala Asp Glu Met Trp Asn Tyr Met Arg Ala Phe Gly Tyr Gly
305                     310                 315                 320
Leu Arg Val Leu Pro Tyr Asp Gln Trp Leu Ser Glu Leu Gly Ser Ala
                325                 330                 335
Ala Ser Ser Asp Ser Glu Leu Gly Asp Leu Met Phe Leu Gln Gln
                340                 345                 350
Val Pro Pro Glu Asp Arg Ser Val Gly Pro Arg Met Val Val Cys
            355                 360                 365
Asp Ser Gly Asp Thr Leu Lys Ala Leu Gly Gly Thr Gly Thr Ser Cys
            370                 375                 380
Pro Ser Val Asp Ala Ser Leu Ile Ser Thr Tyr Leu Ser Ser Leu Val
385                     390                 395                 400
His Arg Gly Phe Leu Lys Ala Pro Glu Val
                405                 410
```

<210> SEQ ID NO 54

```
<211> LENGTH: 398
<212> TYPE: PRT
<213> ORGANISM: Stigmatella aurantiaca

<400> SEQUENCE: 54

Ile Ser Lys Ala Met Leu Ala Asp Ala Glu Leu Pro Glu Glu Ile Val
1               5                   10                  15

Pro Arg Leu Pro Thr Pro Gly Ala Glu Ala Pro Leu Ala Pro Ser Pro
            20                  25                  30

Gly Pro Ala Ala Pro Leu Arg Gln Val Leu Leu Thr Gly Ala Thr Gly
        35                  40                  45

Phe Val Gly Ala His Leu Leu Asp Gln Leu Leu Arg Gln Thr Gln Ala
50                  55                  60

Lys Val Val Cys Leu Val Arg Ala Arg Asp Glu Ala His Ala Met Glu
65                  70                  75                  80

Arg Leu Arg Glu Ala Met Thr Ser Gln Arg Leu Ser Thr Ala Ser Leu
                85                  90                  95

Ser Glu Arg Val Leu Ala Leu Pro Ala Asp Leu Gly Gln Pro Trp Leu
            100                 105                 110

Gly Leu Ser Ser Ala Arg Phe His Gly Leu Ala Ala Glu Cys Asp Met
        115                 120                 125

Ile Leu His Asn Ala Ala Val Val Ser Val Val Arg Glu Tyr Gly Ser
130                 135                 140

Leu Gln Ala Thr Asn Val Arg Gly Thr Arg Glu Leu Leu Arg Leu Ala
145                 150                 155                 160

Ala Ser Val Arg Pro Lys Pro Leu His Tyr Val Ser Thr Leu Ala Val
                165                 170                 175

Ala Pro Gln Ala Asn Leu Ser Pro Glu Val Pro Glu Ala Phe Val Pro
            180                 185                 190

Ala His Pro Gly Leu Arg Asp Gly Tyr Gln Gln Ser Lys Trp Ala Ala
        195                 200                 205

Glu Arg Leu Val Glu Gln Ala Ser Glu Arg Gly Leu Pro Val Thr Val
210                 215                 220

Tyr Arg Leu Gly Arg Val Ser Gly Ala Leu Asp Ser Gly Ile Val Asn
225                 230                 235                 240

Pro Gln Asp Leu Val Trp Arg Ile Leu Leu Ala Gly Ile Pro Ala Gly
                245                 250                 255

Ala Leu Pro Gln Leu Asp Val Gly Glu Val Trp Thr Pro Val Asp Tyr
            260                 265                 270

Val Ala Arg Ala Leu Val Arg Leu Ser Leu Val Pro Arg Pro Gly Thr
        275                 280                 285

Val Phe Asn Leu Thr Pro Ala Pro Glu Val Arg Leu Ser Glu Val Phe
290                 295                 300

Gly Trp Val Gln Asp Tyr Gly Tyr Pro Val Ala Leu Cys Pro Val Pro
305                 310                 315                 320

Glu Trp Arg Thr Arg Val Ala Gln Ser Thr Gly Ser Ala Glu Asn Ser
                325                 330                 335

Thr Thr Leu Ala Phe Phe Asp Leu Arg Ala Gly Ala Ala Glu Pro Thr
            340                 345                 350

Phe Gly Leu Gly Thr Ile Arg Ser Glu Arg Val Leu Gln Ala Leu Ser
        355                 360                 365

Asp Thr Gly Ile Ser Cys Pro Arg Thr Asp Arg Pro Leu Leu His Arg
370                 375                 380

Tyr Leu Asp Tyr Cys Val Gly Gln Gly Leu Leu Gln Arg Pro
```

<210> SEQ ID NO 55
<211> LENGTH: 487
<212> TYPE: PRT
<213> ORGANISM: Brevibacillus brevis

<400> SEQUENCE: 55

| | | | | | | | | | | | | | | |
|---|---|---|---|---|---|---|---|---|---|---|---|---|---|---|
| Pro | Asn | Asn | Val | Ala | Ile | Val | Cys | Glu | Asn | Glu | Gln | Leu | Thr | Tyr | His |
| 1 | | | | 5 | | | | | 10 | | | | | 15 | |
| Glu | Leu | Asn | Val | Lys | Ala | Asn | Gln | Leu | Ala | Arg | Ile | Phe | Ile | Glu | Lys |
| | | | 20 | | | | | 25 | | | | | 30 | | |
| Gly | Ile | Gly | Lys | Asp | Thr | Leu | Val | Gly | Ile | Met | Met | Glu | Lys | Ser | Ile |
| | | | | 35 | | | | | 40 | | | | | 45 | |
| Asp | Leu | Phe | Ile | Gly | Ile | Leu | Ala | Val | Leu | Lys | Ala | Gly | Gly | Ala | Tyr |
| | | 50 | | | | | 55 | | | | | 60 | | | |
| Val | Pro | Ile | Asp | Ile | Glu | Tyr | Pro | Lys | Glu | Arg | Ile | Gln | Tyr | Ile | Leu |
| 65 | | | | | 70 | | | | | 75 | | | | | 80 |
| Asp | Asp | Ser | Gln | Ala | Arg | Met | Leu | Leu | Thr | Gln | Lys | His | Leu | Val | His |
| | | | | 85 | | | | | 90 | | | | | 95 | |
| Leu | Ile | His | Asn | Ile | Gln | Phe | Asn | Gly | Gln | Val | Glu | Ile | Phe | Glu | Glu |
| | | | 100 | | | | | 105 | | | | | 110 | | |
| Asp | Thr | Ile | Lys | Ile | Arg | Glu | Gly | Thr | Asn | Leu | His | Val | Pro | Ser | Lys |
| | | | | 115 | | | | | 120 | | | | | 125 | |
| Ser | Thr | Asp | Leu | Ala | Tyr | Val | Ile | Tyr | Thr | Ser | Gly | Thr | Thr | Gly | Asn |
| | 130 | | | | | 135 | | | | | 140 | | | | |
| Pro | Lys | Gly | Thr | Met | Leu | Glu | His | Lys | Gly | Ile | Ser | Asn | Leu | Lys | Val |
| 145 | | | | | 150 | | | | | 155 | | | | | 160 |
| Phe | Phe | Glu | Asn | Ser | Leu | Asn | Val | Thr | Glu | Lys | Asp | Arg | Ile | Gly | Gln |
| | | | | 165 | | | | | 170 | | | | | 175 | |
| Phe | Ala | Ser | Ile | Ser | Phe | Asp | Ala | Ser | Val | Trp | Glu | Met | Phe | Met | Ala |
| | | | 180 | | | | | 185 | | | | | 190 | | |
| Leu | Leu | Thr | Gly | Ala | Ser | Leu | Tyr | Ile | Ile | Leu | Lys | Asp | Thr | Ile | Asn |
| | | | | 195 | | | | | 200 | | | | | 205 | |
| Asp | Phe | Val | Lys | Phe | Glu | Gln | Tyr | Ile | Asn | Gln | Lys | Glu | Ile | Thr | Val |
| | 210 | | | | | 215 | | | | | 220 | | | | |
| Ile | Thr | Leu | Pro | Pro | Thr | Tyr | Val | Val | His | Leu | Asp | Pro | Glu | Arg | Ile |
| 225 | | | | | 230 | | | | | 235 | | | | | 240 |
| Leu | Ser | Ile | Gln | Thr | Leu | Ile | Thr | Ala | Gly | Ser | Ala | Thr | Ser | Pro | Ser |
| | | | | 245 | | | | | 250 | | | | | 255 | |
| Leu | Val | Asn | Lys | Trp | Lys | Glu | Lys | Val | Thr | Tyr | Ile | Asn | Ala | Tyr | Gly |
| | | | 260 | | | | | 265 | | | | | 270 | | |
| Pro | Thr | Glu | Thr | Thr | Ile | Cys | Ala | Thr | Thr | Cys | Val | Ala | Thr | Lys | Glu |
| | | | | 275 | | | | | 280 | | | | | 285 | |
| Thr | Ile | Gly | His | Ser | Val | Pro | Ile | Gly | Ala | Pro | Ile | Gln | Asn | Thr | Gln |
| | 290 | | | | | 295 | | | | | 300 | | | | |
| Ile | Tyr | Ile | Val | Asp | Glu | Asn | Leu | Gln | Leu | Lys | Ser | Val | Gly | Glu | Ala |
| 305 | | | | | 310 | | | | | 315 | | | | | 320 |
| Gly | Glu | Leu | Cys | Ile | Gly | Gly | Glu | Gly | Leu | Ala | Arg | Gly | Tyr | Trp | Lys |
| | | | | 325 | | | | | 330 | | | | | 335 | |
| Arg | Pro | Glu | Leu | Thr | Ser | Gln | Lys | Phe | Val | Asp | Asn | Pro | Phe | Val | Pro |
| | | | 340 | | | | | 345 | | | | | 350 | | |
| Gly | Glu | Lys | Leu | Tyr | Lys | Thr | Gly | Asp | Gln | Ala | Arg | Trp | Leu | Ser | Asp |
| | | | | 355 | | | | | 360 | | | | | 365 | |

```
Gly Asn Ile Glu Tyr Leu Gly Arg Ile Asp Asn Gln Val Lys Ile Arg
    370                 375                 380

Gly His Arg Val Glu Leu Glu Glu Val Glu Ser Ile Leu Leu Lys His
385                 390                 395                 400

Met Tyr Ile Ser Glu Thr Ala Val Ser Val His Lys Asp His Gln Glu
                405                 410                 415

Gln Pro Tyr Leu Cys Ala Tyr Phe Val Ser Glu Lys His Ile Pro Leu
            420                 425                 430

Glu Gln Leu Arg Gln Phe Ser Ser Glu Glu Leu Pro Thr Tyr Met Ile
        435                 440                 445

Pro Ser Tyr Phe Ile Gln Leu Asp Lys Met Pro Leu Thr Ser Asn Gly
    450                 455                 460

Lys Ile Asp Arg Lys Gln Leu Pro Glu Pro Asp Leu Thr Phe Gly Met
465                 470                 475                 480

Arg Val Asp Tyr Glu Ala Pro
                485

<210> SEQ ID NO 56
<211> LENGTH: 429
<212> TYPE: PRT
<213> ORGANISM: Artificial sequence
<220> FEATURE:
<223> OTHER INFORMATION: Consensus seq based on alignment of Fig 11
      reductase domains
<220> FEATURE:
<221> NAME/KEY: misc_feature
<222> LOCATION: (1)..(2)
<223> OTHER INFORMATION: Xaa may be any amino acid or may be absent
<220> FEATURE:
<221> NAME/KEY: misc_feature
<222> LOCATION: (4)..(5)
<223> OTHER INFORMATION: Xaa may be any amino acid
<220> FEATURE:
<221> NAME/KEY: misc_feature
<222> LOCATION: (15)..(15)
<223> OTHER INFORMATION: Xaa may be any amino acid
<220> FEATURE:
<221> NAME/KEY: misc_feature
<222> LOCATION: (26)..(26)
<223> OTHER INFORMATION: Xaa may be any amino acid
<220> FEATURE:
<221> NAME/KEY: misc_feature
<222> LOCATION: (32)..(33)
<223> OTHER INFORMATION: Xaa may be any amino acid
<220> FEATURE:
<221> NAME/KEY: misc_feature
<222> LOCATION: (34)..(34)
<223> OTHER INFORMATION: Xaa may be any amino acid or may be absent
<220> FEATURE:
<221> NAME/KEY: misc_feature
<222> LOCATION: (35)..(35)
<223> OTHER INFORMATION: Xaa may be any amino acid or may be absent
<220> FEATURE:
<221> NAME/KEY: misc_feature
<222> LOCATION: (41)..(41)
<223> OTHER INFORMATION: Xaa may be any amino acid
<220> FEATURE:
<221> NAME/KEY: misc_feature
<222> LOCATION: (43)..(43)
<223> OTHER INFORMATION: Xaa may be any amino acid or may be absent
<220> FEATURE:
<221> NAME/KEY: misc_feature
<222> LOCATION: (60)..(60)
<223> OTHER INFORMATION: Xaa may be any amino acid
<220> FEATURE:
<221> NAME/KEY: misc_feature
<222> LOCATION: (64)..(64)
<223> OTHER INFORMATION: Xaa may be any amino acid
<220> FEATURE:
<221> NAME/KEY: misc_feature
<222> LOCATION: (70)..(70)
```

```
<223> OTHER INFORMATION: Xaa may be any amino acid
<220> FEATURE:
<221> NAME/KEY: misc_feature
<222> LOCATION: (80)..(80)
<223> OTHER INFORMATION: Xaa may be any amino acid
<220> FEATURE:
<221> NAME/KEY: misc_feature
<222> LOCATION: (97)..(97)
<223> OTHER INFORMATION: Xaa may be any amino acid
<220> FEATURE:
<221> NAME/KEY: misc_feature
<222> LOCATION: (100)..(100)
<223> OTHER INFORMATION: Xaa may be any amino acid or may be absent
<220> FEATURE:
<221> NAME/KEY: misc_feature
<222> LOCATION: (102)..(102)
<223> OTHER INFORMATION: Xaa may be any amino acid
<220> FEATURE:
<221> NAME/KEY: misc_feature
<222> LOCATION: (127)..(127)
<223> OTHER INFORMATION: Xaa may be any amino acid
<220> FEATURE:
<221> NAME/KEY: misc_feature
<222> LOCATION: (131)..(131)
<223> OTHER INFORMATION: Xaa may be any amino acid
<220> FEATURE:
<221> NAME/KEY: misc_feature
<222> LOCATION: (135)..(135)
<223> OTHER INFORMATION: Xaa may be any amino acid
<220> FEATURE:
<221> NAME/KEY: misc_feature
<222> LOCATION: (150)..(150)
<223> OTHER INFORMATION: Xaa may be any amino acid
<220> FEATURE:
<221> NAME/KEY: misc_feature
<222> LOCATION: (169)..(170)
<223> OTHER INFORMATION: Xaa may be any amino acid
<220> FEATURE:
<221> NAME/KEY: misc_feature
<222> LOCATION: (186)..(186)
<223> OTHER INFORMATION: Xaa may be any amino acid
<220> FEATURE:
<221> NAME/KEY: misc_feature
<222> LOCATION: (192)..(192)
<223> OTHER INFORMATION: Xaa may be any amino acid or may be absent
<220> FEATURE:
<221> NAME/KEY: misc_feature
<222> LOCATION: (193)..(193)
<223> OTHER INFORMATION: Xaa may be any amino acid or may be absent
<220> FEATURE:
<221> NAME/KEY: misc_feature
<222> LOCATION: (195)..(195)
<223> OTHER INFORMATION: Xaa may be any amino acid
<220> FEATURE:
<221> NAME/KEY: misc_feature
<222> LOCATION: (201)..(201)
<223> OTHER INFORMATION: Xaa may be any amino acid
<220> FEATURE:
<221> NAME/KEY: misc_feature
<222> LOCATION: (204)..(204)
<223> OTHER INFORMATION: Xaa may be any amino acid
<220> FEATURE:
<221> NAME/KEY: misc_feature
<222> LOCATION: (207)..(207)
<223> OTHER INFORMATION: Xaa may be any amino acid
<220> FEATURE:
<221> NAME/KEY: misc_feature
<222> LOCATION: (222)..(222)
<223> OTHER INFORMATION: Xaa may be any amino acid
<220> FEATURE:
<221> NAME/KEY: misc_feature
<222> LOCATION: (225)..(226)
<223> OTHER INFORMATION: Xaa may be any amino acid
<220> FEATURE:
<221> NAME/KEY: misc_feature
<222> LOCATION: (248)..(248)
<223> OTHER INFORMATION: Xaa may be any amino acid
<220> FEATURE:
<221> NAME/KEY: misc_feature
```

```
<222> LOCATION: (257)..(257)
<223> OTHER INFORMATION: Xaa may be any amino acid
<220> FEATURE:
<221> NAME/KEY: misc_feature
<222> LOCATION: (269)..(271)
<223> OTHER INFORMATION: Xaa may be any amino acid or may be absent
<220> FEATURE:
<221> NAME/KEY: misc_feature
<222> LOCATION: (272)..(272)
<223> OTHER INFORMATION: Xaa may be any amino acid
<220> FEATURE:
<221> NAME/KEY: misc_feature
<222> LOCATION: (275)..(276)
<223> OTHER INFORMATION: Xaa may be any amino acid
<220> FEATURE:
<221> NAME/KEY: misc_feature
<222> LOCATION: (295)..(295)
<223> OTHER INFORMATION: Xaa may be any amino acid
<220> FEATURE:
<221> NAME/KEY: misc_feature
<222> LOCATION: (298)..(298)
<223> OTHER INFORMATION: Xaa may be any amino acid or may be absent
<220> FEATURE:
<221> NAME/KEY: misc_feature
<222> LOCATION: (301)..(302)
<223> OTHER INFORMATION: Xaa may be any amino acid
<220> FEATURE:
<221> NAME/KEY: misc_feature
<222> LOCATION: (310)..(310)
<223> OTHER INFORMATION: Xaa may be any amino acid
<220> FEATURE:
<221> NAME/KEY: misc_feature
<222> LOCATION: (328)..(328)
<223> OTHER INFORMATION: Xaa may be any amino acid
<220> FEATURE:
<221> NAME/KEY: misc_feature
<222> LOCATION: (336)..(336)
<223> OTHER INFORMATION: Xaa may be any amino acid
<220> FEATURE:
<221> NAME/KEY: misc_feature
<222> LOCATION: (338)..(338)
<223> OTHER INFORMATION: Xaa may be any amino acid
<220> FEATURE:
<221> NAME/KEY: misc_feature
<222> LOCATION: (341)..(342)
<223> OTHER INFORMATION: Xaa may be any amino acid
<220> FEATURE:
<221> NAME/KEY: misc_feature
<222> LOCATION: (347)..(347)
<223> OTHER INFORMATION: Xaa may be any amino acid
<220> FEATURE:
<221> NAME/KEY: misc_feature
<222> LOCATION: (350)..(351)
<223> OTHER INFORMATION: Xaa may be any amino acid
<220> FEATURE:
<221> NAME/KEY: misc_feature
<222> LOCATION: (353)..(353)
<223> OTHER INFORMATION: Xaa may be any amino acid
<220> FEATURE:
<221> NAME/KEY: misc_feature
<222> LOCATION: (355)..(355)
<223> OTHER INFORMATION: Xaa may be any amino acid
<220> FEATURE:
<221> NAME/KEY: misc_feature
<222> LOCATION: (357)..(358)
<223> OTHER INFORMATION: Xaa may be any amino acid
<220> FEATURE:
<221> NAME/KEY: misc_feature
<222> LOCATION: (360)..(360)
<223> OTHER INFORMATION: Xaa may be any amino acid
<220> FEATURE:
<221> NAME/KEY: misc_feature
<222> LOCATION: (364)..(364)
<223> OTHER INFORMATION: Xaa may be any amino acid
<220> FEATURE:
<221> NAME/KEY: misc_feature
<222> LOCATION: (368)..(368)
<223> OTHER INFORMATION: Xaa may be any amino acid
<220> FEATURE:
```

-continued

```
<221> NAME/KEY: misc_feature
<222> LOCATION: (373)..(378)
<223> OTHER INFORMATION: Xaa may be any amino acid or may be absent
<220> FEATURE:
<221> NAME/KEY: misc_feature
<222> LOCATION: (379)..(379)
<223> OTHER INFORMATION: Xaa may be any amino acid
<220> FEATURE:
<221> NAME/KEY: misc_feature
<222> LOCATION: (381)..(381)
<223> OTHER INFORMATION: Xaa may be any amino acid or may be absent
<220> FEATURE:
<221> NAME/KEY: misc_feature
<222> LOCATION: (390)..(390)
<223> OTHER INFORMATION: Xaa may be any amino acid
<220> FEATURE:
<221> NAME/KEY: misc_feature
<222> LOCATION: (400)..(400)
<223> OTHER INFORMATION: Xaa may be any amino acid
<220> FEATURE:
<221> NAME/KEY: misc_feature
<222> LOCATION: (423)..(429)
<223> OTHER INFORMATION: Xaa may be any amino acid or may be absent

<400> SEQUENCE: 56

Xaa Xaa Ile Xaa Xaa Ala Ala Gly Thr Asp Ala Val Leu Ala Xaa Asp
 1               5                  10                  15

Val Thr Val Arg Leu Asp Ala Asp Ala Xaa Leu Ala Pro Leu Ile Xaa
            20                  25                  30

Xaa Xaa Xaa Gly Leu Pro Pro Ala Xaa Gly Xaa Ala Leu Arg Ser Val
        35                  40                  45

Leu Leu Thr Gly Ala Thr Gly Phe Leu Gly Ala Xaa Leu Leu Glu Xaa
 50                  55                  60

Leu Leu Arg Arg Thr Xaa Ala Arg Val Tyr Cys Leu Val Arg Ala Xaa
65                  70                  75                  80

Asp Glu Ala Glu Ala Met Asp Arg Leu Arg Ala Ala Met Glu Ser Tyr
                85                  90                  95

Xaa Leu Trp Xaa Glu Xaa Leu Ala Glu Arg Ile Val Pro Leu Val Gly
           100                 105                 110

Asp Leu Gly Gln Pro Arg Leu Gly Leu Ser Glu Ala Glu Phe Xaa Arg
            115                 120                 125

Leu Ala Xaa Glu Leu Asp Xaa Ile Tyr His Asn Gly Ala Leu Val Asn
130                 135                 140

Phe Val Tyr Pro Tyr Xaa Ser Leu Arg Ala Thr Asn Val His Gly Thr
145                 150                 155                 160

Arg Glu Val Leu Arg Leu Ala Ala Xaa Xaa Arg Leu Lys Pro Leu His
                165                 170                 175

Tyr Val Ser Thr Leu Ala Val Leu Pro Xaa Gly His Met Pro Pro Xaa
            180                 185                 190

Xaa Ile Xaa Glu Asp Ala Pro Leu Xaa Gly Pro Xaa Ser Leu Xaa Gly
        195                 200                 205

Gly Tyr Thr Gln Ser Lys Trp Val Ala Glu Lys Leu Val Xaa Gln Ala
    210                 215                 220

Xaa Xaa Arg Gly Leu Pro Val Thr Ile Tyr Arg Pro Gly Arg Ile Thr
225                 230                 235                 240

Gly His Ser Arg Thr Gly Ala Xaa Asn Thr Asp Asp Leu Val Trp Arg
                245                 250                 255

Xaa Leu Lys Gly Tyr Val Pro Met Gly Ile Ile Pro Xaa Xaa Xaa Xaa
            260                 265                 270

Val Asp Xaa Xaa Leu Asp Leu Thr Pro Val Asp Tyr Val Ala Arg Ala
        275                 280                 285
```

```
Ile Val Arg Leu Ser Met Xaa Pro Glu Xaa Leu Gly Xaa Xaa Phe His
    290                 295                 300

Leu Phe Asn Pro Gln Xaa Val Arg Leu Ser Glu Met Trp Asp Trp Ile
305                 310                 315                 320

Arg Ala Tyr Gly Tyr Ala Val Xaa Ile Val Pro Phe Asp Glu Trp Xaa
                325                 330                 335

Ser Xaa Leu Gly Xaa Xaa Ala Gly Ser Asp Xaa Asn Leu Xaa Xaa Leu
            340                 345                 350

Xaa Pro Xaa Ile Xaa Xaa Ala Xaa Ala Glu Asp Xaa Ser Val Gly Xaa
        355                 360                 365

Pro Thr Phe Ile Xaa Xaa Xaa Xaa Xaa Xaa Glu Xaa Gly Arg Thr
    370                 375                 380

Leu Lys Ala Leu Ala Xaa Thr Gly Ile Ser Cys Pro Pro Met Asp Xaa
385                 390                 395                 400

Glu Leu Ile His Arg Tyr Leu Asp Tyr Leu Val Gly Ile Gly Phe Leu
                405                 410                 415

Gln Arg Pro Glu Val Leu Xaa Xaa Xaa Xaa Xaa Xaa Xaa
                420                 425

<210> SEQ ID NO 57
<211> LENGTH: 500
<212> TYPE: PRT
<213> ORGANISM: Artificial sequence
<220> FEATURE:
<223> OTHER INFORMATION: Consensus seq based on alignment of Fig 12
      adenylation domains
<220> FEATURE:
<221> NAME/KEY: misc_feature
<222> LOCATION: (3)..(4)
<223> OTHER INFORMATION: Xaa may be any amino acid
<220> FEATURE:
<221> NAME/KEY: misc_feature
<222> LOCATION: (8)..(8)
<223> OTHER INFORMATION: Xaa may be any amino acid
<220> FEATURE:
<221> NAME/KEY: misc_feature
<222> LOCATION: (11)..(12)
<223> OTHER INFORMATION: Xaa may be any amino acid
<220> FEATURE:
<221> NAME/KEY: misc_feature
<222> LOCATION: (19)..(21)
<223> OTHER INFORMATION: Xaa may be any amino acid
<220> FEATURE:
<221> NAME/KEY: misc_feature
<222> LOCATION: (24)..(24)
<223> OTHER INFORMATION: Xaa may be any amino acid
<220> FEATURE:
<221> NAME/KEY: misc_feature
<222> LOCATION: (28)..(28)
<223> OTHER INFORMATION: Xaa may be any amino acid
<220> FEATURE:
<221> NAME/KEY: misc_feature
<222> LOCATION: (30)..(30)
<223> OTHER INFORMATION: Xaa may be any amino acid
<220> FEATURE:
<221> NAME/KEY: misc_feature
<222> LOCATION: (36)..(36)
<223> OTHER INFORMATION: Xaa may be any amino acid
<220> FEATURE:
<221> NAME/KEY: misc_feature
<222> LOCATION: (38)..(39)
<223> OTHER INFORMATION: Xaa may be any amino acid
<220> FEATURE:
<221> NAME/KEY: misc_feature
<222> LOCATION: (52)..(53)
<223> OTHER INFORMATION: Xaa may be any amino acid
<220> FEATURE:
<221> NAME/KEY: misc_feature
<222> LOCATION: (63)..(63)
```

```
<223> OTHER INFORMATION: Xaa may be any amino acid
<220> FEATURE:
<221> NAME/KEY: misc_feature
<222> LOCATION: (69)..(69)
<223> OTHER INFORMATION: Xaa may be any amino acid
<220> FEATURE:
<221> NAME/KEY: misc_feature
<222> LOCATION: (71)..(71)
<223> OTHER INFORMATION: Xaa may be any amino acid
<220> FEATURE:
<221> NAME/KEY: misc_feature
<222> LOCATION: (81)..(81)
<223> OTHER INFORMATION: Xaa may be any amino acid
<220> FEATURE:
<221> NAME/KEY: misc_feature
<222> LOCATION: (92)..(93)
<223> OTHER INFORMATION: Xaa may be any amino acid
<220> FEATURE:
<221> NAME/KEY: misc_feature
<222> LOCATION: (95)..(96)
<223> OTHER INFORMATION: Xaa may be any amino acid
<220> FEATURE:
<221> NAME/KEY: misc_feature
<222> LOCATION: (98)..(98)
<223> OTHER INFORMATION: Xaa may be any amino acid or may be absent
<220> FEATURE:
<221> NAME/KEY: misc_feature
<222> LOCATION: (100)..(100)
<223> OTHER INFORMATION: Xaa may be any amino acid
<220> FEATURE:
<221> NAME/KEY: misc_feature
<222> LOCATION: (102)..(104)
<223> OTHER INFORMATION: Xaa may be any amino acid
<220> FEATURE:
<221> NAME/KEY: misc_feature
<222> LOCATION: (109)..(109)
<223> OTHER INFORMATION: Xaa may be any amino acid
<220> FEATURE:
<221> NAME/KEY: misc_feature
<222> LOCATION: (111)..(111)
<223> OTHER INFORMATION: Xaa may be any amino acid
<220> FEATURE:
<221> NAME/KEY: misc_feature
<222> LOCATION: (114)..(114)
<223> OTHER INFORMATION: Xaa may be any amino acid
<220> FEATURE:
<221> NAME/KEY: misc_feature
<222> LOCATION: (116)..(116)
<223> OTHER INFORMATION: Xaa may be any amino acid
<220> FEATURE:
<221> NAME/KEY: misc_feature
<222> LOCATION: (118)..(120)
<223> OTHER INFORMATION: Xaa may be any amino acid
<220> FEATURE:
<221> NAME/KEY: misc_feature
<222> LOCATION: (122)..(122)
<223> OTHER INFORMATION: Xaa may be any amino acid or may be absent
<220> FEATURE:
<221> NAME/KEY: misc_feature
<222> LOCATION: (125)..(125)
<223> OTHER INFORMATION: Xaa may be any amino acid or may be absent
<220> FEATURE:
<221> NAME/KEY: misc_feature
<222> LOCATION: (126)..(127)
<223> OTHER INFORMATION: Xaa may be any amino acid
<220> FEATURE:
<221> NAME/KEY: misc_feature
<222> LOCATION: (129)..(129)
<223> OTHER INFORMATION: Xaa may be any amino acid
<220> FEATURE:
<221> NAME/KEY: misc_feature
<222> LOCATION: (132)..(132)
<223> OTHER INFORMATION: Xaa may be any amino acid
<220> FEATURE:
<221> NAME/KEY: misc_feature
<222> LOCATION: (144)..(144)
<223> OTHER INFORMATION: Xaa may be any amino acid
<220> FEATURE:
<221> NAME/KEY: misc_feature
```

```
<222> LOCATION: (151)..(151)
<223> OTHER INFORMATION: Xaa may be any amino acid
<220> FEATURE:
<221> NAME/KEY: misc_feature
<222> LOCATION: (159)..(159)
<223> OTHER INFORMATION: Xaa may be any amino acid
<220> FEATURE:
<221> NAME/KEY: misc_feature
<222> LOCATION: (161)..(163)
<223> OTHER INFORMATION: Xaa may be any amino acid
<220> FEATURE:
<221> NAME/KEY: misc_feature
<222> LOCATION: (164)..(164)
<223> OTHER INFORMATION: Xaa may be any amino acid or may be absent
<220> FEATURE:
<221> NAME/KEY: misc_feature
<222> LOCATION: (165)..(165)
<223> OTHER INFORMATION: Xaa may be any amino acid
<220> FEATURE:
<221> NAME/KEY: misc_feature
<222> LOCATION: (168)..(170)
<223> OTHER INFORMATION: Xaa may be any amino acid
<220> FEATURE:
<221> NAME/KEY: misc_feature
<222> LOCATION: (174)..(174)
<223> OTHER INFORMATION: Xaa may be any amino acid
<220> FEATURE:
<221> NAME/KEY: misc_feature
<222> LOCATION: (179)..(179)
<223> OTHER INFORMATION: Xaa may be any amino acid
<220> FEATURE:
<221> NAME/KEY: misc_feature
<222> LOCATION: (187)..(187)
<223> OTHER INFORMATION: Xaa may be any amino acid
<220> FEATURE:
<221> NAME/KEY: misc_feature
<222> LOCATION: (191)..(192)
<223> OTHER INFORMATION: Xaa may be any amino acid
<220> FEATURE:
<221> NAME/KEY: misc_feature
<222> LOCATION: (200)..(200)
<223> OTHER INFORMATION: Xaa may be any amino acid
<220> FEATURE:
<221> NAME/KEY: misc_feature
<222> LOCATION: (202)..(202)
<223> OTHER INFORMATION: Xaa may be any amino acid
<220> FEATURE:
<221> NAME/KEY: misc_feature
<222> LOCATION: (204)..(207)
<223> OTHER INFORMATION: Xaa may be any amino acid or may be absent
<220> FEATURE:
<221> NAME/KEY: misc_feature
<222> LOCATION: (208)..(208)
<223> OTHER INFORMATION: Xaa may be any amino acid
<220> FEATURE:
<221> NAME/KEY: misc_feature
<222> LOCATION: (211)..(212)
<223> OTHER INFORMATION: Xaa may be any amino acid
<220> FEATURE:
<221> NAME/KEY: misc_feature
<222> LOCATION: (215)..(215)
<223> OTHER INFORMATION: Xaa may be any amino acid
<220> FEATURE:
<221> NAME/KEY: misc_feature
<222> LOCATION: (217)..(219)
<223> OTHER INFORMATION: Xaa may be any amino acid
<220> FEATURE:
<221> NAME/KEY: misc_feature
<222> LOCATION: (221)..(222)
<223> OTHER INFORMATION: Xaa may be any amino acid
<220> FEATURE:
<221> NAME/KEY: misc_feature
<222> LOCATION: (225)..(225)
<223> OTHER INFORMATION: Xaa may be any amino acid
<220> FEATURE:
<221> NAME/KEY: misc_feature
<222> LOCATION: (229)..(229)
<223> OTHER INFORMATION: Xaa may be any amino acid
<220> FEATURE:
```

```
<221> NAME/KEY: misc_feature
<222> LOCATION: (233)..(235)
<223> OTHER INFORMATION: Xaa may be any amino acid or may be absent
<220> FEATURE:
<221> NAME/KEY: misc_feature
<222> LOCATION: (236)..(237)
<223> OTHER INFORMATION: Xaa may be any amino acid
<220> FEATURE:
<221> NAME/KEY: misc_feature
<222> LOCATION: (241)..(242)
<223> OTHER INFORMATION: Xaa may be any amino acid
<220> FEATURE:
<221> NAME/KEY: misc_feature
<222> LOCATION: (244)..(244)
<223> OTHER INFORMATION: Xaa may be any amino acid
<220> FEATURE:
<221> NAME/KEY: misc_feature
<222> LOCATION: (247)..(248)
<223> OTHER INFORMATION: Xaa may be any amino acid
<220> FEATURE:
<221> NAME/KEY: misc_feature
<222> LOCATION: (258)..(261)
<223> OTHER INFORMATION: Xaa may be any amino acid or may be absent
<220> FEATURE:
<221> NAME/KEY: misc_feature
<222> LOCATION: (263)..(266)
<223> OTHER INFORMATION: Xaa may be any amino acid
<220> FEATURE:
<221> NAME/KEY: misc_feature
<222> LOCATION: (269)..(269)
<223> OTHER INFORMATION: Xaa may be any amino acid
<220> FEATURE:
<221> NAME/KEY: misc_feature
<222> LOCATION: (271)..(271)
<223> OTHER INFORMATION: Xaa may be any amino acid
<220> FEATURE:
<221> NAME/KEY: misc_feature
<222> LOCATION: (273)..(273)
<223> OTHER INFORMATION: Xaa may be any amino acid
<220> FEATURE:
<221> NAME/KEY: misc_feature
<222> LOCATION: (276)..(276)
<223> OTHER INFORMATION: Xaa may be any amino acid
<220> FEATURE:
<221> NAME/KEY: misc_feature
<222> LOCATION: (286)..(286)
<223> OTHER INFORMATION: Xaa may be any amino acid
<220> FEATURE:
<221> NAME/KEY: misc_feature
<222> LOCATION: (292)..(293)
<223> OTHER INFORMATION: Xaa may be any amino acid
<220> FEATURE:
<221> NAME/KEY: misc_feature
<222> LOCATION: (295)..(295)
<223> OTHER INFORMATION: Xaa may be any amino acid
<220> FEATURE:
<221> NAME/KEY: misc_feature
<222> LOCATION: (297)..(298)
<223> OTHER INFORMATION: Xaa may be any amino acid
<220> FEATURE:
<221> NAME/KEY: misc_feature
<222> LOCATION: (301)..(301)
<223> OTHER INFORMATION: Xaa may be any amino acid
<220> FEATURE:
<221> NAME/KEY: misc_feature
<222> LOCATION: (302)..(302)
<223> OTHER INFORMATION: Xaa may be any amino acid or may be absent
<220> FEATURE:
<221> NAME/KEY: misc_feature
<222> LOCATION: (303)..(304)
<223> OTHER INFORMATION: Xaa may be any amino acid
<220> FEATURE:
<221> NAME/KEY: misc_feature
<222> LOCATION: (312)..(313)
<223> OTHER INFORMATION: Xaa may be any amino acid
<220> FEATURE:
<221> NAME/KEY: misc_feature
<222> LOCATION: (317)..(317)
<223> OTHER INFORMATION: Xaa may be any amino acid
```

```
<220> FEATURE:
<221> NAME/KEY: misc_feature
<222> LOCATION: (322)..(322)
<223> OTHER INFORMATION: Xaa may be any amino acid
<220> FEATURE:
<221> NAME/KEY: misc_feature
<222> LOCATION: (325)..(328)
<223> OTHER INFORMATION: Xaa may be any amino acid
<220> FEATURE:
<221> NAME/KEY: misc_feature
<222> LOCATION: (330)..(331)
<223> OTHER INFORMATION: Xaa may be any amino acid
<220> FEATURE:
<221> NAME/KEY: misc_feature
<222> LOCATION: (343)..(343)
<223> OTHER INFORMATION: Xaa may be any amino acid
<220> FEATURE:
<221> NAME/KEY: misc_feature
<222> LOCATION: (347)..(348)
<223> OTHER INFORMATION: Xaa may be any amino acid
<220> FEATURE:
<221> NAME/KEY: misc_feature
<222> LOCATION: (353)..(353)
<223> OTHER INFORMATION: Xaa may be any amino acid
<220> FEATURE:
<221> NAME/KEY: misc_feature
<222> LOCATION: (358)..(359)
<223> OTHER INFORMATION: Xaa may be any amino acid
<220> FEATURE:
<221> NAME/KEY: misc_feature
<222> LOCATION: (365)..(365)
<223> OTHER INFORMATION: Xaa may be any amino acid
<220> FEATURE:
<221> NAME/KEY: misc_feature
<222> LOCATION: (376)..(378)
<223> OTHER INFORMATION: Xaa may be any amino acid
<220> FEATURE:
<221> NAME/KEY: misc_feature
<222> LOCATION: (381)..(381)
<223> OTHER INFORMATION: Xaa may be any amino acid
<220> FEATURE:
<221> NAME/KEY: misc_feature
<222> LOCATION: (383)..(383)
<223> OTHER INFORMATION: Xaa may be any amino acid
<220> FEATURE:
<221> NAME/KEY: misc_feature
<222> LOCATION: (385)..(385)
<223> OTHER INFORMATION: Xaa may be any amino acid
<220> FEATURE:
<221> NAME/KEY: misc_feature
<222> LOCATION: (388)..(388)
<223> OTHER INFORMATION: Xaa may be any amino acid
<220> FEATURE:
<221> NAME/KEY: misc_feature
<222> LOCATION: (402)..(402)
<223> OTHER INFORMATION: Xaa may be any amino acid
<220> FEATURE:
<221> NAME/KEY: misc_feature
<222> LOCATION: (406)..(407)
<223> OTHER INFORMATION: Xaa may be any amino acid
<220> FEATURE:
<221> NAME/KEY: misc_feature
<222> LOCATION: (411)..(411)
<223> OTHER INFORMATION: Xaa may be any amino acid
<220> FEATURE:
<221> NAME/KEY: misc_feature
<222> LOCATION: (413)..(413)
<223> OTHER INFORMATION: Xaa may be any amino acid
<220> FEATURE:
<221> NAME/KEY: misc_feature
<222> LOCATION: (416)..(416)
<223> OTHER INFORMATION: Xaa may be any amino acid
<220> FEATURE:
<221> NAME/KEY: misc_feature
<222> LOCATION: (420)..(420)
<223> OTHER INFORMATION: Xaa may be any amino acid
<220> FEATURE:
<221> NAME/KEY: misc_feature
<222> LOCATION: (424)..(426)
```

```
<223> OTHER INFORMATION: Xaa may be any amino acid or may be absent
<220> FEATURE:
<221> NAME/KEY: misc_feature
<222> LOCATION: (430)..(431)
<223> OTHER INFORMATION: Xaa may be any amino acid
<220> FEATURE:
<221> NAME/KEY: misc_feature
<222> LOCATION: (434)..(434)
<223> OTHER INFORMATION: Xaa may be any amino acid
<220> FEATURE:
<221> NAME/KEY: misc_feature
<222> LOCATION: (437)..(438)
<223> OTHER INFORMATION: Xaa may be any amino acid
<220> FEATURE:
<221> NAME/KEY: misc_feature
<222> LOCATION: (445)..(446)
<223> OTHER INFORMATION: Xaa may be any amino acid
<220> FEATURE:
<221> NAME/KEY: misc_feature
<222> LOCATION: (447)..(447)
<223> OTHER INFORMATION: Xaa may be any amino acid or may be absent
<220> FEATURE:
<221> NAME/KEY: misc_feature
<222> LOCATION: (450)..(450)
<223> OTHER INFORMATION: Xaa may be any amino acid
<220> FEATURE:
<221> NAME/KEY: misc_feature
<222> LOCATION: (453)..(455)
<223> OTHER INFORMATION: Xaa may be any amino acid
<220> FEATURE:
<221> NAME/KEY: misc_feature
<222> LOCATION: (458)..(458)
<223> OTHER INFORMATION: Xaa may be any amino acid
<220> FEATURE:
<221> NAME/KEY: misc_feature
<222> LOCATION: (464)..(464)
<223> OTHER INFORMATION: Xaa may be any amino acid
<220> FEATURE:
<221> NAME/KEY: misc_feature
<222> LOCATION: (467)..(467)
<223> OTHER INFORMATION: Xaa may be any amino acid
<220> FEATURE:
<221> NAME/KEY: misc_feature
<222> LOCATION: (470)..(470)
<223> OTHER INFORMATION: Xaa may be any amino acid
<220> FEATURE:
<221> NAME/KEY: misc_feature
<222> LOCATION: (475)..(475)
<223> OTHER INFORMATION: Xaa may be any amino acid
<220> FEATURE:
<221> NAME/KEY: misc_feature
<222> LOCATION: (483)..(483)
<223> OTHER INFORMATION: Xaa may be any amino acid
<220> FEATURE:
<221> NAME/KEY: misc_feature
<222> LOCATION: (485)..(485)
<223> OTHER INFORMATION: Xaa may be any amino acid
<220> FEATURE:
<221> NAME/KEY: misc_feature
<222> LOCATION: (488)..(488)
<223> OTHER INFORMATION: Xaa may be any amino acid
<220> FEATURE:
<221> NAME/KEY: misc_feature
<222> LOCATION: (489)..(498)
<223> OTHER INFORMATION: Xaa may be any amino acid or may be absent
<220> FEATURE:
<221> NAME/KEY: misc_feature
<222> LOCATION: (500)..(500)
<223> OTHER INFORMATION: Xaa may be any amino acid or may be absent

<400> SEQUENCE: 57

Ala Ala Xaa Xaa Ala Val Val Xaa Asp Gly Xaa Xaa Leu Thr Tyr Ala
 1               5                  10                  15

Glu Leu Xaa Xaa Xaa Ala Asn Xaa Val Ala Arg Xaa Leu Xaa Glu Arg
            20                  25                  30

Gly Val Arg Xaa Gly Xaa Xaa Val Gly Val Leu Met Asp Arg Gly Leu
```

```
                  35                  40                  45
Asp Leu Tyr Xaa Xaa Val Leu Gly Ile Leu Lys Ala Gly Gly Xaa Tyr
             50                  55                  60

Val Pro Leu Asp Xaa Asp Xaa Pro Arg Glu Arg Leu Ser Phe Met Leu
 65                  70                  75                  80

Xaa Asp Ser Gly Ala Lys Ile Leu Leu Thr Asp Xaa Xaa Ala Xaa Xaa
                 85                  90                  95

Ala Xaa Val Xaa Leu Xaa Xaa Xaa Met Gln Val Asp Xaa Met Xaa Gly
                100                 105                 110

Asp Xaa Gly Xaa Val Xaa Xaa Xaa Pro Xaa Val Arg Xaa Xaa Xaa Ser
                115                 120                 125

Xaa Asp Asp Xaa Ala Tyr Val Val Tyr Thr Ser Gly Ser Thr Gly Xaa
            130                 135                 140

Pro Lys Gly Val Val Leu Xaa His Arg Gly Ile Thr Asn Leu Xaa Arg
145                 150                 155                 160

Xaa Xaa Xaa Xaa Xaa Leu Ser Xaa Xaa Xaa Arg Asp Arg Xaa Leu Gln
                165                 170                 175

Tyr Ala Xaa Pro Ser Phe Asp Ala Ser Thr Xaa Glu Val Phe Xaa Xaa
            180                 185                 190

Leu Leu Thr Gly Gly Thr Leu Xaa Val Xaa Pro Xaa Xaa Xaa Xaa Xaa
            195                 200                 205

Asp Leu Xaa Xaa Leu Ala Xaa Leu Xaa Xaa Xaa Ile Xaa Xaa Glu Arg
        210                 215                 220

Xaa Thr Val Leu Xaa Leu Pro Leu Xaa Xaa Xaa Xaa Val Val Arg
225                 230                 235                 240

Xaa Xaa Pro Xaa Arg Leu Xaa Xaa Leu Arg Ser Val Ile Val Thr Gly
            245                 250                 255

Glu Xaa Xaa Xaa Xaa Thr Xaa Xaa Xaa Xaa Glu Met Xaa Arg Xaa His
            260                 265                 270

Xaa Gly Ala Xaa Leu Ile Asn Ala Tyr Gly Pro Thr Glu Xaa Ser Leu
        275                 280                 285

Val Ser Ala Xaa Xaa Leu Xaa Thr Xaa Xaa Asp Leu Xaa Xaa Xaa Xaa
        290                 295                 300

Ile Pro Ile Gly Arg Pro Val Xaa Xaa Leu Asp Met Xaa Val Leu Asp
305                 310                 315                 320

Glu Xaa Leu Glu Xaa Xaa Xaa Xaa Gly Xaa Xaa Gly Glu Leu Cys Ile
            325                 330                 335

Ala Gly Asp Gly Leu Ala Xaa Gly Tyr Ile Xaa Xaa Pro Glu Leu Thr
            340                 345                 350

Xaa Gln Lys Phe Val Xaa Xaa Pro Phe Val Pro Gly Xaa Arg Leu Tyr
        355                 360                 365

Arg Thr Gly Asp Val Ala Lys Xaa Xaa Xaa Asp Gly Xaa Ile Xaa Tyr
370                 375                 380

Xaa Gly Arg Xaa Asp Gln Gln Ile Lys Ile Arg Gly Tyr Arg Val Glu
385                 390                 395                 400

Pro Xaa Glu Val Glu Xaa Xaa Leu Glu Arg Xaa Leu Xaa Val Glu Xaa
            405                 410                 415

Ala Ala Val Xaa Ala Val Pro Xaa Xaa Xaa Ala Gly Asp Xaa Xaa Ala
            420                 425                 430

Leu Xaa Ala Phe Xaa Xaa Ser Gly His Glu Leu Pro Xaa Xaa Xaa Leu
        435                 440                 445

Arg Xaa Arg Leu Xaa Xaa Xaa Leu Pro Xaa Tyr Met Ile Pro Ser Xaa
        450                 455                 460
```

```
Ile Leu Xaa Leu Asp Xaa Ile Pro Leu Thr Xaa Asn Gly Lys Ile Asp
465                 470                 475                 480

Arg Arg Xaa Leu Xaa Ala Arg Xaa Xaa Xaa Xaa Xaa Xaa Xaa Xaa Xaa
            485             490                 495

Xaa Xaa Gly Xaa
            500
```

NUCLEIC ACID FRAGMENT ENCODING AN NRPS FOR THE BIOSYNTHESIS OF ANTHRAMYCIN

CROSS-REFERENCING TO RELATED APPLICATION

This application is a continuation-in-part application of U.S. Ser. No. 10/166,087 filed Jun. 11, 2002, now U.S. Pat. No. 7,108,998 which claims benefit under 35 USC § 119 of provisional application U.S. Ser. No. 60/296,744 filed on Jun. 11, 2001 which is hereby incorporated by reference in its entirety for all purposes.

SEQUENCE LISTING ON COMPACT DISK

The content of the following submissions on compact discs are incorporated herein by reference in its entirety: A compact disc copy of the Sequence Listing (COPY 1) (file name: 3014-6US.ST25.txt, date recorded Jul. 6, 2006, size: 210 KB) and a duplicate compact disc copy of the Sequence Listing (COPY 2) (file name: 3014-6US.ST25.txt, date recorded Jul. 6, 2006, size: 210 KB).

FIELD OF INVENTION

The present invention relates to nucleic acids molecules that encode proteins that direct the synthesis of benzodiazepines, and in particular anthramycin. The present invention also is directed to use of DNA to produce compounds exhibiting antibiotic activity based on the anthramycin structures.

BACKGROUND

Anthramycin is a member of a class of natural compounds named pyrrolo[1,4]benzodiazepines (PDBs) or, more simply, the benzodiazepine antibiotics. Members of the benzodiazepine antibiotics include the compounds sibiromycin, tomaymycin, neothramycin, porothramycin, sibanomycin, mazethramycin, DC-81, chicamycin and abbeymycin. Naturally occurring benzodiazepine antibiotics are structurally related tricyclic compounds, consisting of an aromatic-ring, a 1,4-diazepin-5-one-ring bearing a N10-C11 imine-carbinolamine moiety, and a pyrrol-ring, as shown below. Different patterns of substitution of the three rings distinguish the different members of this antibiotic class.

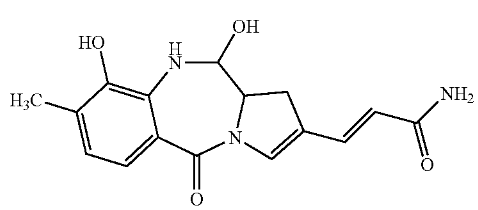

Precursor feeding studies have established the biosynthetic building blocks for anthramycin (Hurley et al., 1975, *J. Am. Chem. Soc.,* 97(15), 4372-4378). The anthranilate moieties of these antibiotics are derived from tryptophan via the kynurenine pathway, with the three antibiotics differing in the pattern of substitution at the aromatic ring (Hurley & Gariola, 1979 Antimicrob. Agents Chemother. 15:42-45). The 2-carbon and 3-carbon proline units of the antibiotics are derived from catabolism of L-tyrosine. The additional carbon atom found in the 3-carbon proline unit of anthramycin and sibiromycin is derived from methionine and is absent in the 2-carbon proline unit of tomaymycin. Despite the precursor feeding studies, the genes and proteins forming the biosynthetic locus for producing anthramycin have remained unidentified.

Benzodiazepine antibiotics have been shown to possess potent biological activitities, including antibiotic, antitumor and antiviral activities (Hurley, 1977, J. Antibiot. 30:349). However, clinical use of benzodiazepine has been compromised primarily because of dose-limiting cardiotoxicity. Consequently, considerable effort has been devoted to creating heterocyclic analogs of the benzodiazepine antibiotics that would retain the desired antitumor activities while avoiding the formation of cardiotoxic quinone-amine products. Elucidation of gene clusters involved in the biosynthesis of benzodiazepines expands the repertoire of genes and proteins useful to produce benzodiazepines via combinatorial biosynthesis.

There is great interest in discovering and developing small molecules capable of binding to DNA in a sequence-selective manner. Anthramycin binds the minor groove of DNA and generates covalent adducts at the 2-amino group of guanine bases. Anthramycin minor groove binding exhibits G-C base specificity. The sequence A-G-A is most favored of all, perhaps because it allows drug binding in either orientation (the acrylamide tail binds at the 5' position of the binding site and prefers the deep minor groove of an AT pair; G-G-G is disfavored because it makes no accommodation for the acrylamide tail in either direction). Compounds having the potential to target and down-regulate individual genes would be useful in the therapy of genetic-based diseases such as cancer. Such compounds would also be useful in diagnostics, functional genomics and target validation (Thurston et al. 1999, J. Med. Chem. 42:1951-1964). Elucidation of the genes and proteins forming the biosynthetic locus for anthramycin provides a means of generating small molecules capable of binding to DNA in a sequence selective manner.

Existing screening methods for identifying benzodiazepine-producing microbes are laborious, time consuming and have not provided sufficient discrimination to date to detect organisms producing benzodiazepine natural products at low levels. There is a need for tools capable of detecting organisms that produce benzodiazepines at levels that are not detected by traditional culture tests.

SUMMARY OF THE INVENTION

The present invention advantageously provides genes and proteins involved in the production of benzodiazepines in general, and anthramycin in particular. Specific embodiments of the genes and proteins are provided in the accompanying sequence listing. SEQ ID NOS: 3, 5, 7, 9, 11, 13, 15, 17, 19, 21, 23, 25, 27, 29, 31, 33, 35, 37, 39, 41, 43, 45, 47, 49, 51 provide nucleic acids responsible for biosynthesis of the benzodiazepine anthramycin. SEQ ID NOS: 2, 4, 6, 8, 10, 12, 14, 16, 18, 20, 22, 24, 26, 28, 30, 32, 34, 36, 38, 40, 42, 44, 46, 48, 50 provide amino acid sequences for proteins responsible for biosynthesis of the benzodiazepine anthramycin. The genes and proteins of the invention provide the machinery for producing novel compounds based on the structure of anthramycins. The invention allows direct manipulation of anthramycin and related chemical structures via chemical engineering of the enzymes involved in the biosynthesis of anthramycin, modifications which may not be presently possible by chemical methodology because of complexity of the structures.

The invention can also be used to introduce "chemical handles" into normally inert positions that permit subsequence chemical modifications. Several general approaches to achieve the development of novel bezodiazapines are facilitated by the methods and reagents of the present invention. Various benzodiazapine structures can be generated by genetic manipulation of the anthramycin gene cluster or use of various genes from the anthramycin gene cluster in accordance with the methods of the invention. The invention can be used to generate a focused library of analogs around a benzodiazepine lead candidate to fine-tune the compound for optimal properties. Genetic engineering methods of the invention can be directed to modify positions of the molecule previously inert to chemical modifications. Known techniques allow one to manipulate a known benzodiazepine gene cluster either to produce the benzodiazepine compound synthesized by that gene cluster at higher levels than occur in nature or in hosts that otherwise do not produce the benzodiazepine. Known techniques allow one to produce molecules that are structurally related to, but distinct from the benzodiazepine compounds produced from known benzodiazepine gene clusters.

Thus, in a first aspect the invention provides an isolated, purified nucleic acid or enriched comprising a sequence selected from the group consisting of SEQ ID NO: 1; the sequences complementary to SEQ ID NO: 1; fragments comprising at least 100, 200, 300, 500, 1000, 2000 or more consecutive nucleotides of SEQ ID NO: 1; and fragments comprising at least 100, 200, 300, 500, 1000, 2000 or more consecutive nucleotides of the sequences complementary to SEQ ID NO: 1. Preferred embodiments of this aspect include isolated, purified or enriched nucleic acids capable of hybridizing to the above sequences under conditions of moderate or high stringency; isolated, purified or enriched nucleic acid comprising at least 100, 200, 300, 500, 1000, 2000 or more consecutive bases of the above sequences; and isolated, purified or enriched nucleic acid having at least 70%, 75%, 80%, 85%, 90%, 95%, 97% or 99% homology to the above sequences as determined by analysis with BLASTN version 2.0 with the default parameters.

Further embodiments of this aspect of the invention include an isolated, purified or enriched nucleic acid comprising a sequence selected from the group consisting of SEQ ID NOS: 3, 5, 7, 9, 11, 13, 15, 17, 19, 21, 23, 25, 27, 29, 31, 33, 35, 37, 39, 41, 43, 45, 47, 49, 51 and the sequences complementary thereto; an isolated, purified or enriched nucleic acid comprising at least 50, 75, 100, 200, 500, 800 or more consecutive bases of a sequence selected from the group consisting of SEQ ID NOS: 3, 5, 7, 9, 11, 13, 15, 17, 19, 21, 23, 25, 27, 29, 31, 33, 35, 37, 39, 41, 43, 45, 47, 49, 51 and the sequences complementary thereto; and an isolated, purified or enriched nucleic acid capable of hybridizing to the above listed nucleic acids under conditions of moderate or high stringency, and isolated, purified or enriched nucleic acid having at least 70%, 75%, 80%, 85%, 90%, 95%, 97% or 99% homology to the nucleic acid of SEQ ID NOS: 3, 5, 7, 9, 11, 13, 15, 17, 19, 21, 23, 25, 27, 29, 31, 33, 35, 37, 39, 41, 43, 45, 47, 49, 51 as determined by analysis with BLASTN version 2.0 with the default parameters.

In a second embodiment, the invention provides an isolated or purified polypeptide comprising a sequence selected from the group consisting of SEQ ID NOS: 2, 4, 6, 8, 10, 12, 14, 16, 18, 20, 22, 24, 26, 28, 30, 32, 34, 36, 38, 40, 42, 44, 46, 48, 50; an isolated or purified polypeptide comprising at least 50, 75, 100, 200, 300 or more consecutive amino acids of the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50; and an isolated or purified polypeptide having at least 70%, 75%, 80%, 85%, 90%, 95%, 97%, or 99% homology to the polypeptide of SEQ ID NOS: 2, 4, 6, 8, 10, 12, 14, 16, 18, 20, 22, 24, 26, 28, 30, 32, 34, 36, 38, 40, 42, 44, 46, 48, 50 as determined by analysis with BLASTP version 2.2.2 with the default parameters. In a further aspect, the invention provides a polypeptide comprising one or two or three or five or more or the above polypeptide sequences.

In a third embodiment, the invention provides an isolated or purified domain of a nonribosomal peptide synthetase system, wherein said nonribosomal peptide synthetase system comprises SEQ ID NO:42 and SEQ ID NO:44, or a polypeptide having at least 80%, 85%, 90% or 95% identity to SEQ ID NO:42 and 44. In a subclass of this embodiment, the domain is selected from an adenylation, a thiolation, a condensation or a reductase domain, wherein said adenylation domain comprises a polypeptide selected from amino acids 35-522 of SEQ ID NO:42 and amino acids 481-962 of SEQ ID NO:44, or a polypeptide at least 80%, 85%, 90% or 95% identical thereto and having adenylation activity; said thiolation domain comprises a polypeptide selected from amino acids 523-600 of SEQ ID NO:42 and 963-1037 of SEQ ID NO:44, or a polypeptide at least 80%, 85%, 90% or 95% identical thereto and having thiolation activity; said condensation domain comprises amino acids 1-480 of SEQ ID NO:44, or a polypeptide at least 80%, 85%, 90% or 95% identical thereto and having condensation activity; and said reductase domain comprises amino acids 1038-1446 of SEQ ID NO:44, or a polypeptide at least 80%, 85%, 90% or 95% identical thereto and having reductase domain activity. In a further aspect, the invention provides an isolated, purified or enriched nucleic acid comprising a polynucleotide encoding at least one domain of said nonribosomal peptide synthetase system, or encoding a polypeptide having at least 80%, 85%, 90% or 95% identity to said domain and having adenylation, thiolation, condensation, or reductase domain activity (Konz and Marahiel (1999), *Chem. Biol.*, vol 6, no 2, R33-R48). In a further aspect, the invention provides an isolated, purified or enriched nucleic acid comprising a polynucleotide encoding at least one domain of said nonribosomal peptide synthetase system a or a nucleotide sequence hybridizable to said nucleic acid, under high stringency conditions, and encoding a polypeptide having adenylation, thiolation, condensation or reductase activity.

The invention also provides recombinant DNA expression vectors containing the above nucleic acids. These genes and the methods of the invention enable one skilled in the art to create recombinant host cells with the ability to produce benzodiazepines. Thus, the invention provides a method of preparing a benzodiazepine compound, said method comprising transforming a heterologous host cell with a recombinant DNA vector that encodes at least one of the above nucleic acids, and culturing said host cell under conditions such that a benzodiazepine is produced. In one aspect, the method is practiced with a *Streptomyces* host cell. In another aspect, the benzodiazepine produced is anthramycin. In another aspect, the benzodiazepine produced is a compound related in structure to anthlramycin.

The invention also encompasses a reagent comprising a probe of the invention for detecting and/or isolating putative anthramycin-producing microorganisms; and a method for detecting and/or isolating putative benzodiazepine-producing microorganisms using a probe of the invention such that hybridization is detected. Cloning, analysis, and manipulation by recombinant DNA technology of genes that encode anthramycin gene products can be performed according to known techniques.

BRIEF DESCRIPTION OF THE DRAWINGS

The present invention will be further understood from the following description with reference to the following figures:

FIGS. 2A, 2B, 2C and 2D are flow diagrams of a sequence comparison software that can be employed for the purpose of comparing a query to a subject, wherein the subject is selected from the reference sequences of the invention, wherein FIG. 2A is the query initialization subprocess of the sequence comparison software, FIG. 2B is the subject datasource initialization subprocess of the sequence comparison software, FIG. 2C illustrates the comparison subprocess and the analysis subprocess of the sequence comparison software, and FIG. 2D is the Display/Report subprocess of the sequence comparison software.

FIG. 11 is an alignment of the reductase domain of anthramycin NRPS (amino acids 1038 to 1446 of SEQ ID NO: 44) with the reductase domain of: Saframycin A synthetase (SEQ ID NO: 52, AAC44129), Myxalamid (SEQ ID NO: 53, AAK57184) and Myxochelin (SEQ ID NO: 54, AAG31130).

FIG. 12 is an adenylation alignment of anthramycin NRPS (amino acids 35-522 of SEQ ID NO: 42 and amino acids 481-962 of SEQ ID NO: 44) with Grsa of Gramicidin (SEQ ID NO: 55).

DETAILED DESCRIPTION OF THE INVENTION

Figure 1:
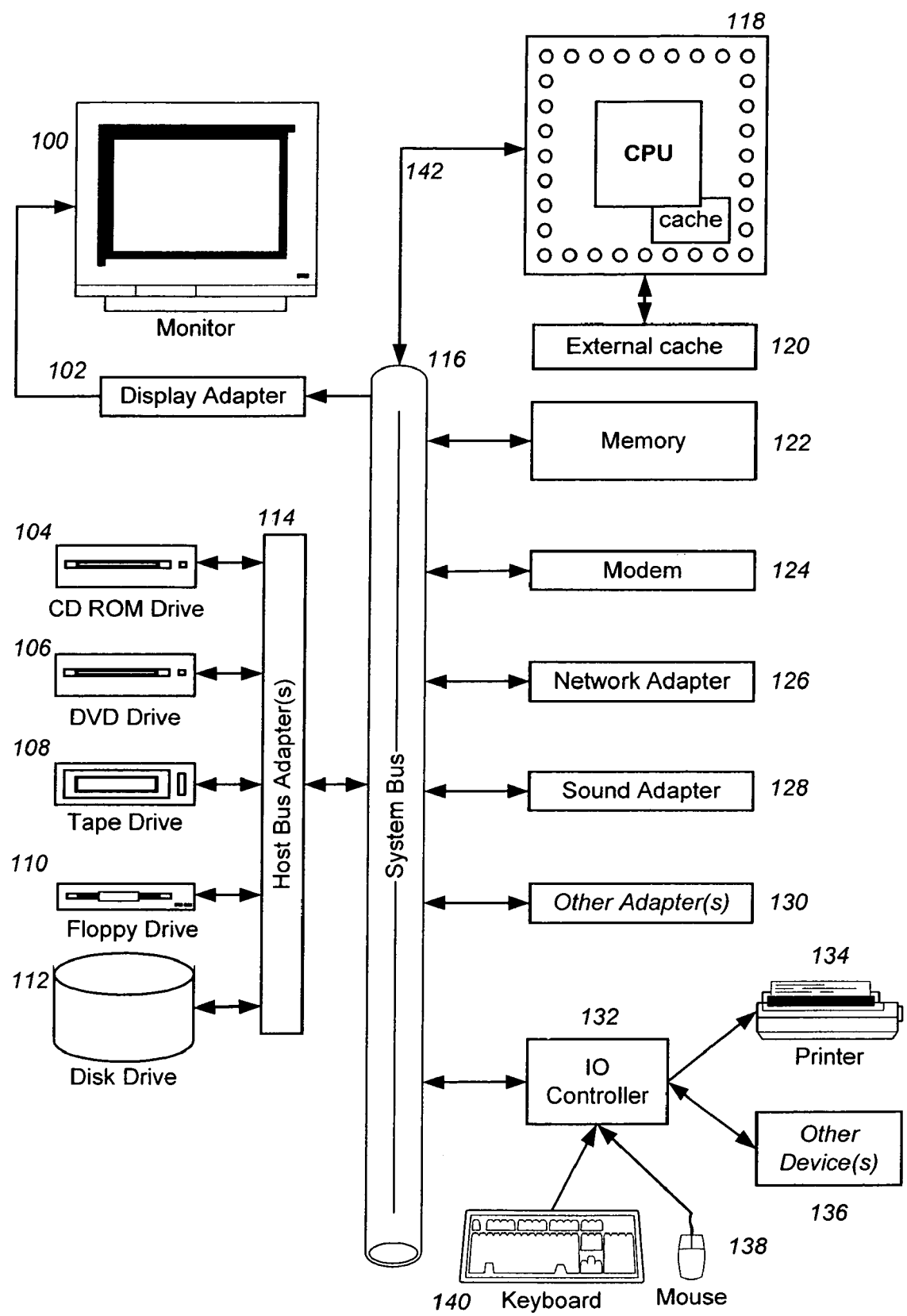
FIG. 1 is a block diagram of a computer system which implements and executes software tools for the purpose of comparing a query to a subject, wherein the subject is selected from the reference sequences of the invention.

Throughout the description and the figures, the biosynthetic locus for anthramycin from *Streptomyces refuineus* var. *thermotolerans* is sometimes referred to as ANTH. The ORFs in ANTH are assigned a putative function sometimes referred to throughout the description and figures by reference to a four-letter designation, as indicated in Table 1.

TABLE 1

| Families | Function |
|---|---|
| AAOB | amine oxidase, flavin-containing; similar to many bacterial L-amino acid oxidases (catalyze the oxidative deamination of amino acids) and eukaryotic monoamine oxidases; domain homology to tryptophan-2-monooxygenases. |
| AOTF | amidotransferase, ATP-dependent [asparaginase; asparagine synthetases class B (glutamine-hydrolyzing)]; glutamine amidotransferase/ asparagine synthase; asparagine synthetases (glutamine amidotransferases); catalyze the transfer of the carboxamide amino group of glutamine to the carboxylate group of aspartate. |
| ATAA | adenylate ligase with C-terminal thiolation domain; part of the anthramycin NRPS system. |
| EATD | domain homology to several bacterial lipases, deacetylases, esterases. |
| EFFA | efflux; transmembrane transporter. |
| ENRP | excision nuclease repair protein; homolog of primary UvrA-like ABC transporter; UvrA is a DNA-binding ATPase that recognizes DNA adducts in the nucleotide excision repair process catalyzed by the Uvr A, B, C excinuclease; contain 2 ABC transporter domains with strong homology to those associated with membrane-bound transporters; contain 1 of the 2 zinc-finger DNA binding motifs found in UvrA; similar to daunorubicin DrrC, mithramycin MtrX, nogalamycin SnoRO. |
| HOXF | monooxygenase, flavin-dependent, NADP-binding site; similar to eukaryotic kynurenine 3-monooxygenase (kynurenine-3-hydroxylase). |
| HOXY | strong similarity to many putative hydroxylases; domain homology to daunorubicin/doxorubicin DnrV protein that somehow cooperates with the DoxA multifunctional P450 monooxygenase to achieve C-13, C-14 hydroxylation of daunorubicin intermediates. |
| HYDE | kynurenine hydrolase family, pyridoxal-phosphate cofactor; the kynureninases cleave L-kynurenine and 3-hydroxykynurenine to generate anthranilic acid and 3-hydroxyanthranilic acid, respectively, and L-alanine, in the biosynthesis of NAD cofactors from tryptophan through the kynurenine pathway. |
| MTFA | methyltransferase, SAM-dependent; includes O-methyltransferases, N,N-dimethyltransferases (e.g. spinosyn SpnS N-dimethyltransferase), C-methyltransferases. |
| NRPS | non-ribosomal peptide synthetase; part of the anthramycin NRPS system. |
| OXBD | oxidoreductase; F420-dependent; similar to LmbY; this reductase probably requires the so-called LCF cofactor (lincomycin cosynthetic factor, identical to the 7,8-didemethyl-8-hydroxy-5-deazariboflavin component of the redox coenzyme F420 of methanogens); this unusual cofactor in its active form contains a gamma-glutamyl moiety in its side chain, a side chain that may be added by the gamma-glutamyl transpeptidase family enzymes. |
| OXBY | flavin-dependent oxidoreductase; strong homology to many plant cytokinin oxidases, which degrade cytokinins by catalyzing the cleavage of the N6-(isopent-2-enyl) side chain resulting in the formation of adenine-type compounds and the corresponding isopentenyl aldehydes; domain homology to other oxidoreductases that covalently |

TABLE 1-continued

| Families | Function |
|---|---|
| | bind FAD; contains the conserved His residue that serves as the site of covalent FAD binding in such diverse oxidoreductases as cytokinin oxidases, 6-deoxy-D-nicotine oxidases, mitomycin McrA, MmcM, MitR, daunorubicin DnrW, and plant berberine bridge enzymes. |
| OXCB | alcohol dehydrogenase; zinc-binding, NAD(+)– dependent alcohol dehydrogenase family. |
| OXCC | NAD-dependent aldehyde dehydrogenase; homology to e.g. Pseudomonas putida p-cumic aldehyde dehydrogenase which converts p-isopropylbenzal- dehyde to p-isopropylbenzoic acid; *Ustilago maydis* indole-3-acetaldehyde dehydrogenase which converts indole-3-acetaldehyde to indole-3-acetic acid; mammalian mitochondrial aldehyde dehydrogenases; vertebrate retinaldehyde- specific dehydrogenases; as well as several plant NAD-dependent aldehyde dehydrogenases. |
| OXRC | oxidoreductase; cytP450 monooxygenase, hydroxylase; similar to PikC, DoxA, FkbD; oxygen-binding site motif: LLxAGx(D, E); heme-binding pocket motif: GxGxHxCxGxxLxR, the cysteine is invariable and coordinates the heme. |
| OXRN | oxidoreductase; homology to tryptophan 2,3- dioxygenases (tryptophan pyrrolase, tryptamin- 2,3-dioxygenase) from diverse organisms; the tryptophan dioxygenases are homotetrameric proteins that bind 2 molecules of protoheme IV, and demonstrate a broad specificity towards tryptamine and derivatives including D- and L-tryptophan, 5-hydroxytryptophan and serotonin. |
| RREA | response regulator; CheY-homologous receiver domain, contains a phosphoacceptor site that is phosphorylated by histidine kinase homologs; similar to JadR1, NisR. |
| UNIQ | unknown. |
| UNKA | unknown; similar to lincomycin LmbX (unassigned function in lincomycin biosynthesis). |
| UNKJ | unknown; similar to LmbA (gammaglutamyl transferase, gamma-glutamyltranspeptidase, involved in generating the FAD-derived lincomycin cosynthetic factor LCF required for lincomycin biosynthesis); GGTs catalyze the transfer of 5-L- glutamyl group from peptides to amino acids and play a key role in the gamma-glutamyl cycle, a pathway for the synthesis and degradation of glutathione; also similar to cephalosporin acylase I, which hydrolyzes 7-beta-(4-carboxybutan-amido)- cephalosporanic acid to 7-aminocephalosporanic acid and glutamic acid, and which also has GGT activity in vitro; may be involved in adding gamma- glutamyl side chains to unusual flavin cofactors. |
| UNKV | unknown; similar to lincomycin LmbB2, putative tyrosine 3-hydroxylase; LmbB1,2 may cooperate to form a L-DOPA extradiol-cleaving 2,3-dioxygenase (L-DOPA converting enzyme) to cleave the aromatic ring of L-DOPA (3,4-dihydroxyphenylalanine; 3- hydroxytyrosine) and create a 5-membered heterocyclic ring that incorporates the amino group of the amino acid; LmbB1 (see UNKW) and LmbB2 together may also act as a tyrosine 3-hydroxylase to convert tyrosine to L-DOPA. |
| UNKW | unknown; similar to lincomycin LmbB1 L-DOPA extradiol-cleaving 2,3-dioxygenase (L-DOPA converting enzyme) subunit, which may work together with LmbB2 (see UNKV) to cleave the aromatic ring of L-DOPA (3,4-dihydroxyphenyl- alanine; 3-hydroxytyrosine) and create a 5- membered heterocyclic ring that incorporates the amino group of the amino acid; LmbB1 and LmbB2 (see UNKV) together may also act as a tyrosine 3-hydroxylase to convert tyrosine to L-DOPA. |

The terms "benzodiazepine producer" and "benzodiazepine-producing organism" refer to a microorganism that carries the genetic information necessary to produce a benzodiazepine compound, whether or not the organism is known to produce a benzodiazepine compound. The terms "anthramycin producer" and "anthramycin-producing organism" refer to a microorganism that carries the genetic information necessary to produce an anthromycin compound, whether or not the organism is known to produce an anthramycin product. The terms apply equally to organisms in which the genetic information to produce the benzodiazepine or anthramycin compound is found in the organism as it exists in its natural environment, and to organisms in which the genetic information is introduced by recombinant techniques. For the sake of particularity, specific organisms contemplated herein include organisms, of the family Micromonosporaceae, of which preferred genera include *Micromonospora*, *Actinoplanes* and *Dactylosporangium*; the family Streptomycetaceae, of which preferred genera include *Streptomyces* and *Kitasatospora*; the family Pseudonocardiaceae, of which preferred genera are *Amycolatopsis* and *Saccharopolyspora*; and the family Actinosynnemataceae, of which preferred genera include *Saccharothrix* and *Actinosynnema*; however the terms are intended to encompass all organisms containing genetic information necessary to produce a benzodiazepine compound.

The term anthramycin biosynthetic gene product refers to any enzyme or polypeptide involved in the biosynthesis of anthramycin. For the sake of particularity, the anthramycin biosynthetic pathway is associated with *Streptomyces refuineus* var. *thermotolerans*. However, it should be understood that this term encompasses anthramycin biosynthetic enzymes (and genes encoding such enzymes) isolated from any microorganism of the genus *Streptomyces*, and furthermore that these genes may have novel homologues in related actinomycete microorganisms or non-actinomycete microorganisms that fall within the scope of the invention. Representative anthramycin biosynthetic genes products include the polypeptides listed in SEQ ID NOS: 2, 4, 6, 8, 10, 12, 14, 16, 18, 20, 22, 24, 26, 28, 30, 32, 34, 36, 38, 40, 42, 44, 46, 48, 50 or homologues thereof.

The term "isolated" means that the material is removed from its original environment, e.g. the natural environment if it is naturally occurring. For example, a naturally-occurring polynucleotide or polypeptide present in a living organism is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The term "purified" does not require absolute purity; rather, it is intended as a relative definition. Individual nucleic acids obtained from a library have been conventionally purified to electrophoretic homogeneity. The purified nucleic acids of the present invention have been purified from the remainder of the genomic DNA in the organism by at least $10^4$ to $10^6$ fold. However, the term "purified" also includes nucleic acids which have been purified from the remainder of the genomic DNA or from other sequences in a library or other environment by at least one order of magnitude, preferably two or three orders of magnitude, and more preferably four or five orders of magnitude.

"Recombinant" means that the nucleic acid is adjacent to "backbone" nucleic acid to which it is not adjacent in its natural environment. "Enriched" nucleic acids represent 5% or more of the number of nucleic acid inserts in a population of nucleic acid backbone molecules. "Backbone" molecules include nucleic acids such as expression vectors, self-replicating nucleic acids, viruses, integrating nucleic acids, and other vectors or nucleic acids used to maintain or manipulate a nucleic acid of interest. Preferably, the enriched nucleic acids represent 15% or more, more preferably 50% or more, and most preferably 90% or more, of the number of nucleic acid inserts in the population of recombinant backbone molecules.

"Recombinant" polypeptides or proteins refers to polypeptides or proteins produced by recombinant DNA techniques, i.e. produced from cells transformed by an exogenous DNA construct encoding the desired polypeptide or protein. "Synthetic" polypeptides or proteins are those prepared by chemical synthesis.

The term "gene" means the segment of DNA involved in producing a polypeptide chain; it includes regions preceding and following the coding region (leader and trailer) as well as, where applicable, intervening regions (introns) between individual coding segments (exons).

A DNA or nucleotide "coding sequence" or "sequence encoding" a particular polypeptide or protein, is a DNA sequence which is transcribed and translated into a polypeptide or protein when placed under the control of appropriate regulatory sequences.

"Oligonucleotide" refers to a nucleic acid, generally of at least 10, preferably 15 and more preferably at least 20 nucleotides, preferably no more than 100 nucleotides, that are hybridizable to a genomic DNA molecule, a cDNA molecule, or an mRNA molecule encoding a gene, mRNA, cDNA or other nucleic acid of interest.

A promoter sequence is "operably linked to" a coding sequence recognized by RNA polymerase which initiates transcription at the promoter and transcribes the coding sequence into mRNA.

"Plasmids" are designated herein by a lower case p preceded or followed by capital letters and/or numbers. The starting plasmids herein are commercially available, publicly available on an unrestricted basis, or can be constructed from available plasmids in accord with published procedures. In addition, equivalent plasmids to those described herein are known in the art and will be apparent to the skilled artisan.

"Digestion" of DNA refers to enzymatic cleavage of the DNA with a restriction enzyme that acts only at certain sequences in the DNA. The various restriction enzymes used herein are commercially available and their reaction conditions, cofactors and other requirements were used as would be known to the ordinary skilled artisan. For analytical purposes, typically 1 μg of plasmid or DNA fragment is used with about 2 units of enzyme in about 20 μl of buffer solution. For the purpose of isolating DNA fragmnents for plasmid construction, typically 5 to 50 μg of DNA are digested with 20 to 250 units of enzyme in a larger volume. Appropriate buffers and substrate amounts for particular enzymes are specified by the manufacturer. Incubation times of about 1 hour at 37° C. are ordinarily used, but may vary in accordance with the supplier's instructions. After digestion the gel electrophoresis may be performed to isolate the desired fragment.

We have now discovered the genes and proteins involved in the biosynthesis of the benzodiazepine anthramycin. Nucleic acid sequences encoding proteins involved in the biosynthesis of anthramycin are provided in the accompanying sequence listing as SEQ ID NOS: 3, 5, 7, 9, 11, 13, 15, 17, 19, 21, 23, 25, 27, 29, 31, 33, 35, 37, 39, 41, 43, 45, 47, 49, 51. Polypeptides involved in the biosynthesis of anthramycin are provided in the accompanying sequence listing as SEQ ID NOS: 2, 4, 6, 8, 10, 12, 14, 16, 18, 20, 22, 24, 26, 28, 30, 32, 34, 36, 38, 40, 42, 44, 46, 48, 50.

One aspect of the present invention is an isolated, purified, or enriched nucleic acid comprising one of the sequences of SEQ ID NOS: 3, 5, 7, 9, 11, 13, 15, 17, 19, 21, 23, 25, 27, 29, 31, 33, 35, 37, 39, 41, 43, 45, 47, 49, 51, the sequences complementary thereto, or a fragment comprising at least 50, 75, 100, 150, 200, 300, 400, 500 or 800 consecutive bases of one of the sequences of SEQ ID NOS: 3, 5, 7, 9, 11, 13, 15, 17, 19, 21, 23, 25, 27, 29, 31, 33, 35, 37, 39, 41, 43, 45, 47, 49, 51 or the sequences complementary thereto. The isolated, purified or enriched nucleic acids may comprise DNA, including CDNA, genomic DNA, and synthetic DNA. The DNA may be double stranded or single stranded, and if single stranded may be the coding (sense) or non-coding (anti-sense) strand. Alternatively, the isolated, purified or enriched nucleic acids may comprise RNA.

As discussed in more detail below, the isolated, purified or enriched nucleic acids of one of SEQ ID NOS: 3, 5, 7, 9, 11, 13, 15, 17, 19, 21, 23, 25, 27, 29, 31, 33, 35, 37, 39, 41, 43, 45, 47, 49, 51 may be used to prepare one of the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50 or fragments comprising at least 50, 75, 100, 200, 300 or more consecutive amino acids of one of the polypeptides of SEQ ID NO: 2, 4, 6, 8, 10, 12, 14, 16, 18, 20, 22, 24, 26, 28, 30, 32, 34, 36, 38, 40, 42, 44, 46, 48, 50.

Accordingly, another aspect of the present invention is an isolated, purified or enriched nucleic acid which encodes one of the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50, or fragments comprising at least 50, 75, 100, 150, 200, 300 or more consecutive amino acids of one of the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50. The coding sequences of these nucleic acids may be identical to one of the coding sequences of one of the nucleic acids of SEQ ID NOS: 3, 5, 7, 9, 11, 13, 15, 17, 19, 21, 23, 25, 27, 29, 31, 33, 35, 37, 39, 41, 43, 45, 47, 49, 51 or a fragment thereof or may be different coding sequences which encode one of the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50, or fragments comprising at least 50, 75, 100, 150, 200, 300 consecutive amino acids of one of the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50 as a result of the redundancy or degeneracy of the genetic code. The genetic code is well known to those of skill in the art and can be obtained, for example, from Stryer, *Biochemistry*, 3$^{rd}$ edition, W. H. Freeman & Co., New York.

The isolated, purified or enriched nucleic acid which encodes one of the polypeptides-of SEQ ID NOS: 2, 4, 6, 8, 10, 12, 14, 16, 18, 20, 22, 24, 26, 28, 30, 32, 34, 36, 38, 40, 42, 44, 46, 48, 50, may include, but is not limited to: (1) only the coding sequences of one of SEQ ID NOS: 3, 5, 7, 9, 11, 13, 15, 17, 19, 21, 23, 25, 27, 29, 31, 33, 35, 37, 39, 41, 43, 45, 47, 49, 51; (2) the coding sequences of SEQ ID NOS: 3, 5, 7, 9, 11, 13, 15, 17, 19, 21, 23, 25, 27, 29, 31, 33, 35, 37, 39, 41, 43, 45, 47, 49, 51 and additional coding sequences, such as leader sequences or proprotein; and (3) the coding sequences of SEQ ID NOS: 3, 5, 7, 9, 11, 13, 15, 17, 19, 21, 23, 25, 27, 29, 31, 33, 35, 37, 39, 41, 43, 45, 47, 49, 51 and non-coding sequences, such as introns or non-coding sequences 5' and/or 3' of the coding sequence. Thus, as used herein, the term "polynucleotide encoding a polypeptide" encompasses a polynucleotide which includes only coding sequence for the polypeptide as well as a polynucleotide which includes additional coding and/or non-coding sequence.

The invention relates to polynucleotides based on SEQ ID NOS: 3, 5, 7, 9, 11, 13, 15, 17, 19, 21, 23, 25, 27, 29, 31, 33, 35, 37, 39, 41, 43, 45, 47, 49, 51 but having polynucleotide changes that are "silent", for example changes which do not alter the amino acid sequence encoded by the polynucleotides of SEQ ID NOS: 3, 5, 7, 9, 11, 13, 15, 17, 19, 21, 23, 25, 27, 29, 31, 33, 35, 37, 39, 41, 43, 45, 47, 49, 51. The invention also relates to polynucleotides which have nucleotide changes which result in amino acid substitutions, additions, deletions, fusions and truncations of the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50. Such nucleotide changes may be introduced using techniques such as site directed mutagenesis, random chemical mutagenesis, exonuclease III deletion, and other recombinant DNA techniques.

The isolated, purified or enriched nucleic acids of SEQ ID NOS: 3, 5, 7, 9, 11, 13, 15, 17, 19, 21, 23, 25, 27, 29, 31, 33, 35, 37, 39, 41, 43, 45, 47, 49, 51, the sequences complementary thereto, or a fragment comprising at least 10, 15, 20, 25, 30, 35, 40, 50, 75, 100, 150, 200, 300, 400 or 500 consecutive bases of one of the sequence of SEQ ID NOS: 3, 5, 7, 9, 11, 13, 15, 17, 19, 21, 23, 25, 27, 29, 31, 33, 35, 37, 39, 41, 43, 45, 47, 49, 51, or the sequences complementary thereto may be used as probes to identify and isolate DNAs encoding the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50 respectively. In such procedures, a genomic DNA library is constructed from a sample microorganism or a sample containing a microorganism capable of producing a benzodiazepine. The genomic DNA library is then contacted with a probe comprising a coding sequence or a fragment of the coding sequence, encoding one of the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50, or a fragment thereof under conditions which permit the probe to specifically hybridize to sequences complementary thereto. In a preferred embodiment, the probe is an oligonucleotide of about 10 to about 30 nucleotides in length designed based on a nucleic acid of SEQ ID NOS: 3, 5, 7, 9, 11, 13, 15, 17, 19, 21, 23, 25, 27, 29, 31, 33, 35, 37, 39, 41, 43, 45, 47, 49, 51. Genomic DNA clones which hybridize to the probe are then detected and isolated. Procedures for preparing and identifying DNA clones of interest are disclosed in Ausubel et al., Current Protocols in Molecular Biology, John Wiley 503 Sons, Inc. 1997; and Sambrook et al., Molecular Cloning: A Laboratory Manual 2d Ed., Cold Spring Harbor Laboratory Press, 1989. In another embodiment, the probe is a restriction fragments or a PCR amplified nucleic acid derived from SEQ ID NOS: 3, 5, 7, 9, 11, 13, 15, 17, 19, 21, 23, 25, 27, 29, 31, 33, 35, 37, 39, 41, 43, 45, 47, 49, 51.

The isolated, purified or enriched nucleic acids of SEQ ID NOS: 3, 5, 7, 9, 11, 13, 15, 17, 19, 21, 23, 25, 27, 29, 31, 33, 35, 37, 39, 41, 43, 45, 47, 49, 51, the sequences complementary thereto, or a fragment comprising at least 10, 15, 20, 25, 30, 35, 40, 50, 75, 100, 150, 200, 300, 400 or 500 consecutive bases of one of the sequences of SEQ ID NOS: 3, 5, 7, 9, 11, 13, 15, 17, 19, 21, 23, 25, 27, 29, 31, 33, 35, 37, 39, 41, 43, 45, 47, 49, 51, or the sequences complementary thereto may be used as probes to identify and isolate related nucleic acids. In some embodiments, the related nucleic acids may be genomic DNAs (or cDNAs) from potential benzodiazepine producers. In such procedures, a nucleic acid sample containing nucleic acids from a potential benzodiazepine-producer or anthramycin-producer is contacted with the probe under conditions that permit the probe to specifically hybridize to related sequences. The nucleic acid sample may be a genomic DNA (or cDNA) library from the potential benzodiazepine-producer. Hybridization of the probe to nucleic acids is then detected using any of the methods described above.

Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM NaH$_2$PO$_4$, pH 7.0, 5.0 mM Na$_2$EDTA, 0.5% SDS, 10× Denhardt's, and 0.5 mg/ml polyriboadenylic acid. Approximately 2×10$^7$ cpm (specific activity 4-9×10$^8$ cpm/ug) of $^{32}$P end-labeled oligonucleotide probe are then added to the solution. After 12-16 hours of incubation, the membrane is washed for 30 minutes at room temperature in 1×SET (150 mM NaCl, 20 mM Tris hydrochloride, pH 7.8, 1 mM Na$_2$EDTA) containing 0.5% SDS, followed by a 30 minute wash in fresh 1×SET at Tm-10 C for the oligonucleotide probe where Tm is the melting temperature. The membrane is then exposed to auto-radiographic film for detection of hybridization signals.

By varying the stringency of the hybridization conditions used to identify nucleic acids, such as genomic DNAs or cDNAs, which hybridize to the detectable probe, nucleic acids having different levels of homology to the probe can be identified and isolated. Stringency may be varied by conducting the hybridization at varying temperatures below the melting temperatures of the probes. The melting temperature of the probe may be calculated using the following formulas:

For oligonucleotide probes between 14 and 70 nucleotides in length the melting temperature (Tm) in degrees Celcius may be calculated using the formula:

$$Tm=81.5+16.6(\log [Na+])+0.41(\text{fraction } G+C)-(600/N)$$

where N is the length of the oligonucleotide.

If the hybridization is carried out in a solution containing formamide, the melting temperature may be calculated using the equation Tm=81.5+16.6(log [Na+])+0.41(fraction G+C)−(0.63% formamide)−(600/N) where N is the length of the probe.

Prehybridization may be carried out in 6×SSC, 5× Denhardt's reagent, 0.5% SDS, 0.1 mg/ml denatured fragmented salmon sperm DNA or 6×SSC, 5× Denhardt's reagent, 0.5% SDS, 0.1 mg/ml denatured fragmented salmon sperm DNA, 50% formamide. The composition of the SSC and Denhardt's solutions are listed in Sambrook et al., supra.

Hybridization is conducted by adding the detectable probe to the hybridization solutions listed above. Where the probe comprises double stranded DNA, it is denatured by incubating at elevated temperatures and quickly cooling before addition to the hybridization solution. It may also be desirable to similarly denature single stranded probes to eliminate or diminish formation of secondary structures or oligomerization. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the Tm. For shorter probes, such as oligonucleotide probes, the hybridization may be conducted at 5-10° C. below the Tm. Preferably, the hybridization is conducted in 6×SSC, for shorter probes.

Preferably, the hybridization is conducted in 50% formamide containing solutions, for longer probes.

All the foregoing hybridizations would be considered to be examples of hybridization performed under conditions of high stringency.

Following hybridization, the filter is washed for at least 15 minutes in 2×SSC, 0.1% SDS at room temperature or higher, depending on the desired stringency. The filter is then washed with 0.1×SSC, 0.5% SDS at room temperature (again) for 30 minutes to 1 hour.

Nucleic acids which have hybridized to the probe are identified by conventional autoradiography and non-radioactive detection methods.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate stringency" conditions above 50° C. and "low stringency" conditions below 50° C. A specific example of "moderate stringency" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate stringency" conditions above 25% formamide and "low stringency" conditions below 25% formamide. A specific example of "moderate stringency" hybridization conditions is when the above hybridization is conducted at 30% formamide. A specific example of "low stringency" hybridization conditions is when the above hybridization is conducted at 10% formamide. Examples of conditions of different stringency are also provided in Table 2.

TABLE 2

| Very High Stringency (detects sequences sharing at least 90% identity) | | | |
|---|---|---|---|
| Hybridization | in | 5× SCC at 65° C. | 16 hours |
| Wash twice | in | 2× SCC at room temperature | 15 minutes each |
| Wash twice | in | 0.5× SCC at 65° C. | 20 minutes each |
| High Stringency (detects sequences sharing at least 80% identity) | | | |
| Hybridization | in | 5× SCC at 65° C. | 16 hours |
| Wash twice | in | 2× SCC at room temperature | 20 mnutes each |
| Wash once | in | 1× SCC at 55° C. | 30 minutes each |
| Low Stringency (detects sequences sharing at least 50% identity) | | | |
| Hybridization | in | 6× SCC at room temperature | 16 hours |
| Wash twice | in | 3× SCC at room temperature | 20 minutes each |

Nucleic acids which have hybridized to the probe are identified by conventional autoradiography and non-radioactive detection methods.

For example, the preceding methods may be used to isolate nucleic acids having a sequence with at least 97%, at least 95%, at least 90%, at least 85%, at least 80%, or at least 70% homology to a nucleic acid sequence selected from the group consisting of the sequences of SEQ ID NOS: 3, 5, 7, 9, 11, 13, 15, 17, 19, 21, 23, 25, 27, 29, 31, 33, 35, 37, 39, 41, 43, 45, 47, 49, 51, fragments comprising at least 10, 15, 20, 25, 30, 35, 40, 50, 75, 100, 150, 200, 300, 400, or 500 consecutive bases thereof, and the sequences complementary thereto. Homology may be measured using BLASTN version 2.0 with the default parameters. For example, the homologous polynucleotides may have a coding sequence that is a naturally occurring allelic variant of one of the coding sequences described herein. Such allelic variant may have a substitution, deletion or addition of one or more nucleotides when compared to the nucleic acids of SEQ ID NOS: 3, 5, 7, 9, 11, 13, 15, 17, 19, 21, 23, 25, 27, 29, 31, 33, 35, 37, 39, 41, 43, 45, 47, 49, 51, or the sequences complementary thereto.

Additionally, the above procedures may be used to isolate nucleic acids which encode polypeptides having at least 99%, 95%, at least 90%, at least 85%, at least 80%, or at least 70% homology to a polypeptide having the sequence of one of SEQ ID NOS: 2, 4, 6, 8, 10, 12, 14, 16, 18, 20, 22, 24, 26, 28, 30, 32, 34, 36, 38, 40, 42, 44, 46, 48, 50, or fragments comprising at least 50, 75, 100, 150, 200, 300 consecutive amino acids thereof as determined using the BLASTP version 2.2.2 algorithm with default parameters.

Another aspect of the present invention is an isolated or purified polypeptide comprising the sequence of one of SEQ ID NOS: 2, 4, 6, 8, 10, 12, 14, 16, 18, 20, 22, 24, 26, 28, 30, 32, 34, 36, 38, 40, 42, 44, 46, 48, 50 or fragments comprising at least 50, 75, 100, 150, 200 or 300 consecutive amino acids thereof. As discussed herein, such polypeptides may be obtained by inserting a nucleic acid encoding the polypeptide into a vector such that the coding sequence is operably linked to a sequence capable of driving the expression of the encoded polypeptide in a suitable host cell. For example, the expression vector may comprise a promoter, a ribosome binding site for translation initiation and a transcription terminator. The vector may also include appropriate sequences for modulating expression levels, an origin of replication and a selectable marker.

Promoters suitable for expressing the polypeptide or fragment thereof in bacteria include the *E.coli* lac or trp promoters, the lacI promoter, the lacZ promoter, the T3 promoter, the T7 promoter, the gpt promoter, the lambda PR promoter, the lambda $P_L$ promoter, promoters from operons encoding glycolytic enzymes such as 3-phosphoglycerate kinase (PGK), and the acid phosphatase promoter. Fungal promoters include the α factor promoter. Eukaryotic promoters include the CMV immediate early promoter, the HSV thymidine kinase promoter, heat shock promoters, the early and late SV40 promoter, LTRs from retroviruses, and the mouse metallothionein-l promoter. Other promoters known to control expression of genes in prokaryotic or eukaryotic cells or their viruses may also be used.

Mammalian expression vectors may also comprise an origin of replication, any necessary ribosome binding sites, a polyadenylation site, splice donors and acceptor sites, transcriptional termination sequences, and 5' flanking non-transcribed sequences. In some embodiments, DNA sequences derived from the SV40 splice and polyadenylation sites may be used to provide the required nontranscribed genetic elements.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin bp 100 to 270, the cytomegalovirus early promoter enhancer, the polyoma enhancer on the late side of the replication origin, and the adenovirus enhancers.

In addition, the expression vectors preferably contain one or more selectable marker genes to permit selection of host cells containing the vector. Examples of selectable markers that may be used include genes encoding dihydrofolate reductase or genes conferring neomycin resistance for eukaryotic cell culture, genes conferring tetracycline or ampicillin resistance in *E. coli*, and the *S. cerevisiae* TRP1 gene.

In some embodiments, the nucleic acid encoding one of the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50, or fragments comprising at least 50, 75, 100, 150, 200 or 300 consecutive amino acids thereof is assembled in appropriate phase with a leader sequence capable of directing secretion of the translated polypeptides or fragments thereof. Optionally, the nucleic acid can encode a fusion polypeptide in which one of the polypeptide of SEQ ID NOS: 2, 4, 6, 8, 10, 12, 14, 16, 18, 20, 22, 24, 26, 28, 30, 32, 34, 36, 38, 40, 42, 44, 46, 48, 50 or fragments comprising at least 5, 10, 15, 20, 25, 30, 35, 40, 50, 75, 100, or 150 consecutive amino acids thereof is fused to heterologous peptides or polypeptides, such as N-terminal identification peptides which impart desired characteristics such as increased stability or simplified purification or detection.

The appropriate DNA sequence may be inserted into the vector by a variety of procedures. In general, the DNA sequence is ligated to the desired position in the vector following digestion of the insert and the vector with appropriate restriction endonucleases. Alternatively, appropriate restriction enzyme sites can be engineered into a DNA sequence by PCR. A variety of cloning techniques are disclosed in Ausbel et al. Current Protocols in Molecular Biology, John Wiley 503 Sons, Inc. 1997 and Sambrook et al., Molecular Cloning: A Laboratory Manual 2d Ed., Cold Spring Harbour Laboratory Press, 1989. Such procedures and others are deemed to be within the scope of those skilled in the art.

The vector may be, for example, in the form of a plasmid, a viral particle, or a phage. Other vectors include derivatives of chromosomal, nonchromosomal and synthetic DNA sequences, viruses, bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by Sambrook, et al., Molecular Cloning: A Laboratory Manual, Second Edition, Cold Spring Harbor, N.Y., (1989).

Particular bacterial vectors which may be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, pDR540, pRIT5 (Pharmacia), pKK232-8 and pCM7. Particular eukaryotic vectors include pSV2CAT, pOG44, pXT1, pSG (Stratagene) pSVK3, pBPV, pMSG, and PSVL (Pharmacia). However, any other vector may be used as long as it is replicable and stable in the host cell.

The host cell may be any of the host cells familiar to those skilled in the art, including prokaryotic cells or eukaryotic cells. As representative examples of appropriate hosts, there may be mentioned: bacteria cells, such as *E. coli, Streptomyces, Bacillus subtilis, Salmonella typhimurium* and various species within the genera *Pseudomonas, Streptomyces*, and *Staphylococcus*, fungal cells, such as yeast, insect cells such as *Drosophila* S2 and *Spodoptera* Sf9, animal cells such as CHO, COS or Bowes melanoma, and adenoviruses. The selection of an appropriate host is within the abilities of those skilled in the art.

The vector may be introduced into the host cells using any of a variety of techniques, including electroporation transformation, transfection, transduction, viral infection, gene guns, or Ti-mediated gene transfer. Where appropriate, the engineered host cells can be cultured in conventional nutrient media modified as appropriate for activating promoters, selecting transformants or amplifying the genes of the present invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells are typically harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts (described by Gluzman, Cell, 23:175 (1981), and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptide produced by host cells containing the vector may be glycosylated or may be non-glycosylated. Polypeptides of the invention may or may not also include an initial methionine amino acid residue.

Alternatively, the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50, or fragments comprising at least 50, 75, 100, 150, 200 or 300 consecutive amino acids thereof can be synthetically produced by conventional peptide synthesizers. In other embodiments, fragments or portions of the polynucleotides may be employed for producing the corresponding full-length polypeptide by peptide synthesis; therefore, the fragments may be employed as intermediates for producing the full-length polypeptides.

Cell-free translation systems can also be employed to produce one of the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50, or fragments comprising at least 50, 75, 100, 150, 200 or 300 consecutive amino acids thereof using mRNAs transcribed from a DNA construct comprising a promoter operably linked to a nucleic acid encoding the polypeptide or fragment therof. In some embodiments, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The present invention also relates to variants of the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50, or fragments comprising at least 50, 75, 100, 150, 200 or 300 consecutive amino acids thereof. The term "variant" includes derivatives or analogs of these polypeptides. In particular, the variants may differ in amino acid sequence from the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50, by one or more substitutions, additions, deletions, fusions and truncations, which may be present in any combination.

The variants may be naturally occurring or created in vitro. In particular, such variants may be created using genetic engineering techniques such as site directed mutagenesis, random chemical mutagenesis, Exonuclease IIII deletion procedures, and standard cloning techniques. Alternatively, such variants, fragments, analogs, or derivatives may be created using chemical synthesis or modification procedures.

Other methods of making variants are also familiar to those skilled in the art. These include procedures in which nucleic acid sequences obtained from natural isolates are modified to generate nucleic acids that encode polypeptides having characteristics which enhance their value in industrial or laboratory applications. In such procedures, a large number of variant sequences having one or more nucleotide differences with respect to the sequence obtained from the natural isolate are generated and characterized. Preferably, these nucleotide differences result in amino acid changes with respect to the polypeptides encoded by the nucleic acids from the natural isolates.

For example, variants may be created using error prone PCR. In error prone PCR, DNA amplification is performed under conditions where the fidelity of the DNA polymerase is low, such that a high rate of point mutation-is obtained along the entire length of the PCR product. Error prone PCR is described in Leung, D. W., et al., Technique, 1:11 -15 (1989) and Caldwell, R. C. & Joyce G. F., PCR Methods Applic., 2:28-33 (1992). Variants may also be created using site directed mutagenesis to generate site-specific mutations in any cloned DNA segment of interest. Oligonucleotide mutagenesis is described in Reidhaar-Olson, J. F. & Sauer, R. T., et al., Science, 241:53-57 (1988). Variants may also be created using directed evolution strategies such as those described in U.S. Pat. Nos. 6,361,974 and 6,372,497. The variants of the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50, may be (i) variants in which one or more of the amino acid residues of the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50, are substituted with a conserved or non-conserved amino acid residue (preferably a conserved amino acid residue) and such substituted amino acid residue may or may not be one encoded by the genetic code.

Conservative substitutions are those that substitute a given amino acid in a polypeptide by another amino acid of like characteristics. Typically seen as conservative substitutions are the following replacements: replacements of an aliphatic amino acid such as Ala, Val, Leu and Ile with another aliphatic amino acid; replacement of a Ser with a Thr or vice versa; replacement of an acidic residue such as Asp or Glu with another acidic residue; replacement of a residue bearing an amide group, such as Asn or Gln, with another residue bearing an amide group; exchange of a basic residue such as Lys or Arg with another basic residue; and replacement of an aromatic residue such as Phe or Tyr with another aromatic residue.

Other variants are those in which one or more of the amino acid residues of the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50 includes a substituent group.

Still other variants are those in which the polypeptide is associated with another compound, such as a compound to increase the half-life of the polypeptide (for example, polyethylene glycol).

Additional variants are those in which additional amino acids are fused to the polypeptide, such as leader sequence, a secretory sequence, a proprotein sequence or a sequence which facilitates purification, enrichment, or stabilization of the polypeptide.

In some embodiments, the fragments, derivatives and analogs retain the same biological function or activity as the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50. In other embodiments, the fragment, derivative or analogue includes a fused heterologous sequence which facilitates purification, enrichment, detection, stabilization or secretion of the polypeptide that can be enzymatically cleaved, in whole or in part, away from the fragment, derivative or analogue.

Another aspect of the present invention are polypeptides or fragments thereof which have at least 70%, at least 80%, at least 85%, at least 90%, or more than 95% homology to one of the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50, or a fragment comprising at least 50, 75, 100, 150, 200 or 300 consecutive amino acids thereof. Homology may be determined using a program, such as BLASTP version 2.2.2 with the default parameters, which aligns the polypeptides or fragments being compared and determines the extent of amino acid identity or similarity between them. It will be appreciated that amino acid "homology" includes conservative substitutions such as those described above.

The polypeptides or fragments having homology to one of the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50, or a fragment comprising at least 50, 75, 100, 150, 200 or 300 consecutive amino acids thereof may be obtained by isolating the nucleic acids encoding them using the techniques described above.

Alternatively, the homologous polypeptides or fragments may be obtained through biochemical enrichment or purification procedures. The sequence of potentially homologous polypeptides or fragments may be determined by proteolytic digestion, gel electrophoresis and/or microsequencing. The sequence of the prospective homologous polypeptide or fragment can be compared to one of the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50, or a fragment comprising at least 5, 10, 15, 20, 25, 30, 35, 40, 50, 75, 100, or 150 consecutive amino acids thereof using a program such as BLASTP version 2.2.2 with the default parameters.

The polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50, or fragments, derivatives or analogs thereof comprising at least 40, 50, 75, 100, 150, 200 or 300 consecutive amino acids thereof invention may be used in a variety of application. For example, the polypeptides or fragments, derivatives or analogs thereof may be used to catalyze certain biochemical reactions. In particular, the polypeptides of the ATAA family, namely SEQ ID NO: 42, and its adenylation (A) and thiolation (T) domains, or fragments, derivatives or analogs thereof; the NRPS family, namely SEQ ID NO: 44, and its condensation (C), adenylation (A), thiolation (T), and reductase (Re) domains, or fragments, derivatives or analogs thereof may be used in any combination, in vitro or in vivo, to direct the synthesis or modification of a polypeptide or a substructure thereof, more specifically a benzodiazepine compound or substructure thereof. Polypeptides of the AOTF family, namely SEQ ID NO: 2 or fragments, derivatives or analogs thereof; the OXCC family, namely SEQ ID NO: 4 or fragments, derivatives or analogs thereof; the OXCB family, namely SEQ ID NO: 6 or fragments, derivatives or analogs thereof; the OXRC family, namely SEQ ID NO: 8 or fragments, derivatives or analogs thereof; the MTFA family, namely SEQ ID NO: 10 or fragments, derivatives or analogs thereof; the UNKJ family, namely SEQ ID NO: 12 or fragments, derivatives or analogs thereof; the OXBY family, namely SEQ ID NO: 14 or fragments, derivatives or analogs thereof; the HOXY family, namely SEQ ID NO: 18 or fragments, derivatives or analogs thereof; the UNKW family, namely SEQ ID NO: 24 or fragments, derivatives or analogs thereof; the UNKV family, namely SEQ ID NO: 26 or fragments, derivatives or analogs thereof; the OXBD family, namely SEQ ID NO: 28 or fragments, derivatives or analogs thereof; the UNKA family, namely SEQ ID NO: 30 or fragments, derivatives or analogs thereof; the UNIQ family, namely SEQ ID NO: 22 or fragments, derivatives or analogs thereof; the EATD family, namely SEQ ID NO: 40 or fragments, derivatives or analogs thereof may be used in any combination, in vitro or in vivo, to direct the synthesis or modification of an amino acid, particularly a proline analogue from precursors that are either endogenously present in the host, supplemented to the growth medium, or added to a cell-free, purified or enriched preparation of the said polypeptides. Polypeptides of the HYDE family, namely SEQ ID NO: 32 or fragments, derivatives or analogs thereof; the OXRN family, namely SEQ ID NO: 34 or fragments, derivatives or analogs thereof; the UNIQ family, namely SEQ ID NO: 36 or fragments, derivatives or analogs thereof; the MTFA family, namely SEQ ID NO: 38 or fragments, derivatives or analogs thereof; the HOXF family, namely SEQ ID NO: 46 or fragments, derivatives or analogs thereof; the MOB family, namely SEQ ID NO: 48 or fragments, derivatives or analogs thereof; the UNIQ family, namely SEQ ID NO: 22 or fragments, derivatives or analogs thereof; the EATD family, namely SEQ ID NO: 40 or fragments, derivatives or analogs thereof may be used in any combination, in vitro or in vivo, to direct the synthesis or modification of an amino acid, particularly an anthranilate or analogue thereof from precursors that are either endogenously present in the host, supplemented to the growth medium, or added to a cell-free, purified or enriched preparation of the said polypeptides. Polypeptides of the ENRP family, namely SEQ ID NO: 16 or fragments, derivatives or analogs thereof; the EFFA family, namely SEQ ID NO: 20 or fragments, derivatives or analogs thereof; the RREA family, namely SEQ ID NO: 50 or fragments, derivatives or analogs thereof; the UNIQ family, namely SEQ ID NO: 22 or fragments, derivatives or analogs thereof; the EATD family, namely SEQ ID NO: 40 or fragments, derivatives or analogs thereof may be used in any combination to confer or enhance resistance to natural products, more specifically to benzodiazepines and even more specifically to anthramycins.

The polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50, or fragments, derivatives or analogues thereof comprising at least 5, 10, 15, 20, 25, 30, 35, 40, 50, 75, 100, or 150 consecutive amino acids thereof, may also be used to generate antibodies which bind specifically to the polypeptides or fragments, derivatives or analogues. The antibodies generated from SEQ ID NOS: 2, 4, 6, 8, 10, 12, 14, 16, 18, 20, 22, 24, 26, 28, 30, 32, 34, 36, 38, 40, 42, 44, 46, 48, 50 may be used to determine whether a biological sample contains *Streptomyces refuineus* or a related microorganism.

In such procedures, a biological sample is contacted with an antibody capable of specifically binding to one of the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50, or fragments comprising at least 5, 10, 15, 20, 25, 30, 35, 40, 50, 75, 100, or 150 consecutive amino acids thereof. The ability of the biological sample to bind to the antibody is then determined. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. A variety of assay protocols which may be used to detect the presence of an anthramycin-producer or of *Streptomyces refuineus* or of polypeptides related to SEQ ID NOS: 2, 4, 6, 8, 10, 12, 14, 16, 18, 20, 22, 24, 26, 28, 30, 32, 34, 36, 38, 40, 42, 44, 46, 48, 50, in a sample are familiar to those skilled in the art. Particular assays include ELISA assays, sandwich assays, radioimmunoassays, and Western Blots. Alternatively, antibodies generated from SEQ ID NOS: 2, 4, 6, 8, 10, 12, 14, 16, 18, 20, 22, 24, 26, 28, 30, .32, 34, 36, 38, 40, 42, 44, 46, 48, 50, may be used to determine whether a biological sample contains related polypeptides that may be involved in the biosynthesis of natural products of the anthramycin class or other benzodiazepines.

Polyclonal antibodies generated against the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50, or fragments comprising at least 5, 10, 15, 20, 25, 30, 35, 40, 50, 75, 100, or 150 consecutive amino acids thereof can be obtained by direct injection of the polypeptides into an animal or by administering the polypeptides to an animal, preferably a nonhuman. The antibody so obtained will then bind the polypeptide itself. In this manner, even a sequence encoding only a fragment of the polypeptide can be used to generate antibodies which may bind to the whole native polypeptide. Such antibodies. can then be used to isolate the polypeptide from cells expressing that polypeptide.

For preparation of monoclonal antibodies, any technique which provides antibodies produced by continuous cell line cultures can be used. Examples include the hybridoma technique (Kholer and Milstein, 1975, Nature, 256:495-497), the trioma technique, the human B-cell hybridoma technique (Kozbor et al., 1983, Immunology Today 4:72), and the EBV-hybridoma technique (Cole, et al., 1985, in Monoclonal Antibodies and Cancer Therapy, Alan R. Liss, Inc., pp. 77-96).

Techniques described for the production of single chain antibodies (U.S. Pat. No. 4,946,778) can be adapted to produce single chain antibodies to the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50, or fragments comprising at least 5, 10, 15, 20, 25, 30, 35, 40, 50, 75, 100, or 150 consecutive amino acids thereof. Alternatively, transgenic mice may be used to express humanized antibodies to these polypeptides or fragments thereof.

Antibodies generated against the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50, or fragments comprising at least 5, 10, 15, 20, 25, 30, 35, 40, 50, 75, 100, or 150 consecutive amino acids thereof may be used in screening for similar polypeptides from a sample containing organisms or cell-free extracts thereof. In such techniques, polypeptides from the sample is contacted with the antibodies and those polypeptides which specifically bind the antibody are detected. Any of the procedures described above may be used to detect antibody binding. One such screening assay is described in "Methods for measuring Cellulase Activities", Methods in Enzymology, Vol 160, pp. 87-116.

As used herein, the term "nucleic acid codes of SEQ ID NOS: 3, 5, 7, 9, 11, 13, 15, 17, 19, 21, 23, 25, 27, 29, 31, 33, 35, 37, 39, 41, 43, 45, 47, 49, 51" encompass the nucleotide sequences of SEQ ID NOS: 3, 5, 7, 9, 11, 13, 15, 17, 19, 21, 23, 25, 27, 29, 31, 33, 35, 37, 39, 41, 43, 45, 47, 49, 51, fragments of SEQ ID NOS: 3, 5, 7, 9, 11, 13, 15, 17, 19, 21, 23, 25, 27, 29, 31, 33, 35, 37, 39, 41, 43, 45, 47, 49, 51, nucleotide sequences homologous to SEQ ID NOS: 3, 5, 7, 9, 11, 13, 15, 17, 19, 21, 23, 25, 27, 29, 31, 33, 35, 37, 39, 41, 43, 45, 47, 49, 51, or homologous to fragments of SEQ ID NOS: 3, 5, 7, 9, 11, 13, 15, 17, 19, 21, 23, 25, 27, 29, 31, 33, 35, 37, 39, 41, 43, 45, 47, 49, 51, and sequences complementary to all of the preceding sequences. The fragments include portions of SEQ ID NOS: 3, 5, 7, 9, 11, 13, 15, 17, 19, 21, 23, 25, 27, 29, 31, 33, 35, 37, 39, 41, 43, 45, 47, 49, 51, comprising at least 10, 15, 20, 25, 30, 35, 40, 50, 75, 100, 150, 200, 300, 400 or 500 consecutive nucleotides of SEQ ID NOS: 3, 5, 7, 9, 11, 13, 15, 17, 19, 21, 23, 25, 27, 29, 31, 33, 35, 37, 39, 41, 43, 45, 47, 49, 51. Preferably, the fragments are novel fragments. Homologous sequences and fragments of SEQ ID NOS: 3, 5, 7, 9, 11, 13, 15, 17, 19, 21, 23, 25, 27, 29, 31, 33, 35, 37, 39, 41, 43, 45, 47, 49, 51 refer to a sequence having at least 99%, 98%, 97%, 96%, 95%, 90%, 80%, 75% or 70% identity to these sequences. Homology may be determined using any of the computer programs and parameters described herein, including BLASTN and TBLASTX with the default parameters. Homologous sequences also include RNA sequences in which uridines replace the thymines in the nucleic acid codes of SEQ ID NOS: 3, 5, 7, 9, 11, 13, 15, 17, 19, 21, 23, 25, 27, 29, 31, 33, 35, 37, 39, 41, 43, 45, 47, 49, 51.

The homologous sequences may be obtained using any of the procedures described herein or may result from the correction of a sequencing error. It will be appreciated that the nucleic acid codes of SEQ ID NOS: 3, 5, 7, 9, 11, 13, 15, 17, 19, 21, 23, 25, 27, 29, 31, 33, 35, 37, 39, 41, 43, 45, 47, 49, 51 can be represented in the traditional single character format in which G, A, T and C denote the guanine, adenine, thymine and cytosine bases of the deoxyribonucleic acid (DNA) sequence respectively, or in which G, A, U and C denote the guanine, adenine, uracil and cytosine bases of the ribonucleic acid (RNA) sequence (see the inside back cover of Stryer, Biochemistry, 3$^{rd}$ edition, W. H. Freeman & Co., New York) or in any other format which records the identity of the nucleotides in a sequence.

"Polypeptide codes of SEQ ID NOS: 2, 4, 6, 8, 10, 12, 14, 16, 18, 20, 22, 24, 26, 28, 30, 32, 34, 36, 38, 40, 42, 44, 46, 48, 50" encompass the polypeptide sequences of SEQ ID NOS: 2, 4, 6, 8, 10, 12, 14, 16, 18, 20, 22, 24, 26, 28, 30, 32, 34, 36, 38, 40, 42, 44, 46, 48, 50 which are encoded by the nucleic acid sequences of SEQ ID NOS: 3, 5, 7, 9, 11, 13, 15, 17, 19, 21, 23, 25, 27, 29, 31, 33, 35, 37, 39, 41, 43, 45, 47, 49, 51, polypeptide sequences homologous to the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50, or fragments of any of the preceding sequences. Homologous polypeptide sequences refer to a polypeptide sequence having at least 99%, 98%, 97%, 96%, 95%, 90%, 85%, 80%, 75% or 70% identity to one of the polypeptide sequences of SEQ ID NOS: 2, 4, 6, 8, 10, 12, 14, 16, 18, 20, 22, 24, 26, 28, 30, 32, 34, 36, 38, 40, 42, 44, 46, 48, 50. Polypeptide sequence homology may be determined using any of the computer programs and parameters described herein, including BLASTP version 2.2.1 with the default parameters or with any user-specified parameters. The homologous sequences may be obtained using any of the procedures described herein or may result from the correction of a sequencing error. The polypeptide fragments comprise at least 5, 10, 15, 20, 25, 30, 35, 40, 50, 75, 100 or 150 consecutive amino acids of the polypeptides of SEQ ID NOS: 2, 4, 6, 8, 10, 12, 14, 16, 18, 20, 22, 24, 26, 28, 30, 32, 34, 36, 38, 40, 42, 44, 46, 48, 50. Preferably the fragments are novel fragments. It will be appreciated that the polypeptide codes of the SEQ ID NOS: 2, 4, 6, 8, 10, 12, 14, 16, 18, 20, 22, 24, 26, 28, 30, 32, 34, 36, 38, 40, 42, 44, 46, 48, 50 can be represented in the traditional single character format or three letter format (see the inside back cover of Stryer, Biochemistry, 3$^{rd}$ edition, W.H. Freeman & Co., New York) or in any other format which relates the identity of the polypeptides in a sequence.

It will be readily appreciated by those skilled in the art that the nucleic acid codes of SEQ ID NOS: 3, 5, 7, 9, 11, 13, 15, 17, 19, 21, 23, 25, 27, 29, 31, 33, 35, 37, 39, 41, 43, 45, 47, 49 and 51, and the polypeptide codes of SEQ ID NOS: 2, 4, 6, 8, 10, 12, 14, 16, 18, 20, 22, 24, 26, 28, 30, 32, 34, 36, 38, 40, 42, 44, 46, 48, and 50 can be stored, recorded and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate manufactures comprising one or more of the nucleic acid codes of SEQ ID NOS: 3, 5, 7, 9, 11, 13, 15, 17, 19, 21, 23, 25, 27, 29, 31, 33, 35, 37, 39, 41, 43, 45, 47, 49 and 51, and the polypeptide codes of SEQ ID NOS: 2, 4, 6, 8, 10, 12, 14, 16, 18, 20, 22, 24, 26, 28, 30, 32, 34, 36, 38, 40, 42, 44, 46, 48, and 50.

Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of media known to those skilled in the art.

The nucleic acid codes of SEQ ID NOS: 3, 5, 7, 9, 11, 13, 15, 17, 19, 21, 23, 25, 27, 29, 31, 33, 35, 37, 39, 41, 43, 45, 47, 49, 51, a subset thereof, the polypeptide codes of SEQ ID NOS: 2, 4, 6, 8, 10, 12, 14, 16, 18, 20, 22, 24, 26, 28, 30, 32, 34, 36, 38, 40, 42, 44, 46, 48, and 50, and a subset thereof may be stored and manipulated in a variety of data processor programs in a variety of formats. For example, one or more of the nucleic acid codes of SEQ ID NOS: 3, 5, 7, 9, 11, 13, 15, 17, 19, 21, 23, 25, 27, 29, 31, 33, 35, 37, 39, 41, 43, 45, 47, 49, 51, and one or more of the polypeptide codes of SEQ ID NOS: 2, 4, 6, 8, 10, 12, 14, 16, 18, 20, 22, 24, 26, 28, 30, 32, 34, 36, 38, 40, 42, 44, 46, 48, and 50 may be stored as ASCII or text in a word processing file, such as Microsoft-WORD or WORDPERFECT in a variety of database programs familiar to those of skill in the art, such as DB2 or ORACLE. In addition, many computer programs and databases may be used as sequence comparers, identifiers or sources of query nucleotide sequences or query polypeptide sequences to be compared to one or more of the nucleic acid codes of SEQ ID NOS: 3, 5, 7, 9, 11, 13, 15, 17, 19, 21, 23, 25, 27, 29, 31, 33, 35, 37, 39, 41, 43, 45, 47, 49 and 51, and one or more of the polypeptide codes of SEQ ID NOS: 2, 4, 6, 8, 10, 12, 14, 16, 18, 20, 22, 24, 26, 28, 30, 32, 34, 36, 38, 40, 42, 44, 46, 48, and 50.

The following list is intended not to limit the invention but to provide guidance to programs and databases useful with one or more of the nucleic acid codes of SEQ ID NOS: 3, 5, 7, 9, 11, 13, 15, 17, 19, 21, 23, 25, 27, 29, 31, 33, 35, 37, 39, 41, 43, 45, 47, 49, 51, and the polypeptide codes of SEQ ID NOS: 2, 4, 6, 8, 10, 12, 14, 16, 18, 20, 22, 24, 26, 28, 30, 32, 34, 36, 38, 40, 42, 44, 46, 48, and 50. The program and databases which may be used include, but are not limited to: MacPattern (EMBL), DiscoveryBase (Molecular Applications Group), GeneMine (Molecular Applications Group) Look (Molecular Applications Group), MacLook (Molecular Applications Group), BLAST and BLAST2 (NCBI), BLASTN and BLASTX (Altschul et al., *J. Mol. Biol.* 215:403 (1990)), FASTA (Person and Lipman, *Proc. Nalt. Acad. Sci. USA,* 85:2444 (1988)), FASTDB (Brutlag et al. *Comp. App. Biosci.* 6-237-245, 1990), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II (Molecular Simulations Inc.), Discover (Molecular Simulations Inc.), CHARMm (Molecular Simulations Inc.), Felix (Molecular Simulations Inc.), DelPhi (Molecular Simulations Inc.), QuanteMM (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WetLab (Molecular Simulations Inc.), WetLab Diversity Explorer (Molecular Simulations Inc.), Gene Explorer (Molecular Simulations Inc.), SeqFold (Molecular Simulations Inc.), the MDL Available Chemicals Directory database, the MDL Drug Data Report data base, the Comprehensive Medicinal Chemistry database, Derwents' World Drug Index database, the BioByteMasterFile database, the Genbank database, and the Gensyqn database. Many other programs and databases would be apparent to one of skill in the art given the present disclosure.

Embodiments of the present invention include systems, particularly computer systems that store and manipulate the sequence information described herein. As used herein, "a computer system", refers to the hardware components, software components, and data storage components used to analyze one or more of the nucleic acid codes of SEQ ID NOS: 3, 5, 7, 9, 11, 13, 15, 17, 19, 21, 23, 25, 27, 29, 31, 33, 35, 37, 39, 41, 43, 45, 47, 49, and 51, and the polypeptide codes of SEQ ID NOS: 2, 4, 6, 8, 10, 12, 14, 16, 18, 20, 22, 24, 26, 28, 30, 32, 34, 36, 38, 40, 42, 44, 46, 48, and 50.

Preferably, the computer system is a general purpose system that comprises a processor and one or more internal data storage components for storing data, and one or more data retrieving devices for retrieving the data stored on the data storage components. A skilled artisan can readily appreciate that any one of the currently available computer systems are suitable.

The computer system of FIG. 1 illustrates components that be present in a conventional computer system. One skilled in the art will readily appreciate that not all components illustrated in FIG. 1 are required to practice the invention and, likewise, additional components not illustrated in FIG. 1 may be present in a computer system contemplated for use with the invention. Referring to the computer system of FIG. 1, the components are connected to a central system bus 116. The components include a central processing unit 118 with internal 118 and/or external cache memory 120, system memory 122, display adapter 102 connected to a monitor 100, network adapter 126 which may also be referred to as a network interface, internal modem 124, sound adapter 128, IO controller 132 to which may be connected a keyboard 140 and mouse 138, or other suitable input device such as a trackball or tablet, as well as external printer 134, and/or any number of external devices such as external modems, tape storage drives, or disk drives 136. One or more host bus adapters 114 may be connected to the system bus 116. To host bus adapter 114 may optionally be connected one or more storage devices such as disk drives 112 (removable or fixed), floppy drives 110, tape drives 108, digital versatile disk DVD drives 106, and compact disk CD ROM drives 104. The storage devices may operate in read-only mode and/or in read-write mode. The computer system may optionally include multiple central processing units 118, or multiple banks of memory 122. Arrows 142 in FIG. 1 indicate the interconnection of internal components of the computer system. The arrows are illustrative only and do not specify exact connection architecture.

Software for accessing and processing the one or more of the nucleic acid codes of SEQ ID NOS: 3, 5, 7, 9, 11, 13, 15, 17, 19, 21, 23, 25, 27, 29, 31, 33, 35, 37, 39, 41, 43, 45, 47, 49, and 51, and the polypeptide codes of SEQ ID NOS: 2, 4, 6, 8, 10, 12, 14, 16, 18, 20, 22, 24, 26, 28, 30, 32, 34, 36, 38, 40, 42, 44, 46, 48, and 50 (such as sequence comparison software, analysis software as well as search tools, annotation tools, and modeling tools etc.) may reside in main memory 122 during execution.

In one embodiment, the computer system further comprises a sequence comparison software for comparing the nucleic acid codes of a query sequence stored on a computer readable medium to a subject sequence which is also stored on a computer readable medium; or for comparing the polypeptide code of a query sequence stored on a computer readable medium to a subject sequence which is also stored on computer readable medium. A "sequence comparison software" refers to one or more programs that are implemented on the computer system to compare nucleotide sequences with other nucleotide sequences stored within the data storage means. The design of one example of a sequence comparison software is provided in FIGS. 2A, 2B, 2C and 2D.

Figure 3:
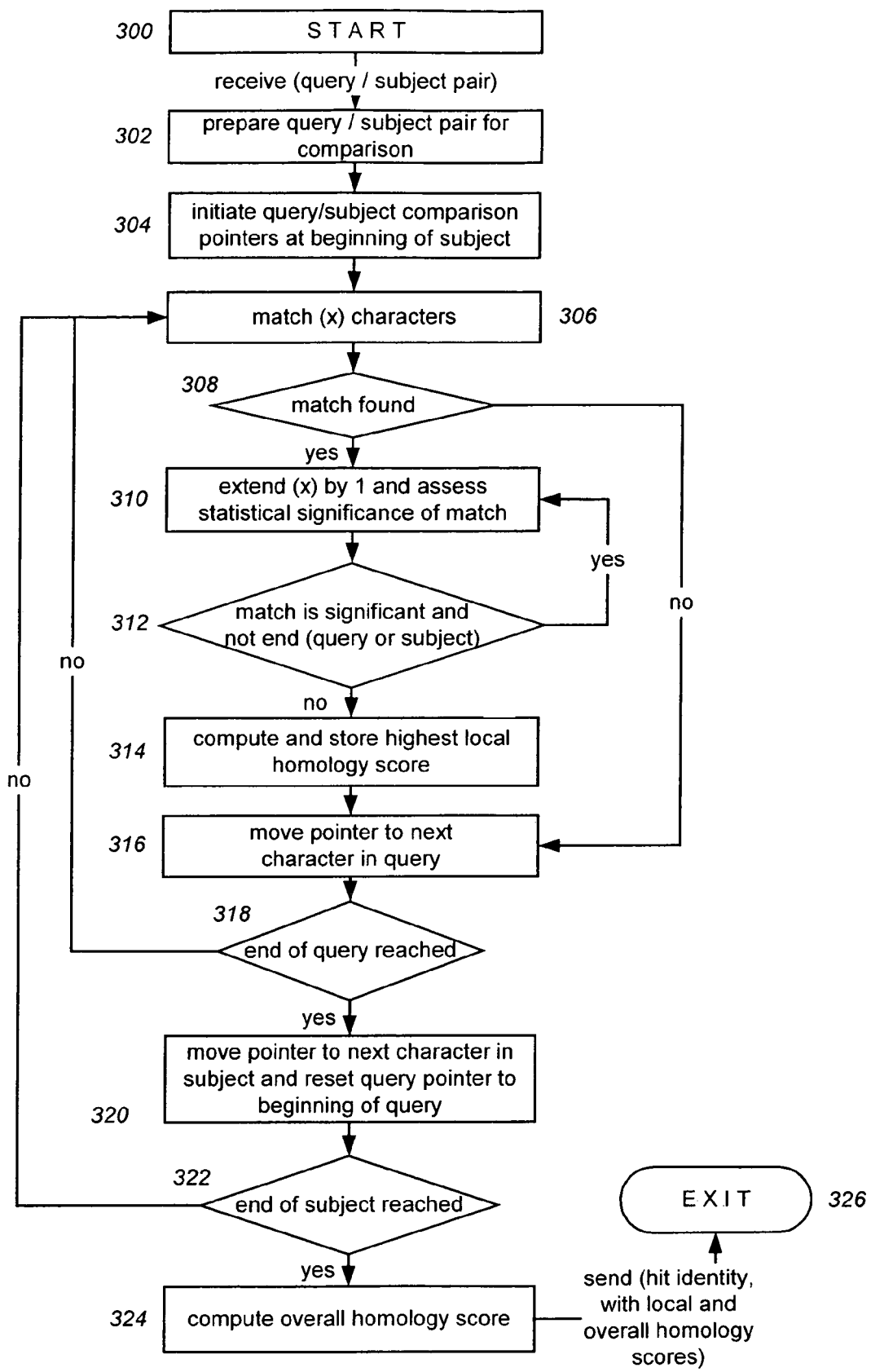
FIG. 3 is a flow diagram of the comparator algorithm (238) of FIG. 2C which is one embodiment of a comparator algorithm that can be used for pairwise determination of similarity between a query/subject pair.

The sequence comparison software will typically employ one or more specialized comparator algorithms. Protein and/or nucleic acid sequence similarities may be evaluated using any of the variety of sequence comparator algorithms and programs known in the art. Such algorithms and programs include, but are no way limited to, TBLASTN, BLASTN, BLASTP, FASTA, TFASTA, CLUSTAL, HMMER, MAST, or other suitable algorithm known to those skilled in the art. (Pearson and Lipman, 1988, *Proc. Natl. Acad. Sci USA* 85(8): 2444-2448; Altschul et al, 1990, *J. Mol. Biol.* 215(3):403-410; Thompson et al., 1994, *Nucleic Acids Res.* 22(2):4673-4680; Higgins et al., 1996, *Methods Enzymol.* 266:383-402; Altschul et al., 1990, *J. Mol. Biol.* 215(3):403-410; Altschul et al., 1993, *Nature Genetics* 3:266-272; Eddy S. R., Bioinformatics 14:755-763, 1998; Bailey T L et al, *J Steroid Biochem Mol Biol* 1997 May; 62(1):29-44). One example of a comparator algorithm is illustrated in FIG. 3. Sequence comparator algorithms identified in this specification are particularly contemplated for use in this aspect of the invention.

Figure 4:
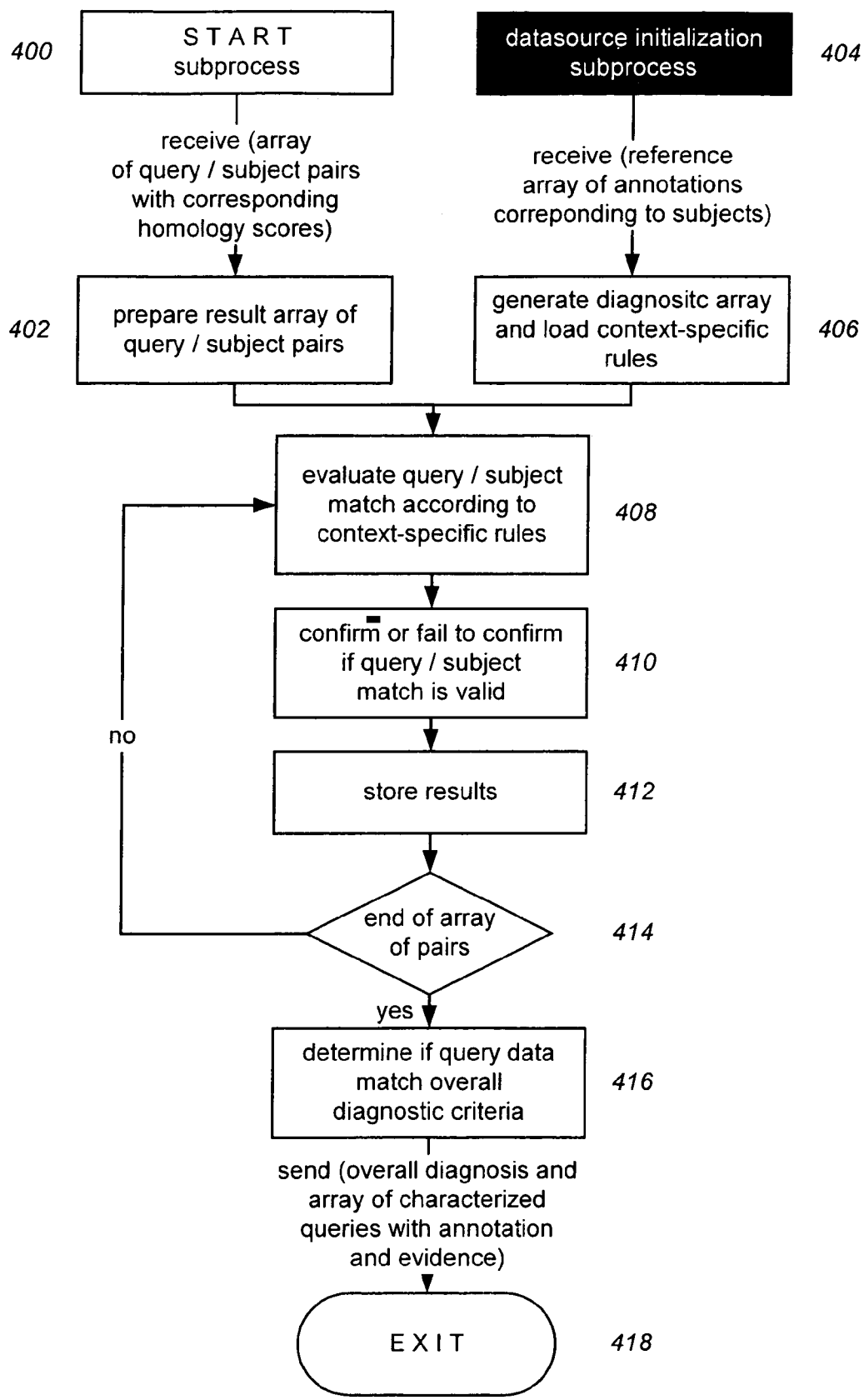
FIG. 4 is a flow diagram of the analyzer algorithm (244) of FIG. 2C which is one embodiment of an analyzer algorithm that can be used to assign identity to a query sequence, based on similarity to a subject sequence, where the subject sequence is a reference sequence of the invention.

The sequence comparison software will typically employ one or more specialized analyzer algorithms. One example of an analyzer algorithm is illustrated in FIG. 4. Any appropriate analyzer algorithm can be used to evaluate similarities, determined by the comparator algorithm, between a query sequence and a subject sequence (referred to herein as a query/subject pair). Based on context specific rules, the annotation of a subject sequence may be assigned to the query sequence. A skilled artisan can readily determine the selection of an appropriate analyzer algorithm and appropriate context specific rules. Analyzer algorithms identified elsewhere in this specification are particularly contemplated for use in this aspect of the invention.

FIGS. 2A, 2B, 2C and 2D together provide a flowchart of one example of a sequence comparison software for comparing query sequences to a subject sequence. The software determines if a gene or set of genes represented by their nucleotide sequence, polypeptide sequence or other representation (the query sequence) is significantly similar to the one or more of the nucleic acid codes of SEQ ID NOS: 3, 5, 7, 9, 11, 13, 15, 17, 19, 21, 23, 25, 27, 29, 31, 33, 35, 37, 39, 41, 43, 45, 47, 49, 51, and the corresponding polypeptide codes of SEQ ID NOS: 2, 4, 6, 8, 10, 12, 14, 16, 18, 20, 22, 24, 26, 28, 30, 32, 34, 36, 38, 40, 42, 44, 46, 48, and 50 of the invention (the subject sequence). The software may be implemented in the C or C++ programming language, Java, Perl or other suitable programming language known to a person skilled in the art.

One or more query sequence(s) are accessed by the program by means of input from the user 210, accessing a database 208 or opening a text file 206 as illustrated in the query initialization subprocess (FIG. 2A). The query initialization subprocess allows one or more query sequence(s) to be loaded into computer memory 122, or under control of the program stored on a disk drive 112 or other storage device in the form of a query sequence array 216. The query array 216 is one or more query nucleotide or polypeptide sequences accompanied by some appropriate identifiers.

A dataset is accessed by the program by means of input from the user 228, accessing a database 226, or opening a text file 224 as illustrated in the subject datasource initialization subprocess (FIG. 2B). The subject data source initialization process refers to the method by which a reference dataset containing one or more sequence selected from the nucleic acid codes of SEQ ID NOS: 3, 5, 7, 9, 11, 13, 15, 17, 19, 21, 23, 25, 27, 29, 31, 33, 35, 37, 39, 41, 43, 45, 47, 49, 51, and the corresponding polypeptide codes of SEQ ID NOS: 2, 4, 6, 8, 10, 12, 14, 16, 18, 20, 22, 24, 26, 28, 30, 32, 34, 36, 38, 40, 42, 44, 46, 48, and 50 is loaded into computer memory 122, or under control of the program stored on a disk drive 112 or other storage device in the form of a subject array 234. The subject array 234 comprises one or more subject nucleotide or polypeptide sequences accompanied by some appropriate identifiers.

The comparison subprocess of FIG. 2C illustrates a process by which the comparator algorithm 238 is invoked by the software for pairwise comparisons between query elements in the query sequence array 216, and subject elements in the subject array 234. The "comparator algorithm" of FIG. 2C refers to the pair-wise comparisons between a query sequence and subject sequence, i.e. a query/subject pair from their respective arrays 216, 234. Comparator algorithm 238 may be any algorithm that acts on a query/subject pair, including but not limited to homology algorithms such as BLAST, Smith Waterman, Fasta, or statistical representation/probabilistic algorithms such as Markov models exemplified by HMMER, or other suitable algorithm known to one skilled in the art. Suitable algorithms would generally require a query/subject pair as input and return a score (an indication of likeness between the query and subject), usually through the use of appropriate statistical methods such as Karlin Altschul statistics used in BLAST, Forward or Viterbi algorithms used in Markov models, or other suitable statistics known to those skilled in the art.

The sequence comparison software of FIG. 2C also comprises a means of analysis of the results of the pair-wise comparisons performed by the comparator algorithm 238. The "analysis subprocess" of FIG. 2C is a process by which the analyzer algorithm 244 is invoked by the software. The "analyzer algorithm" refers to a process by which annotation of a subject is assigned to the query based on query/subject similarity as determined by the comparator algorithm 238 according to context-specific rules coded into the program or dynamically loaded at runtime. Context-specific rules are what the program uses to determine if the annotation of the subject can be assigned to the query given the context of the comparison. These rules allow the software to qualify the overall meaning of the results of the comparator algorithm 238.

In one embodiment, context-specific rules may state that for a set of query sequences to be considered representative of an anthramycin biosynthetic locus, the comparator algorithm 238 must determine that the set of query sequences contains at least five query sequences that shows a statistical similarity to a subject sequence corresponding to the polypeptide codes of SEQ ID NOS: 2, 4, 6, 8, 10, 12, 14, 16, 18, 20, 22, 24, 26, 28, 30, 32, 34, 36, 38, 40, 42, 44, 46, and 48. Of course preferred context specific rules may specify a wide variety of thresholds for identifying anthramycin-biosynthetic genes or anthramycin-producing organisms without departing from the scope of the invention. Some thresholds contemplate that at least one query sequence in the set of query sequences show a statistical similarity to the nucleic acid code corresponding to 5, 6, 7, 8 or more of the polypeptide codes of SEQ ID NOS: 2, 4, 6, 8, 10, 12, 14, 16, 18, 20, 22, 24, 26, 28, 30, 32, 34, 36, 38, 40, 42, 44, 46, 48, and 50. Other context specific rules set the level of homology required in each of the group may be set at 70%, 80%, 85%, 90%, 95% or 98% in regards to any one or more of the subject sequences.

In another embodiment context-specific rules may state that for a query sequence to be considered indicative of an benzodiazepine, the comparator algorithm 238 must determine that the query sequence shows a statistical similarity to subject sequences corresponding to a nucleic acid sequence code for a polypeptide of SEQ ID NO: 42 or 44, polypeptides having at least 75% homology to a polypeptide of SEQ ID NOS: 42 or 44 and fragment comprising at least 400 consecutive amino acids of the polypeptides of SEQ ID NOS: 42 and 44. Of course preferred context specific rules may specify a wide variety of thresholds for identifying a bezodiazepine non-ribosomal peptide synthetase protein without departing from the scope of the invention. Some context specific rules set level of homology required of the query sequence at 70%, 80%, 85%, 90%, 95% or 98%.

Thus, the analysis subprocess may be employed in conjunction with any other context specific rules and may be adapted to suit different embodiments. The principal function of the analyzer algorithm 244 is to assign meaning or a diagnosis to a query or set of queries based on context specific rules that are application specific and may be changed without altering the overall role of the analyzer algorithm 244.

Finally the sequence comparison software of FIG. 2 comprises a means of returning of the results of the comparisons by the comparator algorithm 238 and analyzed by the analyzer algorithm 244 to the user or process that requested the comparison or comparisons. The "display/report subprocess" of FIG. 2D is the process by which the results of the comparisons by the comparator algorithm 238 and analyses by the analyzer algorithm 244 are returned to the user or process that requested the comparison or comparisons. The results 240, 246 may be written to a file 252, displayed in some user interface such as a console, custom graphical interface, web interface, or other suitable implementation specific interface, or uploaded to some database such as a relational database, or other suitable implementation specific database. Once the results have been returned to the user or process that requested the comparison or comparisons the program exits.

The principle of the sequence comparison software of FIG. 2 is to receive or load a query or queries, receive or load a reference dataset, then run a pair-wise comparison by means of the comparator algorithm 238, then evaluate the results using an analyzer algorithm 244 to arrive at a determination if the query or queries bear significant similarity to the reference sequences, and finally return the results to the user or calling program or process.

FIG. 3 is a flow diagram illustrating one embodiment of comparator algorithm 238 process in a computer for determining whether two sequences are homologous. The comparator algorithm receives a query/subject pair for comparison, performs an appropriate comparison, and returns the pair along with a calculated degree of similarity.

Referring to FIG. 3, the comparison is initiated at the beginning of sequences 304. A match of (x) characters is attempted 306 where (x) is a user specified number. If a match is not found the query sequence is advanced 316 by one character with respect to the subject, and if the end of the query has not been reached 318 another match of (x) characters is attempted 306. Thus if no match has been found the query is incrementally advanced in entirety past the initial position of the subject, once the end of the query is reached 318, the subject pointer is advanced by 1 character and the query pointer is set to the beginning of the query 318. If the end of the subject has been reached and still no matches have been found a null homology result score is assigned 324 and the algorithm returns the pair of sequences along with a null score to the calling process or program. The algorithm then exits 326. If instead a match is found 308, an extension of the matched region is attempted 310 and the match is analyzed statistically 312. The extension may be unidirectional or bidirectional. The algorithm continues in a loop extending the matched region and computing the homology score, giving penalties for mismatches taking into consideration that given the chemical properties of the amino acid side chains not all mismatches are equal. For example a mismatch of a lysine with an arginine both of which have basic side chains receive a lesser penalty than a mismatch between lysine and glutamate which has an acidic side chain. The extension loop stops once the accumulated penalty exceeds some user specified value, or of the end of either sequence is reached 312. The maximal score is stored 314, and the query sequence is advanced 316 by one character with respect to the subject, and if the end of the query has not been reached 318 another match of (x) characters is attempted 306. The process continues until the entire length of the subject has been evaluated for matches to the entire length of the query. All individual scores and alignments are stored 314 by the algorithm and an overall score is computed 324 and stored. The algorithm returns the pair of sequences along with local and global scores to the calling process or program. The algorithm then exits 326.

Comparator algorithm 238 algorithm may be represented in pseudocode as follows:

```
INPUT:      Q[m]:     query, m is the length
            S[n]:     subject, n is the length
            x:        x is the size of a segment
START:
for each i in [1,n] do
    for each j in [1,m] do
        if ( j + x - 1 ) <= m and ( i + x - 1 ) <= n then
            if Q(j, j+x-1) = S(i, i+x-1) then
                k=1;
                while Q(j, j+x-1+k ) = S(i, i+x-1+ k) do
                    k++;
                Store highest local homology
Compute overall homology score
Return local and overall homology scores
END.
```

The comparator algorithm 238 may be written for use on nucleotide sequences, in which case the scoring scheme would be implemented so as to calculate scores and apply penalties based on the chemical nature of nucleotides. The comparator algorithm 238 may also provide for the presence of gaps in the scoring method for nucleotide or polypeptide sequences.

BLAST is one implementation of the comparator algorithm 238. HMMER is another implementation of the comparator algorithm 238 based on Markov model analysis. In a HMMER implementation a query sequence would be compared to a mathematical model representative of a subject sequence or sequences rather than using sequence homology.

FIG. 4 is a flow diagram illustrating an analyzer algorithm 244 process for detecting the presence of an anthramycin biosynthetic locus. The analyzer algorithm of FIG. 4 may be used in the process by which the annotation of a subject is assigned to the query based on their similarity as determined by the comparator algorithm 238 and according to context-specific rules coded into the program or dynamically loaded at runtime. Context sensitive rules are what determines if the annotation of the subject can be assigned to the query given the context of the comparison. Context specific rules set the thresholds for determining the level and quality of similarity that would be accepted in the process of evaluating matched pairs.

The analyzer algorithm 244 receives as its input an array of pairs that had been matched by the comparator algorithm 238. The array consists of at least a query identifier, a subject identifier and the associated value of the measure of their similarity. To determine if a group of query sequences includes sequences diagnostic of an anthramycin biosynthetic gene cluster, a reference or diagnostic array 406 is generated by accessing a data source and retrieving anthramycin specific information 404 relating to nucleic acid codes of SEQ ID NOS: 3, 5, 7, 9, 11, 13, 15, 17, 19, 21, 23, 25, 27, 29, 31, 33, 35, 37, 39, 41, 43, 45, 47, 49, 51 and the corresponding polypeptide codes of SEQ ID NOS: 2, 4, 6, 8, 10, 12, 14, 16, 18, 20, 22, 24, 26, 28, 30, 32, 34, 36, 38, 40, 42, 44, 46, 48, and 50. Diagnostic array 406 consists at least of subject identifiers and their associated annotation. Annotation may include reference to the protein families ATAA, NRPS, AOTF, OXCC, OXCB, OXRC, MTFA, UNKJ, OXBY, HOXY, UNKW, UNKV, OXBD, UNKA, UNIQ, EATD, HYDE, OXRN, UNIQ, MTFA, HOXF, AAOB, UNIQ, EATD, ENRP, EFFA, RREA, UNIQ, and EATD. Annotation may also include information regarding exclusive presence in loci of a specific structural class or may include previously computed matches to other databases, for example databases of motifs.

Once the algorithm has successfully generated or received the two necessary arrays 402, 406, and holds in memory any context specific rules, each matched pair as determined by the comparator algorithm 238 can be evaluated. The algorithm will perform an evaluation 408 of each matched pair and based on the context specific rules confirm or fail to confirm the match as valid 410. In cases of successful confirmation of the match 410 the annotation of the subject is assigned to the query. Results of each comparison are stored 412. The loop ends when the end of the query/subject array is reached. Once all query/subject pairs have been evaluated against one or more of the nucleic acid codes of SEQ ID NOS: 3, 5, 7, 9, 11, 13, 15, 17, 19, 21, 23, 25, 27, 29, 31, 33, 35, 37, 39, 41, 43, 45, 47, 49, and the polypeptide codes of SEQ ID NOS: 2, 4, 6, 8, 10, 12, 14, 16, 18, 20, 22, 24, 26, 28, 30, 32, 34, 36, 38, 40, 42, 44, 46, 48, and 50 in the subject array, a final determination can be made if the query set of ORFs represents an anthramycin locus 416. The algorithm then returns the overall diagnosis and an array of characterized query/subject pairs along with supporting evidence to the calling program or process and then terminates 418.

The analyzer algorithm 244 may be configured to dynamically load different diagnostic arrays and context specific rules. It may be used for example in the comparison of query/subject pairs with diagnostic subjects for other biosynthetic pathways, such as benzodiazepine biosynthetic pathways.

Thus one embodiment of the present invention is a computer readable medium having stored thereon a sequence selected from the group consisting of a nucleic acid code of SEQ ID NOS: 3, 5, 7, 9, 11, 13, 15, 17, 19, 21, 23, 25, 27, 29, 31, 33, 35, 37, 39, 41, 43, 45, 47, 49, 51 and a polypeptide code of SEQ ID NOS: 2, 4, 6, 8, 10, 12, 14, 16, 18, 20, 22, 24, 26, 28, 30, 32, 34, 36, 38, 40, 42, 44, 46, 48, 50. Another aspect of the present invention is a computer readable medium having recorded thereon one or more nucleic acid codes of SEQ ID NOS: 3, 5, 7, 9, 11, 13, 15, 17, 19, 21, 23, 25, 27, 29, 31, 33, 35, 37, 39, 41, 43, 45, 47, 49, 51, preferably at least 2, 5, 10, 15, or 20 nucleic acid codes of SEQ ID NOS: 3, 5, 7, 9, 11, 13, 15, 17, 19, 21, 23, 25, 27, 29, 31, 33, 35, 37, 39, 41, 43, 45, 47, 49, 51. Another aspect of the invention is a computer readable medium having recorded thereon one or more of the polypeptide codes of SEQ ID NOS: 2, 4, 6, 8, 10, 12, 14, 16, 18, 20, 22, 24, 26, 28, 30, 32, 34, 36, 38, 40, 42, 44, 46, 48, 50, preferably at least 2, 5, 10, 15 or 20 polypeptide codes of SEQ ID NOS: 2, 4, 6, 8, 10, 12, 14, 16, 18, 20, 22, 24, 26, 28, 30, 32, 34, 36, 38, 40, 42, 44, 46, 48, 50.

Another embodiment of the present invention is a computer system comprising a processor and a data storage device wherein said data storage device has stored thereon a reference sequence selected from the group consisting of a nucleic acid code of SEQ ID NOS: 3, 5, 7, 9, 11, 13, 15, 17, 19, 21, 23, 25, 27, 29, 31, 33, 35, 37, 39, 41, 43, 45, 47, 49, 51 and a polypeptide code of SEQ ID NOS: 2, 4, 6, 8, 10, 12, 14, 16, 18, 20, 22, 24, 26, 28, 30, 32, 34, 36, 38, 40, 42, 44, 46, 48, 50.

Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of media known to those skilled in the art.

The present invention will be further described with reference to the following examples; however, it is to be understood that the present invention is not limited to such examples.

EXAMPLE 1

Identification and Sequencing of the Anthramycin Biosynthetic Gene Cluster

*Streptomyces refuineus* subsp. *thermotolerans* NRRL 3143 was obtained from the Agricultural Research Service collection (National Center for Agricultural Utilization Research, 1815 N. University Street, Peoria, Ill. 61604) and cultured using standard microbiological techniques (Kieser et al., (1982) *Mol. Gen. Genet* 185(2), 223-228). This organism was propagated on oatmeal agar medium at 28 degrees Celsius for several days. For isolation of high molecular weight genomic DNA, cell mass from three freshly grown, near confluent 100 mm petri dishes was used. The cell mass was collected by gentle scraping with a plastic spatula. Residual agar medium was removed by repeated washes with STE buffer (75 mM NaCl; 20 mM Tris-HCl, pH 8.0; 25 mM EDTA). High molecular weight DNA was isolated by established protocols (Kieser et al. (1982), *Mol. Gen. Genet.* 185(2), 223-228) and its integrity was verified by field inversion gel electrophoresis (FIGE) using the preset program number 6 of the FIGE MAPPER™ power supply (BIORAD). This high molecular weight genomic DNA was used to prepare a small size fragment genomic sampling library (GSL) and a large size fragment cluster identification library (CIL). Both libraries contained randomly generated *Streptomyces refuineus* genomic DNA fragments and were considered representative of the entire genome of this organism.

To generate the GSL library, genomic DNA was randomly sheared by sonication. DNA fragments having a size range between 1.5 and 3 kb were fractionated on a agarose gel and isolated using standard molecular biology techniques (Sambrook et al., supra). The ends of the DNA fragments were repaired using T4 DNA polymerase (Roche) as described by the supplier. T4 DNA polymerase creates DNA fragments with blunt ends that can be subsequently cloned into an appropriate vector. The repaired DNA fragments were subcloned into a derivative of pBluescript SK+ vector (Stratagene) which does not allow transcription of cloned DNA fragments. This vector was selected because it contains a convenient polylinker region surrounded by sequences corresponding to universal sequencing primers such as T3, T7, SK, and KS (Stratagene). The unique EcoRV restriction site found in the polylinker region was used as it allows insertion of blunt-end DNA fragments. Ligation of the inserts, use of the ligation products to transform *E. coli* DH10B (Invitrogen) host and selection for recombinant clones were performed as previously described (Sambrook et al., supra). Plasmid DNA carrying the *Streptomyces refuineus* genomic DNA fragments was extracted by the alkaline lysis method (Sambrook et al., supra) and the insert size of 1.5 to 3 kb was confirmed by electrophoresis on agarose gels. Using this procedure, a library of small size random genomic DNA fragments representative of the entire *Streptomyces refuineus* was generated.

A CIL library was constructed from the *Streptomyces refuineus* high molecular weight genomic DNA using the SUPERCOS-1 cosmid vector (STRATAGENE™). The cosmid arms were prepared as specified by the manufacturer. The high molecular weight DNA was subjected to partial digestion at 37 degrees Celsius with approximately one unit of Sau3AI restriction enzyme (New England Biolabs) per 100 micrograms of DNA in the buffer supplied by the manufacturer. This enzyme generates random fragments of DNA ranging from the initial undigested size of the DNA to short fragments of which the length is dependent upon the frequency of the enzyme DNA recognition site in the genome and the extent of the DNA digestion. At various timepoints, aliquots of the digestion were transferred to new microfuge tubes and the enzyme was inactivated by adding a final concentration of 10 mM EDTA and 0.1% SDS. Aliquots judged by FIGE analysis to contain a significant fraction of DNA in the desired size range (30-50 kb) were pooled, extracted with phenol/chloroform (1:1 vol:vol), and pelletted by ethanol precipitation. The 5' ends of Sau3AI DNA fragments were dephosphorylated using alkaline phosphatase (Roche) according to the manufacturer's specifications at 37 degrees Celsius for 30 min. The phosphatase was heat inactivated at 70 degrees Celsius for 10 min and the DNA was extracted with phenol/chloroform (1:1 vol:vol), pelletted by ethanol precipitation, and resuspended in sterile water. The dephosphorylated Sau3AI DNA fragments were then ligated overnight at room temperature to the SuperCos-1 cosmid arms in a reaction containing approximately four-fold molar excess SuperCos-1 cosmid arms. The ligation products were packaged using GIGAPACK III$^R$ XL packaging extract (STRATAGENE™) according to the manufacturer's specifications. The CIL library consisted of 864 isolated cosmid clones in *E. coli* DH10B (Invitrogen). These clones were picked and inoculated into nine 96-well microtiter plates containing LB broth (per liter of water: 10.0 g NaCl; 10.0 g tryptone; 5.0 g yeast extract) which were grown overnight and then adjusted to contain a final concentration of 25% glycerol. These microtiter plates were stored at −80 degrees Celsius and served as glycerol stocks of the CIL library. Duplicate microtiter plates were arrayed onto nylon membranes as follows. Cultures grown on microtiter plates were concentrated by pelleting and resuspending in a small volume of LB broth. A 3×3 96-pin grid was spotted onto nylon membranes. These membranes representing the complete CIL library were then layered onto LB agar and incubated overnight at 37 degrees Celsius to allow the colonies to grow. The membranes were layered onto filter paper pre-soaked with 0.5 N NaOH/1.5 M NaCl for 10 min to denature the DNA and then neutralized by transferring onto filter paper pre-soaked with 0.5 M Tris (pH 8)/1.5 M NaCl for 10 min. Cell debris was gently scraped off with a plastic spatula and the DNA was crosslinked onto the membranes by UV irradiation using a GS GENE LINKER™ UV Chamber (BIORAD). Considering an average size of 8 Mb for an actinomycete genome and an average size of 35 kb of genomic insert in the CIL library, this library represents roughly a 4-fold coverage of the microorganism's entire genome.

The GSL library was analyzed by sequence determination of the cloned genomic DNA inserts. The universal primers KS or T7, referred to as forward (F) primers, were used to initiate polymerization of labeled DNA. Extension of at least 700 bp from the priming site can be routinely achieved using the TF, BDT v2.0 sequencing kit as specified by the supplier (Applied Biosystems). Sequence analysis of the small genomic DNA fragments (Genomic Sequence Tags, GSTs) was performed using a 3700 ABI capillary electrophoresis DNA sequencer (Applied Biosystems). The average length of the DNA sequence reads was ~700 bp. Further analysis of the obtained GSTs was performed by sequence homology comparison to various protein sequence databases. The DNA sequences of the obtained GSTs were translated into amino acid sequences and compared to the National Center for Biotechnology Information (NCBI) nonredundant protein database and the Decipher™ database of natural product biosynthetic gene (Ecopia BioSciences Inc. St.-Laurent, QC, Canada) using known algorithms (Altschul et al. (1990), *J. Mol. Biol.*, 215(3), 403-410 and (1993), *Nature genetics* 3, 266-272).

A total of 486 *Streptomyces refuineus* GSTs were generated and analyzed by sequence comparison using the Blast algorithm (Altschul et al. (1990), *J. Mol. Biol.*, 215(3), 403-410 and (1993), *Nature genetics* 3, 266-272). Sequence alignments displaying an E value of at least e-5 were considered as significantly homologous and retained for further evaluation. GSTs showing similarity to a gene of interest can be at this point selected and used to identify larger segments of genomic DNA from the CIL library that include the gene(s) of interest. One GST clone identified by Blast analysis as encoding a fragment of a nonribosomal peptide synthetase (NRPS) enzyme was selected for the generation of an oligonucleotide probe which was then used to identify the gene cluster harboring this specific NRPS gene(s) in the CIL library.

Hybridization oligonucleotide probes were radiolabeled with $P^{32}$ using T4 polynucleotide kinase (New England Biolabs) in 15 microliter reactions containing 5 picomoles of oligonucleotide and 6.6 picomoles of [γ-$P^{32}$]ATP in the kinase reaction buffer supplied by the manufacturer. After 1 hour at 37 degrees Celsius, the kinase reaction was terminated by the addition of EDTA to a final concentration of 5 mM. The specific activity of the radiolabeled oligonucleotide probes was estimated using a Model 3 Geiger counter (Ludlum Measurements Inc., Sweetwater, Tex.) with a built-in integrator feature. The radiolabeled oligonucleotide probes were heat-denatured by incubation at 85 degrees Celsius for 10 minutes and quick-cooled in an ice bath immediately prior to use.

The CIL library membranes were pretreated by incubation for at least 2 hours at 42 degrees Celsius in Prehyb Solution (6×SSC; 20 mM $NaH_2PO_4$; 5× Denhardt's; 0.4% SDS; 0.1 mg/ml sonicated, denatured salmon sperm DNA) using a hybridization oven with gentle rotation. The membranes were then placed in Hyb Solution (6×SSC; 20 mM NaH$_2$PO$_4$; 0.4% SDS; 0.1 mg/ml sonicated, denatured salmon sperm DNA) containing 1×10$^6$ cpm/ml of radiolabeled oligonucleotide probe and incubated overnight at 42 degrees Celsius using a hybridization oven with gentle rotation. The next day, the membranes were washed with Wash Buffer (6×SSC, 0.1% SDS) for 45 minutes each at 46, 48, and 50 degrees Celsius using a hybridization oven with gentle rotation. The membranes were then exposed to X-ray film to visualize and identify the positive cosmid clones. Positive clones were identified, cosmid DNA was extracted from 30 ml cultures using the alkaline lysis method (Sambrook et al., supra) and the inserts were entirely sequenced using a shotgun sequencing approach (Fleischmann et al. (1995), *Science,* 269:496-512).

Sequencing reads were assembled using the PHRED-PHRAP™ algorithm (University of Washington, Seattle, USA) recreating the entire DNA sequence of the cosmid insert. Reiterations of hybridizations of the CIL library with probes derived from the ends of the original cosmid allow indefinite extension of sequence information on both sides of the original cosmid sequence until the complete sought-after gene cluster is obtained. To date, two overlapping cosmid clones that were detected by the oligonucleotide probe derived from the original NRPS GST clone have been completely sequenced to provide approximately 60 Kb of information. The sequence of these cosmids and analysis of the proteins encoded by them undoubtedly demonstrated that the gene cluster obtained was indeed responsible for the production of anthramycin, sometimes referred to herein as ANTH. Subsequent inspection of the ANTH biosynthetic cluster sequence (~60 kb) by Blast analysis with a database of GST sequences revealed that a total of 8 GSTs from the *Streptomyces refuineus* GSL library were contained within this cluster.

EXAMPLE 2

Genes and Proteins Involved in Biosynthesis of Anthramycin

The anthramycin locus includes the 32,539 base pairs provided in SEQ ID NO: 1 and contains the 25 ORFs provided SEQ ID NOS: 3, 5, 7, 9, 11, 13, 15, 17, 19, 21, 23, 25, 27, 29, 31, 33, 35, 37, 39, 41, 43, 45, 47, 49, 51. More than 15 kilobases of DNA sequence were analyzed on each side of the anthramycin locus and these regions contain primary metabolic genes. The accompanying sequence listing provides the nucleotide sequence of the 25 ORFs regulating the biosynthesis of anthramycin and the corresponding deduced polypeptides, wherein ORF 1 (SEQ ID NO: 3) represents the polynucleotide drawn from residues 1863 to 1 (antisense strand) of SEQ ID NO: 1, and SEQ ID NO: 2 represents the polypeptide deduced from SEQ ID NO: 3; ORF 2 (SEQ ID NOS: 5) represents the polynucleotide drawn from residues 3388 to 1886 (antisense strand) of SEQ ID NO: 1 and SEQ ID NO: 4 represents the polypeptide deduced from SEQ ID NO: 5; ORF 3 (SEQ ID NOS: 7) represents the polynucleotide drawn from residues 4449 to 3385 (antisense strand) of SEQ ID NO: 1 and SEQ ID NO: 6 represents the polypeptide deduced from SEQ ID NO: 7; ORF 4 (SEQ ID NOS: 9) represents the polynucleotide drawn from residues 5703 to 4471 (antisense strand) of SEQ ID NO: 1 and SEQ ID NO: 8 represents the polypeptide deduced from SEQ ID NO: 9; ORF 5 (SEQ ID NOS: 11) represents the polynucleotide drawn from residues 6758 to 5700 (antisense strand) of SEQ ID NO: 1 and SEQ ID NO: 10 represents the polypeptide deduced from SEQ ID NO: 11; ORF 6 (SEQ ID NOS: 13) represents the polynucleotide drawn from residues 8657 to 6792 (antisense strand) of SEQ ID NO: 1 and SEQ ID NO: 12 represents the polypeptide deduced from SEQ ID NO: 13; ORF 7 (SEQ ID NOS: 15) represents the polynucleotide drawn from residues 10117 to 8654 (antisense strand) of SEQ ID NO: 1 and SEQ ID NO: 14 represents the polypeptide deduced from SEQ ID NO: 15; ORF 8 (SEQ ID NOS: 17) represents the polynucleotide drawn from residues 10517 to 12811 (sense strand) of SEQ ID NO: 1 and SEQ ID NO:16 represents the polypeptide deduced from SEQ ID NO: 17; ORF 9 (SEQ ID NOS: 19) represents the polynucleotide drawn from residues 12858 to 13628 (sense strand) of SEQ ID NO: 1 and SEQ ID NO: 18 represents the polypeptide deduced from SEQ ID NO: 19; ORF 10 (SEQ ID NOS: 21) represents the polynucleotide drawn from residues 13657 to 14850 (sense strand) of SEQ ID NO: 1 and SEQ ID NO: 20 represents the polypeptide deduced from SEQ ID NO: 21; ORF 11 (SEQ ID NOS: 23) represents the polynucleotide drawn from residues 14970 to 15239 (sense strand) of SEQ ID NO: 1 and SEQ ID NO: 22 represents the polypeptide deduced from SEQ ID NO: 23; ORF 12 (SEQ ID NOS: 25) represents the polynucleotide drawn from residues 15323 to 15832 (sense strand) of SEQ ID NO: 1 and SEQ ID NO: 24 represents the polypeptide deduced from SEQ ID NO: 25; ORF 13 (SEQ ID NOS: 27) represents the polynucleotide drawn from residues 15829 to 16737 (sense strand) of SEQ ID NO: 1 and SEQ ID NO: 26 represents the polypeptide deduced from SEQ ID NO: 27; ORF 14 (SEQ ID NOS: 29) represents the polynucleotide drawn from residues 16734 to 17627 (sense strand) of SEQ ID NO: 1 and SEQ ID NO: 28 represents the polypeptide deduced from SEQ ID NO: 29; ORF 15 (SEQ ID NOS: 31) represents the polynucleotide drawn from residues 17624 to 18448 (sense strand) of SEQ ID NO: 1 and SEQ ID NO: 30 represents the polypeptide deduced from SEQ ID NO: 31; ORF 16 (SEQ ID NOS: 33) represents the polynucleotide drawn from residues 18445 to 19686 (sense strand) of SEQ ID NO: 1 and SEQ ID NO: 32 represents the polypeptide deduced from SEQ ID NO: 33; ORF 17 (SEQ ID NOS: 35) represents the polynucleotide drawn from residues 19697 to 20482 (sense strand) of SEQ ID NO: 1 and SEQ ID NO: 34 represents the polypeptide deduced from SEQ ID NO: 35; ORF 18 (SEQ ID NOS: 37) represents the polynucleotide drawn from residues 20517 to 20693 (sense strand) of SEQ ID NO: 1 and SEQ ID NO: 36 represents the polypeptide deduced from SEQ ID NO: 37; ORF 19 (SEQ ID NOS: 39) represents the polynucleotide drawn from residues 20690 to 21733 (sense strand) of SEQ ID NO: 1 and SEQ ID NO: 38 represents the polypeptide deduced from SEQ ID NO: 39; ORF 20 (SEQ ID NOS: 41) represents the polynucleotide drawn from residues 21726 to 22616 (sense strand) of SEQ ID NO: 1 and SEQ ID NO: 40 represents the polypeptide deduced from SEQ ID NO: 41; ORF 21 (SEQ ID NOS: 43) represents the polynucleotide drawn from residues 22613 to 24415 (sense strand) of SEQ ID NO: 1 and SEQ ID NO: 42 represents the polypeptide deduced from SEQ ID NO: 43; ORF 22 (SEQ ID NOS: 45) represents the polynucleotide drawn from residues 24417 to 28757 (sense strand) of SEQ ID NO: 1 and SEQ ID NO: 44 represents the polypeptide deduced from SEQ ID NO: 45; ORF 23 (SEQ ID NOS: 47) represents the polynucleotide drawn from residues 28774 to 30138 (sense strand) of SEQ ID NO: 1 and SEQ ID NO: 46 represents the polypeptide deduced from SEQ ID NO: 47; ORF 24 (SEQ ID NOS: 49) represents the polynucleotide drawn from residues 31687 to 30251 (antisense strand) of SEQ ID NO: 1 and SEQ ID NO: 48 represents the polypeptide deduced from SEQ ID NO: 49; ORF 25 (SEQ ID NOS: 51) represents the polynucleotide drawn from residues 32539 to 31718 (antisense strand) of SEQ ID NO: 1 and SEQ ID NO: 50 represents the polypeptide deduced from SEQ ID NO: 51.

Some open reading frames listed herein initiate with non-standard initiation codons (e.g. GTG—Valine or CTG—Leucine) rather than the standard initiation codon ATG, namely ORFs 2, 3, 4, 9, 11, 12, 13, 15, 19, 23, 24 and 25. All ORFs are listed with the appropriate M, V or L amino acids at the amino-terminal position to indicate the specificity of the first codon of the ORF. It is expected, however, that in all cases the biosynthesized protein will contain a methionine residue, and more specifically a formylmethionine residue, at the amino terminal position, in keeping with the widely accepted principle that protein synthesis in bacteria initiates with methionine (formylmethionine) even when the encoding gene specifies a non-standard initiation codon (e.g. Stryer, Biochemistry $3^{rd}$ edition, 1998, W.H. Freeman and Co., New York, pp. 752-754).

Two deposits, namely E. coli DH10B (024CA) strain and E. coli DH10B (024CO) strain each harbouring a cosmid clone of a partial biosynthetic locus for anthramycin from Streptomyces refuineus subsp. thermotolerans have been deposited with the International Depositary Authority of Canada, Bureau of Microbiology, Health Canada, 1015 Arlington Street, Winnipeg, Manitoba, Canada R3E 3R2 on Jun. 4, 2002 and were assigned deposit accession number IDAC 040602-1 and 040602-2 respectively. The E. coli strain deposits are referred to herein as "the deposited strains".

The cosmids harbored in the deposited strains comprise a complete biosynthetic locus for anthramycin. The sequence of the polynucleotides comprised in the deposited strains, as well as the amino acid sequence of any polypeptide encoded thereby are controlling in the event of any conflict with any description of sequences herein.

The deposit of the deposited strains has been made under the terms of the Budapest Treaty on the International Recognition of the Deposit of Micro-organisms for Purposes of Patent Procedure. The deposited strains will be irrevocably and without restriction or condition released to the public upon the issuance of a patent. The deposited strains are provided merely as convenience to those skilled in the art and are not an admission that a deposit is required for enablement, such as that required under 35 U.S.C. §112. A license may be required to make, use or sell the deposited strains, and compounds derived therefrom, and no such license is hereby granted.

Figure 6:
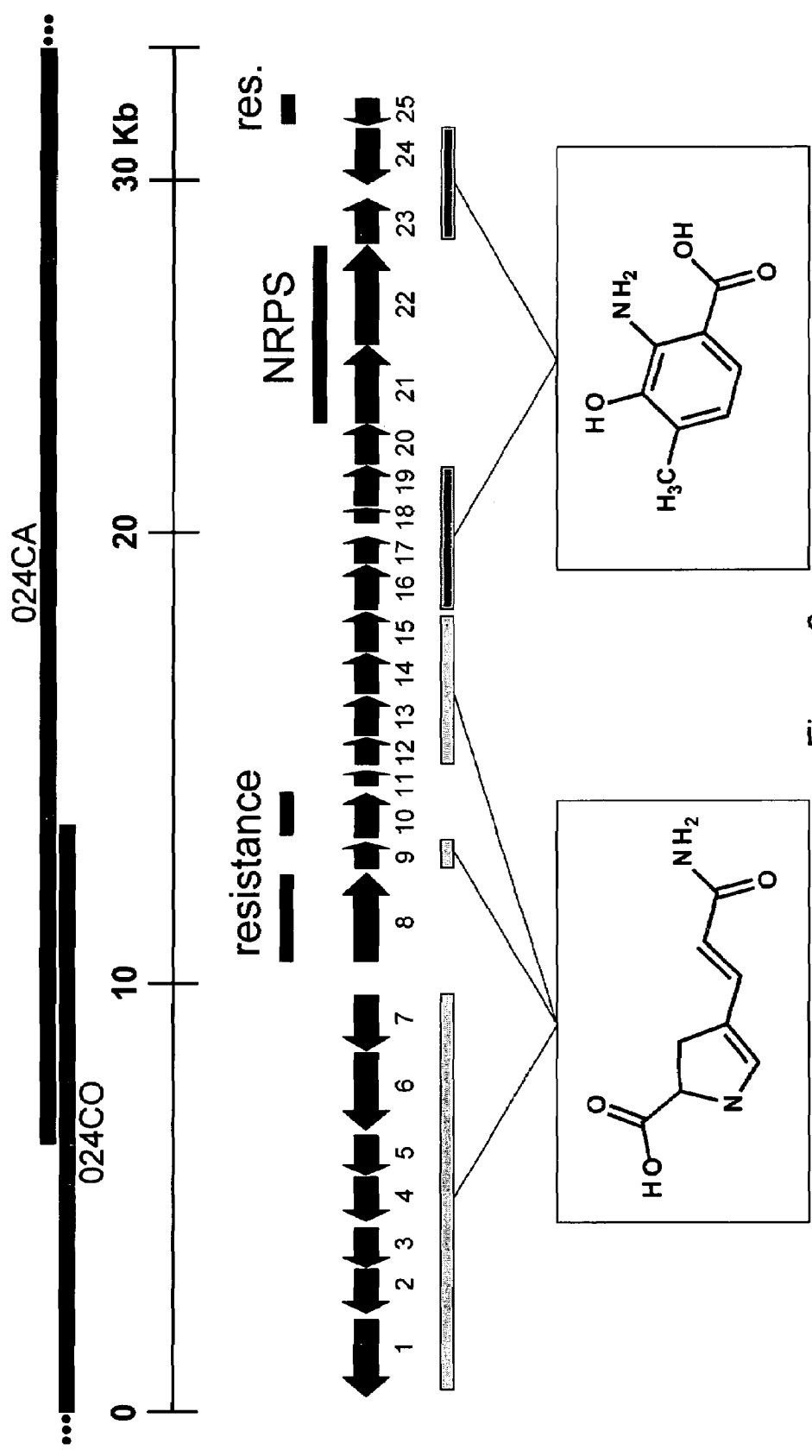
FIG. 6 is a graphical depiction of the anthramycin biosynthetic locus showing coverage of the locus by the deposited strains (024CA and 024CO), a scale in kb, the relative position and orientation of the 25 ORFs, and their role in the biosynthesis of anthramycin.

The order and relative position of the 25 open reading frames and the corresponding polypeptides of the biosynthetic locus for anthramycin are provided in FIG. 6. The arrows represent the orientatation of the ORFs of the anthramycin biosynthetic locus. The top line in FIG. 6 provides a scale in kilobase pairs. The black bars depict the part of the locus covered by each of the deposited cosmids 024CA and 024CO.

In order to identify the function of the genes in the anthramycin locus, SEQ ID NOS: 2, 4, 6, 8, 10, 12, 14, 16, 18, 20, 22, 24, 26, 28, 30, 32, 34, 36, 38, 40, 42, 44, 46, 48, 50 were compared, using the BLASTP version 2.2.1 algorithm with the default parameters, to sequences in the National Center for Biotechnology Information (NCBI) nonredundant protein database and the DECIPHER™ database of microbial genes, pathways and natural products (Ecopia BioSciences Inc. St.-Laurent, QC, Canada).

The accession numbers of the top GenBank hits of this BLAST analysis are presented in Table 3 along with the corresponding E value. The E value relates the expected number of chance alignments with an alignment score at least equal to the observed alignment score. An E value of 0.00 indicates a perfect homolog or nearly perfect homolog. The E values are calculated as described in Altschul et al. J. Mol. Biol., Oct. 5, 1990; 215(3) 403-10, the teachings of which is incorporated herein by reference. The E value assists in the determination of whether two sequences display sufficient similarity to justify an inference of homology.

TABLE 3

| ORF no. | SEQ ID NO | Family | #aa | GenBank homology | probability | % identity | % similarity | proposed function of GenBank match |
|---|---|---|---|---|---|---|---|---|
| 1 | 2 | AOTF | 620 | BAB12569.1, 609aa | 1e-166 | 326/620 (52.58%) | 387/620 (62.42%) | asparagine synthase homolog, Streptomyces aureofaciens |
| | | | | NP_248741.1, 610aa | 1e-146 | 278/618 (44.98%) | 371/618 (60.03%) | probable glutamine amidotransferase, Pseudomonas aeruginosa |
| | | | | AAF17502.1, 610aa | 1e-145 | 276/619 (44.59%) | 367/619 (59.29%) | PhzH, Pseudomonas chlororaphis |
| 2 | 4 | OXCC | 500 | CAD30313.1, 494aa | 1e-124 | 242/480 (50.42%) | 297/480 (61.88%) | aldehyde dehydrogenase, Geobacillus stearothermophilus |
| | | | | NP_241405.1, 498aa | 1e-116 | 229/485 (47.22%) | 295/485 (60.82%) | NADP-dependent aldehyde dehydrogenase, Bacillus halodurans |
| | | | | NP_389813.1, 495aa | 1e-115 | 225/483 (46.58%) | 288/483 (59.63%) | aldehyde dehydrogenase, Bacillus subtilis |
| 3 | 6 | OXCB | 354 | NP_532825.1, 347aa | 8e-72 | 144/318 (45.28%) | 186/318 (58.49%) | alcohol dehydrogenase, Agrobacterium tumefaciens |
| | | | | NP_643135.1, 356aa | 2e-69 | 144/318 (45.28%) | 178/318 (55.97%) | alcohol dehydrogenase, Xanthomonas axonopodis |
| | | | | NP_102793.1, 346aa | 5e-69 | 136/318 (42.77%) | 183/318 (57.55%) | alcohol dehydrogenas, Mesorhizobium loti |
| 4 | 8 | OXRC | 410 | BAA23268.1, 397aa | 6e-88 | 170/388 (43.81%) | 234/388 (60.31%) | hypothetical protein, Nocardioides sp. |
| | | | | AAL25730.1, 400aa | 5e-87 | 167/385 (43.38%) | 226/385 (58.7%) | EthB, Rhodococcus ruber |
| | | | | NP_627830.1, 411aa | 3e-41 | 125/412 (30.34%) | 180/412 (43.69%) | putative cytochrome P-450 hydroxylase, Streptomyces coelicolor |

TABLE 3-continued

| ORF no. | SEQ ID NO | Family | #aa | GenBank homology | probability | % identity | % similarity | proposed function of GenBank match |
|---|---|---|---|---|---|---|---|---|
| 5 | 10 | MTFA | 352 | S44970, 318aa | 1e-135 | 233/318 (73.27%) | 257/318 (80.82%) | ImbW protein, *Streptomyces lincolnensis* |
| 6 | 12 | UNKJ | 621 | S19874, 601aa | 0.0 | 434/603 (71.97%) | 476/603 (78.94%) | lincomycin-condensing protein ImbA, *Streptomyces lincolnensis* |
| | | | | NP_630529.1, 647aa | 1e-151 | 304/642 (47.35%) | 377/642 (58.72%) | putative gamma-glutamyl transferase, *Streptomyces coelicolor* |
| | | | | AAG42852.1, 621aa | 1e-150 | 298/623 (47.83%) | 372/623 (59.71%) | putative gamma-glutamyl transferase, *Streptomyces nogalater* |
| 7 | 14 | OXBY | 487 | P46377, 438aa | 3e-53 | 135/440 (30.68%) | 203/440 (46.14%) | hypothetical oxidoreductase, *Rhodococcus fascians* |
| | | | | Q9LDE6, 532aa | 1e-34 | 154/500 (30.8%) | 212/500 (42.4%) | probable cytokinin oxidase precursor, *Oryza sativa* |
| | | | | AAG30907.1, 524aa | 2e-30 | 126/495 (25.45%) | 205/495 (41.41%) | cytokinin oxidase, *Arabidopsis thaliana* |
| 8 | 16 | ENRP | 764 | NP_630792.1, 752aa | 0.0 | 470/748 (62.83%) | 569/748 (76.07%) | UvrA-like ABC transporter, *Streptomyces coelicolor* |
| | | | | AAB39274.1, 764aa | 0.0 | 415/748 (55.48%) | 540/748 (72.19%) | daunorubicin resistance protein, *Streptomyces peucetius* |
| | | | | NP_465574.1, 746aa | 0.0 | 388/744 (52.15%) | 544/744 (73.12%) | (probable excinuclease ABC, *Listeria monocytogenes* |
| 9 | 18 | HOXY | 256 | NP_624595.1, 263aa | 4e-11 | 66/243 (27.16%) | 97/243 (39.92%) | putative hydroxylase, *Streptomyces coelicolor* |
| | | | | NP_386943.1, 253aa | 9e-10 | 60/252 (23.81%) | 90/252 (35.71%) | hypothetical protein, *Sinorhizobium meliloti* |
| | | | | NP_630787.1, 263aa | 1e-08 | 60/252 (23.81%) | 99/252 (39.29%) | putative hydroxylase, *Streptomyces coelicolor* |
| 10 | 20 | EFFA | 397 | NP_252026.1, 388aa | 1e-72 | 158/391 (40.41%) | 209/391 (53.45%) | probable transporter, *Pseudomonas aeruginosa* |
| | | | | NP_631570.1, 403aa | 5e-54 | 126/377 (33.42%) | 180/377 (47.75%) | chloramphenicol resistance protein, *Streptomyces coelicolor* |
| | | | | AAB36568.1, 436aa | 1e-48 | 120/378 (31.75%) | 178/378 (47.09%) | chloramphenicol resistance protein, *Streptomyces venezuelae* |
| 11 | 22 | UNIQ | 89 | | | | | No homolog by blastp in GenBank nr protein database |
| 12 | 24 | UNKW | 169 | S44948, 158aa | 5e-24 | 59/143 (41.26%) | 76/143 (53.15%) | ImbBI protein, *Streptomyces lincolnensis* |
| 13 | 26 | UNKV | 302 | S44949, 317aa | 3e-34 | 87/199 (43.72%) | 112/199 (56.28%) | ImbB2 protein, *Streptomyces lincolnensis* |
| 14 | 28 | OXBD | 297 | S44973, 295aa | 4e-75 | 138/287 (48.08%) | 173/287 (60.28%) | ImbY protein, *Streptomyces lincolnensis* |
| | | | | NP_628135.1, 320aa | 1e-58 | 128/301 (42.52%) | 165/301 (54.82%) | hypothetical protein, *Streptomyces coelicolor* |
| | | | | NP_216371.1, 307aa | 8e-11 | 60/222 (27.03%) | 91/222 (40.99%) | hypothetical protein, *Mycobacterium tuberculosis* |
| 15 | 30 | UNKA | 274 | S44972, 296aa | 9e-11 | 66/209 (31.58%) | 76/209 (36.36%) | ImbX protein, *Streptomyces lincolnensis* |
| 16 | 32 | HYDE | 413 | NP_627839.1, 410aa | 3e-75 | 164/393 (41.73%) | 218/393 (55.47%) | putative hydrolase, *Streptomyces coelicolor* |
| | | | | NP_518880.1, 417aa | 3e-66 | 140/373 (37.53%) | 208/373 (55.76%) | probable hydrolase, *Ralstonia solanacearum* |
| | | | | NP_102390.1, 415aa | 2e-64 | 146/378 (38.62%) | 204/378 (53.97%) | probable kyurenine hydrolase, *Mesorhizobium loti* |
| 17 | 34 | OXRN | 261 | NP_518879.1, 294aa | 7e-39 | 88/262 (33.59%) | 135/262 (51.53%) | putative oxidoreductase, *Ralstonia solanacearum* |
| | | | | NP_421682.1, 263aa | 2e-38 | 86/257 (33.46%) | 136/257 (52.92%) | hypothetical protein, *Caulobacter crescentus* |
| | | | | NP_627840.1, 271aa | 8e-35 | 88/257 (34.24%) | 126/257 (49.03%) | putative oxidoreductase, *Streptomyces coelicolor* |
| 18 | 36 | UNIQ | 58 | | | | | No homolog by blastp in GenBank nr protein database |
| 19 | 38 | MTFA | 347 | AAM33664.1, 343aa | 2e-21 | 84/323 (26.01%) | 132/323 (40.87%) | methyltransferase, *Streptomyces sp.* |
| | | | | P39896, 339aa | 9e-17 | 57/159 (35.85%) | 78/159 (49.06%) | O-methyltransferase, *Streptomyces glaucescens* |
| | | | | P10950, 345aa | 4e-15 | 69/245 (28.16%) | 106/245 (43.27%) | hydroxyindole O-methyltransferase, *Bos taurus* |
| 20 | 40 | EATD | 296 | BAB32459.1, 289aa | 5e-24 | 83/287 (28.92%) | 117/287 (40.77%) | hypothetical protein, *Pseudomonas sp.* |
| | | | | NP_435384.1, 281aa | 2e-16 | 74/263 (28.14%) | 99/263 (37.64%) | hypothetical protein, *Sinorhizobium meliloti* |
| | | | | NP_106326.1, 309aa | 3e-14 | 61/241 (25.31%) | 93/241 (38.59%) | hypothetical protein, *Mesorhizobium loti* |

TABLE 3-continued

| ORF no. | SEQ ID NO | Family | #aa | GenBank homology | probability | % identity | % similarity | proposed function of GenBank match |
|---|---|---|---|---|---|---|---|---|
| 21 | 42 | ATAA | 600 | T17484, 4077aa | 3e−76 | 197/576 (34.2%) | 285/576 (49.48%) | hypothetical protein, *Amycolatopsis orientalis* |
| | | | | CAB93684.1, 1086aa | 2e−74 | 212/585 (36.24%) | 290/585 (49.57%) | tripeptide synthetase, *Streptomyces viridochromogenes* |
| | | | | NP_627443.1, 7463aa | 1e−73 | 210/609 (34.48%) | 289/609 (47.45%) | CDA peptide synthetase I, *Streptomyces coelicolor* |
| 22 | 44 | NRPS | 1446 | AAK57184.1, 1515aa | 1e−140 | 445/1460 (30.48%) | 658/1460 (45.07%) | MxaA, *Stigmatella aurantiaca* |
| | | | | BAB69380.1, 1440aa | 1e−111 | 426/1482 (28.74%) | 588/1482 (39.68%) | non-ribosomal peptide synthetase, *Streptomyces avermitilis* |
| | | | | T18552, 2605aa | 1e−111 | 429/1485 (28.89%) | 617/1485 (41.55%) | saframycin Mx1 synthetase A, *Myxococcus xanthus* |
| 23 | 46 | HOXF | 454 | NP_506025.1, 461aa | 9e−42 | 128/435 (29.43%) | 198/435 (45.52%) | monooxygenase, *Caenorhabditis elegans* |
| | | | | AAF80481.1, 478aa | 1e−40 | 128/418 (30.62%) | 194/418 (46.41%) | L-kynurenine 3-monooxygenase, *Sus scrofa* |
| | | | | XP_050663.1, 486aa | 2e−40 | 129/426 (30.28%) | 196/426 (46.01%) | kynurenine 3-hydroxylase, *Homo sapiens* |
| 24 | 48 | AAOB | 478 | NP_389783.1, 446aa | 9e−32 | 127/458 (27.73%) | 200/458 (43.67%) | putative L-amino acid oxidase, *Bacillus subtilis* |
| | | | | CAA88452.1, 495aa | 8e−26 | 119/464 (25.65%) | 193/464 (41.59%) | L-amino acid oxidase, *Synechococcus* sp. |
| | | | | CAA72047.1, 485aa | 1e−25 | 129/502 (25.7%) | 215/502 (42.83%) | hypothetical protein, *Bacillus cereus* |
| 25 | 50 | RREA | 273 | AAB36584.1, 234aa | 3e−45 | 101/234 (43.16%) | 142/234 (60.68%) | JadR1, *Streptomyces venezuelae* |
| | | | | NP_561558.1, 231aa | 1e−25 | 79/229 (34.5%) | 119/229 (51.97%) | response regulator, *Clostridium perfringens* |
| | | | | NP_627235.1, 229aa | 5e−25 | 78/224 (34.82%) | 120/224 (53.57%) | putative response regulator, *Streptomyces coelicolor* |

EXAMPLE 3

Formation of Anthramycin

Figure 5:
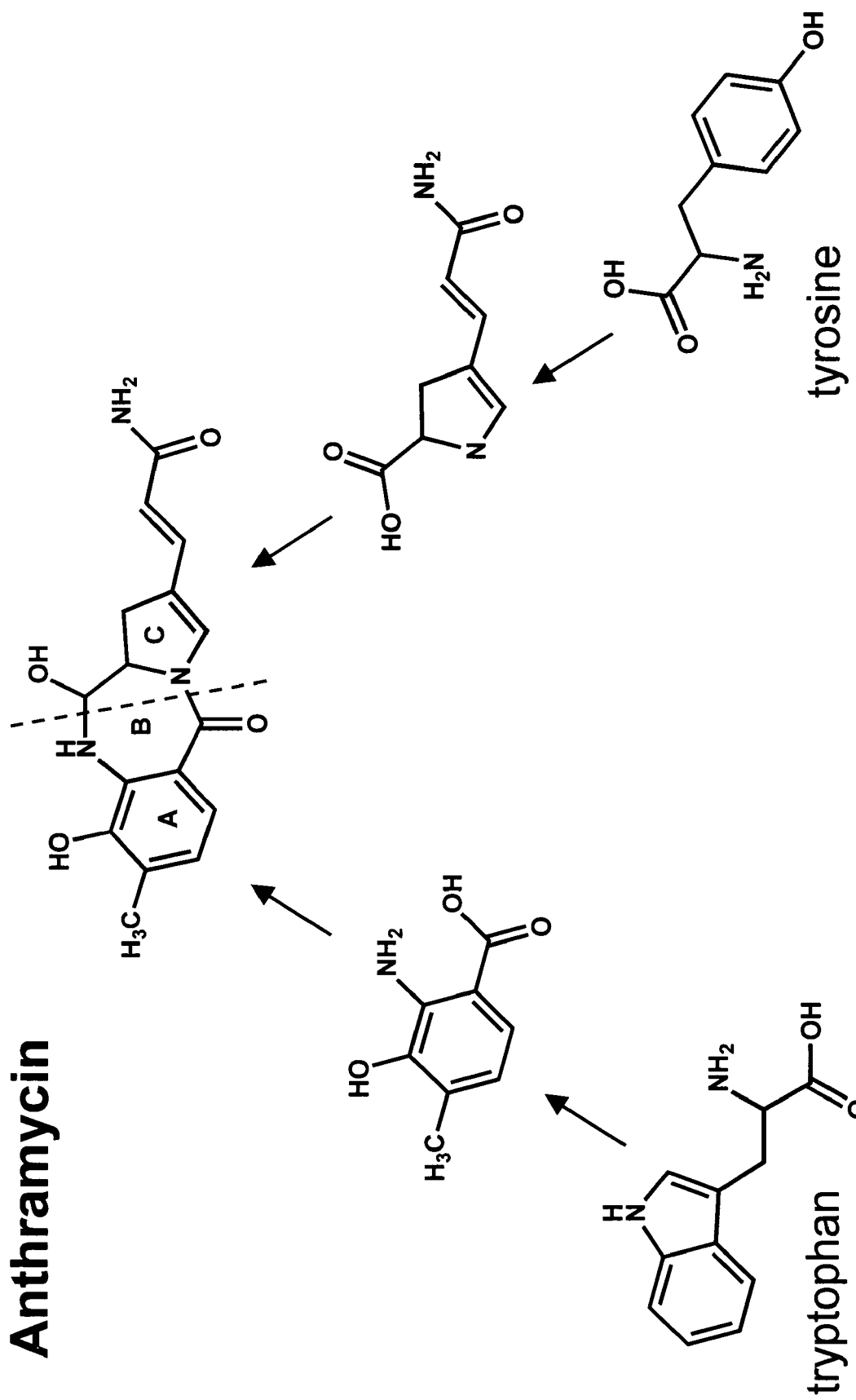
FIG. 5 illustrates the structure of anthramycin identifying its aromatic A-ring, 7-membered diazepine B-ring, and proline-like C-ring, and also showing the precursors and intermediates to formation of the A-ring and C-ring moieties of the anthramycin molecule.

The chemical structure of anthramycin contains an aromatic ring (ring A in FIG. 5), a 7-member diazepine ring (ring B in FIG. 5) and a proline-like ring (ring C in FIG. 5). The genes and proteins of the invention explain formation of anthramycin. The aromatic ring of anthramycin is derived from the amino acid L-tryptophan and the proline-like ring of anthramycin is derived from the amino acid L-tyrosine via the intermediates shown in FIG. 5. Twelve genes, ORFs 1 to 7, 9 and 12 to 15 (SEQ ID NOS: 3, 5, 7, 9, 11, 13, 15, 19, 25, 27, 29 and 31 respectively), encode enzymes involved in transformation of L-tyrosine into the proline-like precursor that forms the C-ring of anthramycin. Six genes, ORFs 16 to 19, 23 and 24 (SEQ ID NOS: 33, 35, 37, 39, 47 and 49) encode enzymes involved in the conversion of L-tryptophan into the substituted anthanilate precursor that becomes the aromatic-ring of the compound. Two genes, ORFs 21 and 22 (SEQ ID NOS: 43 and 45) encode nonribosomal peptide synthetases and are responsible for activating and joining the two precursors and creating the benzodiazepine ring.

Based upon precursor feeding studies, a model has been proposed for the biosynthesis of the 2-carbon and 3-carbon proline units of the anthramycin group antibiotics and a similar structural unit found in another class of antibiotics, the lincomycins (Hurley et al., 1979, Biochemistry 18:4230-4237; Brahme et al., 1984, J. Am. Chem. Soc. 106:7873-7878; Kuo etal., 1992, J. Antibiot. 45:1773-1777). Without intending to be limited to any particular biosynthetic schemes or mechanism of action, the genes of the invention can explain formation of anthramycin in a manner consistent with the precursor feeding studies.

Figure 7:
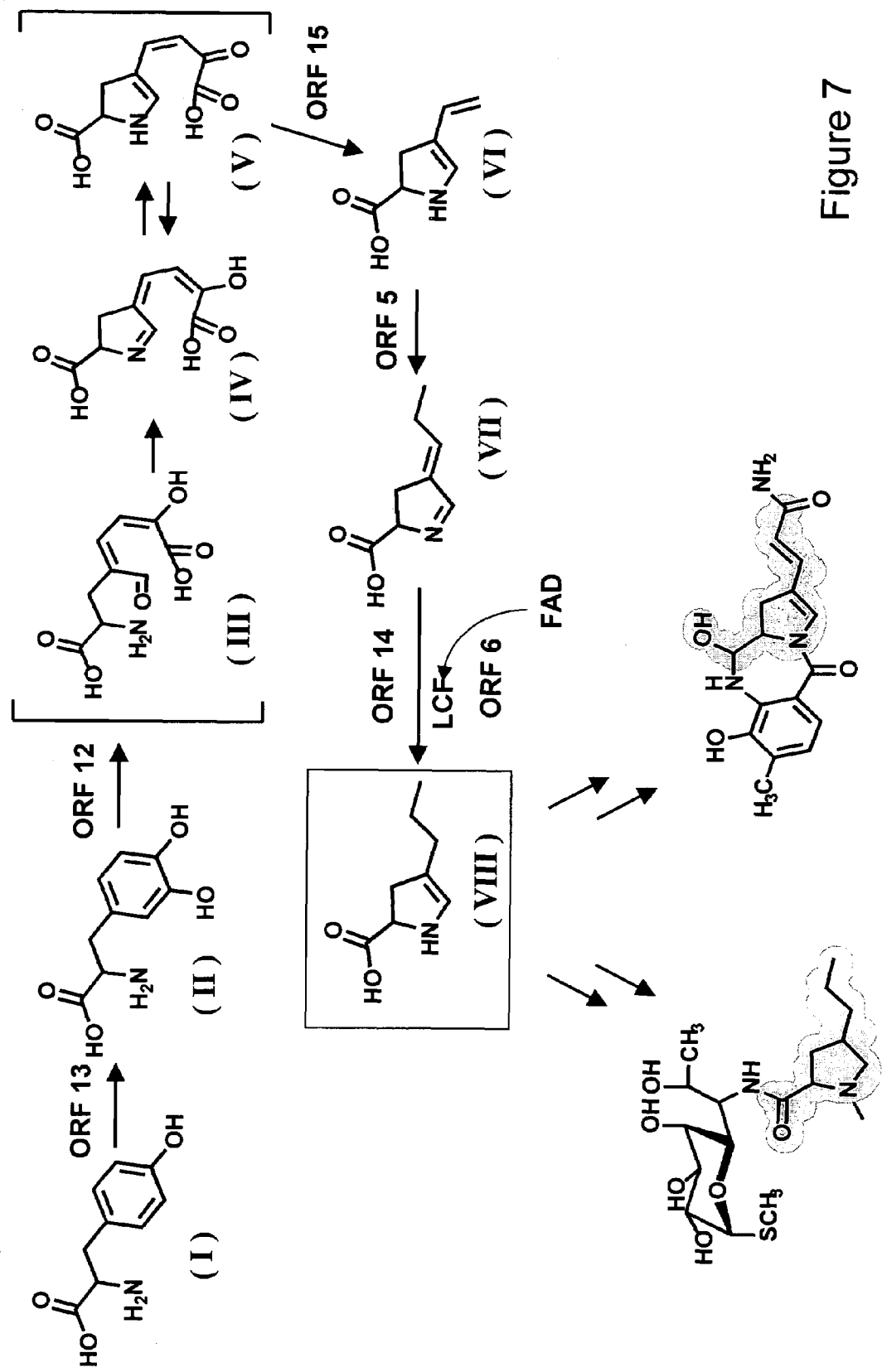
FIG. 7 is a biosynthetic scheme for the formation of a common intermediate generated during the biosynthetic of anthramycin and lincomycin.

The gene products of ORFs 1, 2, 3, 4, 5, 6, 7, 9, 12, 13, 14 and 15 (SEQ ID NOS: 2, 4, 6, 8, 10, 12, 14, 16, 18, 24, 26, 28 and 30 respectively) are involved in the formation of the 3-carbon proline-like substructure found in anthramycin. FIG. 7 illustrates a scheme for formation of the early stage precursors of the 2- and 3-carbon proline-like moieties found in the anthramycins and the lincomycins; the biosynthetic pathways for anthramycin and lincomycin diverge after the formation of a common intermediate (VIIII) of FIG. 7. The gene products of ORFs 5, 6, 12, 13, 14 and 15 (SEQ ID NOS: 10, 12, 24, 26, 28 and 30 respectively) encode proteins that are similar in amino acid sequence to proteins encoded by the lincomycin biosynthetic locus (GenBank accession X79146) and can be assigned to biosynthetic steps leading to the formation of common intermediate VIII of FIG. 7. The gene products of ORFs 1, 2, 3, 4, 7 and 9 (SEQ ID NOS: 2, 4, 6, 8, 14 and 18) show no significant similarity to proteins encoded by the lincomycin biosynthetic locus and are expected to catalyze the reactions leading from the common biosynthetic intermediate to the anthramycins, as illustrated in FIG. 8.

Referring to FIG. 7, L-tyrosine (I) is hydroxylated to L-3,4-dihydroxyphenylalanine (DOPA, II) by ORF 13 protein (SEQ ID NOS: 26), a protein with strong homology to the lincomycin LmbB2 protein which has been proposed to catalyze the 3-hydroxylation of tyrosine (Neusser et al., 1998, Arch. Microbiol. 169:322-332). Proximal extradiol cleavage of the DOPA aromatic ring to generate compound IIII is catalyzed by the ORF 12 protein (SEQ ID NO: 24) which shows homology to lincomycin LmbB1 L-DOPA extradiol-cleaving 2,3-dioxygenase. Ring cleavage is followed by a condensation reaction to form a Schiff's base between the alpha-amino group and the aldehydic group of (III) to generate the five-membered ring and a conjugated enol system (IV). The conjugated enol then undergoes enolization to yield the alpha-keto acid (V), which in turn loses 2 carbon atoms in a stepwise fashion to form the diene (VI) through the action of the ORF 15 protein (SEQ ID NOS: 30), which shows homology to the lincomycin LmbX protein and the PhzF protein involved in phenazine biosynthesis. The diene (VI) undergoes a 1,4-addition reaction resulting in the transfer of a methyl group from S-adenosyl methionine in a reaction catalyzed by the ORF 5 protein (SEQ ID NO: 10), a protein with strong homology to the lincdmycin LmbW methyltransferase. Finally, the diene (VII) is converted to the biosynthetic pathway branchpoint intermediate (VIII) by the ORF 14 reductase (SEQ ID NO: 28), which shows homology to the lincomycin LmbY reductase and to many N5,N10-methylene-tetrahydromethanopterin reductases found in methanogenic archaebacteria. The ORF 14 protein (SEQ ID NO: 28) and the LmbY proteins are reductase enzymes that are expected to utilize a special flavin cofactor referred to as the lincomycin cosynthetic factor or LCF (Kuo et al., 1989, J. Antibiot. 42:475-478). The LCF is identical in structure to the 7,8-didemethyl-8-hydroxy-5-deazariboflavin component of the redox coenzyme F420 of methanogens, which in its active form contains a gamma-glutamyl moiety in its side chain (Peschke et al., 1995, Molec. Microbiol. 15:1137-1156). Thus the ORF 6 protein (SEQ ID NO: 12), which shows homology to the lincomycin LmbA protein and to many bacterial gamma-glutamyltransferases, is likely to generate the active form of the unusual F420 flavanoid cofactor used by the ORF 14 reductase (SEQ ID NO: 28).

Figure 8:
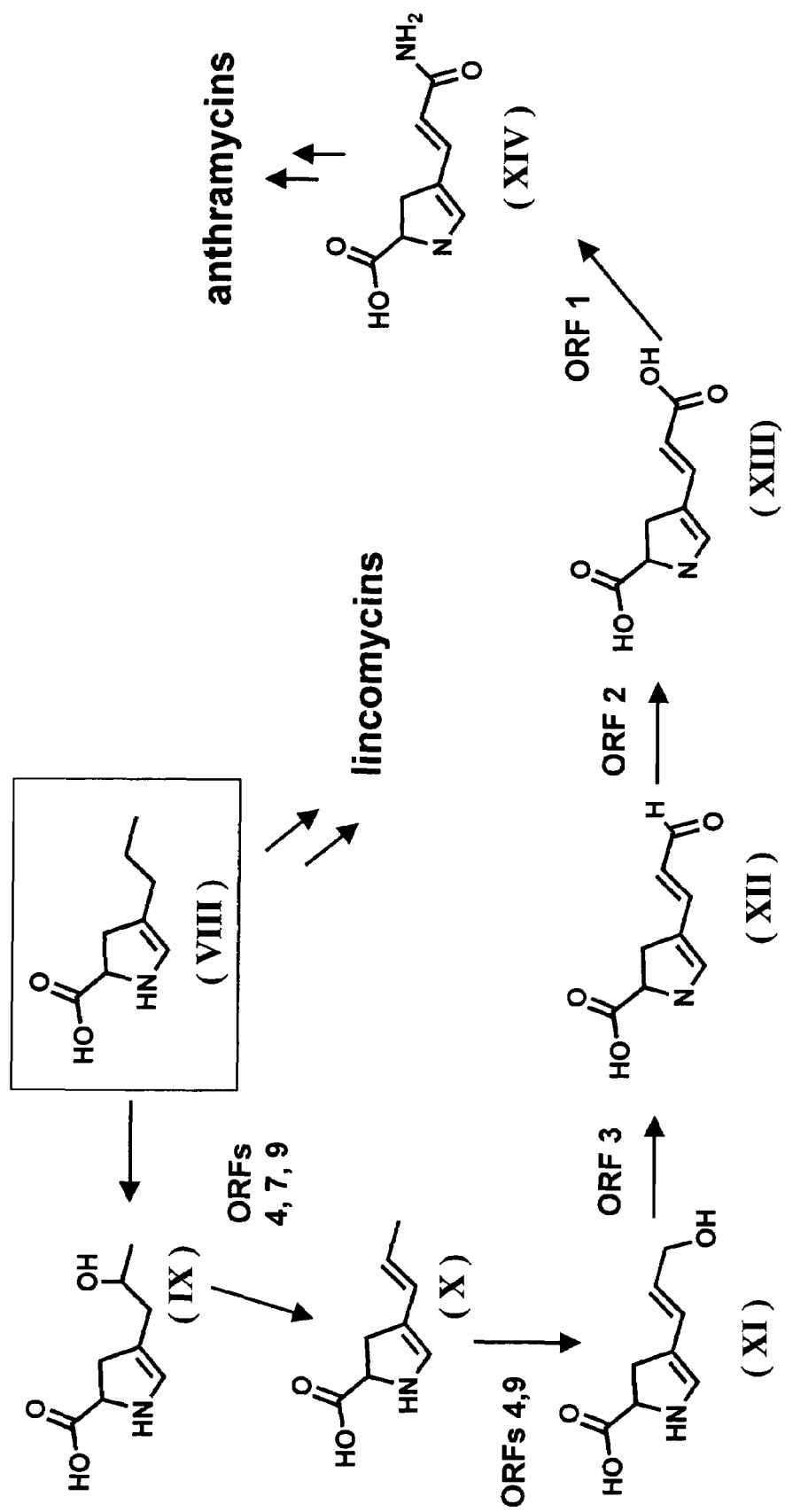
FIG. 8 is a biosynthetic scheme for formation of anthramycin from the common intermediate formed in FIG. 7.

FIG. 8 illustrates a scheme from intermediate (VIII) to the anthramycins, involving ORFs 1, 2, 3, 4, 7 and 9 (SEQ ID NOS: 2, 4, 6, 8, 14 and 18). ORFs 1, 2, 3, 4, 7 and 9 (SEQ ID NOS: 2, 4, 6, 8, 14 and 18) show no significant similarity to proteins encoded by the lincomycin biosynthetic locus. The ORF 4 protein (SEQ ID NO: 2) is similar to many bacterial cytochrome P450 monooxygenases. The ORF 7 protein (SEQ ID NO: 14) is a flavin-dependent oxidase that is similar to many plant cytokinin oxidases. The ORF 9 protein (SEQ ID NO: 18) shows homology to putative bacterial hydroxylases and to the daunorubicin DnrV protein, which has been shown to cooperate with the daunorubicin DoxA in the hydroxylation of daunorubicin biosynthetic intermediates (Lomovskaya et al., 1999, J. Bacteriol. 181:305-318). The ORF 4, ORF 7 and ORF 9 proteins (SEQ ID NOS: 8, 14 and 18) are expected to act individually or in concert to catalyze the hydroxylation of the allylic carbon of (VIII) to generate the alcohol (IX) followed by the subsequent elimination of water to generate the diene (X). The ORF 4 protein (SEQ ID NO: 8), either alone or in combination with the ORF 9 protein (SEQ ID NO: 18), is expected to catalyze the hydroxylation of the allylic carbon of (X) to generate the alcohol (XI). The ORF 3 protein (SEQ ID NO: 6) shows homology to many bacterial zinc-binding, NADP-dependent alcohol dehydrogenases and catalyzes the oxidation of the alcohol (XI) to the aldehyde (XII). The ORF 2 protein (SEQ ID NO: 4) is similar to many bacterial and eukaryotic NAD-dependent aldehyde dehydrogenases, and catalyzes the oxidation of the aldehyde (XII) to generate the carboxylic acid (XIII). Finally, the ORF 1 protein (SEQ ID NO: 2), which shows homology to many glutamine-dependent asparagine synthetases, catalyzes the transfer of the amine group of glutamine to the carboxylic acid (XIII) to generate the carbamide intermediate (XIV).

Figure 9:
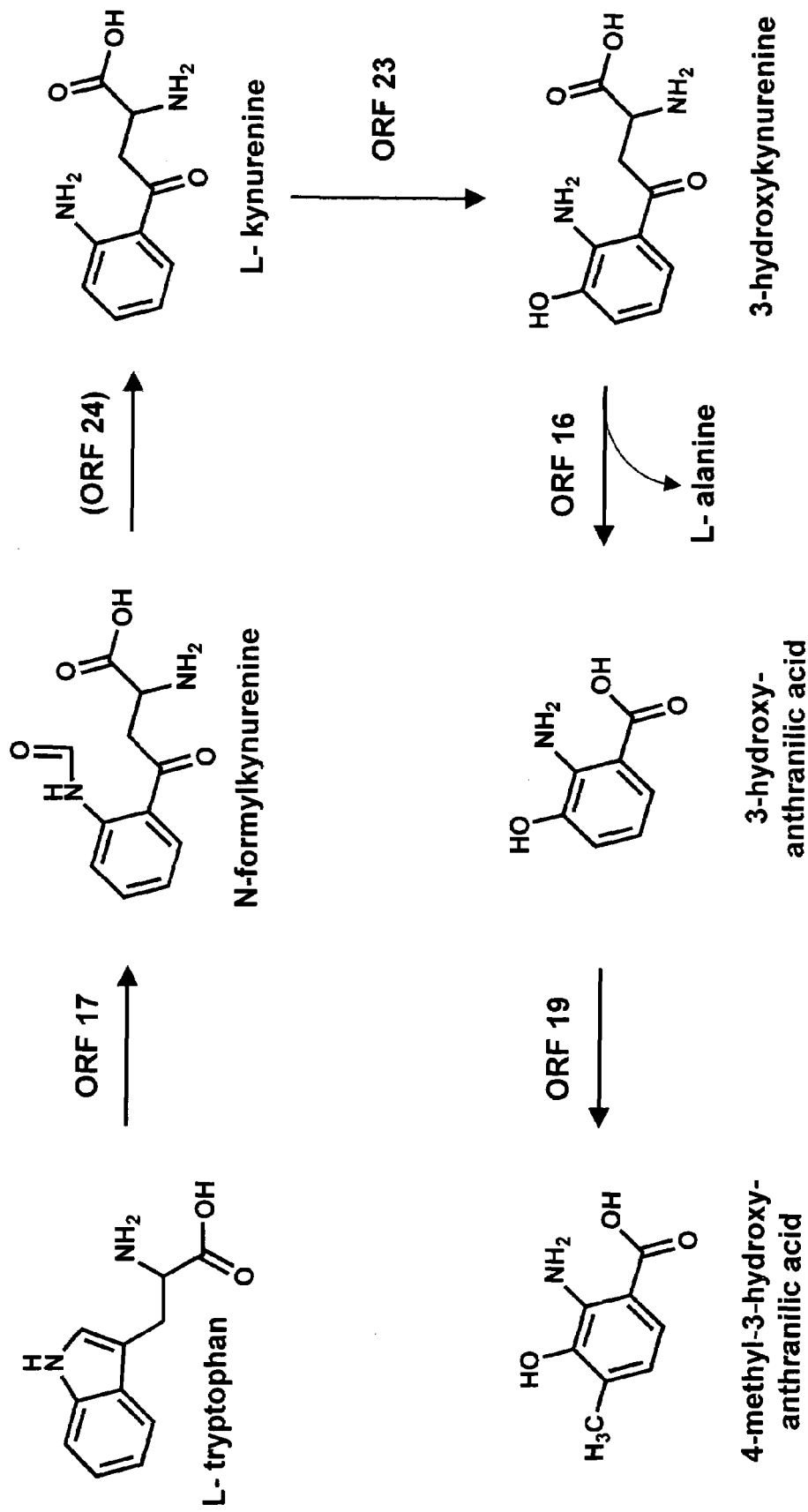
FIG. 9 is a biosynthetic scheme for formation of 4-methyl-3-hydroxyanthranilic acid from L-tryptophan, which 4-methyl-3-hydroxyanthranilic acid is one of the anthranilate precursors shown in FIG. 1.

Biosynthetic precursor feeding studies, suggest that the anthranilate moiety of the anthramycins is generated via the kynurenine pathway of tryptophan catabolism (Hurley et al., 1975, J. Am. Chem. Soc. 97:4372-4378; Hurley and Gairola, 1979, Antimicrob. Agents Chemother. 15:42-45). ORFs 16, 17, 18, 19, 23 and 24 (SEQ ID NOS: 32, 34, 36, 38, 46 and 48) are expected to be involved in the formation of the anthranilate precursor, as indicated in the scheme illustrated in FIG. 9. The ORF 17 protein (SEQ ID NO: 34) is similar to many tryptophan-2,3-dioxygenases and catalyzes the cleavage of the pyrrole ring of tryptophan to generate N-formylkynurenine. The ORF 24 protein (SEQ ID NO: 48) is similar to many prokaryotic and eukaryotic FAD-binding amine oxidases including L-amino acid oxidases and may catalyze the oxidative deformylation of N-formylkynurenine to generate L-kynurenine. The ORF 23 protein (SEQ ID NO: 46) is a flavin-dependent monooxygenase similar to mammalian L-kynurenine 3-monooxygenases and catalyzes the conversion of L-kynurenine to 3-hydroxykynurenine. The ORF 16 protein (SEQ ID NO: 32) is a pyridoxal phosphate-dependent kynureninase similar to many prokaryotic and eukaryotic kynurenine hydrolases and catalyzes the cleavage of 3-hydroxykynurenine to generate 3-hydroxyanthranilic acid and L-alanine. The ORF 19 protein (SEQ ID NO: 38) is a S-adenosylmethionine-dependent methyltransferase similar to many bacterial methyltransferases involved in secondary metabolism as well as mammalian hydroxyindole O-methyltransferases, and catalyzes the methylation of 3-hydroxyanthranilic acid to generate 3-hydroxy-4-methylanthranilic acid. The ORF 18 protein (SEQ ID NO: 36) encodes a small protein with a cluster of cysteine and histidine residues that may be involved in binding metals. The ORF 18 protein (SEQ ID NO: 36) is expected to be involved in the biosynthesis of the 3-hydroxy-4-methylanthranilic acid precursor, as it is transcriptionally coupled to the other ORFs in this pathway.

The ORF 21 protein (SEQ ID NO: 42) has two domains, an A domain and a T domain, and is similar to bacterial adenylate ligases that activate aromatic carboxylic acid precursors. The A domain of the ORF 21 protein (SEQ ID NO: 42) is unusual in containing an alanine residue at a position of the protein that is normally occupied by an aspartate residue in other A domains. X-ray crystal structure studies indicate that the highly conserved aspartate residue is involved in forming a salt-bridge with the free amine on the alpha carbon of amino acid substrates. The substitution of the highly conserved aspartate is only found in A domains that activate carboxylic acids that lack an amino group at the alpha carbon. The substitution of the highly conserved aspartate residue in the ORF 21 (SEQ ID NO: 42) A domain is consistent with the activation of a substituted anthranilate substrate, as this substrate has no amino group at the alpha carbon.

Figure 10:
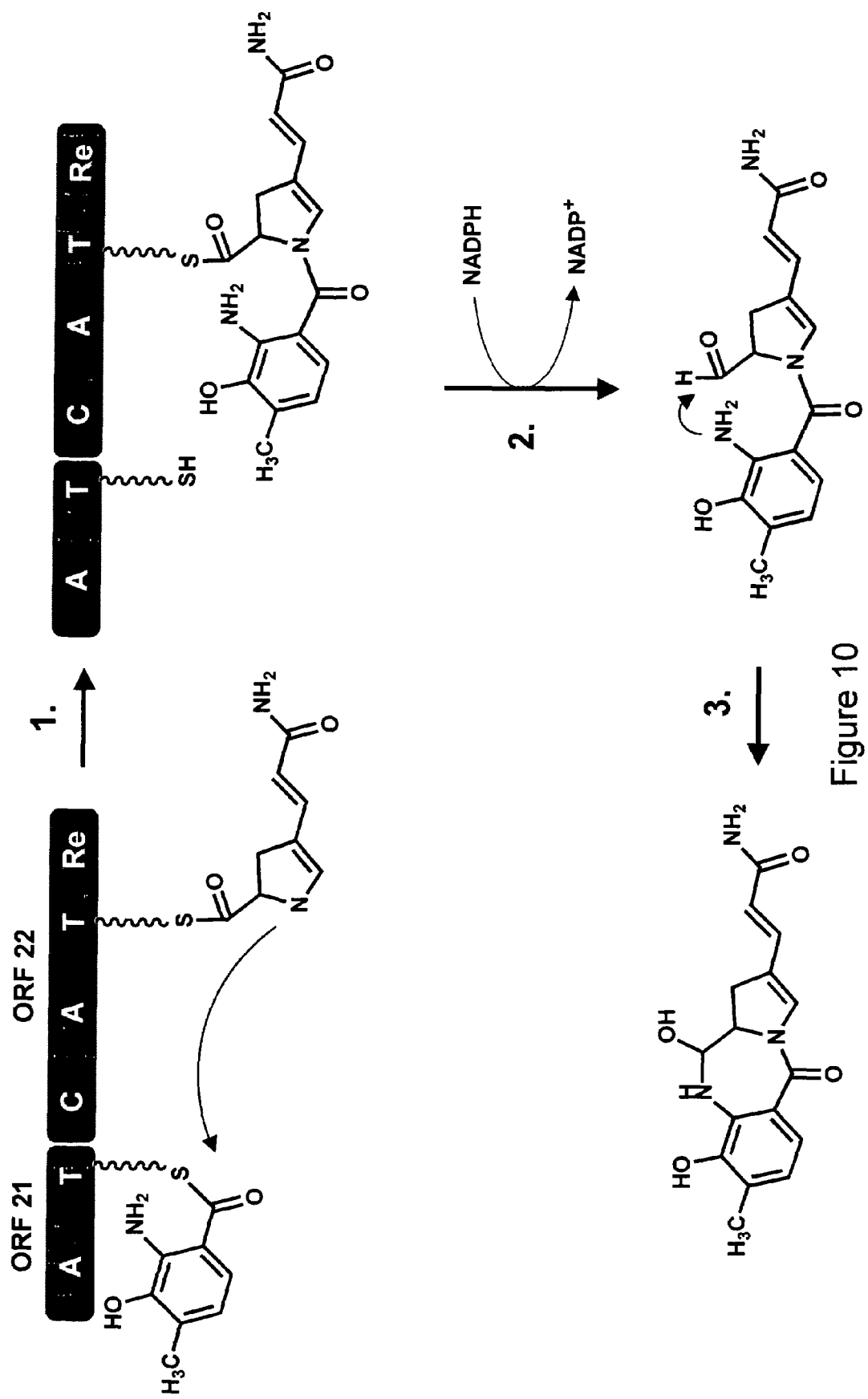
FIG. 10 is a model for the formation of the anthramycin backbone by the ORF 21 and ORF 22 peptide synthetase system.

The ORF 21 and ORF 22 proteins (SEQ ID NOS: 42 and 44) encode the components of a simple peptide synthetase system responsible for activating and joining a proline-like substrate and a substituted anthranilate substrate. As illustrated in FIG. 10, the A domain of ORF 21 (SEQ ID NO: 42) activates an anthranilate substrate and tethers it to the T domain of the protein. The A domain of the ORF 21 protein (SEQ ID NO: 42) is similar to the A domains of other bacterial adenylate ligases that activate aromatic carboxylic acid precursors. These A domains differ from those of other peptide synthetase A domains in carrying a substitution of a highly conserved aspartate residue that interacts with the amino group located at the alpha carbon of amino acid substrates (see FIG. 12; May et al., 2001, J. Biol. Chem. 276:7209-7217). The substitution of this highly conserved residue in the ORF 21 (SEQ ID NO: 42) A domain is consistent with the activation of substituted anthranilate substrates, as these substrates have no amino group at the alpha carbon. The ORF 22 protein (SEQ ID NO: 44) contains four domains, a C domain, an A domain, a T domain and a reductase domain. The A domain of the ORF 22 protein activates a proline-like substrate and tethers it to the T domain of the protein. The C domain of the ORF 22 protein (SEQ ID NO: 44) catalyzes the formation of an amide linkage between two substrates tethered to the T domains of the ORF 21 and ORF 22 synthetases (SEQ ID NOS: 42 and 44) as indicated in step 1 of FIG. 10. The reductase domain of ORF 22 (SEQ ID NO: 44) is similar to the reductase domains in other peptide synthetases that catalyze the reductive release of peptide intermediates (see FIG. 11; Keating et al., 2001, Chembiochem 2:99-107). The reductase domain of ORF 22 (SEQ ID NO: 44) catalyzes the NAD(P)-dependent reductive release of the dipeptide intermediate from the T domain of the protein (step 2 in FIG. 10), generating a free peptidyl aldehyde that undergoes spontaneous condensation of the primary amine with the reactive aldehyde carbonyl to form the diazepine ring (step 3 in FIG. 10). The presence of these domains was also confirmed by the identification of highly conserved motifs found in NRPS domains (see Konz and Marahiel (1999), Chem. Biol., vol 6, no 2, R39-R48). Examples of these conserved motifs are exemplified in FIG. 11, where R1-R7 reductase motifs are shown, and in FIG. 12, where A1-A10 adenylation motifs are demonstrated. Table 4 shows the coordinates of the domains of the nonribosomal peptide synthetase system of ORF 21 and ORF 22 proteins (SEQ ID NO:42 and 44), together with the corresponding coordinates of ORF 21 and 22 encoding nucleic acid.

TABLE 4

NRPS system domain coordinates

| ORF no. | SEQ ID NO (a.a./n.a.) | Amino acids | Nucleic acids | Domain Type |
|---------|----------------------|-------------|---------------|-------------|
| 21      | 42/43                | 35-522      | 103-1566      | A           |
|         | 42/43                | 523-600     | 1567-1800     | T           |
| 22      | 44/45                | 1-480       | 1-1440        | C           |
|         | 44/45                | 481-962     | 1441-2886     | A           |
|         | 44/45                | 963-1037    | 2887-3111     | T           |
|         | 44/45                | 1038-1446   | 3112-4338     | Re          |

The ORF 8 protein, (SEQ ID NO: 16) is expected to confer upon the producing organism resistance to the toxic effects of anthramycin. The ORF 8 protein (SEQ ID NO: 16) shows strong homology to UvrA subunits of bacterial ABC excinucleases and the DrrC daunorubicin resistance protein. Purified *E. coli* UvrA and UvrB proteins have been shown to reverse the formation of anthramycin-DNA adducts in vitro (Tang et al., 1991, J. Mol. Biol. 220:855-866). The DrrC protein has been proposed to bind to DNA regions intercalated by daunorubicin and thereby release the drug from DNA or block its ability to damage DNA (Furuya and Hutchinson, 1998, FEMS Microbiol. Lett. 168:243-249). Similarly, the ORF 8 protein (SEQ ID NO: 16) may act together with the cellular UvrB protein to reverse or prevent DNA damage that may result from the production of anthramycin or its intermediates.

The ORF 10 protein (SEQ ID NO: 20) is a membrane-associated protein that is expected to be involved in anthramycin efflux. The ORF 10 protein (SEQ ID NO: 20) is similar to many bacterial chloramphenicol resistance transporters involved in conferring resistance to the antibiotic chloramphenicol, as well as to some bacterial membrane transport proteins of the major facilitator superfamily of sugar transporters.

The ORF 25 protein (SEQ ID NO: 50) is expected to be involved in the regulation of anthramycin biosynthesis. ORF 25 (SEQ ID NO: 50) shows similarity to a number of response regulator receiver domain proteins involved in transcriptional regulation of gene expression in response to environmental or cellular signals.

The ORF 20 protein is expected to function as an esterase, as the protein contains histidine (aa 76) and serine residues (at amino acid positions 76 and 149, respectively) found in the active sites of many prokaryotic and eukaryotic esterases.

EXAMPLE 4

In vitro Production of 1,4-benzodiazePine-2,5-dione

In Vitro Production of Anthramycin and Derivatives:

Anthramycin is a potent, biologically active natural product that results from the condensation of two amino acid-derived substrates by a simple 2-enzyme NRPS system. NRPSs are multidomain proteins that contain sets of functional domains arranged into units called modules. The formation of a dipeptide requires a minimum of two NRPS modules, with each module consisting of an adenylation (A) domain and a thiolation (T) domain. Each T domain is posttranslationally modified with a 4'-phosphopantheteinyl (Ppant) group derived from coenzyme A (CoA) in a reaction catalyzed by a phosphopantheteinyl transferase. Peptide formation requires each module to load a specific amino acid or other carboxylic acid substrate onto its T domain, a process that involves activation of the substrate by the A domain as an acyl-adenylate intermediate and subsequent reaction of the acyl-adenylate with the P-pant thiol group to form an acyl-thioester. In this way the substrates to be joined are covalently bound to the protein modules through their T domains. Peptide bond formation is catalyzed by a condensation (C) domain. The C domain directs the nucleophilic attack of the amino group found on the substrate bound to downstream T domain onto the activated acyl thioester of the substrate bound to the upstream T domain. The resulting dipeptide product remains covalently tethered to the downstream module via thioester linkage to the T domain (dipeptidyl-S-T product). Thus the minimal dipeptide-forming NRPS system consists of the following protein domains: A-T-C-A-T. These domains may be contained on a single polypeptide or, as in the anthramycin ORF 21-ORF 22 system, on two polypeptides that cooperate through protein: protein interactions.

The ORF 21-ORF 22 gene products (SEQ ID NOS: 42 and 44) provide a system for the production of anthramycin and derivatives in vitro using purified enzymes. This system may also be used to create structurally diverse dipeptide-based products using purified enzymes and represents an advance over similar dipeptide-forming enzyme systems described previously.

The two-protein NRPS system comprising the ORF 21 and ORF 22 proteins (SEQ ID NOS: 42 and 44) represents one of the simplest natural product biosynthesis systems described to date and provides an attractive system for the production of anthramycin and anthramycin derivatives using purified protein components. Reconstitution of anthramycin synthesis in vitro using purified ORF 21 (SEQ ID NO: 42) and ORF 22 (SEQ ID NO: 44) can be achieved using methods similar to those used to achieve the in vitro synthesis of the peptide natural product enterobactin (Gehring et al., 1998, Biochemistry 37: 2648-2659). In the enterobactin system, incubation of purified EntE protein (which contains an A domain and activates the substrate 2,3-dihydroxybenzoate, DHB), purified hoLo-EntB protein (which contains an aryl-carrier protein that is functionally analogous to the T domain of other NRPS modules) and purified holo-EntF protein (a four-domain protein containing a C domain, an A domain specific for serine, a T domain and a thioesterase or Te domain) along with the substrates DHB, serine and ATP results in the reconstitution of enterobactin synthetase activity and the production of enterobactin.

The construction of expression vectors directing the expression of the apo and holo forms of ORF 21 (SEQ ID NO: 42) and ORF 22 (SEQ ID NO: 44) is achieved using standard methods (Sambrook, et al., 1989, Molecular Cloning: A Laboratory Manual, Cold Spring Harbor Laboratory, Cold Spring Harbor, N.Y.). For example, the genes encoding ORF 21 (SEQ ID NO: 43) and ORF 22 (SEQ ID NO: 45) are amplified by PCR and cloned into a commonly used vector such as the pQE vector system (Qiagen) or the pET vector system (Novagen). NRPS T domains require covalent attachment of the Ppant moiety of CoA to a conserved serine in order to be active (Walsh et al., 1997, Curr. Opin. Chem. Biol. 1:301-315). The Sfp Ppant transferase from *Bacillus subtilis* is capable of converting the apo forms of many heterologous recombinant proteins into the holo form and can be coexpressed with recombinant proteins in order to generate holo enzyme preparations (Lambalot et al., 1996, Chem. Biol. 3:923-936; Quadri et al., 1998, Biochemistry 37:1585-1595). The apo and holo forms of recombinant ORF 21 and ORF 22 are produced in *E. coli* as C-terminal hexahistidine-tagged fusion proteins and purified to homogeneity by nickel affinity chromatography, using methods similar to those described in Admiraal et al., 2001, Biochemistry 40:6116-6123. For the heterologous expression and isolation of apo forms of ORF 21 and ORF 22, *E. coli* strain M15(pREP4) is used, whereas *E. coli* strain BL21 (pREP4-gsp) is used to produce the holo enzyme forms, using methods similar to those described in May et al., 2001, J. Biol. Chem. 276:7209-7217. Alternatively, the *E. coli* strain BL21 strain is used for the the production of apo enzyme forms, while *E. coli* strain BL21 (pRSG56) is used to produce holo enzyme forms, using methods similar to those described in Admiraal et al., 2001, Biochemistry 40:6116-6123. As an alternative for the preperation of holo. forms of the recombinant proteins, the corresponding apo forms are incubated in a reaction mixture containing CoA and purified Sfp Ppant transferase, using methods similar to those described in Lambalot and Walsh, 1995, J. Biol. Chem. 270:24658-24661.

To determine the range of substrates that may be recognized and activated by the ORF 21 and ORF 22 enzymes (SEQ ID NOS: 42 and 44), reactions containing radiolabeled substrates and apo or holo forms of the recombinant proteins are incubated in the presence or absence of magnesium-ATP and subsequently analyzed by SDS-polyacrylamide gel electrophoresis (SDS-PAGE) followed by gel autoradiography, or by trichloroacetic acid precipitation of protein fractions followed by scintillation counting of the precipitate. The apo forms of the recombinant proteins, lacking the Ppant cofactor, are not covalently labeled with substrate. In contrast, holo forms of the recombinant proteins are covalently loaded with radiolabeled substrate in reactions that also require the presence of magnesium-ATP.

ORF 21 (SEQ ID NOS: 42) is expected to recognize and covalently tether a variety of benzoate, anthranilate and heterocyclic aromatic substrates. ORF 22 (SEQ ID NO: 44) is expected to recognize and covalently tether a variety of proline-like or pyrrol-containing substrates. The loading reaction consists of two steps, the formation of a substrate-adenylate intermediate mediated by the A domains of the recombinant proteins followed by substrate loading onto the thiol of the Ppant cofactor of the T domains. Additional substrates that can be loaded onto the recombinant proteins are identified by radiolabel chase experiments, using methods similar to those described in Admiraal et al., 2001, *Biochemistry* 40:6116-6123. Briefly, the holo form of the recombinant protein is first incubated with a putative substrate. The protein components are separated from putative unreactive substrates by microspin gel filtration. Radiolabeled forms of a known substrate, such as a substituted anthranilate in the case of ORF 21 or a proline-like substrate in the case of ORF 22, are then added to the protein fractions and the mixtures incubated briefly under reaction conditions (the chase period) prior to SDS-PAGE autoradiography. Protein samples that are originally incubated with a compound that is competent to serve as a substrate contain covalently loaded protein which is not available to react with radiolabeled substrates during the chase period, resulting in little or no detectable radiolabeled protein by SDS-PAGE autoradiography. In contrast, protein samples that are incubated with a compound that serves as a poor substrate or a non-substrate contain primarily free forms of the holo protein, which then readily react with radiolabeled substrate during the chase period to generate radiolabeled protein that is readily detected by SDS-PAGE autoradiography. Control experiments are used to rule out the possibility that a putative substrate acts as a tight-binding competitive inhibitor of subsequent loading with radiolabeled substrate by measuring the relative rate constants for reaction of putative substrates with respect to a known substrate over time in a mixed reaction.

Determination of the substrate selectivity of the A domains of ORF 21 and ORF 22 proteins (SEQ ID NOS: 42 and 44) is also accomplished by using the well-known A domain ATP-pyrophosphate exchange assay that monitors the formation of acyl-adenylates, using methods similar to those described in Stachelhaus et al., 1998, J. Biol. Chem. 273:22773-22781. Briefly, purified recombinant proteins are incubated with putative substrates in the presence of ATP and radiolabeled pyrophosphate and the incorporation of radiolabel into ATP is measured.

The anthramycin ORF 21 protein (SEQ ID NO: 42) is structurally and functionally similar to the A-T loading didomain of the RifA rifamycin synthetase. The natural substrate of the ORF 21 protein is a substituted anthranilate, while the natural substrate for the A-T loading didomain of the RifA synthetase is 3-amino-5-hydroxybenzoate. The rifamycin A-T loading didomain, when expressed and purified from a heterologous expression system independently from the remainder of the RifA synthetase, is able to activate and tether many additional substrates, including 3,5-diaminobenzoate, 3-hydroxybenzoate, 3-aminobenzoate, 3,5-dibromobenzoate, 3,5-dichlorobenzoate, 3,5-dihydroxybenzoate, 3-chlorobenzoate, 3-bromobenzoate, benzoate, 2-aminobenzoate, 3-methoxybenzoate, 3-fluorobenzoate and 3,5-difluorobenzoate (Admiraal et al., 2001, Biochemistry 40:6116-6123). It is similarly expected that the ORF 21 protein (SEQ ID NOS: 42) is able to activate and tether these and other substrates, including the corresponding anthranilate derivatives of all of the compounds listed as well as heterocyclic aromatic ring-containing substrates and present them for peptide bond formation to substrates tethered to the T domain of recombinant ORF 22 (SEQ ID NO: 44).

Reconstitution of peptide synthesis in vitro using NRPS modules provides a method to produce libraries of compounds derived from the condensation of amino acid and other carboxylic acid substrates. Reconstitution of one peptide bond-forming reaction to produce a dipeptidyl—S-T product requires two T domains primed with Ppant and loaded with an amino acid on the downstream T domain and an amino acid or other carboxylic acid group on the upstream T domain. Such two-module reconstitutions have recently been achieved with purified proteins. In one example, described in Stachelhaus et al., 1998, J. Biol. Chem. 273:22773-22781, the isolated first module of gramicidin S synthetase GrsA [A(Phe)-T-E domains] and the isolated first module of tyrocidine synthetase TycB [C-A (Pro)-T domains] function together to form a peptide bond, yielding the dipeptidyl product covalently tethered to the TycB module (D-Phe-Pro-S-TycB) which, in the absence of downstream modules, undergoes a slow intramolecular cyclization and release from the TycB module to generate free D-Phe-D-Pro diketopiperazine. In the absence of downstream domains the dipeptidyl-S-T condensation product remains covalently tethered to the enzyme (except in special cases) so that enzymatic turnover cannot occur, limiting the usefulness of this system. Doekel and Marahiel, 2000, Chem. Biol. 7:373-384 demonstrate that hybrid synthetases containing modules from heterologous NRPS systems can be constructed using protein engineering techniques to construct two-module systems capable of forming dipeptide products. For example, a hybrid synthetase consisting of the native initiation module of the bacitracin synthetase BacA1 [A(Ile) domain] and the carboxy-terminal module of the tyrocidine synthetase TycC [T-C-A(Leu)-T-Te domains] produced the dipeptides Ile-Leu and Ile-Ile when incubated with the substrates isoleucine and leucine in an in vitro reaction. Analysis of the reaction kinetics of the hybrid synthetase systems indicates that both the condensation reaction and the hydrolytic release of dipeptide product are slow processes, also limiting the usefulness of these systems for the production of dipeptide products in vitro.

In contrast to the system described above, the ORF 21-ORF 22 system represents a naturally-occurring 2-module system for the efficient production of anthramycin, anthramycin derivatives and other dipeptide products. Efficient product release and catalytic turnover results from the activity of the reductase domain found at the C-terminus of the ORF 22 protein. The unusual reductive cleavage mechanism catalyzed by the ORF 22 reductase domain results in the formation of a reactive aldehyde that can be captured intramolecularly in stable hemiaminal linkage, as found in anthramycin. A variety of hemiaminal or imine and other heteroatom cyclic forms can thus be produced depending on the nature of the nucleophilic substituents appended onto the upstream substrate activated by the ORF 21 protein, resulting in the formation of dipeptide products consisting of substrates linked by a diverse range of heterocyclic ring structures. Alternatively the reactive aldehyde may be reduced to the alcohol.

To assay for the production of dipeptide products by the recombinant ORF 21-ORF 22 system, methods similar to those described in Doekel and Marahiel, 2000, Chem. Biol. 7:373-384, are used. Briefly, purified holo enzymes are incubated with carboxylic acid and amino acid substrates in the presence of magnesium-ATP and suitable buffers to allow peptide bond formation to occur. Negative controls are performed with no ATP or only one substrate. Product detection is achieved using thin-layer chromatography and reverse phase high-performance liquid chromatography (HPLC) and coupled HPLC-mass spectrometric methods.

The ORF 21-ORF 22 system has applications in the production of many products containing heterocyclic ring structures, including benzodiazepine derivatives. For example, the 1,4-benzodiazepine-2,5-diones are an important class of compounds as derivatives of this class have shown promise as antithrombolitic agents, they serve as the synthetic precursors to the anthramycin antitumor compounds as well as to the benzodiazepine receptor antagonist flumazenil, and they have also shown utility as herbicides (Boojamre et al., 1997, J. Org. Chem. 62:1240-1256). The formation of 1,4-benzodiazepine-2,5-dione derivatives in vitro can be achieved using recombinant forms of the ORF 21 and ORF 22 proteins. It is expected that replacement of the reductase domain of ORF 22 by a hydrolyzing thioesterase domain will result in the release of products from the ORF 22 protein by simple hydrolysis of the dipeptidyl thioester to the corresponding free carboxylate rather than reductive cleavage to generate the aldehyde. Mootz et al. (2000, Proc. Natl. Acad. Sci. USA 97:5848-5853) describe methods for appending Te domains to heterologous NRPS modules for the purpose of effecting the release of nascent peptide chains from the recombinant synthetase. Using similar methods, the reductase domain of ORF 22 is replaced with a Te domain from a heterologous NRPS system that normally releases the peptide chain as a carboxylate, such as the AcvA Te domain involved in the release of aminoadipoyl-cysteine-valine tripeptide via water hydrolysis during the biosynthesis of penicillin, or the hydrolyzing Te domain of the vancomycin synthetase. Such a domain replacement results in the release of the anthramycin precursor dipeptide as a linear species containing vicinal carboxylate (generated by hydrolytic release) and amino (anthranilate substituent) groups. Cyclization of this compound to form the corresponding 1,4-benzodiazepine-2,5-dione structure is expected to occur following incubation under conditions that favor amide bond formation between the free amino and carboxylate groups.

An alternative scheme for the in vitro production of the 1,4-benzodiazepine-2,5-dione follows from the replacement of the reductase domain of ORF 22 with a lactam-forming Te domain, such as the Te domain of the TycC tyrocidine synthetase, that naturally catalyzes the intramolecular coupling of a free amino group to the carbonyl involved in thioester Inkage to the synthetase. The TycC Te domain exhibits a broad flexibility toward nonnative substrates (Trauger et al., 2000, Nature 407:215-218). In this case, transfer of the dipeptide intermediate onto the Te active site serine residue is followed by intramolecular amide formation and release of product from the recombinant synthetase. Other NRPS Te domains that are likely to catalyze a chain-releasing lactam-forming reaction, such as the Te domain of the gramicidin S GrsB synthetase protein, are also potential substitutes. Replacement of the ORF 22 reductase domain with such Te domains using standard protein engineering techniques thus results in the simultaneous formation of the second amide bond and release of the cyclic 1,4-benzodiazepine-2,5-dione product from the recombinant ORF 22 protein.

Another scheme for the in vitro production of the 1,4-benzodiazepine-2,5-dione follows from the replacement of the reductase domain of ORF 22 with an amide-forming C domain, such as the carboxy-terminal C domain of the cyclosporin synthetase, that naturally catalyzes the intramolecular coupling of a free amino group to the carbonyl involved in thioester linkage to the synthetase. Other NRPS C domains that are likely to catalyze a chain-releasing amide synthase reaction, such as the amide synthase C domain of the vibriobactin VibF protein, are also suitable substitutes. Replacement of the ORF 22 reductase domain with such amide synthase C domains thus results in the simultaneous formation of the second amide bond and release of the cyclic 1,4-benzodiazepine-2,5-dione product from the recombinant ORF 22 protein.

Yet another scheme for the production of the 1,4-benzodiazepine-2,5-dione follows from the inactivation or removal of the reductase domain of ORF 22 using standard protein engineering techniques. In this case the tethered dipeptidyl intermediate undergoes slow release from the ORF 22 protein via a nonenzymatic cyclization and release that results from the nucleophilic attack of the free amine group appended to the ring A substituent onto the activated carbonyl thioester, using a mechanism similar to the diketopiperazine-forming chain-release mechanism proposed for the biosynthesis and release of the natural product ergotamine from the LPS1 synthetase (Walzel et a., 1997, Chem. Biol. 4:223-230). Such cyclization and release is facilitated by the cyclic pyrrol-compound substituent naturally tethered to the ORF 22 protein, and is expected to be further enhanced by the loading of more conformationally flexible proline derivatives onto the ORF 22 T domain.

Ehmann et al. (2000, Chem. Biol. 7:765-772) demonstrate the feasibility of using small molecule substrate analogs to mimic the covalently tethered upstream and downstream acyl thioester substrates. Thus, rather than loading an acyl substrate onto a T domain, it is possible to activate the same substrate as the N-acetylcysteamine (NAC) thioester (acyl-S-NAC). For example, in a reaction containing purified EntF subunit of the enterobactin synthetase [C-A(Ser)-T-Te domains], purified EntB subunit (A domain) loaded with the 2,3-dihydroxybenzoyl donor (upstream) substrate group and the acceptor (downstream) substrate L-serine-SNAC, the formation of the condensation products 2,3-dihydroxybenzoyl -L-serine-SNAC and 2,3-dihydroxybenzoyl-L-serine (which results from thioester hydrolysis during the reaction and subsequent purification) were observed. Dipeptidyl condensation products were also observed when other L-amino acid-SNACs were used as the downstream substrate, albeit at lower levels than those observed with the natural substrate analog serine-SNAC. In another example, a reaction containing purified first module of tyrocidine synthetase TycB (C-A(Pro)-T), the natural proline acceptor (downstream) substrate for this module and D-phenylalanine-SNAC (the SNAC analog of the natural donor or upstream substrate of this module), resulted in the formation of the condensation product D-phenylalanine-proline diketopiperazine.

Using methods similar to those described in Ehmann et al., 2000, Chem. Biol. 7:765-772, the natural specificity of the ORF 21 and ORF 22 (SEQ ID NOS: 42 and 44) A domains may be bypassed to achieve condensation of an increased range of carboxylic acid and amino acid substrates by the ORF 21-ORF 22 NRPS system, thus increasing the range of unusual dipeptide compounds produced by this system.

Alternative carboxylic acid substrates may also be loaded onto the T domains of ORF 21 and ORF 22 proteins (SEQ ID NOS: 42 and 44) using methods similar to those described by Belshaw et al. (1999, *Science* 284:486-489). Such methods also bypass the editing function of the A domains and allow the loading of noncognate carboxylic acid and amino acid groups onto the ORF 21 and ORF 22 (SEQ ID NOS: 42 and 44) T domains. The ORF 21-ORF 22 system has the advantage that the upstream (donor) and downstream (acceptor) T domains reside on separate enzymes, allowing each to be loaded independently, and the activity of the reductase domain of ORF 22 ensures that dipeptide products are released from the enzyme following condensation, thus allowing enzymatic turnover and facilitating the detection of products. The loading and joining of noncognate substrates by the ORF 21-ORF 22 system includes the following three steps: 1) synthesis of acyl- or aminoacyl-S-coenzyme A molecules (aa-S-CoAs) to serve as potential substrates for loading onto the T domains of purified ORF 21 and ORF 22 proteins; 2) enzymatic loading of acyl- or aminoacyl-S-Ppant groups onto the apo forms of upstream and downstream T domains using the *Bacillus subtilis* Ppant transferase enzyme, with transfer of the aa-S-Ppant moiety to the apo T domains being monitored by mass spectrometric analysis or native PAGE gel-shift assays capable of resolving apo and holo forms of the ORF 21 and ORF 22 proteins; and 3) measuring the formation of dipeptide product resulting from peptide bond formation mediated by the C domain of the ORF 22 protein using thin-layer chromatography and reverse phase high-performance liquid chromatography (HPLC) and coupled HPLC-mass spectrometric methods.

EXAMPLE 5

Production of Anthramycin Derivatives by in Vivo Expression of Recombinant ORF 21 and ORF 22 Proteins The production of anthramycin derivatives by fermentation may also be accomplished by in vivo expression of recombinant ORF 21 and ORF 22 proteins (SEQ ID NOS: 42 and 44).

By analogy to the first condensation domain of the tyrocidine synthetase (Belshaw et al., 1999, Science 284: 486-489), the C domain of ORF 22 is likely to show low selectivity at the upstream (donor) residue (which is normally a substituted anthranilate for anthramycin biosynthesis). The experiments described in Doekel and Marahiel, 2000 Chem. Biol. 7:373-384 further confirm that recombinant NRPS modules show a considerable degree of tolerance toward noncognate substrates for the condensation reaction at the upstream (donor) position. Thus it is expected that the loading of noncognate substrates onto the ORF 21-ORF 22 proteins will be useful in generating anthramycin derivatives that carry numerous modifications of the A-ring structure, such as highly substituted aromatic rings, including heterocyclic rings, as well as unsaturated ring systems. The tyrocidine synthetase and other recombinant NRPS modules described by Doekel and Marahiel show a greater selectivity at the downstream (acceptor) site, reflecting a selectivity in the size of the R-group linked to the amino acid chain. However, the ORF 22 protein (SEQ ID NO: 42) represents an ideal catalyst for the activation and condensation of highly substituted proline-like and pyrrol-containing substrates, as the A domain of this protein naturally accepts a substrate containing the bulky acrylamide substituent on the pyrrol-ring, indicating that a wide variety of chemical groups can be substituted at this position without adversely affecting the catalytic suitability of the substrate amine and carbonyl functionalities involved in peptide bond formation and enzymatic release of products. It is therefore expected that the ORF 21-ORF 22 system will be useful in generating anthramycin derivatives that carry modifications of the C3-pyrrol-group that forms the C-ring of anthramycin.

For example, this is achieved by supplementing the growth medium with analogs of the natural substrates of the ORF 21 and ORF 22 system. This may be carried out in either a natural anthramycin-producing microorganism such as *Streptomyces refuineus*, or, preferably, a recombinant microorganism that is genetically engineered to over-express the ORF 21-ORF 22 system. The latter is preferred as higher levels of the ORF 21-ORF 22 enzymes will increase yields and the absence of the biosynthetic genes for the natural substrates of the ORF 21-ORF 22 system will overcome any potential substrate competition that may arise in a natural anthramycin-producing microorganism. Similar results may be obtained with natural anthramycin-producing strains that have either been genetically engineered or selected or mutagenized to (i) produce higher levels of the ORF 21-ORF 22 system and/or (ii) to be deficient in the biosynthesis of one or both of the natural substrates of the ORF 21-ORF 22 system. In both naturally producing and heterologously producing microorganisms, co-expression or increased expression of resistance determinants, such as the gene products of ORF 8, ORF 10 or ORF 25 (SEQ ID NOS: 16, 20 and 50) may be beneficial.

Many peptide natural products produced by NRPS systems have important medical and agricultural applications and there is great interest in methods for generating derivatives of peptide natural products that may have improved therapeutic and agricultural applications. For example, Doekel and Marahiel (2000 Chem. Biol. 7:373-384) have described protein engineering methods that can be used to join heterologous NRPS modules and generate hybrid synthetases capable of producing novel peptide products. Similar methods are used to append the domains of ORF 21 and ORF 22 to other NRPS modules in order to generate hybrid synthetases that produce novel peptide products and structural derivatives of known natural products. The ORF 21 and ORF 22 proteins are particularly useful in this regard as they naturally recognize and activate unusual, non-proteinogenic carboxylic acid and amino acid substrates and can therefore be used to incorporate these unusual substrates into other peptide natural products.

The ORF 21 A-T didomain provides a module that may be appended to other peptide synthetases or polyketide synthases in order to generate derivatives of peptide and polyketide natural products. For example, the ORF 21 A-T didomain may be used to prime the synthesis of polyketides by appending the protein or portions thereof to polyketide synthases (PKSs) by protein engineering in order to generate new natural product derivatives. Several polyketide-based natural products are synthesized by enzyme systems that contain an NRPS-like loading module fused to the first condensing module of the PKS. Biosynthetic gene clusters for the natural products rifamycin (Admiralet al., 2001, Biochemistry 40:6116-6123), rapamycin (Lowden et al., 1996, Agnes. Chem. Int. Ed. Engl. 35:2249-2251), FK506 (Motamedi and Shafiee, 1998, Eur. J. Biochem. 256:528-534), ansatrienin (Chen et al., 1999, Eur. J. Biochem. 261:98-107), FK520 (Wu et al., 2000, Gene 251:81-90), microcystin (Tillett et al., 2000, Chem. Biol. 7:753-764), and pimaricin (Aparicio et al., 2000, Chem. Biol. 7:895-905) all encode loading modules that are structurally and functionally similar to the ORF 21 A-T didomain. These naturally-occurring systems are likely to prime the biosynthesis of the corresponding natural products using an adenylation-thiolation mechanism similar to that used by the ORF 21 protein in anthramycin biosynthesis (Admira-al et al., 2001, Biochemistry 40:6116-6123). Thus, it is likely that substitution of the naturally occurring loading module of these systems with the module of ORF 21 will generate new products that result from priming with 4-methyl-3-hydroxyanthranilate or other benzoate- or anthranilate-based units or heterocylic ring structures. The production of derivatives of natural products by appending the ORF 21 loading module to other peptide synthetases or PKSs is achieved using methods similar to those described in Marsden et al., 1998, Science 279:199-202, in which the endogenous loading module of 6-deoxyerythronolide B PKS producing the polyketide backbone of the erythromycins is replaced by the loading module of the avermectin PKS such that the resulting hybrid synthase produced erythromycin derivatives that had incorporated branched starter units characteristic of the avermectin family.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all sizes and all molecular weight or mass values are approximate, and are provided for description.

Patents, patent publications, procedures and publications cited throughout this application are incorporated herein in their entirety for all purposes.

The invention claimed is:

1. An isolated, purified or enriched polynucleotide comprising a polynucleotide selected from the group consisting of: (a) a polynucleotide comprising nucleotides 1-1440 of SEQ ID NO:45, (b) a polynucleotide having at least 95% identity to a polynucleotide comprising nucleotides 1-1440 of SEQ ID NO:45 and encoding condensation activity, (c) a polynucleotide comprising nucleotides 2887-3111 of SEQ ID NO:45, and (d) a polynucleotide having at least 95% identity to a polynucleotide comprising nucleotides 2887-3111 of SEQ ID NO:45 and encoding thiolation activity.

2. The isolated, purified or enriched polynucleotide of claim 1, wherein said polynucleotide comprises nucleotides 1-1440 of SEQ ID NO:45 or nucleotides 2887-3111 of SEQ ID NO:45.

3. An expression vector comprising a nucleic acid of claim 1.

4. An isolated host cell transformed with the expression vector of claim 3.

5. A method of preparing anthramycin or an anthramycin analog, comprising transforming an isolated host cell with the expression vector of claim 4, culturing said host cell under conditions such that an anthramycin synthetase is produced and catalyzes the synthesis of said anthramycin or anthramycin analog.

6. An isolated, purified or enriched polynucleotide comprising a polynucleotide encoding the condensation domain of amino acids 1-480 of SEQ ID NO:44 or the thiolation domain of amino acids 963-1037 of SEQ ID NO:44.

7. An expression vector comprising a nucleic acid of claim 1.

8. An isolated host cell transformed with the expression vector of claim 7.

9. A method of preparing anthramycin or an anthramycin analog, comprising transforming an isolated host cell with the expression vector of claim 7, culturing said host cell under conditions such that an anthramycin synthetase is produced and catalyzes the synthesis of said anthramycin or anthramycin analog.

10. The method of claim 9, wherein said host cell is selected from species of the genera *Pseudomonas* and *Streptomyces*.

11. The method of claim 9, wherein said host cell is *E. coli*.

12. Cosmid 024CA comprised in the *E. coli* DH10B strain having accession number IDAC 040602-1.

13. Cosmid 024CO comprised in the *E. coli* DH10B strain having accession number IDAC 040602-2.

* * * * *